(12) United States Patent
Monath et al.

(10) Patent No.: US 11,214,598 B2
(45) Date of Patent: Jan. 4, 2022

(54) VACCINES AGAINST HEPATITIS B VIRUS

(71) Applicant: Hookipa Biotech GmbH, Vienna (AT)

(72) Inventors: Thomas Monath, Harvard, MA (US); Katherine Cohen, Vienna (AT); Vera Baumgartl-Strasser, Purkersdorf (AT)

(73) Assignee: Hookipa Biotech GmbH, Vienna (AT)

( * ) Notice: Subject to any disclaimer, the term of this patent is extended or adjusted under 35 U.S.C. 154(b) by 0 days.

(21) Appl. No.: 15/773,512

(22) PCT Filed: Nov. 3, 2016

(86) PCT No.: PCT/EP2016/076591
§ 371 (c)(1),
(2) Date: May 3, 2018

(87) PCT Pub. No.: WO2017/076988
PCT Pub. Date: May 11, 2017

(65) Prior Publication Data
US 2018/0319845 A1    Nov. 8, 2018

Related U.S. Application Data

(60) Provisional application No. 62/250,639, filed on Nov. 4, 2015.

(51) Int. Cl.
| | | |
|---|---|---|
| C07K 14/005 | (2006.01) | |
| C12N 15/86 | (2006.01) | |
| A61P 31/20 | (2006.01) | |
| A61K 9/00 | (2006.01) | |
| A61K 39/29 | (2006.01) | |
| A61K 39/00 | (2006.01) | |

(52) U.S. Cl.
CPC .......... *C07K 14/005* (2013.01); *A61K 9/0019* (2013.01); *A61K 39/292* (2013.01); *A61P 31/20* (2018.01); *C12N 15/86* (2013.01); *A61K 2039/5256* (2013.01); *A61K 2039/54* (2013.01); *A61K 2039/575* (2013.01); *C07K 2319/00* (2013.01); *C12N 2730/10134* (2013.01); *C12N 2760/10022* (2013.01); *C12N 2760/10034* (2013.01); *C12N 2760/10043* (2013.01)

(58) Field of Classification Search
CPC .. C07K 14/005; C07K 2319/00; C12N 15/86; C12N 2760/10043; C12N 2760/10034; C12N 2760/10022; C12N 2730/10134; A61P 31/20; A61K 9/0019; A61K 39/292; A61K 2039/54; A61K 2039/575; A61K 2039/5256; A61K 48/00
See application file for complete search history.

(56) References Cited

U.S. PATENT DOCUMENTS

| | | |
|---|---|---|
| 5,057,540 A | 10/1991 | Kensil et al. |
| 8,592,205 B2 | 11/2013 | Pinschewer et al. |
| 9,309,289 B2 | 4/2016 | Pinschewer et al. |
| 9,809,801 B2 | 11/2017 | Belnoue et al. |
| 9,944,952 B2 | 4/2018 | Pinschewer et al. |
| 10,111,945 B2 | 10/2018 | Orlinger et al. |
| 10,669,315 B2 | 6/2020 | Orlinger et al. |
| 2003/0129202 A1* | 7/2003 | Trepo ................... C07K 14/005 424/225.1 |
| 2010/0297172 A1 | 11/2010 | Pinschewer et al. |
| 2014/0050760 A1* | 2/2014 | Pinschewer .............. C12N 7/00 424/204.1 |
| 2016/0194663 A1 | 7/2016 | Pinschewer et al. |
| 2016/0206724 A1 | 7/2016 | De la Torre et al. |
| 2016/0296619 A1 | 10/2016 | Orlinger et al. |
| 2017/0319673 A1* | 11/2017 | Pinschewer ........ A61K 39/0011 |
| 2018/0179257 A1 | 6/2018 | Orlinger et al. |
| 2018/0319845 A1 | 11/2018 | Monath et al. |
| 2018/0344830 A1 | 12/2018 | Schmidt et al. |
| 2019/0062784 A1 | 2/2019 | Pinschewer et al. |
| 2019/0135875 A1 | 5/2019 | Bonilla et al. |
| 2019/0247493 A1 | 8/2019 | Orlinger et al. |
| 2020/0113995 A1 | 4/2020 | Orlinger et al. |
| 2020/0206334 A1 | 7/2020 | Schmidt et al. |
| 2021/0024584 A1 | 1/2021 | Orlinger et al. |
| 2021/0071198 A1 | 3/2021 | Pinschewer et al. |

FOREIGN PATENT DOCUMENTS

| | | |
|---|---|---|
| JP | A-H10-1084967 | 4/1998 |
| WO | WO 2006/125983 A1 | 11/2006 |
| WO | WO 2007/109812 A2 | 9/2007 |
| WO | WO 2007/109813 A1 | 9/2007 |
| WO | WO 2009/083210 A1 | 7/2009 |

(Continued)

OTHER PUBLICATIONS

Gutierrez C, et. al. Hepatitis B virus isolate 98678 core protein gene, partial cds. GenBank: AY254515.1, Dep. Apr. 1, 2004.*
Kimbi GC, et. al. Hepatitis B virus isolate 2 complete genome. GenBank: AY233280.1, Apr. 23, 2004.*
Salvato M, et. al. Lymphocytic choriomeningitis virus envelope glycoprotein (GP-C) and nucleoprotein (NP) genes, complete cds. GenBank: M20869.1. Pub. Aug. 2, 1993.*
Chakraborty AK, et. al. Synthetic construct isolate L1.1 Hepatitis B virus precore (precore), polymerase-reverse transcriptase (Pol), PreS1 (PreS1), and X protein (X) genes, complete cds. GenBank: DQ219811.1, Pub. Oct. 23, 2005.*

(Continued)

*Primary Examiner* — Rachel B Gill
(74) *Attorney, Agent, or Firm* — Jones Day

(57) ABSTRACT

The present application provides immunotherapies for Hepatitis B virus infections. Provided herein are genetically modified arenaviral vectors suitable as vaccines for prevention and treatment of Hepatitis B virus infections. Also provided herein are pharmaceutical compositions and methods for the treatment of Hepatitis B virus infections. Specifically, provided herein are pharmaceutical compositions, vaccines, and methods of treating Hepatitis B virus infection.

Figure 1:
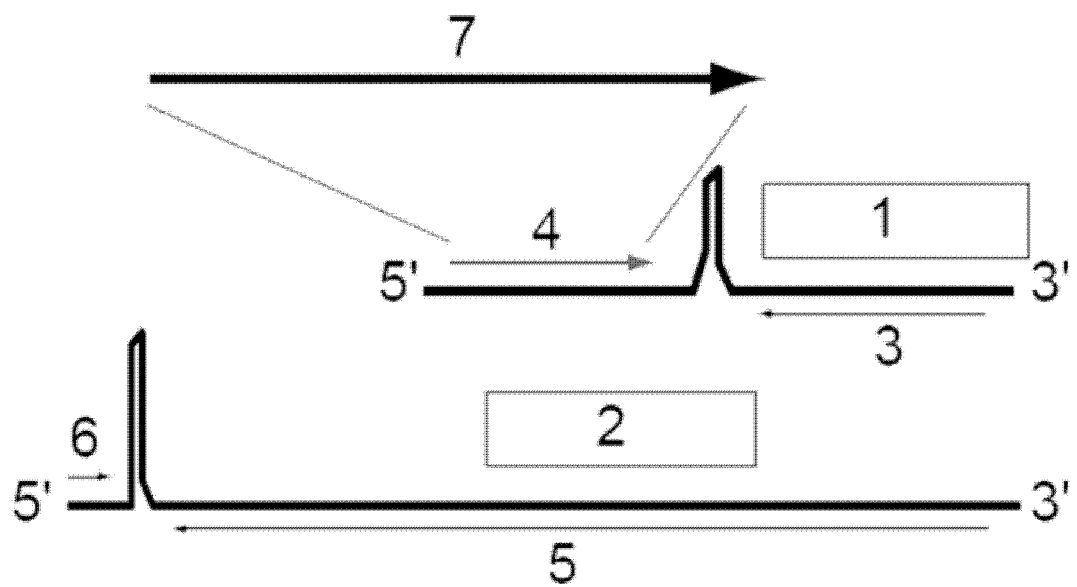

34 Claims, 4 Drawing Sheets
Specification includes a Sequence Listing.

(56) References Cited

FOREIGN PATENT DOCUMENTS

| | | |
|---|---|---|
| WO | WO 2011/015656 | 2/2011 |
| WO | WO 2012/162428 A1 | 11/2012 |
| WO | WO 2013/112549 A1 | 8/2013 |
| WO | WO 2014/140301 A1 | 9/2014 |
| WO | WO 2014/155076 A1 | 10/2014 |
| WO | WO 2015/082570 A1 | 6/2015 |
| WO | WO 2015/183895 A1 | 12/2015 |
| WO | WO 2016/048949 A1 | 3/2016 |
| WO | WO 2016/071683 A2 | 5/2016 |
| WO | WO 2016/075250 A1 | 5/2016 |
| WO | WO 2016/166285 A1 | 10/2016 |
| WO | WO 2016/198531 A2 | 12/2016 |
| WO | WO 2017/068190 A1 | 4/2017 |
| WO | WO 2017/076988 A1 | 5/2017 |
| WO | WO 2017/080920 A1 | 5/2017 |
| WO | WO 2017/190074 A1 | 11/2017 |
| WO | WO 2017/198726 A1 | 11/2017 |
| WO | WO 2018/083220 A2 | 5/2018 |
| WO | WO 2018/185307 A1 | 10/2018 |

OTHER PUBLICATIONS

Flatz L, Hegazy AN, et. al. Nabel GJ, Pinschewer DD. Development of replication-defective lymphocytic choriomeningitis virus vectors for the induction of potent CD8+ T cell immunity. Nat Med. Mar. 2010;16(3):339-45. Epub Feb. 7, 2010.*
Knudsen KB, Northeved H, Kumar PE, Permin A, Gjetting T, Andresen TL, Larsen S, Wegener KM, Lykkesfeldt J, Jantzen K, Loft S , Møller P, Roursgaard M. In vivo toxicity of cationic micelles and liposomes. Nanomedicine. Feb. 2015;11(2):467-77. Epub Aug. 25, 2014.*
Akbar et al., "HBsAg, HBcAg, and combined HBsAg/HBcAg-based therapeutic vaccines in treating chronic hepatitis B virus infection," *Hepatobiliary Pancreat. Dis. Int.*, 12(4):363-369 (2013).
Albarino et al., "Efficient rescue of recombinant Lassa virus reveals the influence of S segment noncoding regions on virus replication and virulence," *J. Virol.*, 85(8):4020-4024 (2011).
Altman et al., "Phenotypic analysis of antigen-specific T lymphocytes," *Science*, 274:94-96 (1996).
Beasley et al., "Overview on the Epidemiology of Hepatocellular Carcinoma," *Viral Hepatitis and Liver Disease: Proceedings of the 1990 International Symposium on Viral Hepatitis and Liver Disease: Contemporary Issued and Future Prospects*, Hollinger et al. eds., Williams & Wilkins, Baltimore MD, 532-535 (1991).
Bertoletti et al., "Innate and adaptive immune responses in chronic hepatitis B virus infections: towards restoration of immune control of viral infection," *Gut*, 61(12):1754-1764 (2012).
Boni et al., "Transient restoration of anti-viral T cell responses induced by lamivudine therapy in chronic hepatitis B," *J. Hepatol.*, 39:595-605 (2003).
Bonilla et al., "Interpretation of lymphocyte proliferation tests," *Ann. Allergy Asthma Immunol.*, 101:101-104 (2008).
Bonilla et al., "Practice parameter for the diagnosis and management of primary immunodeficiency," *Ann. Allergy Asthma Innumol.*, 94(5 Supp 1):S1-63 (2005).
Bourgine et al., "Optimization of immune responses induced by therapeutic vaccination with cross-reactive antigens in a humanized hepatitis B surface antigen transgenic mouse model," *Virology*, 430(1):10-19 (2012).
Buchmeier et al., "Arenaviridae: The Viruses and Their Replication," *Fields Virol.*, 2:1635-1668 (2001).
Caruso et al., "Flow cytometric analysis of activation markers on stimulated T cells and their correlation with cell proliferation," *Cytometry*, 27:71-76 (1997).
Cheng et al., "Arenavirus Genome Rearrangement for the Development of Live Attenuated Vaccines," J. Virol., 89(14):7373-7384 (2015).
Cheng et al., "Generation of recombinant arenavirus for vaccine development in FDA-approved Vero cells," *J. Vis. Exp.*, 78: 50662 (2013).

Couillin et al., "Specific vaccine therapy in chronic hepatitis B: induction of T cell proliferative responses specific for envelope antigens," *J. Infect. Dis.*, 180:15-26 (1999).
Czerkinsky et al., "A solid-phase enzyme-linked immunospot (ELISPOT) assay for enumeration of specific antibody-secreting cells," *J. Immunol. Methods*, 65:109-121 (1983).
De La Hoz et al., "Eight years of hepatitis B vaccination in Colombia with a recombinant vaccine: factors influencing hepatitis B virus infection and effectiveness," *Int. J. Infet. Dis.*, 12:183-189 (2008).
Dhanwani et al., "A Novel Live Pichinde Virus-Based Vaccine Vector Induces Enhanced Humoral and Cellular Immunity after a Booster Dose," J. Virol., 90(5):2551-2560 (2015).
Emonet et al., "Generation of recombinant lymphocytic choriomeningitis viruses with trisegmented genomes stably expressing two additional genes of interest," *Proc. Natl. Acad. Sci. U.S.A.*, 106(9):3473-3478 (2009).
Emonet et al., "Arenavirus reverse genetics: new approaches for the investigation of arenavirus biology and development of antiviral strategies," Virology, 411(2):416-425 (2011).
Emonet et al., "Rescue from Cloned cDNAs and In Vivo Characterization of Recombinant Pathogenic Romero and Live-Attenuated Candid #1 Strains of Junin Virus, the Causative Agent of Argentine Hemorrhagic Fever Disease," *J. Virol.*, 85(4):1473-1483 (2011).
Flatz et al., "Development of replication-defective lymphocytic choriomeningitis virus vectors for the induction of potent CD8+ T cell immunity," *Nat. Med.*, 16(3):339-345 (2010).
Flatz et al., "Recovery of an arenavirus entirely from RNA polymerase I/II-driven cDNA," *Proc. Natl. Acad. Sci. U.S.A.*, 103(12):4663-4668 (2006).
Ghanekar et al., "Gamma interferon expression in CD8(+) T cells is a marker for circulating cytotoxic T lymphocytes that recognize an HLA A2-restricted epitope of human cytomegalovirus phosphoprotein pp65," *Clin. Diagn. Lab Immunol.*, 8(3):628-631 (2001).
Goldstein et al., "A mathematical model to estimate global hepatitis B disease burden and vaccination impact," *Int. J. Epidemiol.*, 34(6):1329-1339 (2005).
Goldstein et al., "Incidence and risk factors for acute hepatitis B in the United States, 1982-1998: implications for vaccination programs," *J. Infet. Dis.*, 185:713-719 (2002).
Guidotti et al., "High-level hepatitis B virus replication in transgenic mice," *J. Virol.*, 69(10):6158-6169 (1995).
Hicks et al., "Age-related changes in mitogen-induced lymphocyte function from birth to old age," *Am. J. Clin. Pathol.*, 80(2):159-163 (1983).
Hong et al., "Lentivector expressing HBsAg and immunoglobulin Fc fusion antigen induces potent immune responses and results in seroconversion in HBsAg transgenic mice," *Vaccine*, 29(22):3909-3916 (2011).
Hutchings et al., "The detection and enumeration of cytokine-secreting cells in mice and man and the clinical application of these assays," *J. Immunol. Methods*, 120(1):1-8 (1989).
Hyams, "Risks of chronicity following acute hepatitis B virus infection: a review," *Clin. Infect. Dis.*, 20(4):992-1000 (1995).
Iwasaki et al., "General Molecular Strategy for Development of Arenavirus Live-Attenuated Vaccines," J. Virol., 89(23):12166-12177 (2015).
Jenne et al., "Immune surveillance by the liver," *Nat. Immunol.*, 14(10):996-1006 (2013).
Kallert et al., "Replicating viral vector platform exploits alarmin signals for potent CD8+ T cell-mediated tumour immunotherapy," *Nat. Comm.*, 8:15327 (2017).
Karwacz et al., "Nonintegrating Lentivector Vaccines Stimulate Prolonged T-Cell and Antibody Responses and Are Effective in Tumor Therapy," *J. Virol.*, 83(7):3094-3103 (2009).
Kosinska et al., "Therapeutic vaccination in chronic hepatitis B: preclinical studies in the woodchuck," *Hepat. Res. Treat.*, 2010:817580 (2010).
Liu et al., "New therapeutic vaccination strategies for the treatment of chronic hepatitis B," *Virol. Sin.*, 29:10-16 (2014).
Margolis et al., "Prevention of hepatitis B virus transmission by immunization. An economic analysis of current recommendations," *JAMA*, 274(15):1201-1208 (1995).

(56) References Cited

OTHER PUBLICATIONS

Mayer et al., "Hepatitis B assays in serum, plasma and whole blood on filter paper," *BMC Clin. Pathol.*, 12:8 (2012).
Mendy et al., "Hepatitis B viral load and risk for liver cirrhosis and hepatocellular carcinoma in the Gambia, West Africa," *J. Viral. Hepat.*, 17(2):115-122 (2010).
Michel et al., "Hepatitis B vaccines: protective efficacy and therapeutic potential," *Pathol. Biol.*, 58:288-295 (2010).
Michel et al., "Therapeutic vaccines and immune-based therapies for the treatment of chronic hepatitis B: perspectives and challenges," *J. Hepatol.*, 54:1286-1296 (2011).
Michel et al., "Therapeutic vaccines in treating chronic hepatitis B: the end of the beginning or the beginning of the end?," *Med. Microbiol. Immunol.*, 204:121-129 (2015).
Moshkani et al., "A Highly Attenuated Vesicular Stomatitis Virus-Based Vaccine Platform Controls Hepatitis B Virus Replication in Mouse Models of Hepatitis B," *J. Virol.*, 93(5): e01586 (2019).
Murali-Krishna et al., "Counting antigen-specific CD8 T cells: a reevaluation of bystander activation during viral infection," *Immunity*, 8(2):177-187 (1998).
Nomura et al., "Optimization of whole blood antigen-specific cytokine assays for CD4(+) T cells," *Cytometry*, 40:60-68 (2000).
Ortiz-Riano et al., "Arenavirus reverse genetics for vaccine development," *J. Gen. Virol.*, 94:1175-1188 (2013).
Perez et al., "Characterization of the genomic promoter of the prototypic arenavirus lymphocytic choriomeningitis virus," *J. Virol.*, 77(2):1184-1194 (2003).
Perfetto et al., "Seventeen-colour flow cytometry: unravelling the immune system," *Nat. Rev. Immunol.*, 4(8):648-655 (2004).
Popkin et al., "Expanded Potential for Recombinant Trisegmented Lymphocytic Choriomeningitis Viruses: Protein Production, Antibody Production, and In Vivo Assessment of Biological Function of Genes of Interest," *J. Virol.*, 85(15):7928-7932 (2011).
Rapicetta et al., "New perspectives for hepatitis B vaccines and immunization," *Vaccine*, 27(25-26):3271-3275 (2009).
Sanchez et al., "Rescue of the prototypic Arenavirus LCMV entirely from plasmid," *Virology*, 350(2):370-380 (2006).
Shanmugham et al., "Immunocapture enzyme-linked immunosorbent assay for assessment of in vitro potency of recombinant hepatitis B vaccines," *Clin. Vaccine Immunol.*, 17(8):1252-1260 (2010).
Stoute et al., "A preliminary evaluation of a recombinant circumsporozoite protein vaccine against plasmodium falciparum malaria," *N. Eng. J. Med.*, 336:86-91 (1997).
Suni et al., "Detection of antigen-specific T cell cytokine expression in whole blood by flow cytometry," *J. Immunol. Methods*, 212(1):89-98 (1998).
Van Helden et al., "Performance of hepatitis B assays on the Bayer ADVIA Centaur Immunoassay System," *Clin. Lab.*, 50(1-2):63-73 (2004).
Villar et al., "Assessment of dried blood spot samples as a simple method for detection of hepatitis B virus markers," *J. Med. Virol.*, 83(9):1522-1529 (2011).
Wong et al., "Prevention of the HBsAg carrier state in newborn infants of mothers who are chronic carriers of HBsAg and HBeAg by administration of hepatitis-B vaccine and hepatitis-B immunoglobulin. Double-blind randomised placebo-controlled study," *Lancet*, 1:921-926 (1984).
Stahl et al., "Immunogenicity of peptide fusions to hepatitis B virus core antigen," *Proc. Natl. Acad. Sci. USA*, 86(16):6283-6287 (1989).
Chen et al., 2008, "Genomic and biological characterization of aggressive and docile strains of lymphocytic choriomeningitis virus rescued from a plasmidbased reverse-genetics system", J of Gen. Virology, vol. 89: 1421-1433.
Opposition Brief filed on Apr. 16, 2021 in European Pat. App. No. 15794900.9 (26 pages).

\* cited by examiner

Fig. 2A- 2C

VACCINES AGAINST HEPATITIS B VIRUS

This application is a U.S. National Stage Application under 35 U.S.C. § 371 of International Patent Application No. PCT/EP2016/076591, filed Nov. 3, 2016, which claims benefit of U.S. Provisional Patent Application No. 62/250,639, filed Nov. 4, 2015, the disclosure of which is incorporated by reference herein in its entirety.

REFERENCE TO SEQUENCE LISTING SUBMITTED ELECTRONICALLY

This application incorporates by reference a Sequence Listing submitted with this application as text file entitled "Sequence_Listing_13194-014-228.TXT" created on Nov. 2, 2016 and having a size of 128,899 bytes.

1. INTRODUCTION

Provided herein are genetically modified arenaviruses suitable as vaccines for prevention and treatment of Hepatitis B virus infections. Also provided herein are pharmaceutical compositions and methods for the treatment of Hepatitis B virus infections. Specifically, provided herein are pharmaceutical compositions, vaccines, and methods of treating Hepatitis B virus infections. As such, the present application provides immunotherapies for Hepatitis B virus infections.

2. BACKGROUND

2.1 the Pathogen and the Disease

Hepatitis B virus (HBV) is a double-stranded enveloped virus of the Hepadnaviridae family. The virus particle consists of an outer lipid envelope and an icosahedral nucleocapsid core composed of protein. The nucleocapsid encloses the viral DNA and a DNA polymerase that has reverse transcriptase activity. The outer envelope contains embedded proteins which are involved in viral binding of, and entry into, susceptible cells. HBV replicates in the hepatocytes of humans and other higher primates, but does not grow in artificial cell cultures.

The outcomes of HBV infection are age-dependent and include asymptomatic infection, acute hepatitis B, chronic HBV infection, cirrhosis and hepatocellular carcinoma (HCC). Acute hepatitis B occurs in approximately 1% of perinatal infections, 10% of early childhood infections (children aged 1-5 years) and 30% of late infections (people aged >5 years). Fulminant hepatitis develops in 0.1-0.6% of acute hepatitis cases; mortality from fulminant hepatitis B is approximately 70%. The development of chronic HBV infection is inversely related to the age of acquisition, occurring in approximately 80-90% of people infected perinatally, about 30% of children infected before the age of 6 years, and in <5% of infections occurring in otherwise healthy adults (Hyams et al., 1995, Clinical Infections Diseases 20:992-1000). Comorbidities, including concurrent HIV infection and ingestion of alcohol or aflotoxins, or both, may have an important role in the development of morbidity related to hepatitis B. It is estimated that 10% of the 40 million people infected with HIV worldwide are coinfected with HBV.

People with chronic HBV infection have a 15-25% risk of dying prematurely from HBV-related cirrhosis and HCC (Beasley and Hwang, 1991, Proceedings of the 1990 International Symposium on Viral Hepatitis and Liver Disease: Contemporary Issues and Future Prospects 532-535). Acute HBV infection is characterized by the presence of HBsAg, the surface antigen of HBV, and immunoglobulin M (IgM) antibody to the core antigen, HBcAg. During the initial, highly replicative phase of infection, patients are also seropositive for HBeAg, the extracellular and secreted form of HBcAg which can be found in the serum of patients where it serves as a marker of active replication in chronic hepatitis. Antibody to HBsAg (anti-HBs) is discernible after a few weeks and is followed by clearance of the HBsAg. Chronic infection is characterized by the persistence (>6 months) of HBsAg (with or without concurrent HBeAg). Persistence of HBsAg is the principal marker of risk for developing chronic liver disease and HCC later in life. The presence of HBeAg indicates that the blood and body fluids of the infected individual are highly contagious.

2.2 Epidemiology and Public Health

Diseases caused by the hepatitis B virus have a worldwide distribution. It is estimated that two billion people have at some time been infected with HBV. Of these, approximately 360 million individuals are chronically infected and at risk of serious illness and death, mainly from liver cirrhosis and hepatocellular carcinoma (HCC). Mathematical modeling for the year 2000 estimated the number of deaths from HBV-related diseases at about 600 000 each year worldwide (Goldstein et al., 2005, International J. Epidemiology 34:1329-1339). Humans are the only reservoir of HBV. The virus is transmitted by percutaneous and permucosal exposure to infected blood and other body fluids, mainly semen and vaginal fluid. The incubation period is 75 days on average, but may vary from about 30 days to 180 days. The surface antigen of HBV (HBsAg) may be detected in serum 30-60 days following infection and may persist for widely variable periods of time. The endemicity of hepatitis B is described by the prevalence of HBsAg in the general population of a defined geographical area, and it varies considerably globally: HBsAg prevalences of >8% are typical of highly endemic areas, prevalences of 2-7% are found in areas of intermediate endemicity, whereas in areas with low endemicity <2% of the population is HBsAg-positive.

In highly endemic areas, HBV is most commonly spread from mother to child at birth, or from person to person in early childhood (Goldstein et al., 2005, International J. Epidemiology 34:1329-1339; Wong et al., 1984, Lancet 1:921-926; de la Hoz et al., 2008 International J. Infectious Diseases 12:183-189). Perinatal or early childhood transmission may also account for more than one third of chronic infections in areas of low endemicity (Margolis et al., 1995, JAMA 274:1201-1208) although in those settings, sexual transmission and the use of contaminated needles, especially among injecting drug users, are the major routes of infection (Goldstein et al., 2002, J. Infectious Diseases 185:713-719).

2.3 Current Treatment

Universal hepatitis B vaccination has been shown to reduce the rates of HBV infection and HCC significantly. However, once chronic HBV infection is established, treatment still poses a major challenge as traditional therapies usually fail to provide sustained control of viral replication and liver damage in most patients.

Currently approved antiviral treatments for chronic hepatitis B include pegylated (PEG) recombinant interferon-α and viral DNA polymerase inhibitors. These agents decrease viral replication and have been shown to delay progression of cirrhosis, reduce the incidence of HCC and improve long-term survival. However, treatment is complicated by the toxicity of the agents and it can only cure a small subset of chronically infected individuals. Although viral levels in the blood plummet to almost undetectable levels in individuals receiving standard therapies, reductions of intrahepatic viral DNA are only modest. As a consequence, rebound of viraemia frequently occurs after discontinuation of treatment and people with chronic HBV infections must stay on lifelong treatment. However, even after ten years on antiviral therapy, drugs reduce liver failure by only 40-70%, and mortality from cirrhosis and liver cancer remains high.

2.4 Hepatitis B and the Immune System

Chronic hepatitis B infection is characterized by dysfunctional innate and adaptive antiviral immunity (Bertoletti & Ferrari, 2012, Gut 61:1754-1764). In contrast, HBV-specific immunity in patients with resolved HBV infection is robust and multifunctional. Several mechanisms might contribute to the dysfunction of HBV-specific T-cell immunity in chronic hepatitis B patients, including high levels of viral antigenaemia, and the tolerizing microenvironment of the liver (Jenne & Kubes, 2013, Nat. Immunol. 14:996-1006). Previous studies have demonstrated that suppression of viral replication can transiently and partially restore antiviral T-cell immunity, which supports the hypothesis that long-term exposure to high levels of antigenaemia might cause dysfunction of antiviral T cells (Boni et al., 2003, J. Hepatol. 39:595-605).

Therapeutic vaccines that could reverse the dysfunctional immune state of chronic hepatitis B and restore antiviral immunity, would theoretically have the potential to eliminate viremia and reduce intrahepatic levels of HBV DNA to zero, thus holding great promise for HBV cure.

Recently, HBV vaccines have been identified as a promising therapeutic strategy for treatment and control of HBV infection in HBV carriers and persistently infected patients (Michel & Tiollais, 2010, Pathol. Biol. (Paris) 58:288-295; Liu et al., 2014, Virol. Sin. 29:10-16). In about 50% of chronic active HBV patients specific therapy by conventional anti-HBV vaccination effectively reduced the replication of HBV and inhibited the immune tolerance to HBsAg protein (Couillin et al., 1999, J. Infect. Dis. 180:15-26). However, so far monotherapy with HBsAg based vaccines did not lead to sustained control of HBV replication and/or liver damage (Akbar et al., 2013, Hepatobiliary Pancreat. Dis. Int. 12:363-369) and new therapy strategies are needed to provide potent and durable antiviral immune responses and long-term control of HBV replication.

The failure of previous therapeutic vaccine approaches highlights the challenges and limitations of current knowledge regarding immune responses in chronic HBV infection (Michel et al., 2011, J. Hepatol. 54:1286-1296). The combination of a high viral load condition such as chronic hepatitis B with the tolerizing liver microenvironment might make it difficult to achieve full recovery of antiviral T-cell immunity.

Intensive research is currently concentrated on a better understanding of immune responses in hepatocytes, on mechanisms by which HBV evades innate immunity and on proper selection of patients susceptible to benefit from immune therapy, which could increase the efficacy of therapeutic vaccination (Michel et al., 2015, Med. Microbiol. Immunol. 204:121-129).

3. SUMMARY OF THE INVENTION

The present application provides immunotherapies for Hepatitis B virus infections. Provided herein is an infectious arenavirus viral vector comprising a nucleotide sequence selected from the group consisting of:
 a. a nucleotide sequence encoding an HBV pre-S2/S protein or an antigenic fragment thereof;
 b. a nucleotide sequence encoding an HBV HBc protein or an antigenic fragment thereof;
 c. a nucleotide sequence encoding an HBV HBs protein or an antigenic fragment thereof;
 d. a nucleotide sequence encoding a fusion of HBV HBs and HBc proteins or antigenic fragments thereof; and
 e. a nucleotide sequence encoding an HBV HBe protein or an antigenic fragment thereof.

In certain embodiments, the infectious arenavirus viral vector is replication-deficient (See Section 6.1(a)). In certain embodiments, the infectious arenavirus viral vector is replication-competent (See Section 6.1(b)). In certain embodiments, the infectious, replication-deficient arenavirus viral vector is bisegmented. In certain embodiments, the infectious, replication-deficient arenavirus viral vector is trisegmented. In certain embodiments, the infectious, replication-competent arenavirus viral vector is trisegmented.

In certain embodiments, provided herein is an arenavirus viral vector comprising a nucleotide sequence selected from the group consisting of:
 a. a nucleotide sequence encoding an HBV pre-S2/S protein or an antigenic fragment thereof;
 b. a nucleotide sequence encoding an HBV HBc protein or an antigenic fragment thereof;
 c. a nucleotide sequence encoding an HBV HBs protein or an antigenic fragment thereof;
 d. a nucleotide sequence encoding a fusion of HBV HBs and HBc proteins or antigenic fragments thereof; and
 e. a nucleotide sequence encoding an HBV HBe protein or an antigenic fragment thereof.

In certain embodiments, the arenavirus viral vector is replication-deficient. In certain embodiments, the arenavirus viral vector is replication-competent.

In certain embodiments, a viral vector as provided herein is infectious, i.e., is capable of entering into or injecting its genetic material into a host cell. In certain more specific embodiments, a viral vector as provided herein is infectious, i.e., is capable of entering into or injecting its genetic material into a host cell followed by amplification and expression of its genetic information inside the host cell. In certain embodiments, the viral vector is an infectious, replication-deficient arenavirus viral vector engineered to contain a genome with the ability to amplify and express its genetic information in infected cells but unable to produce further infectious progeny particles in normal, not genetically engineered cells. In certain embodiments, provided herein is a cell line that supports viral growth of a wild type virus but does not express the complementing viral protein, thus is unable to produce further infectious viral progeny particles. In certain embodiments, the infectious arenavirus viral vector is replication-competent and able to produce further infectious progeny particles in normal, not genetically engineered cells.

In certain embodiments, the pre-S2/S protein or the antigenic fragment thereof comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 1. In certain embodiments, the fragment is antigenic when it is capable of (i) eliciting an antibody immune response in a host (e.g., mouse, rabbit, goat, or donkey) wherein the resulting antibodies bind specifically to human HBV pre-S2/S protein; and/or (ii) eliciting a specific T cell immune response.

In certain embodiments, the HBc protein or the antigenic fragment thereof comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 2. In certain embodiments, the fragment is antigenic when it is capable of (i) eliciting an antibody immune response in a host (e.g., mouse, rabbit, goat, or donkey) wherein the resulting antibodies bind specifically to human HBV HBc protein; and/or (ii) eliciting a specific T cell immune response.

In certain embodiments, the fusion of HBV HBs and HBc proteins or antigenic fragments thereof comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 3. In certain embodiments, the fragment is antigenic when it is capable of (i) eliciting an antibody immune response in a host (e.g., mouse, rabbit, goat, or donkey) wherein the resulting antibodies bind specifically to human HBV HBs, HBc or both HBs and HBc; and/or (ii) eliciting a specific T cell immune response.

In certain embodiments, the HBe protein or the antigenic fragment thereof comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 26. In certain embodiments, the fragment is antigenic when it is capable of (i) eliciting an antibody immune response in a host (e.g., mouse, rabbit, goat, or donkey) wherein the resulting antibodies bind specifically to human HBV HBe protein; and/or (ii) eliciting a specific T cell immune response.

In certain embodiments, the viral vector comprises at least two of:
 a. a nucleotide sequence encoding an HBV pre-S2/S protein or an antigenic fragment thereof;
 b. a nucleotide sequence encoding an HBV HBc protein or an antigenic fragment thereof;
 c. a nucleotide sequence encoding an HBV HBs protein or an antigenic fragment thereof;
 d. a nucleotide sequence encoding a fusion of HBV HBs and HBc proteins or antigenic fragments thereof; and
 e. a nucleotide sequence encoding an HBV HBe protein or an antigenic fragment thereof.

In certain embodiments, the viral vector comprises at least three of:
 a. a nucleotide sequence encoding an HBV pre-S2/S protein or an antigenic fragment thereof;
 b. a nucleotide sequence encoding an HBV HBc protein or an antigenic fragment thereof;
 c. a nucleotide sequence encoding an HBV HBs protein or an antigenic fragment thereof;
 d. a nucleotide sequence encoding a fusion of HBV HBs and HBc proteins or antigenic fragments thereof; and
 e. a nucleotide sequence encoding an HBV HBe protein or an antigenic fragment thereof.

In certain embodiments, an open reading frame (ORF) of the arenavirus is deleted or functionally inactivated and replaced with a nucleic acid encoding an HBV antigen as described herein. In a specific embodiment, the ORF that encodes the glycoprotein GP of the arenavirus is deleted or functionally inactivated. In certain embodiments, functional inactivation of a gene eliminates any translation product. In certain embodiments, functional inactivation refers to a genetic alteration that allows some translation, the translation product, however, is not longer functional and cannot replace the wild type protein.

In certain embodiments, the viral vector can amplify and express its genetic information in a cell that has been infected by the viral vector but the viral vector is unable to produce further infectious progeny particles in a non-complementing cell. In certain embodiments, a viral vector as provided herein is infectious, i.e., is capable of entering into or injecting its genetic material into a host cell. In certain more specific embodiments, a viral vector as provided herein is infectious, i.e., is capable of entering into or injecting its genetic material into a host cell followed by amplification and expression of its genetic information inside the host cell.

In certain embodiments, the genomic information encoding the infectious arenavirus particle is derived from the lymphocytic choriomeningitis virus (LCMV) Clone 13 strain or the LCMV MP strain. The nucleotide sequence of the S segment and of the L segment of Clone 13 are set forth in SEQ ID NOs: 12 and 7, respectively.

In certain embodiments, provided herein is a viral vector whose genome is or has been derived from the genome of Clone 13 (SEQ ID NOs: 12 and 7) by deleting an ORF of the Clone 13 genome (e.g., the ORF of the GP protein) and replacing it with a heterologous ORF that encodes an antigen (e.g., an HBV antigen) such that the remaining LCMV genome is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the nucleotide sequence of Clone 13 (SEQ ID NOs: 12 and 7).

In certain embodiments, provided herein is a viral vector whose genome has been derived from the genome of the LCMV strain MP (SEQ ID NOs: 13 and 14) by deleting an ORF of the LCMV strain MP genome (e.g., the ORF of the GP protein) and replacing it with a heterologous ORF that encodes an antigen (e.g., an HBV antigen) such that the remaining LCMV genome is at least 80%, 81%, 82%, 83%, 84%, 85%, 86%, 87%, 88%, 89%, 90%, 91%, 92%, 93%, 94%, 95%, 96%, 97%, 98%, at least 99%, 99.1%, 99.2%, 99.3%, 99.4%, 99.5%, 99.6%, 99.7%, 99.8%, at least 99.9% or 100% identical to the nucleotide sequence of LCMV strain MP (SEQ ID NOs: 13 and 14).

In a more specific embodiment, the viral vector comprises a genomic segment, wherein the genomic segment comprises a nucleotide sequence that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the sequence of nucleotide 1639 to 3315 of SEQ ID NO: 11 or 1640 to 3316 of SEQ ID NO: 12. In certain embodiments, the viral vector comprises a genomic segment comprising a nucleotide sequence encoding an expression product whose amino acid sequence is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the amino acid sequence encoded by 1639 to 3315 of SEQ ID NO: 11 or 1640 to 3316 of SEQ ID NO: 12.

Also provided herein are isolated nucleic acids, wherein the nucleic acid is a cDNA of an arenavirus genomic segment wherein one ORF of the genomic segment is deleted or functionally inactivated and wherein the genomic segment comprises one or any combination of:
 a. a nucleotide sequence encoding an HBV pre-S2/S protein or an antigenic fragment thereof;
 b. a nucleotide sequence encoding an HBV HBc protein or an antigenic fragment thereof;
 c. a nucleotide sequence encoding an HBV HBs protein or an antigenic fragment thereof;

d. a nucleotide sequence encoding a fusion of HBV HBs and HBc proteins or antigenic fragments thereof; and
e. a nucleotide sequence encoding an HBV HBe protein or an antigenic fragment thereof.

In certain embodiments, the genomic segment is the short segment, wherein the ORF encoding the GP is deleted.

In one aspect, provided herein are methods for generating an infectious, replication-deficient arenavirus particle comprising:
a. transfecting into a host cell a nucleic acid described herein;
b. maintaining the host cell under conditions suitable for virus formation; and
c. harvesting the infectious, replication-deficient arenavirus particle;

wherein the host cell expresses the ORF that is deleted or functionally inactivated on the genomic segment. In certain embodiments, any additional nucleic acids required for the rescue of a viral particle are also transfected into the host cell in step a. Such additional nucleic acids can be: the cDNA of the second arenavirus genomic segment, a nucleic acid comprising the L ORF, and/or a nucleic acid comprising the NP ORF.

In another aspect, provided herein are compositions, e.g., pharmaceutical, immunogenic or vaccine compositions, comprising a viral vector described herein and a pharmaceutically acceptable carrier. Also provided herein are compositions (e.g., vaccine compositions) that comprise two or more different viral vectors described herein (i.e., wherein the viral vectors encode different HBV antigens). In certain embodiments, the pharmaceutical composition comprises a nucleic acid or fusion protein described herein.

In a further aspect, provided herein are methods of treating or preventing HBV infection in a patient, comprising administering to the patient a viral vector, a pharmaceutical composition, an immunogenic composition, or a vaccine described herein. In yet another aspect, provided herein is use of a viral vector, a pharmaceutical composition, an immunogenic composition, or a vaccine described herein for the treatment or prevention of HBV. In certain embodiments, an infectious arenavirus expressing an HBV antigen or a fragment thereof is capable of preventing transmission and/or infection of HBV from a mother to an unborn child. In certain embodiments, one or more infectious arenaviruses expressing an HBV antigen or a fragment thereof are capable of preventing transmission and/or infection of HBV from a mother to an unborn child. In certain embodiments, the infectious arenavirus viral vector is replication-deficient (See Section 6.1(a)). In certain embodiments, the infectious arenavirus viral vector is replication-competent (See Section 6.1(b)).

In certain embodiments, administering to a patient an infectious arenavirus expressing an HBV antigen or a fragment thereof induces a long-lasting immune response. In certain embodiments, the infectious arenavirus viral vector is replication-deficient (See Section 6.1(a)). In certain embodiments, the infectious arenavirus viral vector is replication-competent (See Section 6.1(b)).

In certain embodiments, provided herein are methods of treating and or preventing HBV infection in a patient, comprising administering to the patient two or more arenaviruses expressing an HBV antigen or fragment thereof. In a more specific embodiment, each arenavirus expresses a different HBV antigen or fragment thereof. In other embodiments, each arenavirus expresses an HBV antigen or a derivative thereof. In some embodiments the derivative thereof is an HBV antigen fragment. In yet another embodiment provided herein are compositions that comprise two or more arenaviruses each expressing a different HBV antigen or fragment thereof. In certain embodiments, the infectious arenavirus viral vector is replication-deficient (See Section 6.1(a)). In certain embodiments, the infectious arenavirus viral vector is replication-competent (See Section 6.1(b)).

In certain embodiments, the arenavirus is lymphocytic choriomeningitis virus (LCMV) or Junin virus (JUNV).

In certain embodiments, provided herein is an infectious arenavirus viral vector, wherein an arenavirus open reading frame is removed and replaced by a nucleotide sequence encoding a fusion of HBV HBs and HBc proteins or antigenic fragments thereof. In specific embodiments, the arenavirus is lymphocytic choriomeningitis virus. In specific embodiments, the open reading frame that encodes the glycoprotein of the arenavirus is deleted or functionally inactivated. In specific embodiments, the viral vector is replication-deficient. In specific embodiments, the viral vector is replication-competent. In specific embodiments, the viral vector is trisegmented. In certain embodiments, provided herein is a method of treating or preventing a Hepatitis B virus infection in a patient, wherein said method comprises administering to the patient the viral vector from which an arenavirus open reading frame is removed and replaced by a nucleotide sequence encoding a fusion of HBV HBs and HBc proteins or antigenic fragments thereof.

3.1 Conventions and Abbreviations

| | |
|---|---|
| AFP | Alpha-fetoprotein |
| ALT | Alanine aminotransferase |
| APC | Antigen presenting cells |
| AST | Aspartate aminotransferase |
| C-cell | Complementing cell line |
| CD4 | Cluster of Differentiation 4 |
| CD8 | Cluster of Differentiation 8 |
| CMI | Cell-mediated immunity |
| GS-plasmid | Plasmid expressing genome segments |
| HBc or HBcAg | HBV core antigen |
| HBe or HBeAg | Extracellular HBV core antigen |
| HBs or HBsAg | HBV (large) surface antigen |
| HBV | Hepatitis B virus |
| HCC | Hepatocellular carcinoma |
| HRP | Horse radish peroxidase |
| IFN-γ | Interferon-γ |
| IGR | Intergenic region |
| JUNV | Junin virus |
| LCMV | Lymphocytic choriomeningitis virus |
| LDH | Lactate dehydrogenase |
| MHC | Major Histocompatibility Complex |
| NP | Nucleoprotein |
| ORF | Open reading frame |
| Pre-S2/S | HBV middle surface antigen |
| TF-plasmid | Plasmid expressing transacting factors |
| TNF-α | Tumor necrosis factor-α |
| UTR | Untranslated region |
| Z | Matrix Protein from LCMV |

4. DESCRIPTION OF THE SEQUENCE LISTING

The following sequences are illustrative amino acid sequences and nucleotide sequences that can be used with the methods and compositions described herein. In some instances a DNA sequence is used to describe the RNA sequence of a viral genomic segment. The RNA sequence can be readily deduced from the DNA sequence. The sequences themselves may also be found in Table 3 of Section 6.10.

SEQ ID NO: 1 is the nucleotide sequence of the HBV pre-S2/S ORF.

SEQ ID NO: 2 is the nucleotide sequence of the HBV HBc ORF.

SEQ ID NO: 3 is the nucleotide sequence of the HBV HBs-HBc fusion protein ORF.

SEQ ID NO: 4 is the nucleotide sequence of the LCMV S segment expressing HBV HBs-HBc fusion protein in cDNA form. The genomic segment is RNA, the sequence in SEQ ID NO:4 is shown for DNA; however, exchanging all thymidines ("T") in SEQ ID NO:4 for uridines ("U") provides the RNA sequence.

SEQ ID NO: 5 is the nucleotide sequence of the LCMV S segment expressing the HBc ORF, in cDNA form. The genomic segment is RNA, the sequence in SEQ ID NO:5 is shown for DNA; however, exchanging all thymidines ("T") in SEQ ID NO:5 for uridines ("U") provides the RNA sequence.

SEQ ID NO: 6 is the nucleotide sequence of the LCMV S segment expressing the pre-S2/S ORF, in cDNA form. The genomic segment is RNA, the sequence in SEQ ID NO:6 is shown for DNA; however, exchanging all thymidines ("T") in SEQ ID NO:6 for uridines ("U") provides the RNA sequence.

SEQ ID NO: 7 is the lymphocytic choriomeningitis virus clone 13 segment L, complete sequence (GenBank: DQ361066.1). The genomic segment is RNA, the sequence in SEQ ID NO: 7 is shown for DNA; however, exchanging all thymidines ("T") in SEQ ID NO: 7 for uridines ("U") provides the RNA sequence.

SEQ ID NO: 8 is the amino acid sequence of an HBV HBs protein-derived epitope.

SEQ ID NO: 9 is the amino acid sequence of an HBV HBs protein-derived epitope.

SEQ ID NO: 10 is the amino acid sequence of an HBV HBc protein-derived epitope.

SEQ ID NO: 11 is the lymphocytic choriomeningitis virus segment S, complete sequence. The genomic segment is RNA, the sequence in SEQ ID NO: 11 is shown for DNA; however, exchanging all thymidines ("T") in SEQ ID NO:11 for uridines ("U") provides the RNA sequence.

SEQ ID NO: 12 is the lymphocytic choriomeningitis virus clone 13 segment S, complete sequence (GenBank: DQ361065.2). The genomic segment is RNA, the sequence in SEQ ID NO: 12 is shown for DNA; however, exchanging all thymidines ("T") in SEQ ID NO: 12 for uridines ("U") provides the RNA sequence.

SEQ ID NO: 13 is the lymphocytic choriomeningitis strain MP segment L, complete sequence. The genomic segment is RNA, the sequence in SEQ ID NO:13 is shown for DNA; however, exchanging all thymidines ("T") in SEQ ID NO:13 for uridines ("U") provides the RNA sequence.

SEQ ID NO: 14 is the lymphocytic choriomeningitis strain MP segment S, complete sequence. The genomic segment is RNA, the sequence in SEQ ID NO:14 is shown for DNA; however, exchanging all thymidines ("T") in SEQ ID NO:14 for uridines ("U") provides the RNA sequence.

SEQ ID NO: 15 is the amino acid sequence of the NP protein of the MP strain of LCMV.

SEQ ID NO: 16 is the amino acid sequence of the GP protein of the MP strain of LCMV.

SEQ ID NO: 17 is the amino acid sequence of the L protein of the MP strain of LCMV.

SEQ ID NO: 18 is the amino acid sequence of the Z protein of the MP strain of LCMV.

SEQ ID NO: 19 is Junin virus Candid #1 strain segment L, complete sequence.

SEQ ID NO: 20 is Junin virus Candid #1 strain segment S, complete sequence.

SEQ ID NO: 21 is the amino acid sequence of the NP protein of the Clone 13 strain of LCMV.

SEQ ID NO: 22 is the amino acid sequence of the GP protein of the Clone 13 strain of LCMV.

SEQ ID NO: 23 is the amino acid sequence of the L protein of the Clone 13 strain of LCMV.

SEQ ID NO: 24 is the amino acid sequence of the Z protein of the Clone 13 strain of LCMV SEQ ID NO: 25 is the amino acid sequence of the GP protein of the WE strain of LCMV.

SEQ ID NO: 26 is the nucleotide sequence of the HBV HBe antigen.

5. BRIEF DESCRIPTION OF THE FIGURES

FIG. 1: The genome of wild type arenaviruses consists of a short (1; ~3.4 kb) and a large (2; ~7.2 kb) RNA segment. The short segment carries ORFs encoding the nucleoprotein (3) and glycoprotein (4). The large segment encodes the RNA-dependent RNA polymerase L (5) and the matrix protein Z (6). Wild type arenaviruses can be rendered replication-deficient vaccine vectors by deleting the glycoprotein gene and inserting, instead of the glycoprotein gene, antigens of choice (7) against which immune responses are to be induced.

FIGS. 2A-C: Schematic representation of the genomic organization of bi- and tri-segmented LCMV. The bi-segmented genome of wild-type LCMV consists of one S segment encoding the GP and NP and one L segment encoding the Z protein and the L protein (A). Both segments are flanked by the respective 5' and 3' UTRs. The genome of recombinant tri-segmented LCMVs (r3LCMV) consists of one L and two S segments with one position where to insert a gene of interest (here GFP) into each one of the S segments. r3LCMV-GFP$^{natural}$ (nat) has all viral genes in their natural position (B), whereas the GP ORF in r3LCMV-GFP$^{artificial}$ (art) is artificially juxtaposed to and expressed under control of the 3' UTR (C).

FIG. 3: Hepatitis B virus-specific CD8+ T cells, expressed as a percentage of the total CD8+B220− T cell pool in peripheral blood of C57BL/6 mice (5 mice per group) ten days after intravenous immunization with $10^5$ FFU of rLCMV/HBs-HBc (group 1), rLCMV/HBc (group 3), rLCMV/Pre-S2 (group 4), or with $10^4$ FFU of rLCMV/HBs-HBc (group 2). Control mice were left untreated.

FIG. 4A-B: Hepatitis B virus-specific CD8+ T cells, expressed as (A) a percentage of the total CD8+B220− T cell pool in peripheral blood or, (B) as a percentage of the circulating lymphocytes in the blood, of C57BL/6 mice (5 mice per group) eight days after intravenous immunization with $10^5$ FFU of r3LCMV/HBs-HBc (group 1), r3LCMV/HBc (group 2), r3LCMV/Pre-S2 (group 3), or with $10^5$ FFU of rLCMV/HBs-HBc (group 4). Control mice were left untreated.

6. DETAILED DESCRIPTION OF THE INVENTION

The present application provides immunotherapies for Hepatitis B virus infections. Provided herein are methods and compositions for the treatment or prevention of infection of a subject with HBV. More specifically, provided herein are infectious arenaviruses that comprise a nucleotide sequence encoding an HBV antigen. In certain embodiments, the infectious arenavirus is replication-deficient. In certain embodiments, the infectious arenavirus is replication-competent. These viruses can be administered to a subject for the treatment or prevention of HBV infection. The generation of infectious arenavirus vectors for use with the present invention is described in more detail in Section 6.3.

Provided herein is a genetically modified arenavirus, where the arenavirus:
is infectious;
cannot form infectious progeny virus in a non-complementary cell (i.e., a cell that does not express the functionality that is missing from the replication-deficient arenavirus and causes it to be replication-deficient);
is capable of replicating its genome and expressing its genetic information; and
encodes an HBV antigen or a fragment thereof.

A genetically modified arenavirus described herein is infectious, i.e., it can attach to a host cell and release its genetic material into the host cell. A genetically modified arenavirus described herein may be replication-deficient, i.e., the arenavirus is unable to produce further infectious progeny particles in a non-complementing cell. In particular, to create a replication-deficient arenavirus, the genome of the arenavirus is modified (e.g., by deletion or functional inactivation of an ORF) such that a virus carrying the modified genome can no longer produce infectious progeny viruses. A non-complementing cell is a cell that does not provide the functionality that has been eliminated from the replication-deficient arenavirus by modification of the virus genome (e.g., if the ORF encoding the GP protein is deleted or functionally inactivated, a non-complementing cell does not provide the GP protein). However, a genetically modified replication-deficient arenavirus provided herein is capable of producing infectious progeny viruses in complementing cells. Complementing cells are cells that provide (in trans) the functionality that has been eliminated from the replication-deficient arenavirus by modification of the virus genome (e.g., if the ORF encoding the GP protein is deleted or functionally inactivated, a complementing cell does provide the GP protein). Expression of the complementing functionality (e.g., the GP protein) can be accomplished by any method known to the skilled artisan (e.g., transient or stable expression). A genetically modified arenavirus described herein can amplify and express its genetic information in a cell that has been infected by the virus. A genetically modified arenavirus provided herein comprises a nucleotide sequence that encodes an HBV antigen such as but not limited to the HBV antigens described in Section 6.2.

In certain embodiments, provided herein is a genetically modified arenavirus in which an ORF of the arenavirus genome is deleted or functionally inactivated such that the resulting virus cannot produce further infectious progeny virus particles in non-complementing cells. An arenavirus particle comprising a genetically modified genome in which an ORF is deleted or functionally inactivated can be produced in complementing cells (i.e., in cells that express the arenaviral ORF that has been deleted or functionally inactivated) (see Section 6.3). The genetic material of the resulting arenavirus particles can be transferred upon infection of a host cell into the host cell, wherein the genetic material can be expressed and amplified. In addition, the genome of the genetically modified arenavirus particles provided herein encodes an HBV antigen that can be expressed in the host cell.

In certain embodiments, the ORF that encodes the glycoprotein (GP) of the arenavirus is deleted to generate a replication-deficient arenavirus for use with the present invention. In a specific embodiment, the replication-deficient arenavirus comprises a genomic segment comprising a nucleotide sequence encoding an HBV antigen. Thus, in certain embodiments, a genetically modified arenavirus particle provided herein comprises a genomic segment that a) has a deletion or functional inactivation of an ORF that is present in the wild type form of the genomic segment; and b) encodes (either in sense or antisense) an HBV antigen (see Section 6.3).

In certain embodiments, the antigen encoded by the nucleic acid that is inserted into the genome of the arenavirus can encode, for example, an HBV antigen or combinations of HBV antigens including, but not limited to:
a. a nucleotide sequence encoding an HBV pre-S2/S protein or an antigenic fragment thereof;
b. a nucleotide sequence encoding an HBV HBc protein or an antigenic fragment thereof;
c. a nucleotide sequence encoding an HBV HBs protein or an antigenic fragment thereof;
d. a nucleotide sequence encoding a fusion of HBV HBs and HBc proteins or antigenic fragments thereof;
e. a nucleotide sequence encoding an HBV HBe protein or an antigenic fragment thereof.

In certain embodiments, the infectious arenavirus viral vector is replication-deficient (See Section 6.1(a)). In certain embodiments, the infectious arenavirus viral vector is replication-competent (See Section 6.1(b))

A detailed description of the antigens described herein is provided in Section 6.2.

In certain embodiments, the arenaviruses used according to the invention described herein can be Old World viruses, for example, Lymphocytic choriomeningitis virus (LCMV). More detailed description of the arenaviruses described herein is provided in Section 6.1. In certain embodiments, the arenaviruses used according to the invention described herein can be New World viruses.

Provided herein are nucleic acids comprising the genome of such replication-deficient arenaviruses. In certain aspects, an infectious, replication-deficient arenavirus particle comprises a genomic segment comprising a nucleotide sequence of SEQ ID NO: 1, SEQ ID NO: 2, or SEQ ID NO: 3.

Provided herein is an expression plasmid that encodes one or more components required for the generation of a viral vector described herein. Specifically, provided herein is an expression vector that encodes an LCMV S segment wherein the ORF for the GP protein has been deleted from the S segment and has been replaced with the ORF of human HBV pre-S2/S protein (e.g., having an amino acid sequence encoded by the nucleotide sequence of SEQ ID NO: 1 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 1).

Provided herein is an expression plasmid that encodes one or more components required for the generation of a viral vector described herein. Specifically, provided herein is an expression vector that encodes an LCMV S segment wherein the ORF for the GP protein has been deleted from the S segment and has been replaced with the ORF of human HBV HBc protein (e.g., having an amino acid sequence encoded by the nucleotide sequence of SEQ ID NO: 2 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 2).

Provided herein is an expression plasmid that encodes one or more components required for the generation of a viral vector described herein. Specifically, provided herein is an expression vector that encodes an LCMV S segment wherein the ORF for the GP protein has been deleted from the S segment and has been replaced with the ORF of human HBV HBs and the ORF of human HBV HBc (e.g., having an amino acid sequence encoded by the nucleotide sequence of SEQ ID NO: 3 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 3).

Provided herein are kits comprising one or two of the vector plasmids described herein. In certain embodiments, provided herein is a kit that comprises a) an expression plasmid that comprises the nucleotide sequence of the S segment of an LCMV vector; b) an expression plasmid that comprises the nucleotide sequence of the L segment of an LCMV vector; and c) an expression plasmid that encodes the complementing functionality. In a specific embodiment, provided herein is a kit comprising a) an expression vector that comprises the nucleotide sequence of an LCMV S segment wherein the ORF for the GP protein has been deleted from the S segment and has been replaced with the ORF of human HBV pre-S2/S protein (e.g., having an amino acid sequence encoded by the nucleotide sequence of SEQ ID NO: 1 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 1); b) an expression plasmid that comprises the nucleotide sequence of the L segment of an LCMV vector; and c) an expression plasmid that encodes the LCMV GP protein (or a cell line that expresses LCMV GP protein).

Provided herein are kits comprising one or two of the vector plasmids described herein. In certain embodiments, provided herein is a kit that comprises a) an expression plasmid that comprises the nucleotide sequence of the S segment of an LCMV vector; b) an expression plasmid that comprises the nucleotide sequence of the L segment of an LCMV vector; and c) an expression plasmid that encodes the complementing functionality. In a specific embodiment, provided herein is a kit comprising a) an expression vector that comprises the nucleotide sequence of an LCMV S segment wherein the ORF for the GP protein has been deleted from the S segment and has been replaced with the ORF of human HBV HBc protein (e.g., having an amino acid sequence encoded by the nucleotide sequence of SEQ ID NO: 2 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 2); b) an expression plasmid that comprises the nucleotide sequence of the L segment of an LCMV vector; and c) an expression plasmid that encodes the LCMV GP protein (or a cell line that expresses LCMV GP protein).

Provided herein are kits comprising one or two of the vector plasmids described herein. In certain embodiments, provided herein is a kit that comprises a) an expression plasmid that comprises the nucleotide sequence of the S segment of an LCMV vector; b) an expression plasmid that comprises the nucleotide sequence of the L segment of an LCMV vector; and c) an expression plasmid that encodes the complementing functionality. In a specific embodiment, provided herein is a kit comprising a) an expression vector that comprises the nucleotide sequence of an LCMV S segment wherein the ORF for the GP protein has been deleted from the S segment and has been replaced with the ORF of human HBV HBs and the ORF of human HBV HBc (e.g., having an amino acid sequence encoded by the nucleotide sequence of SEQ ID NO: 3 or an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 3); b) an expression plasmid that comprises the nucleotide sequence of the L segment of an LCMV vector; and c) an expression plasmid that encodes the LCMV GP protein (or a cell line that expresses LCMV GP protein).

Also provided herein are cell lines, cultures and methods of culturing cells infected with nucleic acids, vectors, and compositions provided herein. More detailed description of the nucleic acids, vector systems and cell lines described herein is provided in Section 6.4.

In one aspect, provided herein are such genetically modified replication-deficient arenaviruses suitable as vaccines and methods of using such arenaviruses in vaccination and treatment or prevention of infections by HBV. More detailed description of methods of using such arenaviruses described herein is provided in Section 6.5.

In certain embodiments, immunization with an infectious arenavirus that expresses an HBV antigen or a fragment thereof, as described herein provides a long-lasting immune response. In certain embodiments, maximal antibody levels can be achieved after two immunizations. In another embodiment, a third immunization can be administered for a boosting effect. In more specific embodiments, provided herein are administration schedules using the infectious arenavirus in a vaccination for the treatment and/or prevention of infections by HBV. A more detailed description of administration schedules using an infectious arenavirus as described herein is provided in Section 6.6. In certain embodiments, the infectious arenavirus viral vector is replication-deficient (See Section 6.1(a)). In certain embodiments, the infectious arenavirus viral vector is replication-competent (See Section 6.1(b)).

In certain embodiments, administering to a seronegative subject an infectious arenavirus expressing an HBV antigen or a fragment thereof, as described herein induces a detectable antibody titer for a minimum of at least 4 weeks. In another embodiment, administering to a subject infected with an HBV infection an infectious arenavirus expressing an HBV antigen or a fragment thereof, as described herein increases the antibody titer by at least 100%, at least 200%, at least 300%, at least 400%, at least 500%, or at least 1000%. In certain embodiments, primary antigen exposure, by first immunization with an infectious arenavirus expressing an HBV antigen, elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the primary neutralizing geometric mean antibody titer increases up to a peak value of at least 1:50, at least 1:100, at least 1:200, or at least 1:1000 within at least 4 weeks post-immunization. In another embodiment, immunization with an infectious arenavirus expressing an HBV antigen or a fragment thereof, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization following a single administration of the vaccine. In certain embodiments, the infectious arenavirus viral vector is replication-deficient (See Section 6.1(a)). In certain embodiments, the infectious arenavirus viral vector is replication-competent (See Section 6.1(b)).

In yet another embodiment, secondary antigen exposure by second immunization with an infectious arenavirus expressing an HBV antigen or a fragment thereof increases the antibody titer by at least 100%, at least 200%, at least 300%, at least 400%, at least 500%, or at least 1000%. In another embodiment, secondary antigen exposure elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the secondary neutralizing geometric mean antibody titer increases up to a peak value of at least 1:50, at least 1:100, at least 1:200, or at least 1:1000 within at least 4 weeks post-immunization. In another embodiment, a second immunization with an infectious arenavirus expressing an HBV antigen or a fragment thereof, as described herein produces high titers of antibodies that last for at least 4 weeks, at least 8 weeks, at least 12 weeks, at least 6 months, at least 12 months, at least 2 years, at least 3 years, at least 4 years, or at least 5 years post-immunization. In certain embodiments, the infectious arenavirus viral vector is replication-deficient (See Section 6.1(a)). In certain embodiments, the infectious arenavirus viral vector is replication-competent (See Section 6.1(b)).

In yet another embodiment, a third boosting immunization increases the antibody titer by at least 100%, at least 200%, at least 300%, at least 400%, at least 500%, or at least 1000%. In another embodiment, the boosting immunization elicits a functional, (neutralizing) and minimum antibody titer of at least 50%, at least 100%, at least 200%, at least 300%, at least 400%, at least 500%, or at least 1000% of mean control sera from infection-immune human subjects. In more specific embodiments, the neutralizing geometric mean antibody titer after the third boosting immunization increases up to a peak value of at least 1:50, at least 1:100, at least 1:200, or at least 1:1000 within at least 4 weeks post-immunization. In another embodiment, a third boosting immunization prolongs the antibody titer by at least 4 weeks, at least 8 weeks, at least 12 weeks, at least 6 months, at least 12 months, at least 2 years, at least 3 years, at least 4 years, or at least 5 years post-immunization.

In certain embodiments, the infectious arenavirus expressing an HBV antigen or fragment thereof, elicits a T cell independent or T cell dependent response. In other embodiments, the infectious arenavirus expressing an HBV antigen or a fragment thereof, elicits a T cell response. In other embodiments, the infectious arenavirus expressing an HBV antigen or a fragment thereof, as described herein elicits a T helper response. In another embodiment, the infectious arenavirus expressing an HBV antigen or a fragment thereof, as described herein elicits a Th1-orientated response or a Th2-orientated response. In certain embodiments, the infectious arenavirus viral vector is replication-deficient (See Section 6.1(a)). In certain embodiments, the infectious arenavirus viral vector is replication-competent (See Section 6.1(b)).

In more specific embodiments, the Th1-orientated response is indicated by a predominance of IgG1 antibodies versus IgG2. In other embodiments the ratio of IgG1:IgG2 is greater than 1:1, greater than 2:1, greater than 3:1, or greater than 4:1. In another embodiment the infectious arenavirus expressing an HBV antigen or a fragment thereof, as described herein is indicated by a predominance of IgG3 antibodies. In certain embodiments, the infectious arenavirus viral vector is replication-deficient (See Section 6.1(a)). In certain embodiments, the infectious arenavirus viral vector is replication-competent (See Section 6.1(b)).

In some embodiments, the infectious arenavirus expressing an HBV antigen or a fragment thereof elicits a CD8+ T cell response. In other embodiments, the infectious arenavirus expressing an HBV antigen or a fragment thereof elicits a regulatory T cell response. In more specific embodiments, the regulatory T cell response maintains immune tolerance. In another embodiment, the infectious arenavirus expressing an HBV antigen or a fragment thereof elicits both CD4+ and CD8+ T cell responses. In certain embodiments, the infectious arenavirus viral vector is replication-deficient (See Section 6.1(a)). In certain embodiments, the infectious arenavirus viral vector is replication-competent (See Section 6.1(b)).

In certain embodiments, the infectious arenavirus expressing one or more HBV antigens or fragment thereof, as described herein, elicits high titers of neutralizing antibodies. In another embodiment, the infectious arenavirus expressing two or more HBV antigens or fragments thereof, as described herein, elicits higher titers of neutralizing antibodies than expression of the protein complex components individually. In certain embodiments, the infectious arenavirus viral vector is replication-deficient (See Section 6.1(a)). In certain embodiments, the infectious arenavirus viral vector is replication-competent (See Section 6.1(b)).

In other embodiments, two or more infectious arenaviruses expressing an HBV antigen elicit high titers of neutralizing antibodies. In a more specific embodiment, two or more infectious arenaviruses expressing an HBV antigen elicit higher titers of neutralizing antibodies than an infectious arenavirus expressing one HBV antigen or fragment thereof. In certain embodiments, the infectious arenavirus viral vector is replication-deficient (See Section 6.1(a)). In certain embodiments, the infectious arenavirus viral vector is replication-competent (See Section 6.1(b)).

In another embodiment, the infectious arenavirus expressing two, three, four, five, or more HBV antigens elicits higher titers of neutralizing antibodies than an infectious arenavirus expressing one HBV antigen or fragment thereof. In certain embodiments, the infectious arenavirus viral vector is replication-deficient (See Section 6.1(a)). In certain embodiments, the infectious arenavirus viral vector is replication-competent (See Section 6.1(b)).

6.1 Arenavirus Vectors Expressing an HBV Antigen

Arenaviruses for use with the methods and compositions provided herein can be Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus. The genetically modified arenavirus can be generated as described in Section 6.3.

The wild type arenavirus genome consists of a short (~3.4 kb) and a large (~7.2 kb) RNA segment. The short segment carries the ORFs encoding the nucleoprotein NP and glycoprotein GP genes. The large segment comprises the RNA-dependent RNA polymerase L and the matrix protein Z genes.

(a) Replication-Deficient Arenavirus Vectors

In certain embodiments, the arenavirus vector is a replication-deficient, bisegmented arenavirus vector. In certain embodiments, the arenavirus vector is a replication-deficient, trisegmented arenavirus vector. Wild type arenaviruses can be rendered replication-deficient to generate vaccine vectors by substituting the glycoprotein gene for one or more HBV antigens, against which immune responses are to be induced.

Infectious arenavirus vectors expressing an HBV antigen, or a combination of HBV antigens as described herein, can be used to immunize (in a preventive manner) or treat (in an immunotherapeutic manner) subjects against HBV infection. In a specific embodiment, a combination of HBs and HBc is used.

Arenavirus disease and immunosuppression in wild type arenavirus infection are known to result from unchecked viral replication. By abolishing replication, i.e., the ability to produce infectious progeny virus particles, of arenavirus vectors by deleting from their genome, e.g., the Z gene which is required for particle release, or the GP gene which is required for infection of target cells, the total number of infected cells can be limited by the inoculum administered, e.g., to a vaccine recipient, or accidentally transmitted to personnel involved in medical or biotechnological applications, or to animals. Therefore, abolishing replication of arenavirus vectors prevents pathogenesis as a result of intentional or accidental transmission of vector particles. Provided herein, one important aspect consists in exploiting the above necessity of abolishment of replication in a beneficial way for the purpose of expressing an HBV antigen. In certain embodiments, an arenavirus particle is rendered replication deficient by genetic modification of its genome. Such modifications to the genome can include:

deletion of an ORF (e.g., the ORF encoding the GP, NP, L, or Z protein);

functional inactivation of an ORF (e.g., the ORF encoding the GP, NP, L, or Z protein). For example, this can be achieved by introducing a missense or a nonsense mutation;

change of the sequence of the ORF (e.g., the exchange of an $S11^3$ cleavage site with the cleavage site of another protease);

mutagenesis of one of the 5' or 3' termini of one of the genomic segments;

mutagenesis of an intergenic region (i.e., of the L or the S genomic segment).

In certain embodiments, an infectious arenavirus expressing an HBV antigen described herein is a Lymphocytic choriomeningitis virus (LCMV) wherein the S segment of the virus is modified by substituting the ORF encoding the GP protein with an ORF encoding an HBV antigen.

In certain embodiments, a wild type arenavirus vector genome (FIG. 1) can be designed to retain at least the essential regulatory elements on the 5' and 3' untranslated regions (UTRs) of both segments, and/or also the intergenic regions (IGRs). Without being bound by theory, the minimal transacting factors for gene expression in infected cells remain in the vector genome as ORFs that can be expressed, yet they can be placed differently in the genome and can be placed under control of a different promoter than naturally, or can be expressed from internal ribosome entry sites. In certain embodiments, the nucleic acid encoding an HBV antigen is transcribed from one of the endogenous arenavirus promoters (i.e., 5' UTR, 3' UTR of the S segment, 5' UTR, 3' UTR of the L segment). In other embodiments, the nucleic acid encoding an HBV antigen is expressed from a heterologous introduced promoter sequences that can be read by the viral RNA-dependent RNA polymerase, by cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. In certain embodiments ribonucleic acids coding for HBV antigens are transcribed and translated either by themselves or as read-through by fusion to arenavirus protein ORFs, and expression of proteins in the host cell may be enhanced by introducing in the viral transcript sequence at the appropriate place(s) one or more, e.g., two, three or four, internal ribosome entry sites.

In certain embodiments, for use with the compositions and methods provided herein is a tri-segmented arenavirus particle comprising one L segment and two S segments in which (i) an ORF is in a position other than the wild-type position of the ORF; and (ii) an ORF encoding GP or NP has been removed or functionally inactivated, such that the resulting virus cannot produce further infectious progeny virus particles. In a specific embodiment, one ORF is removed and replaced with a heterologous ORF (e.g., encoding an HBV antigen) from an organism other than an arenavirus. In another specific embodiment, two ORFs are removed and replaced with a heterologous ORF from an organism other than an arenavirus. In other specific embodiments, three ORFs are removed and replaced with a heterologous ORF (e.g., encoding an HBV antigen) from an organism other than an arenavirus. In specific embodiments, the ORF encoding GP is removed and replaced with a heterologous ORF (e.g., encoding an HBV antigen) from an organism other than an arenavirus. In other specific embodiments, the ORF encoding NP is removed and replaced with a heterologous ORF (e.g., encoding an HBV antigen) from an organism other than an arenavirus. In yet more specific embodiments, the ORF encoding NP and the ORF encoding GP are removed and replaced with one or two heterologous ORFs (e.g., encoding one or two HBV antigens) from an organism other than an arenavirus particle. Thus, in certain embodiments the tri-segmented arenavirus particle comprises (i) one L segment and two S segments; (ii) an ORF in a position other than the wild-type position of the ORF; (iii) one or more heterologous ORFs (e.g., encoding one or more HBV antigens) from an organism other than an arenavirus.

In certain embodiments, for use with the compositions and methods provided herein is a tri-segmented arenavirus particle comprising two L segments and one S segment in which (i) an ORF is in a position other than the wild-type position of the ORF; and (ii) an ORF encoding the Z protein, and/or the L protein has been removed or functionally inactivated, such that the resulting virus cannot produce further infectious progeny virus particle. In a specific embodiment, one ORF is removed and replaced with a heterologous ORF (e.g., encoding an HBV antigen) from an organism other than an arenavirus. In another specific embodiment, two ORFs are removed and replaced with a heterologous ORF (e.g., encoding an HBV antigen) from an organism other than an arenavirus. In specific embodiments, the ORF encoding the Z protein is removed and replaced with a heterologous ORF (e.g., encoding an HBV antigen) from an organism other than an arenavirus. In other specific embodiments, the ORF encoding the L protein is removed and replaced with a heterologous ORF (e.g., encoding an HBV antigen) from an organism other than an arenavirus. In yet more specific embodiments, the ORF encoding the Z protein and the ORF encoding the L protein is removed and replaced with a heterologous ORF (e.g., encoding an HBV antigen) from an organism other than an arenavirus particle. Thus, in certain embodiments the tri-segmented arenavirus particle comprises (i) two L segments and one S segment; (ii) an ORF in a position other than the wild-type position of the ORF; (iii) a heterologous ORF (e.g., encoding an HBV antigen) from an organism other than an arenavirus.

Thus, in certain embodiments, the tri-segmented arenavirus particle for use with the compositions and methods provided herein comprises a tri-segmented arenavirus particle (i.e., one L segment and two S segments or two L segments and one S segment) that i) is engineered to carry an ORF in a non-natural position; ii) an ORF encoding GP, NP, Z protein, or L protein is removed; iii) the ORF that is removed is replaced with one or more heterologous ORFs (e.g., encoding one or more HBV antigens) from an organism other than an arenavirus.

In certain embodiments, the vector generated to encode one or more HBV antigens may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, the vector generated to encode one or more HBV antigens may be based on LCMV Clone 13. In other embodiments, the vector generated to encode one or more HBV antigens may be based on LCMV MP strain. The sequence of the S segment of LCMV Clone 13 is listed as SEQ ID NO: 12. In certain embodiments, the sequence of the S segment of LCMV Clone 13 is the sequence set forth in SEQ ID NO: 11. The sequence of the L segment of LCMV Clone 13 is listed as SEQ ID NO: 7. The sequence of the S segment of LCMV strain MP is listed as SEQ ID NO: 14. The sequence of the L segment of LCMV strain MP is listed as SEQ ID NO: 13.

In certain embodiments, the vector generated to encode one or more HBV antigens may be based on a specific strain of Junin virus. Strains of Junin virus include vaccine strains XJ13, XJ#44, and Candid#1 as well as IV4454, a human isolate. In certain embodiments, the vector generated to encode one or more HBV antigens is based on Junin virus Candid #1 strain.

In certain embodiments, described herein is an infectious, replication-deficient arenavirus particle comprising a nucleotide sequence or fragment thereof selected from SEQ ID NO: 13, SEQ ID NO: 14, or a combination thereof.

In certain embodiments, described herein is an infectious, replication-deficient arenavirus particle comprising a nucleotide sequence, or a combination of nucleotide sequences, selected from the group consisting of:
  a nucleotide sequence encoding a Hepatitis B virus pre-S2/S protein or an antigenic fragment thereof;
  a nucleotide sequence encoding a Hepatitis B virus HBc protein or an antigenic fragment thereof;
  a nucleotide sequence encoding a Hepatitis B virus HBs protein or an antigenic fragment thereof;
  a nucleotide sequence encoding a fusion of Hepatitis B virus HBs and HBc proteins or antigenic fragments thereof;
  a nucleotide sequence encoding a Hepatitis B virus HBe protein or an antigenic fragment thereof.

In certain embodiments, the infectious, replication-deficient arenavirus vector is trisegmented.

(b) Replication-Competent Trisegmented Arenavirus Vectors

In certain embodiments, for use with the compositions and methods provided herein is a replication-competent, trisegmented arenavirus vector. In certain embodiments, the arenavirus vector is a tri-segmented arenavirus particle comprising one L segment and two S segments or two L segments and one S segment that do not recombine into a replication-competent bi-segmented arenavirus particle.

In certain embodiments, an infectious arenavirus expressing an HBV antigen for use with the compositions and methods described herein is engineered to carry a viral ORF in a position other than the wild-type position of the ORF. In some embodiments, the arenavirus genomic segment is selected from the group consisting of: (i) an S segment, wherein the ORF encoding the NP is under control of an arenavirus 5' UTR; (ii) an S segment, wherein the ORF encoding the Z protein is under control of an arenavirus 5' UTR; (iii) an S segment, wherein the ORF encoding the L protein is under control of an arenavirus 5' UTR; (iv) an S segment, wherein the ORF encoding the GP is under control of an arenavirus 3' UTR; (v) an S segment, wherein the ORF encoding the L protein is under control of an arenavirus 3' UTR; (vi) an S segment, wherein the ORF encoding the Z protein is under control of an arenavirus 3' UTR; (vii) an L segment, wherein the ORF encoding the GP is under control of an arenavirus 5' UTR; (viii) an L segment, wherein the ORF encoding the NP is under control of an arenavirus 5' UTR; (ix) an L segment, wherein the ORF encoding the L protein is under control of an arenavirus 5' UTR; (x) an L segment, wherein the ORF encoding the GP is under control of an arenavirus 3' UTR; (xi) an L segment, wherein the ORF encoding the NP is under control of an arenavirus 3' UTR; and (xii) an L segment, wherein the ORF encoding the Z protein is under control of an arenavirus 3' UTR.

In some embodiments, the arenavirus 3' UTR is the 3' UTR of the arenavirus S segment or the arenavirus L segment. In certain embodiments, the arenavirus 5' UTR is the 5' UTR of the arenavirus S segment or the arenavirus L segment.

Figures 2A, 2B, 2C:
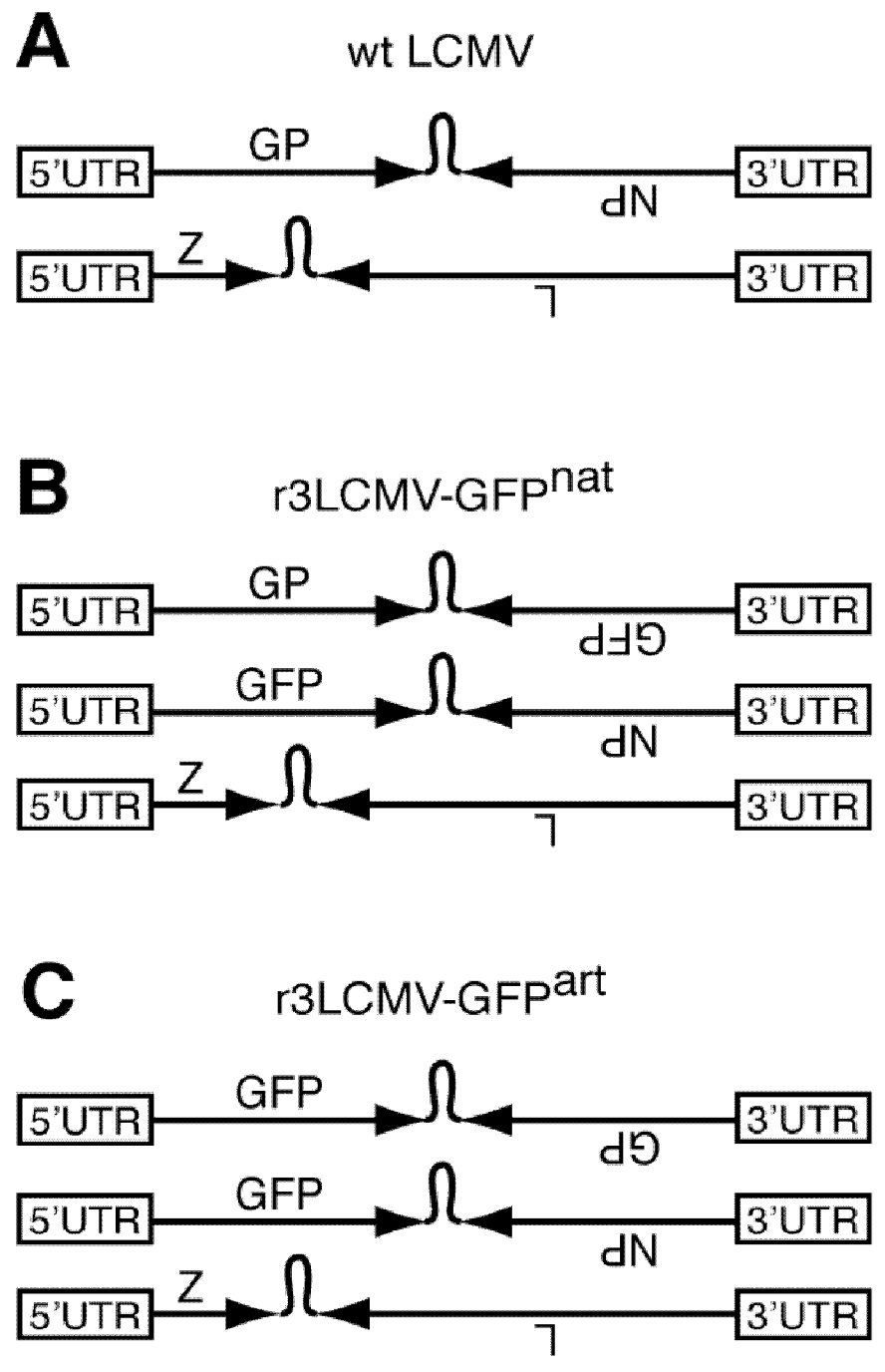

For use with the compositions and methods provided herein are tri-segmented arenavirus particles with rearrangements of their ORFs. In one aspect, for use with the compositions and methods provided herein is a tri-segmented arenavirus particle comprising one L segment and two S segments or two L segments and one S segment. In certain embodiments, the tri-segmented arenavirus particle does not recombine into a replication competent bi-segmented arenavirus particle. In specific embodiments, the tri-segmented arenavirus particle comprises an ORF in a position other than the wild-type position of the ORF. In yet another specific embodiment, the tri-segmented arenavirus particle comprises all four arenavirus ORFs. Thus, in certain embodiments, the tri-segmented arenavirus particle is replication competent and infectious. FIG. 2 shows exemplary schematic representations of the genomic organization of a replication-competent trisegmented LCMV vector (FIGS. 2B-C). FIG. 2C shows an exemplary schematic representation of the genomic organization of replication-competent trisegmented LCMV vector which cannot recombine into a replication-competent bisegmented arenavirus particle. In comparison, FIG. 2A shows the wildtype bisegmented LCMV vector.

In certain embodiments, the ORF encoding GP, NP, Z protein, or the L protein of the tri-segmented arenavirus particle described herein can be under the control of an arenavirus 3' UTR or an arenavirus 5' UTR. In more specific embodiments, the tri-segmented arenavirus 3' UTR is the 3' UTR of an arenavirus S segment(s). In another specific embodiment, the tri-segmented arenavirus 3' UTR is the 3' UTR of an arenavirus L segment(s). In more specific embodiments, the tri-segmented arenavirus 5' UTR is the 5'

UTR of an arenavirus S segment(s). In other specific embodiments, the 5' UTR is the 5' UTR of an arenavirus L segment(s).

In other embodiments, the ORF encoding GP, NP, Z protein, or the L protein of an tri-segmented arenavirus particle described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF encoding GP, NP, Z protein or the L protein of the tri-segmented arenavirus particle can be under the control of the promoter element of the 5' UTR (see e.g., Albarino et al., 2011, J Virol., 85(8): 4020-4). In another embodiment, the ORF encoding GP, NP Z protein, L protein of the tri-segmented arenavirus particle can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment(s) or the L segment(s). In another specific embodiment, the promoter element of the 3' UTR is the 3' UTR the promoter element of the S segment(s) or the L segment(s).

In certain embodiments, the ORF that encoding GP, NP, Z protein or the L protein of the tri-segmented arenavirus particle can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment(s) or L segment(s).

In one aspect, for use with the compositions and methods provided herein is a tri-segmented arenavirus particle comprising one L segment and two S segments. In certain embodiments, propagation of the tri-segmented arenavirus particle comprising one L segment and two S segments does not result in a replication-competent bi-segmented viral particle. In specific embodiments, propagation of the tri-segmented arenavirus particle comprising one L segment and two S segments does not result in a replication-competent bi-segmented viral particle after at least 10 days, at least 20 days, at least 30 days, at least 40 days, at least 50 days, at least 60 days, at least 70 days, at least 80 days, at least 90 days, or at least 100 days of persistent infection in mice lacking type I interferon receptor, type II interferon receptor and recombination activating gene (RAG1), and having been infected with $10^4$ PFU of the tri-segmented arenavirus particle. In other embodiments, propagation of the tri-segmented arenavirus particle comprising one L segment and two S segments does not result in a replication-competent bi-segmented viral particle after at least 10 passages, at least 20 passages, at least 30 passages, at least 40 passages, or at least 50 passages.

The tri-segmented arenavirus particle with all viral genes in their respective wild-type position is known in the art (e.g., Emonet et al., 2011 J. Virol., 85(4):1473; Popkin et al., 2011, J. Virol, 85(15):7928). In particular, the tri-segmented arenavirus genome consists of one L segment and two S segments, in which a heterologous ORF (e.g., a GFP) is inserted into one position on each S segment. More specifically, one S segment encodes GP and GFP, respectively. The other S segment encodes GFP and NP, respectively. The L segment encodes the L protein and Z protein. All segments are flanked by the respective 5' and 3' UTRs.

In certain embodiments, inter-segmental recombination of the two S segments of the tri-segmented arenavirus particle for use with the compositions and methods provided herein, that unities the two arenaviral ORFs on one instead of two separate segments results in a non functional promoter (i.e., a genomic segment of the structure: 5' UTR-----------5' UTR or a 3' UTR------------3' UTR), wherein each UTR forming one end of the genome is an inverted repeat sequence of the other end of the same genome.

In certain embodiments, the tri-segmented arenavirus particle comprising one L segment and two S segments has been engineered to carry an arenavirus ORF in a position other than the wild-type position of the ORF. In other embodiments, the tri-segmented arenavirus particle comprising one L segment and two S segments has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising one L segment and two S segments comprises a full complement of all four arenavirus ORFs. Thus, in some embodiments, the tri-segmented arenavirus particle is an infectious and replication competent tri-segmented arenavirus particle. In specific embodiments, the two S segments of the tri-segmented arenavirus particle have been engineered to carry one of their ORFs in a position other than the wild-type position. In more specific embodiments, the two S segments comprise a full complement of the S segment ORF's. In certain specific embodiments, the L segment has been engineered to carry an ORF in a position other than the wild-type position or the L segment can be the wild-type genomic segment.

In certain embodiments, one of the two S segments can be:

(i) an arenavirus S segment, wherein the ORF encoding the Z protein is under control of an arenavirus 5' UTR;

(ii) an arenavirus S segment, wherein the ORF encoding the L protein is under control of an arenavirus 5' UTR;

(iii) an arenavirus S segment, wherein the ORF encoding the NP is under control of an arenavirus 5' UTR;

(iv) an arenavirus S segment, wherein the ORF encoding the GP is under control of an arenavirus 3' UTR;

(v) an arenavirus S segment, wherein the ORF encoding the L is under control of an arenavirus 3' UTR; and (vi) an arenavirus S segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type S segment ORFs e.g., GP or NP). In specific embodiments, the tri-segmented arenavirus particle comprising one L segment and two S segments can comprise one duplicate ORF (e.g., (GP, GP)) or two duplicate ORFs (e.g., (GP, GP) and (NP, NP)).

Table 1A, below, is an exemplary illustration of the genome organization of a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 3'UTRs instead of a 3' UTR and a 5' UTR).

TABLE 1A

Tri-segmented arenavirus particle comprising one L segment and two S segments

| Position 1 | Position 2 | Position 3 | Position 4 | Position 5 | Position 6 |
|---|---|---|---|---|---|
| *ORF | GP | *ORF | NP | Z | L |
| *ORF | NP | *ORF | GP | Z | L |
| *ORF | NP | *ORF | GP | L | Z |
| *ORF | NP | *ORF | Z | L | GP |
| *ORF | NP | Z | GP | *ORF | Z |
| *ORF | NP | Z | GP | Z | *ORF |
| *ORF | NP | *ORF | L | Z | GP |
| *ORF | L | *ORF | NP | Z | GP |
| *ORF | L | Z | NP | *ORF | GP |
| *ORF | L | *ORF | GP | Z | NP |
| *ORF | L | Z | GP | *ORF | NP |
| *ORF | Z | L | NP | *ORF | GP |
| *ORF | Z | *ORF | GP | L | NP |
| *ORF | Z | L | GP | *ORF | NP |
| L | GP | *ORF | NP | *ORF | Z |
| L | GP | *ORF | *ORF | Z | NP |
| L | GP | *ORF | Z | *ORF | NP |
| L | *ORF | Z | GP | *ORF | NP |
| L | GP | *ORF | NP | *ORF | Z |
| L | GP | *ORF | Z | *ORF | NP |
| L | GP | Z | NP | *ORF | *ORF |
| L | GP | Z | NP | *ORF | *ORF |
| L | *ORF | Z | NP | *ORF | GP |
| L | NP | *ORF | Z | *ORF | GP |
| L | NP | Z | *ORF | GP | *ORF |
| L | *ORF | Z | *ORF | GP | NP |
| L | NP | Z | GP | *ORF | *ORF |
| L | NP | *ORF | Z | *ORF | GP |
| L | *ORF | Z | NP | *ORF | GP |
| L | Z | *ORF | GP | *ORF | NP |
| L | Z | *ORF | NP | *ORF | GP |
| Z | GP | *ORF | NP | *ORF | L |
| Z | GP | *ORF | *ORF | L | NP |
| Z | GP | *ORF | L | *ORF | NP |
| Z | *ORF | L | GP | *ORF | NP |
| Z | GP | *ORF | NP | *ORF | L |
| Z | GP | *ORF | L | *ORF | NP |
| Z | GP | L | NP | *ORF | *ORF |
| Z | GP | L | NP | *ORF | *ORF |
| Z | *ORF | L | NP | *ORF | GP |
| Z | NP | *ORF | *ORF | L | GP |
| Z | NP | *ORF | GP | *ORF | L |
| Z | NP | *ORF | *ORF | L | GP |
| Z | NP | *ORF | L | *ORF | GP |
| Z | NP | L | GP | *ORF | *ORF |
| Z | *ORF | L | GP | *ORF | NP |
| Z | NP | *ORF | GP | *ORF | L |
| Z | NP | *ORF | L | *ORF | GP |
| Z | *ORF | L | NP | *ORF | GP |
| Z | L | *ORF | GP | *ORF | NP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a heterologous ORF, for example, a heterologous ORF encoding an HBV antigen, has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombed S segment is made up of two 5' UTRs instead of a 3' UTR and a 5' UTR).

In certain embodiments, intersegmental recombination of an S segment and an L segment in the tri-segmented arenavirus particle comprising one L segment and two S segments, restores a functional segment with two viral genes on only one segment instead of two separate segments. In other embodiments, intersegmental recombination of an S segment and an L segment in the tri-segmented arenavirus particle comprising one L segment and two S segments does not result in a replication-competent bi-segmented viral particle.

Table 1B, below, is an exemplary illustration of the genome organization of a tri-segmented arenavirus particle comprising one L segment and two S segments, wherein intersegmental recombination of an S segment and an L segment in the tri-segmented arenavirus genome does not result in a replication-competent bi-segmented viral particle and abrogates arenaviral promoter activity (i.e., the resulting recombined S segment is made up of two 3' UTRs instead of a 3' UTR and a 5' UTR).

TABLE 1B

Tri-segmented arenavirus particle comprising one L segment and two S segments

| Position 1 | Position 2 | Position 3 | Position 4 | Position 5 | Position 6 |
|---|---|---|---|---|---|
| L | GP | *ORF | NP | Z | *ORF |
| L | GP | Z | *ORF | *ORF | NP |
| L | GP | *ORF | NP | Z | *ORF |
| L | GP | Z | *ORF | *ORF | NP |
| L | NP | *ORF | GP | Z | *ORF |
| L | NP | Z | *ORF | *ORF | GP |
| L | NP | *ORF | GP | Z | *ORF |
| L | NP | Z | *ORF | *ORF | GP |
| Z | GP | *ORF | NP | L | *ORF |
| Z | GP | L | *ORF | *ORF | NP |
| Z | GP | *ORF | NP | L | *ORF |
| Z | NP | L | *ORF | *ORF | GP |
| Z | NP | *ORF | GP | L | *ORF |
| Z | NP | L | *ORF | *ORF | GP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a heterologous ORF, for example, a heterologous ORF encoding an HBV antigen, has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 5'UTRs instead of a 3' UTR and a 5' UTR).

In one aspect, for use with the compositions and methods provided herein is a tri-segmented arenavirus particle comprising two L segments and one S segment. In certain embodiments, propagation of the tri-segmented arenavirus particle comprising two L segments and one S segment does not result in a replication-competent bi-segmented viral particle. In specific embodiments, propagation of the tri-segmented arenavirus particle comprising two L segments and one S segment does not result in a replication-competent bi-segmented viral particle after at least 10 days, at least 20 days, at least 30 days, at least 40 days, or at least 50 days, at least 60 days, at least 70 days, at least 80 days, at least 90 days, at least 100 days of persistent in mice lacking type I interferon receptor, type II interferon receptor and recombination activating gene (RAG1), and having been infected with $10^4$ PFU of the tri-segmented arenavirus particle. In other embodiments, propagation of the tri-segmented arenavirus particle comprising two L segments and one S segment does not result in a replication-competent bi-segmented viral particle after at least 10 passages, 20 passages, 30 passages, 40 passages, or 50 passages.

In certain embodiments, inter-segmental recombination of the two L segments of the tri-segmented arenavirus particle for use with the compositions and methods provided herein, that unities the two arenaviral ORFs on one instead of two separate genomic segments results in a non functional promoter (i.e., a genomic segment of the structure: 5' UTR-----------5' UTR or a 3' UTR------------3' UTR), wherein each UTR forming one end of the genome is an inverted repeat sequence of the other end of the same genome.

In certain embodiments, the tri-segmented arenavirus particle comprising two L segments and one S segment has been engineered to carry an arenavirus ORF in a position other than the wild-type position of the ORF. In other embodiments, the tri-segmented arenavirus particle comprising two L segments and one S segment has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising two L segments and one S segment comprises a full complement of all four arenavirus ORFs. Thus, in some embodiments, the tri-segmented arenavirus particle is an infectious and replication competent tri-segmented arenavirus particle. In specific embodiments, the two L segments of the tri-segmented arenavirus particle have been engineered to carry one of their ORFs in a position other than the wild-type position. In more specific embodiments, the two L segments comprise a full complement of the L segment ORF's. In certain specific embodiments, the S segment has been engineered to carry one of their ORFs in a position other than the wild-type position or the S segment can be the wild-type genomic segment.

In certain embodiments, one of the two L segments can be:
  (i) an L segment, wherein the ORF encoding the GP is under control of an arenavirus 5' UTR;
  (ii) an L segment, wherein the ORF encoding NP is under control of an arenavirus 5' UTR;
  (iii) an L segment, wherein the ORF encoding the L protein is under control of an arenavirus 5' UTR;
  (iv) an L segment, wherein the ORF encoding the GP is under control of an arenavirus 3' UTR;
  (v) an L segment, wherein the ORF encoding the NP is under control of an arenavirus 3' UTR; and
  (vi) an L segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type L segment ORFs e.g., Z protein or L protein). In specific embodiments, the tri-segmented arenavirus particle comprising two L segments and one S segment can comprise one duplicate ORF (e.g., (Z protein, Z protein)) or two duplicate ORFs (e.g., (Z protein, Z protein) and (L protein, L protein)).

Table 2A, below, is an exemplary illustration of the genome organization of a tri-segmented arenavirus particle comprising two L segments and one S segment, wherein intersegmental recombination of the two L segments in the tri-segmented arenavirus genome does not result in a replication-competent bi-segmented viral particle and abrogates arenaviral promoter activity (i.e., the S segment is made up of two 3'UTRs instead of a 3' UTR and a 5' UTR). Based on Table 3 similar combinations could be predicted for generating an arenavirus particle made up of two 5' UTRs instead of a 3' UTR and a 5' UTR.

TABLE 2A

Tri-segmented arenavirus particle comprising two L segments and one S segment

| Position 1 | Position 2 | Position 3 | Position 4 | Position 5 | Position 6 |
| --- | --- | --- | --- | --- | --- |
| *ORF | Z | *ORF | L | NP | GP |
| *ORF | Z | *ORF | L | GP | NP |
| *ORF | Z | GP | L | *ORF | NP |
| *ORF | Z | *ORF | GP | NP | L |
| *ORF | Z | GP | *ORF | NP | L |
| *ORF | Z | NP | *ORF | GP | L |
| *ORF | *ORF | NP | Z | GP | L |
| *ORF | Z | GP | NP | *ORF | L |
| *ORF | Z | NP | GP | *ORF | L |
| *ORF | L | *ORF | Z | NP | GP |
| *ORF | L | *ORF | Z | GP | NP |
| *ORF | L | *ORF | GP | NP | Z |
| *ORF | L | GP | Z | *ORF | NP |
| *ORF | L | *ORF | GP | NP | Z |
| *ORF | L | NP | Z | *ORF | GP |
| *ORF | L | GP | NP | *ORF | Z |
| *ORF | L | NP | GP | *ORF | Z |
| *ORF | GP | *ORF | L | NP | Z |
| *ORF | GP | NP | L | *ORF | Z |
| *ORF | GP | *ORF | Z | NP | L |
| *ORF | GP | NP | Z | *ORF | L |
| *ORF | NP | *ORF | L | GP | Z |
| *ORF | NP | GP | L | *ORF | Z |
| *ORF | NP | GP | Z | *ORF | L |
| *ORF | NP | *ORF | Z | GP | L |
| *ORF | L | *ORF | Z | NP | GP |
| *ORF | L | *ORF | Z | GP | NP |
| *ORF | L | *ORF | NP | GP | Z |
| *ORF | L | *ORF | GP | NP | Z |
| *ORF | L | NP | Z | *ORF | GP |
| *ORF | Z | *ORF | GP | NP | L |
| *ORF | Z | GP | L | *ORF | NP |
| *ORF | Z | NP | GP | *ORF | L |
| *ORF | Z | GP | NP | *ORF | L |
| *ORF | GP | *ORF | L | NP | Z |
| *ORF | GP | *ORF | L | Z | NP |
| *ORF | GP | *ORF | Z | GP | L |
| *ORF | GP | NP | L | *ORF | Z |
| GP | L | *ORF | Z | *ORF | NP |
| GP | L | *ORF | NP | *ORF | Z |
| GP | Z | *ORF | L | *ORF | NP |
| GP | Z | *ORF | L | *ORF | NP |
| GP | Z | *ORF | NP | *ORF | L |
| GP | NP | *ORF | Z | *ORF | L |
| NP | L | *ORF | Z | *ORF | GP |
| NP | L | *ORF | GP | *ORF | Z |
| NP | L | *ORF | Z | *ORF | GP |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a heterologous ORF, for example, a heterologous ORF encoding an HBV antigen, has been inserted.

In certain embodiments, the IGR between position one and position two cab be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments intersegmental recombination of an L segment and an S segment from the tri-segmented arenavirus particle comprising two L segments and one S segment restores a functional segment with two viral genes on only one segment instead of two separate segments. In other embodiments, intersegmental recombination of an L segment and an S segment in the tri-segmented arenavirus particle comprising two L segments and one S segment does not result in a replication-competent bi-segmeneted viral particle.

Table 2B, below, is an exemplary illustration of the genome organization of a tri-segmented arenavirus particle comprising two L segments and one S segment, wherein intersegmental recombination of an L segment and an S segment in the tri-segmented arenavirus genome does not result in a replication-competent bi-segmented viral particle and abrogates arenaviral promoter activity (i.e., the resulting recombined S segment is made up of two 3' UTRs instead of a 3' UTR and a 5' UTR).

TABLE 2B

Tri-segmented arenavirus particle comprising two L segments and one S segment

| Position 1 | Position 2 | Position 3 | Position 4 | Position 5 | Position 6 |
|---|---|---|---|---|---|
| NP | Z | *ORF | GP | L | *ORF |
| NP | Z | GP | *ORF | *ORF | L |
| NP | Z | *ORF | GP | L | *ORF |
| NP | Z | GP | *ORF | *ORF | L |
| NP | L | *ORF | GP | Z | *ORF |
| NP | L | GP | *ORF | *ORF | Z |
| NP | L | *ORF | GP | Z | *ORF |
| NP | L | GP | *ORF | *ORF | Z |
| GP | Z | *ORF | NP | L | *ORF |
| GP | Z | NP | *ORF | *ORF | L |
| GP | Z | *ORF | NP | L | *ORF |
| GP | L | NP | *ORF | *ORF | Z |
| GP | L | *ORF | NP | Z | *ORF |
| GP | L | NP | *ORF | *ORF | Z |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a heterologous ORF, for example, a heterologous ORF encoding an HBV antigen, has been inserted.

In certain embodiments, the IGR between position one and position two cab be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments, the tri-segmented arenavirus particle as described herein results in a infectious and replication competent arenavirus particle. In specific embodiments, the arenavirus particle described herein is attenuated. In a particular embodiment, the tri-segmented arenavirus particle is attenuated such that the virus remains, at least partially, replication-competent and can replicate in vivo, but can only generate low viral loads resulting in subclinical levels of infection that are non-pathogenic. Such attenuated viruses can be used as an immunogenic composition. In other embodiments, the arenavirus particle is infectious but unable to produce further infectious progeny in non-complementing cells.

In certain embodiments, the arenavirus genomic segment, and the respective arenavirus particle or tri-segmented arenavirus particle can comprise a heterologous ORF. In other embodiments, the arenavirus genomic segment and the respective arenavirus particle or tri-segmented arenavirus particle can comprise a gene of interest. In more specific embodiments, the heterologous ORF or the gene of interest encodes an antigen. In more specific embodiments, the heterologous ORF or the gene or interest encodes an HBV antigen or an antigenic fragment thereof (see Section 6.2).

In certain embodiments, the arenavirus genomic segment, the arenavirus particle or the tri-segmented arenavirus particle can comprise one or more heterologous ORFs or one or more genes of interest. In other embodiments, the arenavirus genomic segment, the arenavirus particle or the tri-segmented arenavirus particle can comprise at least one heterologous ORF, at least two heterologous ORFs, at least three heterologous ORFs, or more heterologous ORFs. In other embodiments, the arenavirus particle or the tri-segmented arenavirus particle comprises at least one gene of interest, at least two genes of interest, at least three genes of interest, or more genes of interest. In more specific embodiments, the one or more heterologous ORFs or the genes of interest encode one or more HBV antigens or antigenic fragments thereof (see Section 6.2).

In certain embodiments, an infectious arenavirus expressing an HBV antigen described herein is a tri-segmented arenavirus particle comprising one L segment and two S segments. In certain embodiments, an infectious arenavirus expressing an HBV antigen described herein is a tri-segmented arenavirus particle comprising two L segments and one S segment.

6.2 HBV Antigens

In certain embodiments, antigens for use with the methods and compositions described herein are HBV antigens.

In certain embodiments, the ORFs of two or more HBV antigens described are transcribed as a single transcript.

In certain embodiments, any genotype or subgenotype of human HBV or any clinical isolate of human HBV can be used with the present invention to obtain the antigens for generation of the arenaviral vectors described herein. Such HBV genotypes and subgenotypes include genotypes A-J, and subgenotypes A1-A6, B1-B4, C1-C6, D1-D7, and F1-F4.

In certain embodiments, the HBV antigen can be an HBV antigen ortholog, e.g., a mammalian (i.e., non-human primate, pig, dog, cat, or horse) HBV antigen.

(a) Pre-S2/S Protein Antigens

In certain embodiments, the antigen is the HBV pre-S2/S protein or a fragment thereof. In certain embodiments, the antigen is a fragment of at least 10, 15, 20, 25, 30, 35, 40, 45, 50, 60, 70, 80, 90, 100, 150 or more amino acids of HBV pre-S2/S protein. In certain embodiments, the antigen is an antigenic fragment of HBV pre-S2/S protein. In certain embodiments, the antigen is encoded by a nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 1. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 1.

(b) HBc Protein Antigens

In certain embodiments, the antigen is the HBV HBc protein or a fragment thereof. In certain embodiments, the antigen is a fragment of at least 10, 15, 20, 25, 50, 75, 100, 125, 150 or more amino acids of the HBV HBc protein. In certain embodiments, the antigen is an antigenic fragment of HBc. In certain embodiments, the antigen is encoded by a nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 2. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 2.

(c) HBs Protein Antigens

In certain embodiments, the antigen is the HBV HBs protein or a fragment thereof. In certain embodiments, the antigen is a fragment of at least 10, 15, 20, 25, 30, 35, 40, 45, 50 or more amino acids of the HBV HBs protein. In certain embodiments, the antigen is an antigenic fragment of HBs.

In certain embodiments, the antigen is the HBV HBs small polypeptide (e.g. "S") or a fragment thereof. In certain embodiments, the antigen is the HBV HBs medium polypeptide (e.g., "pre-S2/S") or a fragment thereof. In certain embodiments, the antigen is the HBV HBs large polypeptide (e.g., "pre-S1/pre-S2/S") or a fragment thereof. In certain embodiments, the antigen is a fragment of at least 10, 15, 20, 25, 30, 35, 40, 45, 50, 60, 70, 80, 90, 100, 150 or more amino acids of the HBV HBs small polypeptide. In certain embodiments, the antigen is a fragment of at least 10, 15, 20, 25, 30, 35, 40, 45, 50, 60, 70, 80, 90, 100, 150 or more amino acids of the HBV HBs medium polypeptide. In certain embodiments, the antigen is a fragment of at least 10, 15, 20, 25, 30, 35, 40, 45, 50, 100, 150, 200, 250, 300, 350 or more amino acids of the HBV HBs large polypeptide.

(d) HBs and HBc Fusion Proteins

In certain embodiments, the antigen is a fusion protein of the HBV HBs and HBc proteins or antigenic fragments thereof. In certain embodiments, the antigen is a fragment of at least 10, 15, 20, 25, 50, 75, 100, 125, 150, 175, 200, 225 or more amino acids of a fusion protein of HBs and HBc. In certain embodiments, the antigen is encoded by a nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 3. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 3.

(e) HBe Protein Antigens

In certain embodiments, the antigen is the HBV HBe protein or a fragment thereof. In certain embodiments, the antigen is a fragment of at least 10, 15, 20, 25, 30, 35, 40, 45, 50, 60, 70, 80, 90, 100, 150 or more amino acids of the HBV HBe protein. In certain embodiments, the antigen is an antigenic fragment of HBe. In certain embodiments, the antigen is encoded by a nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 26. In certain embodiments, the antigen comprises an amino acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence encoded by the nucleotide sequence of SEQ ID NO: 26.

(f) Polymerase Protein Antigens

In certain embodiments, the antigen is an HBV polymerase protein or antigenic fragment thereof. In certain embodiments, the antigen is a fragment of at least 10, 15, 20, 25, 50, 75, 100, 125, 150, 175, 200, 225, 250, 300, 400, 500, 600, 700 or more amino acids of an HBV polymerase protein.

Nucleic acid sequences encoding an HBV antigen can be introduced in the genome of an infectious arenavirus by substitution of the nucleic acid sequence of the ORF of glycoprotein GP, the matrix protein Z, the nucleoprotein NP, or the polymerase protein L. In other embodiments, the nucleic acid sequence encoding the HBV antigen is fused to the ORF of glycoprotein GP, the matrix protein Z, the nucleoprotein NP, or the polymerase protein L. The nucleotide sequence encoding the HBV antigen, once inserted into the genome of an infectious arenavirus, can be transcribed and/or expressed under control of one of the four arenavirus promoters (5' UTR and 3' UTR of the S segment, and 5' UTR and 3' UTR of the L segment), as well as ribonucleic acids that can be inserted with regulatory elements that can be read by the viral RNA-dependent RNA polymerase, cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. The nucleic acids encoding the HBV antigen can be transcribed and/or expressed either by themselves or as read-through by fusion to arenavirus ORFs and genes, respectively, and/or in combination with one or more, e.g., two, three or four, internal ribosome entry sites.

In one embodiment, the antigen is one that is useful for the prevention and/or treatment of infectious disease. In a specific embodiment, the antigen is derived from HBV. In certain embodiments, the ORF that encodes the glycoprotein of the arenavirus is substituted by a nucleic acid sequence encoding HBV pre-S2/S protein. In certain embodiments, the ORF that encodes the glycoprotein of the arenavirus is substituted by a nucleic acid sequence encoding HBV HBc protein. In certain embodiments, the ORF that encodes the glycoprotein of the arenavirus is substituted by a nucleic acid sequence encoding HBV HBs protein. In certain embodiments, the ORF that encodes the glycoprotein of the arenavirus is substituted by a nucleic acid sequence encoding a fusion of HBV HBs and HBc proteins or antigenic fragments thereof.

(g) Substitution of the ORF Encoding the Glycoprotein of the Arenavirus

In certain embodiments, the ORF that encodes the glycoprotein of the arenavirus is substituted by a nucleic acid sequence encoding one, two, or more HBV antigens described herein.

In one embodiment, the ORF that encodes the glycoprotein of the arenavirus is substituted by nucleic acid sequences encoding an HBV antigen. In certain embodiments, the ORF that encodes the glycoprotein of the arenavirus is substituted by nucleic acid sequences encoding antigen that is a fragment of at least 10, 15, 20, 25, 30, 35, 40, 45, 50, or more amino acids of a gene product of a gene of the pre-S2/S protein of HBV or a fragment thereof. In certain embodiments, the ORF that encodes the glycoprotein of the arenavirus is substituted by nucleic acid sequences encoding an antigenic fragment of pre-S2/S. In certain embodiments, the ORF that encodes the glycoprotein of the arenavirus is substituted by nucleic acid sequences encoding antigens including, but not limited to pre-S2/S or a fragment of pre-S2/S.

In certain embodiments, the ORF that encodes the glycoprotein of the arenavirus is substituted by nucleic acid sequences encoding antigen that is a fragment of at least 10, 15, 20, 25, 50, 75, 100, 125, 150 or more amino acids of a gene product of a gene of the HBc protein of HBV or a fragment thereof. In certain embodiments, the ORF that encodes the glycoprotein of the arenavirus is substituted by nucleic acid sequences encoding an antigenic fragment of HBc. In certain embodiments, the ORF that encodes the glycoprotein of the arenavirus is substituted by nucleic acid sequences encoding antigens including, but not limited to HBc or a fragment of HBc.

In certain embodiments, the ORF that encodes the glycoprotein of the arenavirus is substituted by nucleic acid sequences encoding antigen that is a fragment of at least 10, 15, 20, 25, 30, 35, 40, 45, 50 or more amino acids of a gene product of a gene of the HBs protein of HBV or a fragment thereof. In certain embodiments, the ORF that encodes the glycoprotein of the arenavirus is substituted by nucleic acid sequences encoding an antigenic fragment of HBs. In certain embodiments, the ORF that encodes the glycoprotein of the arenavirus is substituted by nucleic acid sequences encoding antigens including, but not limited to HBs or a fragment of HBs.

In certain embodiments, the ORF that encodes the glycoprotein of the arenavirus is substituted by a nucleic acid sequence encoding two or more HBV proteins or fragments of at least 10, 15, 20, 25, 50, 75, 100, 125, 150, 175, 200, 225 or more amino acids thereof. In certain embodiments, the ORF that encodes the glycoprotein of the arenavirus is substituted by a nucleic acid sequence encoding HBs and HBc.

In certain embodiments, the ORF that encodes the glycoprotein of the arenavirus is substituted by a nucleic acid sequence encoding one or more of pre-S2/S protein or an antigenic fragment thereof, HBc protein or an antigenic fragment thereof, HBs protein or an antigenic fragment thereof, and Hbe protein or an antigenic fragment thereof.

6.3 Generation of Infectious Arenavirus Expressing an HBV Antigen

Generally, arenavirus particles can be recombinantly produced by standard reverse genetic techniques as described for LCMV (L. Flatz, A. Bergthaler, J. C. de la Torre, and D. D. Pinschewer, Proc Natl Acad Sci USA 103:4663-4668, 2006; A. B. Sanchez and J. C. de la Torre, Virology 350:370, 2006; E. Ortiz-Riano, B. Y. Cheng, J. C. de la Torre, L. Martinez-Sobrido. J Gen Virol. 94:1175-88, 2013).

(a) Replication-Deficient Arenaviruses

To generate infectious, replication-deficient arenaviruses for use with the present invention these techniques can be used, however, the genome of the rescued virus is modified as described in Section 6.1. These modifications can be: i) one or more, e.g., two, three or four, of the four arenavirus ORFs (glycoprotein (GP); nucleoprotein (NP); the matrix protein Z; the RNA-dependent RNA polymerase L) are removed or functionally inactivated to prevent formation of infectious particles in normal cells albeit still allowing gene expression in arenavirus vector-infected host cells; and ii) nucleic acids coding for HBV antigens can be introduced. Infectious, replication-deficient viruses as described herein can be produced as described in International Patent Application Publication No. WO 2009/083210 (application number PCT/EP2008/010994) and International Patent Application Publication No. WO 2014/140301 (application number PCT/EP2014/055144), each of which is incorporated by reference herein in its entirety.

Once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the viral genes in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids that can be used can be of two types: i) Two plasmids, referred to as TF-plasmids for expressing intracellularly in C-cells the minimal transacting factors of the arenavirus, is derived from e.g., NP and L proteins of LCMV in the present example; and ii) Plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e. the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e. the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., –20° C. or –80° C. depending on how long the arenavirus vector should be stored prior to use. Then the arenavirus vector preparation's infectious titer is assessed by an immunofocus assay on C-cells.

The invention furthermore relates to expression of an HBV antigen in a cell culture wherein the cell culture is infected with an infectious arenavirus expressing an HBV antigen. When used for expression of an HBV antigen in cultured cells, the following two procedures can be used:

i) The cell type of interest is infected with the arenavirus vector preparation described herein at a multiplicity of infection (MOI) of one or more, e.g., two, three or four, resulting in production of the HBV antigen in all cells already shortly after infection.

ii) Alternatively, a lower MOI can be used and individual cell clones can be selected for their level of virally driven HBV antigen expression. Subsequently individual clones can be expanded infinitely owing to the non-cytolytic nature of arenavirus vectors. Irrespective of the approach, the HBV antigen can subsequently be collected (and purified) either from the culture supernatant or from the cells themselves, depending on the properties of the HBV antigen produced. However, the invention is not limited to these two strategies, and other ways of driving expression of HBV antigen using infectious, replication-deficient arenaviruses as vectors may be considered.

Alternatively, a rescue system consisting of three plasmids can be used: (1) the first plasmid expresses the protein NP by transcription via Polymerase II and subsequent translation in transfected cells; (2) the second plasmid gives rise to the (negative-stranded) L-Segment of the LCMV genome by transcription via Polymerase I as well as the L protein by transcription via Polymerase II from the same template in the opposite direction of the Polymerase I promoter; (3) the third plasmid gives rise to the S-segment of the LCMV genome (encoding the antigen coding sequence instead of the LCMV glycoprotein) via transcription by Polymerase I. 3 µg of each plasmid is used for electroporation of C-cells, followed by seeding of cells in 6-well plates and incubation at 37° C. After incubation, cells and supernatant from transfections are combined with freshly seeded C-cells, and vectors are harvested and cleared from cells & debris at a defined timepoint post infection. Once the vector has been generated, a nucleic acid encoding an antigen of an oncogenic virus and/or an immunomodulatory peptide, polypeptide, or protein (see Section 6.2) can be inserted into a plasmid from which a genomic segment of an infectious replication-deficient vector is transcribed by any technique known to the skilled artisan.

Owing to the removal or functional inactivation of one or more of the viral genes in arenavirus vectors (here deletion of the glycoprotein, GP, will be taken as an example) arenavirus vectors can be generated and expanded in cells that provide the deleted or functionally inactivated viral gene(s) (e.g., the GP) in trans. The resulting virus itself is infectious but is unable to produce further infectious progeny particles in non-complementing cells due to the lack of the deleted or functionally inactivated viral gene(s) (e.g., the GP). The complementing cell can provide the missing functionality either by stable transfection, transient transfection, or by infection with a helper virus that expresses the missing functionality.

In certain embodiments, the complementing cell provides the viral gene that has been deleted or functionally inactivated from the arenavirus vector genome. In a specific embodiment, the complementing cell provides the viral gene from a viral strain that is the same as the viral strain that was used to generate the genome of the arenavirus vector. In another embodiment, the complementing cell provides the viral gene from a viral strain that is different from the viral strain that was used to generate the genome of the arenavirus vector. For example, the viral gene provided in the complementing cell is obtained from the MP strain of LCMV and encodes a protein having the amino acid sequence of SEQ ID NO: 15, 16, 17, or 18. In another example, the viral gene provided in the complementing cell is obtained from the Clone 13 strain of LCMV and encodes a protein having the amino acid sequence of SEQ ID NO: 21, 22, 23, or 24. In another example, the viral gene provided in the complementing cell is obtained from the WE strain of LCMV and encodes a protein having the amino acid sequence of SEQ ID NO: 25.

In a specific embodiment, the complementing cell provides the GP of the MP strain of LCMV and the arenavirus vector comprises an ORF of a human HBV antigen as described herein in place of the ORF encoding the GP protein. In an even more specific embodiment, the complementing cell provides the GP of the MP strain of LCMV and the arenavirus vector is obtained from LCMV Clone 13 and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 16.

In a specific embodiment, the complementing cell provides the GP of the Clone 13 strain of LCMV and the arenavirus vector comprises an ORF of a human HBV antigen as described herein in place of the ORF encoding the GP protein. In an even more specific embodiment, the complementing cell provides the GP of the Clone 13 strain of LCMV and the arenavirus vector is obtained from LCMV MP strain and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 22.

In a specific embodiment, the complementing cell provides the GP of the WE strain of LCMV and the arenavirus vector comprises an ORF of a human HBV antigen as described herein in place of the ORF encoding the GP protein. In an even more specific embodiment, the complementing cell provides the GP of the WE strain of LCMV and the arenavirus vector is obtained from LCMV Clone 13 and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 25.

In a specific embodiment, the complementing cell provides the GP of the WE strain of LCMV and the arenavirus vector comprises an ORF of a human HBV antigen as described herein in place of the ORF encoding the GP protein. In an even more specific embodiment, the complementing cell provides the GP of the WE strain of LCMV and the arenavirus vector is obtained from LCMV MP strain and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 25.

In certain embodiments, the infectious, replication-deficient arenavirus is trisegmented.

(b) Replication-Competent, Trisegmented Arenaviruses

For use with the methods and compositions provided herein are methods of generation of replication-competent arenavirus vectors. Infectious, replication-competent trisegmented viruses as described herein can be produced as described in U.S. Provisional Patent Application No. 62/079,493, which is incorporated by reference herein in its entirety.

In certain embodiments, the method of generating a tri-segmented arenavirus particle comprises (i) transfecting into a host cell the cDNAs of the one L segment and two S segments or two L segments and one S segment; (ii) transfecting into a host cell plasmids expressing the arenavirus' minimal trans-acting factors NP and L; (iii) maintaining the host cell under conditions suitable for virus formation; and (iv) harvesting the arenavirus particle.

Once generated from cDNA, the tri-segmented arenavirus particle (i.e., infectious and replication competent) can be propagated. In certain embodiments tri-segmented arenavirus particles can be propagated in any host cell that allows the virus to grow to titers that permit the uses of the virus as described herein. In one embodiment, the host cell allows the tri-segmented arenavirus particle to grow to titers comparable to those determined for the corresponding wild-type.

In certain embodiments, the tri-segmented arenavirus particle may be propagated in host cells. Specific examples of host cells that can be used include BHK-21, HEK 293, VERO or other. In a specific embodiment, the tri-segmented arenavirus particle may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

In specific embodiments, the host cells are kept in culture and are transfected with one or more plasmid(s). The plasmid(s) express the viral gene(s) to be generated under control of one or more expression cassettes suitable for expression in mammalian cells, e.g., consisting of a polymerase I promoter and terminator.

Plasmids that can be used for generating a tri-segmented arenavirus comprising one L segment and two S segments can include: i) two plasmids each encoding the S genome segment e.g., pol-I driven S segment expression plasmids, ii) a plasmid encoding the L genome segment e.g., a pol-I driven L segment expression plasmid. Plasmids needed for the tri-segmented arenavirus comprising two L segments and one S segments are: i) two plasmids each encoding the L genome segment e.g., pol-L, ii) a plasmid encoding the S genome segment e.g., pol-I S.

In certain embodiments, plasmids encoding an arenavirus polymerase that direct intracellular synthesis of the viral L and S segments can be incorporated into the transfection mixture. For example, a plasmid encoding the L protein and a plasmid encoding NP (pC-L and pC-NP, respectively). The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In addition, the plasmid(s) features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Transfection of BHK-21 cells with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

Typically, RNA polymerase I-driven expression cassettes, RNA polymerase II-driven cassettes or T7 bacteriophage RNA polymerase driven cassettes can be used, the latter preferentially with a 3'-terminal ribozyme for processing of the primary transcript to yield the correct end. In certain embodiments, the plasmids encoding the arenavirus genomic segments can be the same, i.e., the genome sequence and transacting factors can be transcribed by T7, polI and polII promoters from one plasmid.

For recovering the tri-segmented arenavirus vector, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore relates to expression of a heterologous ORF (e.g., an HBV antigen), wherein a plasmid encoding the genomic segment is modified to incorporate a heterologous ORF. The heterologous ORF can be incorporated into the plasmid using restriction enzymes. In certain embodiments, the heterologous ORF encodes an HBV antigen. In certain embodiments, the plasmid encoding the genomic segment is modified to incorporate one or more heterologous ORFs. In certain embodiments, the heterologous ORFs encode one or more HBV antigens.

6.4 Nucleic Acids, Vector Systems and Cell Lines

In one embodiment, described herein is a nucleic acid sequence which is the cDNA of the large genomic segment (L segment) of an infectious arenavirus described herein, in which one ORF of the genomic segment is deleted or functionally inactivated, and the genomic segment comprises a nucleotide sequence encoding an HBV antigen. In certain embodiments, the infectious arenavirus viral vector is replication-deficient (See Section 6.1(a)). In certain embodiments, the infectious arenavirus viral vector is replication-competent (See Section 6.1(b)).

In one embodiment, described herein is a nucleic acid sequence that encodes the short genomic segment (S segment) of an infectious arenavirus described herein, in which one ORF of the genomic segment is deleted or functionally inactivated and wherein the short genomic segment comprises a nucleotide sequence encoding an HBV antigen. In another embodiment, described herein is a nucleic acid sequence that encodes the short genomic segment (S segment) of an infectious arenavirus described herein, in which the ORF of the glycoprotein gene is deleted or functionally inactivated and wherein the short genomic segment comprises a nucleotide sequence encoding an HBV antigen. In certain, more specific embodiments, the HBV antigen is an antigen described in Section 6.2.

In certain embodiments, the nucleic acid sequences provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the nucleic acid is derived from LCMV Clone 13. In other specific embodiments, the nucleic acid is derived from LCMV MP strain.

In a more specific embodiment, provided herein is a nucleic acid comprising an arenavirus genomic segment comprising a sequence that is at least 90%, 91%, 92%, 93%, 94%, 95%, 96%, 97%, 98%, at least 99%, or 100% identical to the sequence of SEQ ID NO: 1, SEQ ID NO: 2, or SEQ ID NO: 3. In another embodiment, provided herein is a nucleic acid that comprises an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO: 11; and (ii) a nucleotide sequence encoding an HBV antigen.

In another embodiment, provided herein is a nucleic acid that comprises an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO: 11; and (ii) a nucleotide sequence encoding an HBV antigen.

In another embodiment, provided herein is a nucleic acid that comprises an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO: 12; and (ii) a nucleotide sequence encoding an HBV antigen.

In another embodiment, provided herein is a nucleic acid that comprises an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO: 12; and (ii) a nucleotide sequence encoding an HBV antigen In one embodiment, described herein is a vector system comprising one or more vectors that together comprise the genome of an infectious arenavirus particle described herein. Specifically, provided herein is a vector system wherein the one or more vectors comprise two arenavirus genomic segments, namely an L segment and an S segment, of an infectious arenavirus described herein. Such a vector system can comprise (on one or more separate DNA molecules):

An arenavirus S genomic segment that is modified such that an arenavirus particle carrying this modified S genomic segment cannot produce infectious progeny virus particles and an arenavirus L genomic segment that comprises a nucleotide sequence encoding (in sense or antisense) an HBV antigen;

An arenavirus L genomic segment that is modified such that an arenavirus particle carrying this modified L genomic segment cannot produce infectious progeny virus particles and an arenavirus S genomic segment that comprises a nucleotide sequence encoding (in sense or antisense) an HBV antigen;

An arenavirus S genomic segment that is modified such that an arenavirus particle carrying this modified S genomic segment cannot produce infectious progeny virus particles and wherein the arenavirus S genomic segment comprises a nucleotide sequence encoding (in sense or antisense) an HBV antigen and comprising a wild type arenavirus L genomic segment; or An arenavirus L genomic segment that is modified such that an arenavirus particle carrying this modified L genomic segment cannot produce infectious progeny virus particles and wherein the arenavirus L genomic segment comprises a nucleotide sequence encoding (in sense or antisense) an HBV antigen and comprising a wild type arenavirus S genomic segment.

In certain embodiments, described herein is a nucleic acid sequence comprising an arenavirus (e.g., LCMV) genomic segment in which the ORF encoding the GP of the S genomic segment is substituted with a nucleotide sequence comprising:

a nucleotide sequence encoding a Hepatitis B pre-S2/S protein or an antigenic fragment thereof;

a nucleotide sequence encoding a Hepatitis B virus HBc protein or an antigenic fragment thereof;

a nucleotide sequence encoding a Hepatitis B virus HBs protein or an antigenic fragment thereof;

a nucleotide sequence encoding a fusion of Hepatitis B virus HBs and HBc proteins or antigenic fragments thereof;

a nucleotide sequence encoding a Hepatitis B virus HBe protein or an antigenic fragment thereof.

In certain embodiments, described herein is a nucleic acid sequence comprising an arenavirus (e.g., LCMV) genomic segment in which the ORF encoding the GP of the S genomic segment is substituted with a nucleotide sequence encoding one or more HBV antigens (e.g., one or more of those listed in the above paragraph).

In another embodiment, provided herein is a cell wherein the cell comprises a nucleic acid or a vector system described above in this section. Cell lines derived from such cells, cultures comprising such cells, and methods of culturing such cells infected with nucleic acids or vector systems are also provided herein. In certain embodiments, provided herein is a cell wherein the cell comprises a nucleic acid comprising the large genomic segment (L segment) of an infectious arenavirus described herein, in which one ORF of the genomic segment is deleted or functionally inactivated, and the genomic segment comprises a nucleotide sequence encoding an HBV antigen.

In other embodiments, provided herein is a cell wherein the cell comprises a nucleic acid sequence that comprises the short genomic segment (S segment) of an infectious arenavirus described herein, in which one ORF of the genomic segment is deleted or functionally inactivated and wherein the short genomic segment comprises a nucleotide sequence encoding HBV pre-S2/S protein or an antigenic fragment thereof.

In other embodiments, provided herein is a cell wherein the cell comprises a nucleic acid sequence that comprises the short genomic segment (S segment) of an infectious arenavirus described herein, in which one ORF of the genomic segment is deleted or functionally inactivated and wherein the short genomic segment comprises a nucleotide sequence encoding HBV HBc protein or an antigenic fragment thereof.

In other embodiments, provided herein is a cell wherein the cell comprises a nucleic acid sequence that comprises the short genomic segment (S segment) of an infectious arenavirus described herein, in which one ORF of the genomic segment is deleted or functionally inactivated and wherein the short genomic segment comprises a nucleotide sequence encoding HBV HBs protein or an antigenic fragment thereof.

In other embodiments, provided herein is a cell wherein the cell comprises a nucleic acid sequence that comprises the short genomic segment (S segment) of an infectious arenavirus described herein, in which one ORF of the genomic segment is deleted or functionally inactivated and wherein the short genomic segment comprises a nucleotide sequence encoding a fusion protein comprising at least one domain from HBV HBs protein and HBV HBc protein.

In other embodiments, provided herein is a cell wherein the cell comprises a nucleic acid sequence that comprises the short genomic segment (S segment) of an infectious arenavirus described herein, in which one ORF of the genomic segment is deleted or functionally inactivated and wherein the short genomic segment comprises a nucleotide sequence encoding one or more of HBV antigens.

In another embodiment, provided herein is a cell wherein the cell comprises two nucleic acids or vector systems described herein. Cell lines derived from such cells, cultures comprising such cells, and methods of culturing such cells infected with nucleic acids or vector systems are also provided herein.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13 or SEQ ID NO: 14. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13 or SEQ ID NO: 14. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13 or SEQ ID NO: 14.

In certain embodiments, provided herein is a nucleic acid comprising a nucleotide sequence encoding an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 15, 16, 17, or 18. In certain embodiments, provided herein is an expression vector comprising a nucleotide sequence encoding an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 15, 16, 17, or 18. In certain embodiments, provided herein is a host cell comprising a nucleotide sequence that encodes an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 15, 16, 17, or 18.

In certain embodiments, provided herein is an isolated protein comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 15, 16, 17, or 18. In certain embodiments, provided herein is a host cell that expresses a protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 15, 16, 17, or 18. In certain embodiments, the host cell is cultured in cell culture medium.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 12 or SEQ ID NO: 7. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 12 or SEQ ID NO: 7. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 12 or SEQ ID NO: 7.

In certain embodiments, provided herein is a nucleic acid comprising a nucleotide sequence encoding an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21, 22, 23, or 24. In certain embodiments, provided herein is an expression vector comprising a nucleotide sequence encoding an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21, 22, 23, or 24. In certain embodiments, provided herein is a host cell comprising a nucleotide sequence that encodes an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21, 22, 23, or 24.

In certain embodiments, provided herein is an isolated protein comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21, 22, 23, or 24. In certain embodiments, provided herein is a host cell that expresses a protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 21, 22, 23, or 24. In certain embodiments, the host cell is cultured in cell culture medium.

6.5 Methods of Use

Provided herein are immunotherapies for Hepatitis B virus infections. In one embodiment, provided herein are methods of treating an infection in a subject comprising administering to the subject one or more infectious arenaviruses expressing an HBV antigen as described herein or a composition thereof. In certain embodiments, the infectious arenaviruses are replication-deficient. In certain embodiments, the infectious arenaviruses are replication-competent. In a specific embodiment, a method for treating an infection described herein comprises administering to a subject in need thereof an effective amount of one or more infectious arenaviruses expressing an HBV antigen described herein or a composition thereof. The subject can be a mammal, such as but not limited to a human being, a mouse, a rat, a guinea pig, a domesticated animal, such as, but not limited to, a cow, a horse, a sheep, a pig, a goat, a cat, a dog, a hamster, a donkey. In a specific embodiment, the subject is a human.

In another embodiment, provided herein are methods for inducing an immune response against HBV in a subject comprising administering to the subject an infectious arenavirus expressing an HBV antigen or a composition thereof.

In another embodiment, the subjects to whom an infectious arenavirus expressing an HBV antigen described herein or a composition thereof is administered have, are susceptible to, or are at risk for an HBV infection. In another specific embodiment, the subjects to whom an infectious arenavirus expressing an HBV antigen described herein or a composition thereof is administered are infected with, are susceptible to, or are at risk for, an infection with HBV.

In another embodiment, the subjects to whom an infectious arenavirus expressing an HBV antigen described herein or a composition thereof is administered are suffering from, are susceptible to, or are at risk for, an infection with HBV, e.g., in the liver. In a specific embodiment, the subjects to whom an infectious arenavirus expressing an HBV antigen described herein or a composition thereof is administered are suffering from, are susceptible to, or are at risk for, an infection with HBV in one or more organs of the body, e.g., the liver.

In another embodiment, the subjects to whom an infectious arenavirus expressing an HBV antigen described herein or a composition thereof is administered have test results (e.g., blood test results) indicating liver damage. In certain embodiments, the subjects have alanine aminotransferase (ALT) levels in the blood indicating liver damage. In certain embodiment, the subjects have aspartate aminotransferase (AST) levels in the blood indicating liver damage. In certain embodiments, the subjects have alkaline phosphatase levels in the blood indicating liver damage. In certain embodiments, the subjects have lactate dehydrogenase (LDH) levels in the blood indicating liver damage. In certain embodiments, the subjects have one or more of ALT, AST, alkaline phosphatase, and LDH levels in the blood indicating liver damage.

In certain embodiments, the subjects have alpha-fetoprotein (AFP) levels in the blood indicating liver cancer or susceptibility thereto. In certain embodiments, the subjects have bilirubin (e.g., conjugated bilirubin) levels in the blood indicating liver damage. In certain embodiments, the subjects have albumin levels in the blood indicating liver damage.

In certain embodiments, the subjects have abdominal ultrasound results indicating liver damage. In certain embodiments, the subjects have CAT scan results indicating liver damage. In certain embodiments, the subjects have MRI results indicating liver damage.

In another embodiment, the subjects to whom an infectious arenavirus expressing an HBV antigen described herein or a composition thereof is administered have detectable levels of HBs antigen (HBsAg) in the blood. In certain embodiments, the subjects have detectable levels of IgM antibody against HBc antigen (HBcAg) in the blood. In certain embodiments, the subjects have detectable levels of HBe antigen (HBeAg, the extracellular/secreted version of the HBc protein) in the blood. In certain embodiments, the subjects have detectable levels of antibody to HBsAg in the blood.

In another embodiment, the subjects to whom an infectious arenavirus expressing an HBV antigen described herein or a composition thereof is administered have persistent levels of HBsAg, indicative of chronic hepatitis. In certain embodiments, the subjects have persistent levels of HBeAg, indicative of chronic hepatitis. In certain embodiments, the subjects have persistent levels of HBsAg and HBeAg, indicative of chronic hepatitis.

In another embodiment, the subjects to whom an infectious arenavirus expressing an HBV antigen described herein or a composition thereof is administered are suffering from symptoms of HBV infection, including but not limited to loss of appetite, fatigue, nausea, vomiting, itchiness, abdominal pain, abdominal swelling, or jaundice.

In another embodiment, the subjects to whom an infectious arenavirus expressing an HBV antigen described herein or a composition thereof is administered are suffering from manifestations of HBV, including but not limited to acute hepatitis B, chronic HBV infection, cirrhosis, and hepatocellular carcinoma (HCC). In another embodiment, the infectious arenavirus expressing an HBV antigen described herein or a composition thereof is administered to a subject with asymptomatic HBV.

In another embodiment, an infectious arenavirus expressing an HBV antigen as described herein or a composition thereof is administered to a subject of any age group suffering from, susceptible to, or are at risk for, an infection with HBV. In a specific embodiment, an infectious arenavirus expressing an HBV antigen as described herein or a composition thereof is administered to a subject with a compromised immune system, a pregnant subject, a subject undergoing an organ or bone marrow transplant, a subject taking immunosuppressive drugs, a subject undergoing hemodialysis, a subject who has cancer, or a subject who is suffering from, susceptible to, or at risk for, an infection with HBV. In a more specific embodiment, an infectious arenavirus expressing an HBV antigen as described herein or a composition thereof is administered to a subject with a compromised immune system due to HIV infection, who is suffering from, is susceptible to, or is at risk for, an infection with HBV. In yet another specific embodiment, an infectious arenavirus expressing an HBV antigen as described herein or a composition thereof is administered to a subject who is a child of 0, 1, 2, 3, 4, 5, 6, 7, 8, 9, 10, 11, 12, 13, 14, 15, 16, or 17 years of age suffering from, susceptible to, or at risk for, an infection with HBV. In yet another specific embodiment, an infectious arenavirus expressing an HBV antigen described herein or a composition thereof is administered to a subject who is an infant suffering from, susceptible to, or at risk for, an infection with HBV. In yet another specific embodiment, an infectious arenavirus expressing an HBV antigen described herein or a composition thereof is administered to a subject who is an infant of 0, 1, 2, 3, 4, 5, 6, 7, 8, 9, 10, 11, or 12 months of age suffering from, susceptible to, or at risk for, an infection with HBV. In yet another specific embodiment, an infectious arenavirus expressing an HBV antigen described herein or a composition thereof is administered to an elderly subject who is suffering from, is susceptible to, or is at risk for, an infection with HBV.

In another embodiment, an infectious arenavirus expressing an HBV antigen described herein or a composition thereof is administered to subjects with a heightened risk of disseminated HBV infection. In a specific embodiment, an infectious arenavirus expressing an HBV antigen described herein or a composition thereof is administered to subjects in neonatal period with immature neonatal immune system. In another embodiment, an infectious arenavirus expressing an HBV antigen described herein or a composition thereof is administered to a subject who uses intravenous drugs with a heightened risk of HBV infection.

In another embodiment, an infectious arenavirus expressing an HBV antigen described herein or a composition thereof is administered to subjects infected with one or more genotypes or subgenotypes of HBV. In certain embodiments, the genotype is one or more of genotypes A-J, or another genotype. In certain embodiments, the subgenotype is one or more subgenotypes A1-A6, B1-B4, C1-C6, D1-D7, F1-F4, or another subgenotype.

In another embodiment, administering an infectious arenavirus expressing an HBV antigen as described herein or a composition thereof to subjects confer cell-mediated immunity (CMI) against an infection with HBV. Without being bound by theory, in another embodiment, an infectious arenavirus expressing an HBV antigen as described herein or a composition thereof infects and expresses antigens of interest in antigen presenting cells (APC) of the host (e.g., macrophages) for direct presentation of antigens on Major Histocompatibility Complex (MHC) class I and II. In another embodiment, administering an infectious arenavirus expressing an HBV antigen as described herein or a composition thereof to subjects induces plurifunctional IFN-γ and TNF-α co-producing HBV-specific CD4+ and CD8+ T cell responses (IFN-γ is produced by CD4+ and CD8+ T cells and TNF-α is produced by CD4+ T cells) of high magnitude to treat or prevent an infection with HBV.

In another embodiment, administering an infectious arenavirus expressing an HBV antigen or a composition thereof reduces the risk that an individual will develop an infection with HBV by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection with HBV in the absence of such treatment.

In another embodiment, administering an infectious arenavirus expressing an HBV antigen or a composition thereof reduces the symptoms of an infection with HBV by at least about 10%, at least about 20%, at least about 25%, at least about 30%, at least about 35%, at least about 40%, at least about 50%, at least about 60%, at least about 70%, at least about 80%, at least about 90%, or more, compared to the manifestation of the symptoms of an infection HBV in the absence of such treatment.

In another embodiment, administering an infectious arenavirus expressing an HBV antigen or a composition thereof in subjects with immature neonatal immune system induces cell-mediated immunity (CMI) response against an infection with HBV by at least about 10%, at least about 20%, at least about 25%, at least about 30%, at least about 35%, at least about 40%, at least about 50%, at least about 60%, at least about 70%, at least about 80%, at least about 90%, or more, compared to cell-mediated immunity (CMI) response against an infection with HBV in the absence of such a treatment.

In certain embodiments, administering an infectious arenavirus expressing an HBV antigen or a composition thereof reduces ALT levels in the blood. In certain embodiments, administering an infectious arenavirus expressing an HBV antigen or a composition thereof reduces AST levels in the blood. In certain embodiments, administering an infectious arenavirus expressing an HBV antigen or a composition thereof reduces alkaline phosphatase levels in the blood. In certain embodiments, administering an infectious arenavirus expressing an HBV antigen or a composition thereof reduces LDH levels in the blood. In certain embodiments, administering an infectious arenavirus expressing an HBV antigen or a composition thereof reduces one or more of ALT, AST, alkaline phosphatase, and LDH levels in the blood.

In certain embodiments, administering an infectious arenavirus expressing an HBV antigen or a composition thereof reduces AFP levels in the blood. In certain embodiments, administering an infectious arenavirus expressing an HBV antigen or a composition thereof reduces bilirubin (e.g., conjugated bilirubin) levels in the blood. In certain embodiments, administering an infectious arenavirus expressing an HBV antigen or a composition thereof increases albumin levels in the blood.

In certain embodiments, administering an infectious arenavirus expressing an HBV antigen or a composition thereof reduces levels of HBsAg in the blood. In certain embodiments, administering an infectious arenavirus expressing an HBV antigen or a composition thereof reduces levels of IgM antibody against HBcAg in the blood. In certain embodiments, administering an infectious arenavirus expressing an HBV antigen or a composition thereof reduces levels of HBeAg in the blood. In certain embodiments, administering an infectious arenavirus expressing an HBV antigen or a composition thereof reduces levels of antibody to HBsAg in the blood.

In certain embodiments, administering an infectious arenavirus expressing an HBV antigen or a composition thereof reduces the number of inclusion bodies detected in salivary glands or another histological sample. In certain embodiments, administering an infectious arenavirus expressing an HBV antigen or a composition thereof reduces the number of anti-HBV antibodies detected in a patient blood sample. In certain embodiments, administering an infectious arenavirus expressing an HBV antigen or a composition thereof reduces the amount of HBV detected in urine, saliva, blood, tears, semen, or breast milk. In certain embodiments, administering an infectious arenavirus expressing an HBV antigen or a composition thereof reduces the level of virus cultured from a urine, throat swab, bronchial lavage, or tissue sample. In certain embodiments, administering an infectious arenavirus expressing an HBV antigen or a composition thereof reduces the level of virus detected through quantitative or qualitative PCR tests.

Changes in cell-mediated immunity (CMI) response function against an infection with HBV induced by administering an infectious arenavirus expressing an HBV antigen or a composition thereof in subjects can be measured by any assay known to the skilled artisan including, but not limited to flow cytometry (see, e.g., Perfetto S. P. et al., Nat Rev Immun. 2004; 4(8):648-55), lymphocyte proliferation assays (see, e.g., Bonilla F. A. et al., Ann Allergy Asthma Immunol. 2008; 101:101-4; and Hicks M. J. et al., Am J Clin Pathol. 1983; 80:159-63), assays to measure lymphocyte activation including determining changes in surface marker expression following activation of measurement of cytokines of T lymphocytes (see, e.g., Caruso A. et al., Cytometry. 1997; 27:71-6), ELISPOT assays (see, e.g., Czerkinsky C. C. et al., J Immunol Methods. 1983; 65:109-121; and Hutchings P. R. Et al., J Immunol Methods. 1989; 120:1-8), or Natural killer cell cytotoxicity assays (see, e.g., Bonilla F. A. et al., Ann Allergy Asthma Immunol. 2005 May; 94(5 Suppl 1):S1-63).

In another embodiment, described herein is a method of use with an infectious arenavirus (e.g., LCMV) expressing an HBV antigen as described herein in which the ORF encoding the GP of the S genomic segment is substituted with a nucleotide sequence comprising:

a. a nucleotide sequence encoding an HBV pre-S2/S protein or an antigenic fragment thereof;
b. a nucleotide sequence encoding an HBV HBc protein or an antigenic fragment thereof;
c. a nucleotide sequence encoding an HBV HBs protein or an antigenic fragment thereof;
d. a nucleotide sequence encoding a fusion of HBV HBs and HBc proteins or antigenic fragments thereof;
e. a nucleotide sequence encoding an HBV HBe protein or an antigenic fragment thereof.

In another embodiment, provided herein are methods of preventing transmission and/or infection of HBV from a mother to an unborn child comprising administering to a subject of child-bearing age an infectious arenavirus expressing an HBV antigen as described herein. See Section 6.2. In specific embodiments, provided herein are methods of preventing transmission and/or infection of HBV from a mother to an unborn child comprising administering to a seronegative subject of child-bearing age an infectious arenavirus expressing an HBV antigen as described herein. In yet another embodiment provided herein are methods of preventing transmission and/or infection of HBV from a mother to an unborn child comprising administering to a subject of child-bearing age with the intention to procreate an infectious arenavirus expressing an HBV antigen as described herein.

In another embodiment, provided herein are methods of preventing transmission and/or infection of HBV from a mother to an unborn child comprising administering to a subject of child-bearing age one or more infectious arenaviruses expressing an HBV antigen as described herein. See Section 6.2. In specific embodiments, provided herein are methods of preventing transmission and/or infection of HBV from a mother to an unborn child comprising administering to a seronegative subject of child-bearing age one or more infectious arenaviruses expressing an HBV antigen as described herein. In yet another embodiment, provided herein are methods of preventing transmission and/or infection of HBV from a mother to an unborn child comprising administering to a subject of child-bearing age with the intention to procreate one or more infectious arenaviruses expressing an HBV antigen as described herein.

In another embodiment, provided herein are methods of preventing transmission and/or infection of HBV from a mother to an unborn child comprising administering to a pregnant subject an infectious arenavirus expressing an HBV antigen as described herein. In specific embodiments, provided herein are methods of preventing transmission and/or infection of HBV from a mother to an unborn child comprising administering to a pregnant subject an effective amount of an infectious arenavirus expressing an HBV antigen described herein.

In another embodiment, provided herein are methods of preventing transmission and/or infection of HBV from a mother to an unborn child comprising administering to a pregnant subject one or more infectious arenaviruses expressing an HBV antigen as described herein. In specific embodiments, provided herein are methods of preventing transmission and/or infection of HBV from a mother to an unborn child comprising administering to a pregnant subject an effective amount of one or more infectious arenaviruses expressing an HBV antigen described herein.

In another embodiment, administering an infectious arenavirus expressing an HBV antigen reduces congenital HBV infection. In another embodiment, administering one or more infectious arenaviruses expressing an HBV antigen reduces congenital HBV infection.

In another embodiment, administering an infectious arenavirus expressing an HBV antigen reduces manifestations of congenital HBV infection by at least about 10%, at least about 20%, at least 25%, at least about 30%, at least about 35%, at least about 40%, at least about 50%, at least about 60%, at least about 70%, at least 80%, at least 90%, or more. In another specific embodiment, administering an infectious arenavirus expressing an HBV antigen reduces mortality of newborn infants with congenital HBV infection.

In another embodiment, administering one or more infectious arenaviruses expressing an HBV antigen reduces manifestations of congenital HBV infection by at least about 10%, at least about 20%, at least 25%, at least about 30%, at least about 35%, at least about 40%, at least about 50%, at least about 60%, at least about 70%, at least 80%, at least 90%, or more. In another specific embodiment, administering one or more infectious arenaviruses expressing an HBV antigen reduces mortality of newborn infants with congenital HBV infection.

Such manifestations of congenital HBV include but are not limited to acute hepatitis B, chronic HBV infection, cirrhosis, and hepatocellular carcinoma (HCC).

6.6 Compositions, Administration and Dosage

The invention furthermore relates to vaccines, immunogenic compositions, and pharmaceutical compositions comprising a genetically engineered arenavirus as described herein. Such vaccines and pharmaceutical compositions can be formulated according to standard procedures in the art.

In another embodiment, provided herein are compositions comprising an infectious arenavirus described herein. Such compositions can be used in methods of treatment and prevention of disease. In a specific embodiment, the compositions described herein are used in the treatment of subjects infected with, or susceptible to, an infection with HBV. In another specific embodiment, the immunogenic compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the prevention of infection of subjects (e.g., human subjects) by HBV. In certain embodiments, the infectious arenavirus viral vector is replication-deficient (See Section 6.1(a)). In certain embodiments, the infectious arenavirus viral vector is replication-competent (See Section 6.1(b)).

In certain embodiments, provided herein are immunogenic compositions comprising an arenavirus vector (or a combination of different arenavirus vectors) as described herein. In certain embodiments, such an immunogenic composition further comprises a pharmaceutically acceptable excipient. In certain embodiments, such an immunogenic composition further comprises an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to an infectious arenavirus particle, but when the compound is administered alone does not generate an immune response to the infectious arenavirus particle. In some embodiments, the adjuvant generates an immune response to the infectious arenavirus particle and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)).

The compositions comprise the infectious arenaviruses described herein alone or together with a pharmaceutically acceptable carrier. Suspensions or dispersions of genetically engineered arenaviruses, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2-8° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

The pharmaceutical compositions comprise from about $10^3$ to about $10^{11}$ focus forming units of the genetically engineered arenaviruses. Unit dose forms for parenteral administration are, for example, ampoules or vials, e.g., vials containing from about $10^3$ to $10^{10}$ focus forming units or $10^5$ to $10^{15}$ physical particles of genetically engineered arenaviruses.

In another embodiment, a vaccine or immunogenic composition provided herein is administered to a subject by, including but not limited to, oral, intradermal, intramuscular, intraperitoneal, intravenous, topical, subcutaneous, percutaneous, intranasal and inhalation routes, and via scarification (scratching through the top layers of skin, e.g., using a bifurcated needle). Specifically, subcutaneous, intramuscular or intravenous routes can be used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

The dosage of the active ingredient depends upon the type of vaccination and upon the subject, and their age, weight, individual condition, the individual pharmacokinetic data, and the mode of administration.

Also provided herein are processes and uses of genetically engineered arenaviruses for the manufacture of vaccines in the form of pharmaceutical preparations, which comprise genetically engineered arenaviruses as active ingredient. The pharmaceutical compositions of the present invention are prepared in a manner known per se, for example by means of conventional mixing and/or dispersing processes.

6.7 Optimized Generation of LCMV Vectors

Owing to the removal or functional inactivation of one or more of the viral genes in arenavirus vectors (here deletion of the glycoprotein, GP, will be taken as an example) arenavirus vectors can be generated and expanded in cells that provide the deleted or functionally inactivated viral gene(s) (e.g., the GP) "in trans." The resulting virus itself is infectious but is unable to produce further infectious progeny particles in non-complementing cells due to the lack of the deleted or functionally inactivated viral gene(s) (e.g., the GP). The complementing cell can provide the missing functionality either by stable transfection, transient transfection, or by infection with a helper virus that expresses the missing functionality.

In certain embodiments, the complementing cell provides the viral gene that has been deleted or functionally inactivated from the arenavirus vector genome. In a specific embodiment, the complementing cell provides the viral gene from a viral strain that is the same as the viral strain that was used to generate the genome of the arenavirus vector. In another embodiment, the complementing cell provides the viral gene from a viral strain that is different from the viral strain that was used to generate the genome of the arenavirus vector. For example, the viral gene provided in the complementing cell is obtained from the MP strain of LCMV and encodes a protein having the amino acid sequence of SEQ ID NO: 15, 16, 17, or 18. In another example, the viral gene provided in the complementing cell is obtained from the Clone 13 strain of LCMV and encodes a protein having the amino acid sequence of SEQ ID NO: 21, 22, 23, or 24. In another example, the viral gene provided in the complementing cell is obtained from the WE strain of LCMV and encodes a protein having the amino acid sequence of SEQ ID NO: 25.

In a specific embodiment, the complementing cell provides the GP of the MP strain of LCMV and the arenavirus vector comprises an ORF of a human HBV antigen as described herein in place of the ORF encoding the GP protein. In an even more specific embodiment, the complementing cell provides the GP of the MP strain of LCMV and the arenavirus vector is obtained from LCMV Clone 13 and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 16.

In a specific embodiment, the complementing cell provides the GP of the Clone 13 strain of LCMV and the arenavirus vector comprises an ORF of a human HBV antigen as described herein in place of the ORF encoding the GP protein. In an even more specific embodiment, the complementing cell provides the GP of the Clone 13 strain of LCMV and the arenavirus vector is obtained from LCMV MP strain and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 22.

In a specific embodiment, the complementing cell provides the GP of the WE strain of LCMV and the arenavirus vector comprises an ORF of a human HBV antigen as described herein in place of the ORF encoding the GP protein. In an even more specific embodiment, the complementing cell provides the GP of the WE strain of LCMV and the arenavirus vector is obtained from LCMV Clone 13 and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 25.

In a specific embodiment, the complementing cell provides the GP of the WE strain of LCMV and the arenavirus vector comprises an ORF of a human HBV antigen as described herein in place of the ORF encoding the GP protein. In an even more specific embodiment, the complementing cell provides the GP of the WE strain of LCMV and the arenavirus vector is obtained from LCMV MP strain and comprises an ORF of a human HBV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 25.

6.8 Combination Therapy 6.8 (a) Methods

In one embodiment, provided herein are methods of treating and/or preventing an HBV infection in a subject comprising administering to the subject two or more infectious arenaviruses expressing an HBV antigen as described herein. See, e.g., Section 6.2. In specific embodiments, a method for treating and/or preventing an HBV infection comprises administering a first infectious arenavirus expressing an HBV antigen as described herein, e.g., in which the ORF encoding the GP of the S genomic segment is substituted with a nucleotide sequence encoding the HBV antigen, wherein the HBV antigen can be but is not limited to:

a) a nucleotide sequence encoding an HBV pre-S2/S protein or an antigenic fragment thereof;

b) a nucleotide sequence encoding an HBV HBc protein or an antigenic fragment thereof;

c) a nucleotide sequence encoding an HBV HBs protein or an antigenic fragment thereof;

d) a nucleotide sequence encoding a fusion of HBV HBs and HBc proteins or antigenic fragments thereof;

e) a nucleotide sequence encoding an HBV HBe protein or an antigenic fragment thereof; and a second infectious arenavirus expressing an HBV antigen as described herein, e.g., in which the ORF encoding the GP of the S genomic segment is substituted with a nucleotide sequence encoding the HBV antigen, wherein the HBV antigen can be but is not limited to:

a) a nucleotide sequence encoding an HBV pre-S2/S protein or an antigenic fragment thereof;

b) a nucleotide sequence encoding an HBV HBc protein or an antigenic fragment thereof;

c) a nucleotide sequence encoding an HBV HBs protein or an antigenic fragment thereof;

d) a nucleotide sequence encoding a fusion of HBV HBs and HBc proteins or antigenic fragments thereof;

e) a nucleotide sequence encoding an HBV HBe protein or an antigenic fragment thereof.

In certain embodiments, the first and second infectious arenaviruses are replication-deficient. In certain embodiments, the first and second infectious arenaviruses are replication-competent. In certain embodiments, either the first or second infectious arenavirus is replication-deficient. In certain embodiments, the first and second infectious arenaviruses are bisegmented. In certain embodiments, the first and second infectious arenaviruses are trisegmented. In certain embodiments, either the first or second infectious arenavirus is bisegmented, and the other is trisegmented.

In specific embodiments, provided herein are methods for treating and/or preventing an HBV infection comprising administering a first infectious arenavirus expressing a first HBV antigen, selected from: an HBV pre-S2/S protein or an antigenic fragment thereof; an HBV HBc protein or an antigenic fragment thereof, an HBV HBs protein or an antigenic fragment thereof, or an HBV HBe protein or an antigenic fragment thereof as described herein and a second infectious arenavirus expressing a second HBV antigen, selected from: a nucleotide sequence encoding an HBV pre-S2/S protein or an antigenic fragment thereof; an HBV HBc protein or an antigenic fragment thereof, an HBV HBs protein or an antigenic fragment thereof, or an HBV HBe protein or an antigenic fragment thereof.

In certain embodiments, provided herein are methods for treating and/or preventing an infection comprising administering two arenavirus vector constructs expressing an HBV antigen as described herein. In a specific embodiment, the two arenavirus vector constructs express a different HBV antigen.

In certain embodiments, provided herein are methods for treating and/or preventing an infection comprising administering two or more arenavirus vector constructs expressing an HBV antigen as described herein. In a specific embodiment, provided herein are methods for treating and/or preventing an infection comprising administering three or more arenavirus vector constructs expressing an HBV antigen as described herein. In certain embodiments, the arenavirus vector construct can be based on LCMV.

In certain embodiments, provided herein are methods for treating and/or preventing an infection comprising administering two or more arenavirus vector constructs each expressing a different HBV antigen as described herein. In a specific embodiment, provided herein are methods for treating and/or preventing an infection comprising administering three or more arenavirus vector constructs, each expressing a different HBV antigen as described herein. In certain embodiments, the arenavirus vector construct can be based on LCMV.

In specific embodiments, the antigen is the HBV pre-S2/S protein or a fragment thereof (See, e.g., Section 6.2(a)).

In certain embodiments, the antigen is the HBV HBc protein or a fragment thereof. (See, e.g., Section 6.2(b)).

In certain embodiments, the antigen is the HBV HBs protein or a fragment thereof (See, e.g., Section 6.2(c)).

In certain embodiments, the antigen is a fusion of HBV HBs and HBc proteins or antigenic fragments thereof (See, e.g., Section 6.2(d)).

In certain embodiments, the antigen is the HBV HBe protein or a fragment thereof. (See, e.g., Section 6.2(e)).

In certain embodiments, the vector generated to encode one or more HBV antigens as described herein comprises one or more nucleic acids encoding an HBV antigen and combinations thereof as described. In specific embodiments the HBV antigens as described herein are separated by various linkers, spacers, and cleavage sites as described herein.

In another embodiment, the vector generated to encode one or more HBV antigens as described herein of the first infectious arenavirus may be based on LCMV Clone 13 or LCMV MP strain. (See, e.g., Section 7.1).

In another embodiment, the vector generated to encode one or more HBV antigens as described herein of the second infectious arenavirus may be based on LCMV Clone 13 or LCMV MP strain. (See, e.g., Section 7.1). In another embodiment, the vector generated to encode one or more HBV antigens as described herein of the first infectious arenavirus may be based on Junin virus.

In another embodiment, the vector generated to encode one or more HBV antigens as described herein of the second infectious arenavirus may be based on Junin virus.

In a specific embodiment, provided herein are methods of treating and/or preventing an infection in a subject comprising administering to the subject a first infectious arenavirus expressing an HBV pre-S2/S protein or an antigenic fragment thereof and a second infectious arenavirus expressing an HBV HBc protein or an antigenic fragment thereof.

In a specific embodiment, provided herein are methods of treating and/or preventing an infection in a subject comprising administering sequentially to the subject a first infectious arenavirus expressing an HBV pre-S2/S protein or an antigenic fragment thereof and a second infectious arenavirus expressing an HBV HBs protein or an antigenic fragment thereof.

In a specific embodiment, provided herein are methods of treating and/or preventing an infection in a subject comprising administering simultaneously to the subject a first infectious arenavirus expressing an HBV HBc protein or an antigenic fragment thereof and a second infectious arenavirus expressing an HBV HBs protein or an antigenic fragment thereof.

In a specific embodiment, provided herein are methods of treating and/or preventing an infection in a subject comprising administering sequentially to the subject a first infectious arenavirus expressing an HBV pre-S2/S protein or an antigenic fragment thereof and a second infectious arenavirus expressing a fusion of HBV HBs and HBc proteins or antigenic fragments thereof.

In a specific embodiment, provided herein are methods of treating and/or preventing an infection in a subject comprising administering sequentially to the subject a first infectious arenavirus expressing an HBV HBc protein or an antigenic fragment thereof and a second infectious arenavirus expressing a fusion of HBV HBs and HBc proteins or antigenic fragments thereof.

In a specific embodiment, provided herein are methods of treating and/or preventing an infection in a subject comprising administering sequentially to the subject a first infectious arenavirus expressing an HBV HBc protein or an antigenic fragment thereof and a second infectious arenavirus expressing an HBV pre-S2/S protein or an antigenic fragment thereof.

In a specific embodiment, provided herein are methods of treating and/or preventing an infection in a subject comprising administering sequentially to the subject a first infectious arenavirus expressing a fusion of HBV HBs and HBc proteins or antigenic fragments thereof and a second infectious arenavirus expressing an HBV pre-S2/S protein or an antigenic fragment thereof.

In a specific embodiment, provided herein are methods of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBe protein or an antigenic fragment thereof.

In a specific embodiment, provided herein are methods of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBc protein or an antigenic fragment thereof.

In a specific embodiment, provided herein are methods of treating and/or preventing an infection in a subject comprising administering to the subject a first infectious arenavirus expressing an HBV pre-S2/S protein or an antigenic fragment thereof and a second infectious arenavirus expressing an HBV HBe protein or an antigenic fragment thereof.

In a specific embodiment, provided herein are methods of treating and/or preventing an infection in a subject comprising administering simultaneously to the subject a first infectious arenavirus expressing an HBV HBe protein or an antigenic fragment thereof and a second infectious arenavirus expressing an HBV HBs protein or an antigenic fragment thereof.

In a specific embodiment, provided herein are methods of treating and/or preventing an infection in a subject comprising administering sequentially to the subject a first infectious arenavirus expressing an HBV HBe protein or an antigenic fragment thereof and a second infectious arenavirus expressing a fusion of HBV HBs and HBc proteins or antigenic fragments thereof.

In a specific embodiment, provided herein are methods of treating and/or preventing an infection in a subject comprising administering sequentially to the subject a first infectious arenavirus expressing an HBV HBs protein or an antigenic fragment thereof and a second infectious arenavirus expressing a fusion of HBV HBs and HBc proteins or antigenic fragments thereof.

In a specific embodiment, provided herein are methods of treating and/or preventing an infection in a subject comprising administering sequentially to the subject a first infectious arenavirus expressing an HBV HBe protein or an antigenic fragment thereof and a second infectious arenavirus expressing an HBV pre-S2/S protein or an antigenic fragment thereof.

In a specific embodiment, provided herein are methods of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBs protein or an antigenic fragment thereof.

In a specific embodiment, provided herein are methods of treating and/or preventing an infection in a subject comprising administering sequentially to the subject a first infectious arenavirus expressing an HBV HBs protein or an antigenic fragment thereof and a second infectious arenavirus expressing an HBV pre-S2/S protein or an antigenic fragment thereof.

In a specific embodiment, provided herein are methods of treating and/or preventing an infection in a subject comprising administering simultaneously to the subject a first infectious arenavirus expressing an HBV HBc protein or an antigenic fragment thereof and a second infectious arenavirus expressing an HBV HBe protein or an antigenic fragment thereof.

In a specific embodiment, provided herein are methods of treating and/or preventing an infection in a subject comprising administering simultaneously to the subject a first infectious arenavirus expressing an HBV HBs protein or an antigenic fragment thereof and a second infectious arenavirus expressing an HBV HBe protein or an antigenic fragment thereof.

In a specific embodiment, provided herein are methods of treating and/or preventing an infection in a subject comprising administering simultaneously to the subject a first infectious arenavirus expressing an HBV HBs protein or an antigenic fragment thereof and a second infectious arenavirus expressing an HBV HBc protein or an antigenic fragment thereof.

In a specific embodiment, provided herein are methods of treating and/or preventing an infection in a subject comprising administering simultaneously to the subject a first infectious arenavirus expressing an HBV HBe protein or an antigenic fragment thereof and a second infectious arenavirus expressing an HBV HBc protein or an antigenic fragment thereof.

In another embodiment, the first infectious arenavirus expressing an HBV antigen is a primary vaccine antigen and the second infectious arenavirus expressing another HBV antigen is a secondary vaccine antigen.

In certain embodiments, administering a first infectious arenavirus expressing an HBV pre-S2/S protein or a fragment thereof or an HBV HBc protein and a second infectious arenavirus expressing an HBV pre-S2/S protein or an HBV HBc protein provides a better protective effect to HBV after vaccination than administering a single infectious arenavirus expressing an HBV antigen, e.g., expressing only the pre-S2/S protein (or a fragment thereof) or only the HBc protein. In other embodiments, administering a first infectious arenavirus expressing an HBV pre-S2/S protein or a fragment thereof or an HBV HBc protein and a second infectious arenavirus expressing an HBV pre-S2/S protein or a fragment thereof or an HBV HBc protein elicits a greater immune response than administering a single infectious arenavirus expressing an HBV antigen e.g., expressing only the pre-S2/S protein (or a fragment thereof) or only the HBc protein. In another embodiment, administering a first infectious arenavirus expressing an HBV pre-S2/S protein or a fragment thereof or an HBV HBc protein and a second infectious arenavirus expressing an HBV pre-S2/S protein or a fragment thereof, or an HBV HBc protein elicits a larger CD8+ T cell response than administering a single infectious arenavirus expressing an HBV antigen e.g., expressing only the pre-S2/S protein (or a fragment thereof) or only the HBc protein. In other embodiments, administering a first infectious arenavirus expressing an HBV pre-S2/S protein or a fragment thereof or an HBV HBc protein and a second infectious arenavirus expressing an HBV pre-S2/S protein or a fragment thereof or an HBV HBc protein elicits higher titers of neutralizing antibodies than administering a single infectious arenavirus expressing an HBV antigen e.g., expressing only the pre-S2/S protein (or a fragment thereof) or only the HBc protein.

In certain embodiments, administering a first infectious arenavirus expressing an HBV pre-S2/S protein or a fragment thereof or an HBV HBs protein and a second infectious arenavirus expressing an HBV pre-S2/S protein or an HBV HBs protein provides a better protective effect to HBV after vaccination than administering a single infectious arenavirus expressing an HBV antigen, e.g., expressing only the pre-S2/S protein (or a fragment thereof) or only the HBs protein. In other embodiments, administering a first infectious arenavirus expressing an HBV pre-S2/S protein or a fragment thereof or an HBV HBs protein and a second infectious arenavirus expressing an HBV pre-S2/S protein or a fragment thereof or an HBV HBs protein elicits a greater immune response than administering a single infectious arenavirus expressing an HBV antigen e.g., expressing only the pre-S2/S protein (or a fragment thereof) or only the HBs protein. In another embodiment, administering a first infectious arenavirus expressing an HBV pre-S2/S protein or a fragment thereof or an HBV HBs protein and a second infectious arenavirus expressing an HBV pre-S2/S protein or a fragment thereof, or an HBV HBs protein elicits a larger CD8+ T cell response than administering a single infectious arenavirus expressing an HBV antigen e.g., expressing only the pre-S2/S protein (or a fragment thereof) or only the HBs protein. In other embodiments, administering a first infectious arenavirus expressing an HBV pre-S2/S protein or a fragment thereof or an HBV HBs protein and a second infectious arenavirus expressing an HBV pre-S2/S protein or a fragment thereof or an HBV HBs protein elicits higher titers of neutralizing antibodies than administering a single infectious arenavirus expressing an HBV antigen e.g., expressing only the pre-S2/S protein (or a fragment thereof) or only the HBs protein.

In certain embodiments, administering a first infectious arenavirus expressing an HBV pre-S2/S protein or a fragment thereof or a fusion of HBV HBs and HBc proteins and a second infectious arenavirus expressing an HBV pre-S2/S protein or a fusion of HBV HBs and HBc proteins provides a better protective effect to HBV after vaccination than administering a single infectious arenavirus expressing an HBV antigen, e.g., expressing only the pre-S2/S protein (or a fragment thereof) or only the fusion of HBV HBs and HBc proteins. In other embodiments, administering a first infectious arenavirus expressing an HBV pre-S2/S protein or a fragment thereof or a fusion of HBV HBs and HBc proteins and a second infectious arenavirus expressing an HBV pre-S2/S protein or a fragment thereof or a fusion of HBV HBs and HBc proteins elicits a greater immune response than administering a single infectious arenavirus expressing an HBV antigen e.g., expressing only the pre-S2/S protein (or a fragment thereof) or only the fusion of HBV HBs and HBc proteins. In another embodiment, administering a first infectious arenavirus expressing an HBV pre-S2/S protein or a fragment thereof or a fusion of HBV HBs and HBc proteins and a second infectious arenavirus expressing an HBV pre-S2/S protein or a fragment thereof, or a fusion of HBV HBs and HBc proteins elicits a larger CD8+ T cell response than administering a single infectious arenavirus expressing an HBV antigen e.g., expressing only the pre-S2/S protein (or a fragment thereof) or only the fusion of HBV HBs and HBc proteins. In other embodiments, administering a first infectious arenavirus expressing an HBV pre-S2/S protein or a fragment thereof or a fusion of HBV HBs and HBc proteins and a second infectious arenavirus expressing an HBV pre-S2/S protein or a fragment thereof or a fusion of HBV HBs and HBc proteins elicits higher titers of neutralizing antibodies than administering a single infectious arenavirus expressing an HBV antigen e.g., expressing only the pre-S2/S protein (or a fragment thereof) or only the fusion of HBV HBs and HBc proteins.

In certain embodiments, administering a first infectious arenavirus expressing an HBV pre-S2/S protein or a fragment thereof or an HBV HBe protein and a second infectious arenavirus expressing an HBV pre-S2/S protein or an HBV HBe protein provides a better protective effect to HBV after vaccination than administering a single infectious arenavirus expressing an HBV antigen, e.g., expressing only the pre-S2/S protein (or a fragment thereof) or only the HBe protein. In other embodiments, administering a first infectious arenavirus expressing an HBV pre-S2/S protein or a fragment thereof or an HBV HBe protein and a second infectious arenavirus expressing an HBV pre-S2/S protein or a fragment thereof or an HBV HBe protein elicits a greater immune response than administering a single infectious arenavirus expressing an HBV antigen e.g., expressing only the pre-S2/S protein (or a fragment thereof) or only the HBe protein. In another embodiment, administering a first infectious arenavirus expressing an HBV pre-S2/S protein or a fragment thereof or an HBV HBe protein and a second infectious arenavirus expressing an HBV pre-S2/S protein or a fragment thereof, or an HBV HBe protein elicits a larger CD8+ T cell response than administering a single infectious arenavirus expressing an HBV antigen e.g., expressing only the pre-S2/S protein (or a fragment thereof) or only the HBe protein. In other embodiments, administering a first infectious arenavirus expressing an HBV pre-S2/S protein or a fragment thereof or an HBV HBe protein and a second infectious arenavirus expressing an HBV pre-S2/S protein or a fragment thereof or an HBV HBe protein elicits higher titers of neutralizing antibodies than administering a single infectious arenavirus expressing an HBV antigen e.g., expressing only the pre-S2/S protein (or a fragment thereof) or only the HBe protein.

In yet another embodiment, provided herein is the combined use of the replication-deficient arenavirus expressing an HBV antigen described herein and one or more replication-defective virus vectors. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In yet another embodiment, provided herein is the combined use of the replication-deficient arenavirus expressing an HBV antigen described herein and one or more replication-defective virus vectors expressing an HBV antigen. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In another embodiment, the first infectious arenavirus expressing an HBV antigen as described herein is administered before or after the second infectious arenavirus expressing an HBV antigen as described herein. For example the first infectious arenavirus expressing an HBV antigen is administered around 30-60 minutes before or after the first administration of the second infectious arenavirus.

In another embodiment, the first infectious arenavirus expressing a vaccine antigen is administered before the second infectious arenavirus expressing a vaccine antigen. In certain embodiments there is a period of about 1 hour, 2 hours, 3 hours, 6 hours, 12 hours, 1 day, 2 days, 3 days, 5 days, 1 week, 2 weeks, 1 month, 2 months, 3 months, 4 months, 5 months, 6 months, 7 months, 8 months, 9 months, 10 months, 11 months, 1 year between the administration of the first infectious arenavirus and the second infectious arenavirus.

In another embodiment, two infectious arenaviruses are administered in a treatment regime at molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, the subjects whom two or more infectious arenaviruses expressing an HBV antigen described herein are administered have, are susceptible to, or are at risk for an HBV infection. In another embodiment, the subjects whom two or more infectious arenaviruses expressing an HBV antigen described herein are administered are infected with, are susceptible to, or are at risk for, an infection with HBV.

In another embodiment, the subjects whom two or more infectious arenaviruses expressing an HBV antigen described herein, are administered simultaneously have, are susceptible to, or are at risk for an HBV infection. In another embodiment, the subjects whom two or more infectious arenaviruses expressing an HBV antigen described herein are administered simultaneously are infected with, are susceptible to, or are at risk for, an infection with HBV.

In another embodiment, the subjects whom two or more infectious arenaviruses expressing an HBV antigen described herein, are administered sequentially have, are susceptible to, or are at risk for an HBV infection. In another embodiment, the subjects whom two or more infectious arenaviruses expressing an HBV antigen described herein are administered sequentially are infected with, are susceptible to, or are at risk for, an infection with HBV.

In another embodiment, said two or more infectious arenaviruses expressing an HBV antigen as described herein are further administered in combination with at least one other medicament for treating and/or preventing HBV. Therapeutic medicaments for treating and/or preventing HBV include, but are not limited to entecavir (BARACLUDE®; Bristol-Myers Squibb), lamivudine (EPIVIR HBV®; GlaxoSmithKline), adefovir dipivoxil (HEPSERA®; Gilead Sciences), interferon alpha 2b (INTRON A®; Schering), pegylated interferon (PEGASYS®; Roche), telbivudine (TYZEKA®, Novartis), and tenofovir (VIREAD®; Gilead Sciences).

In another embodiment, said two or more infectious arenaviruses expressing an HBV antigen as described herein are further administered in a combination with at least one other immunomodulator. In a more specific embodiment, said two or more infectious arenaviruses expressing an HBV antigen as described herein are further administered in a combination with at least one Th1-specific adjuvant. In a more specific embodiment the Th-1 specific adjuvant is *Bacillus* Calmette-Guerin (BCG).

In another embodiment, the administration regime can involve administering to a symptomatic subject a second infectious arenavirus expressing an HBV antigen as described herein. In yet another embodiment, the administration regime can involve administering to an subject with a compromised immune system, especially transplant recipients, HIV-infected persons, a pregnant subject, a subject who has cancer, a second infectious arenavirus expressing an HBV antigen as described herein. In another embodiment, two or more infectious arenaviruses expressing an HBV antigen as described herein are administered to a subject who is a child of 0, 1, 2, 3, 4, 5, 6, 7, 8, 9, 10, 11, 12, 13, 14, 15, 16, or 17 years of age suffering from or susceptible to, or at risk for, an infection with HBV.

In another embodiment, the administration regime can involve administering to a subject who is a child, a first arenavirus expressing an HBV antigen, and administering to the same subject who is an adolescent a second arenavirus expressing an HBV antigen. In a specific embodiment, the administration regime can involve administering to a subject who is 0, 1, 2, 3, 4, 5, 6, 7, 8, 9, 10, 11, 12, 13, 14, 15, 16, or 17 years of age a first arenavirus expressing an HBV antigen as described herein, and to the same subject who is 12, 13, 14, 15, 16, 17, 18, 19, 20, 21, 22, 23, 24, 25 years of age a second infectious arenavirus expressing an HBV antigen.

In another embodiment, the administration regime can involve administering to a prepubescent subject a second infectious arenavirus expressing an HBV antigen. In another embodiment, the administration regime can involve administering to an adolescent male, aged 12 to 18 years a second infectious arenavirus expressing an HBV antigen as described herein. In another embodiment, the administration regime can involve administering to a female, aged 12 to 18 years a second infectious arenavirus expressing an HBV antigen.

In another embodiment, administering two or more infectious arenaviruses expressing an HBV antigen reduces the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

In another embodiment, administering two or more infectious arenaviruses expressing an HBV antigen, administered separately, reduces the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

In another embodiment, administering two or more infectious arenaviruses expressing an HBV antigen, administered sequentially, reduces the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

Without being limited by theory, administration of a first infectious arenavirus and subsequently of a second infectious arenavirus vector results in a prime-boost effect.

In certain embodiments, provided herein are methods for treating and/or preventing an HBV infection comprising administering two or more arenavirus vector constructs each expressing the same or a different HBV antigen sequentially. The time interval between each administration can be about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In certain embodiments, the first infectious arenavirus and the second infectious arenavirus are homologous. In certain embodiments, the first infectious arenavirus and the second infectious arenavirus are heterologous.

In certain specific embodiments, the first infectious arenavirus is an Old World arenavirus, and the second infectious arenavirus is an Old World arenavirus. In certain specific embodiments, the first infectious arenavirus is an Old World arenavirus, and the second infectious arenavirus is a New World arenavirus. In certain specific embodiments, the first infectious arenavirus is a New World arenavirus, and the second infectious arenavirus is a New World arenavirus. In certain specific embodiments, the first infectious arenavirus is a New World arenavirus, and the second infectious arenavirus is an Old World arenavirus.

In certain specific embodiments, the first infectious arenavirus is derived from LCMV, and the second infectious arenavirus is derived from LCMV. In certain specific embodiments, the first infectious arenavirus is derived from LCMV, and the second infectious arenavirus is derived from Junin virus. In certain specific embodiments, the first infectious arenavirus is derived from Junin virus, and the second infectious arenavirus is derived from Junin virus. In certain specific embodiments, the first infectious arenavirus is derived from Junin virus, and the second infectious arenavirus is derived from LCMV.

In certain embodiments, provided herein is a method of treating and/or preventing an HBV infection wherein a first infectious arenavirus is administered first as a "prime," and a second infectious arenavirus is administered as a "boost." The first and the second infectious arenavirus vectors can express the same or different HBV antigens. In certain specific embodiments, the "prime" administration is performed with an infectious arenavirus derived from LCMV, and the "boost" is performed with an infectious arenavirus derived from Junin virus. In certain specific embodiments, the "prime" administration is performed with an infectious arenavirus derived from Junin virus, and the "boost" is performed with an infectious arenavirus derived from LCMV.

In certain embodiments, administering a first infectious arenavirus expressing an HBV antigen or a fragment thereof, followed by administering a second infectious arenavirus expressing an HBV antigen or a fragment thereof results in a greater antigen specific CD8+ T cell response than administering a single infectious arenavirus expressing an HBV antigen or a fragment thereof. In certain embodiments, the antigen specific CD8+ T cell count increases by 50%, 100%, 150% or 200% after the second administration compared to the first administration. In certain embodiments, administering a third infectious arenavirus expressing an HBV antigen results in a greater antigen specific CD8+ T cell response than administering two consecutive infectious arenaviruses expressing an HBV antigen. In certain embodiments, the antigen specific CD8+ T cell count increases by about 50%, about 100%, about 150%, about 200% or about 250% after the third administration compared to the first administration.

In certain embodiments, provided herein are methods for treating and/or preventing an infection comprising administering two or more arenavirus vector constructs, wherein the two or more arenavirus vector constructs are homologous, and wherein the time interval between each administration is about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In certain embodiments, administering a first infectious arenavirus expressing an HBV antigen or a fragment thereof and a second, heterologous, infectious arenavirus expressing an HBV antigen or a fragment thereof elicits a greater CD8+ T cell response than administering a first infectious arenavirus expressing an HBV antigen or a fragment thereof and a second, homologous, infectious arenavirus expressing an HBV antigen or a fragment thereof.

In certain specific embodiments, the first infectious arenavirus expressing an HBV pre-S2/S protein is LCMV, and the second, heterologous, infectious arenavirus expressing an HBV pre-S2/S protein is Junin virus. In certain specific embodiments, the first infectious arenavirus expressing an HBV pre-S2/S protein is Junin virus, and the second, heterologous, infectious arenavirus expressing an HBV pre-S2/S protein is LCMV.

In certain specific embodiments, the first infectious arenavirus expressing an HBV HBc protein is LCMV, and the second, heterologous, infectious arenavirus expressing an HBV HBc protein is Junin virus. In certain specific embodiments, the first infectious arenavirus expressing an HBV HBc protein is Junin virus, and the second, heterologous, infectious arenavirus expressing an HBV HBc protein is LCMV.

In certain specific embodiments, the first infectious arenavirus expressing an HBV HBs and HBc fusion protein is LCMV, and the second, heterologous, infectious arenavirus expressing an HBV HBs and HBc fusion protein is Junin virus. In certain specific embodiments, the first infectious arenavirus expressing an HBV HBs and HBc fusion protein is Junin virus, and the second, heterologous, infectious arenavirus expressing an HBV HBs and HBc fusion protein is LCMV.

In certain specific embodiments, the first infectious arenavirus expressing an HBV HBe protein is LCMV, and the second, heterologous, infectious arenavirus expressing an HBV HBe protein is Junin virus. In certain specific embodiments, the first infectious arenavirus expressing an HBV HBe protein is Junin virus, and the second, heterologous, infectious arenavirus expressing an HBV HBe protein is LCMV.

In certain specific embodiments, administering a first infectious arenavirus expressing an HBV pre-S2/S protein and a second, heterologous, infectious arenavirus expressing an HBV pre-S2/S protein elicits a greater CD8+ T cell response than administering a first infectious arenavirus expressing an HBV pre-S2/S protein and a second, homologous, infectious arenavirus expressing HBV pre-S2/S protein. In certain specific embodiments, administering a first infectious arenavirus expressing an HBV pre-S2/S protein and a second, heterologous, infectious arenavirus expressing an HBV pre-S2/S protein elicits a CD8+ T cell response that is about 20%, about 40%, about 60%, about 80%, about 100%, about 120%, about 140%, about 160%, about 180%, or about 200% greater than administering a first infectious arenavirus expressing an HBV pre-S2/S protein and a second, homologous, infectious arenavirus expressing an HBV pre-S2/S protein.

In certain specific embodiments, administering a first infectious arenavirus expressing an HBV HBc protein and a second, heterologous, infectious arenavirus expressing an HBV HBc protein elicits a greater CD8+ T cell response than administering a first infectious arenavirus expressing an HBV HBc protein and a second, homologous, infectious arenavirus expressing HBV HBc protein. In certain specific embodiments, administering a first infectious arenavirus expressing an HBV HBc protein and a second, heterologous, infectious arenavirus expressing an HBV HBc protein elicits a CD8+ T cell response that is about 20%, about 40%, about 60%, about 80%, about 100%, about 120%, about 140%, about 160%, about 180%, or about 200% greater than administering a first infectious arenavirus expressing an HBV HBc protein and a second, homologous, infectious arenavirus expressing an HBV HBc protein.

In certain specific embodiments, administering a first infectious arenavirus expressing an HBV HBs and HBc fusion protein and a second, heterologous, infectious arenavirus expressing an HBV HBs and HBc fusion protein elicits a greater CD8+ T cell response than administering a first infectious arenavirus expressing an HBV HBs and HBc fusion protein and a second, homologous, infectious arenavirus expressing HBV HBs and HBc fusion protein. In certain specific embodiments, administering a first infectious arenavirus expressing an HBV HBs and HBc fusion protein and a second, heterologous, infectious arenavirus expressing an HBV HBs and HBc fusion protein elicits a CD8+ T cell response that is about 20%, about 40%, about 60%, about 80%, about 100%, about 120%, about 140%, about 160%, about 180%, or about 200% greater than administering a first infectious arenavirus expressing an HBV HBs and HBc fusion protein and a second, homologous, infectious arenavirus expressing an HBV HBs and HBc fusion protein.

In certain specific embodiments, administering a first infectious arenavirus expressing an HBV HBe protein and a second, heterologous, infectious arenavirus expressing an HBV HBe protein elicits a greater CD8+ T cell response than administering a first infectious arenavirus expressing an HBV HBe protein and a second, homologous, infectious arenavirus expressing HBV HBe protein. In certain specific embodiments, administering a first infectious arenavirus expressing an HBV HBe protein and a second, heterologous, infectious arenavirus expressing an HBV HBe protein elicits a CD8+ T cell response that is about 20%, about 40%, about 60%, about 80%, about 100%, about 120%, about 140%, about 160%, about 180%, or about 200% greater than administering a first infectious arenavirus expressing an HBV HBe protein and a second, homologous, infectious arenavirus expressing an HBV HBe protein.

In certain embodiments, provided herein are methods for treating and/or preventing an infection comprising administering two or more arenavirus vector constructs, wherein the two or more arenavirus vector constructs are heterologous, and wherein the time interval between each administration is about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In yet another embodiment, provided herein is the combined use of the replication-deficient arenavirus expressing an HBV antigen described herein and one or more replication-defective virus vectors. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In yet another embodiment, provided herein is the combined use of the replication-deficient arenavirus expressing an HBV antigen described herein and one or more replication-defective virus vectors expressing an HBV antigen. In a more specific embodiment the replication-defective virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In another embodiment, the first infectious arenavirus expressing an HBV antigen as described herein is administered before or after the second infectious arenavirus expressing an HBV antigen as described herein. For example the first infectious arenavirus expressing an HBV antigen is administered around 30-60 minutes before or after the first administration of the second infectious arenavirus.

In another embodiment, the first infectious arenavirus expressing a vaccine antigen is administered before the second infectious arenavirus expressing a vaccine antigen. In certain embodiments there is a period of about 1 hour, 2 hours, 3 hours, 6 hours, 12 hours, 1 day, 2 days, 3 days, 5 days, 1 week, 2 weeks, 1 month, 2 months, 3 months, 4 months, 5 months, 6 months, 7 months, 8 months, 9 months, 10 months, 11 months, 1 year between the administration of the first infectious arenavirus and the second infectious arenavirus.

In another embodiment, two infectious arenaviruses are administered in a treatment regime at molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, the subjects to whom two or more infectious arenaviruses expressing an HBV antigen described herein are administered have, are susceptible to, or are at risk for an HBV infection. In another embodiment, the subjects to whom two or more infectious arenaviruses expressing an HBV antigen described herein are administered are infected with, are susceptible to, or are at risk for, an infection with HBV.

The subjects who can be treated with the methods provided herein are susceptible to, or are at risk for an HBV infection.

In another embodiment, said two or more infectious arenaviruses expressing an HBV antigen as described herein further express at least another immunostimulatory peptide, polypeptide or protein. In certain embodiments, the immunostimulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; *Mycobacterium tuberculosis* Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

Heterologous prime-boost methods with infectious replication-defective arenavirus vectors wherein the two infectious replication-defective arenavirus vectors are derived from different arenaviruses (e.g., LCMV and Junin virus) are also provided. These infectious replication-defective arenavirus vectors can express an antigen, such as an antigen of HBV.

Heterologous prime-boost methods with infectious replication-competent arenavirus vectors wherein the two infectious replication-competent arenavirus vectors are derived from different arenaviruses (e.g., LCMV and Junin virus) are also provided. These infectious replication-competent arenavirus vectors can express an antigen, such as an antigen of HBV.

6.8 (b) Compositions

The invention furthermore relates to vaccines, immunogenic compositions, and pharmaceutical compositions comprising a genetically engineered arenavirus as described herein. Such vaccines and pharmaceutical compositions can be formulated according to standard procedures in the art.

In one embodiment, provided herein are compositions comprising two or more infectious arenaviruses expressing an HBV antigen as described herein. See, e.g., Section 6.2. In a specific embodiments, the compositions described herein comprises administering to a subject a first infectious arenavirus expressing an HBV antigen as described herein, e.g., in which the ORF encoding the GP of the S genomic segment is substituted with a nucleotide sequence encoding the HBV antigen. The HBV antigen can be but is not limited to:

a) a nucleotide sequence encoding an HBV pre-S2/S protein or an antigenic fragment thereof;

b) a nucleotide sequence encoding an HBV HBc protein or an antigenic fragment thereof;

c) a nucleotide sequence encoding an HBV HBs protein or an antigenic fragment thereof;

d) a nucleotide sequence encoding a fusion of HBV HBs and HBc proteins or antigenic fragments thereof;

e) a nucleotide sequence encoding an HBV HBe protein or an antigenic fragment thereof;

and a second infectious arenavirus composition expressing an HBV antigen as described herein, e.g., in which the ORF encoding the GP of the S genomic segment is substituted with a nucleotide sequence encoding the HBV antigen. The HBV antigen can be but is not limited to:

a) a nucleotide sequence encoding an HBV pre-S2/S protein or an antigenic fragment thereof;

b) a nucleotide sequence encoding an HBV HBc protein or an antigenic fragment thereof;

c) a nucleotide sequence encoding an HBV HBs protein or an antigenic fragment thereof;

d) a nucleotide sequence encoding a fusion of HBV HBs and HBc proteins or antigenic fragments thereof;

e) a nucleotide sequence encoding an HBV HBe protein or an antigenic fragment thereof. In certain embodiments, the first and second infectious arenaviruses are replication-deficient. In certain embodiments, the first and second infectious arenaviruses are replication-competent. In certain embodiments, either the first or second infectious arenavirus is replication-deficient.

In specific embodiments, provided herein are methods for treating and/or preventing an HBV infection comprising administering a first infectious arenavirus expressing a first HBV antigen, selected from: an HBV pre-S2/S protein or an antigenic fragment thereof; an HBV HBc protein or an antigenic fragment thereof; an HBV HBs protein or an antigenic fragment thereof, a fusion of HBV HBs and HBc proteins or antigenic fragments thereof, or an HBV HBe protein or an antigenic fragment thereof, as described herein and a second infectious arenavirus expressing a second HBV antigen, selected from: an HBV pre-S2/S protein or an antigenic fragment thereof; an HBV HBc protein or an antigenic fragment thereof; or an HBV HBs protein or an antigenic fragment thereof, a fusion of HBV HBs and HBc proteins or antigenic fragments thereof, or an HBV HBe protein or an antigenic fragment thereof.

In certain embodiments, provided herein are compositions suitable for a method of treating and/or preventing an HBV infection comprising administering two arenavirus constructs expressing an HBV antigen as described herein. In a specific embodiment, the two arenavirus vector constructs express an HBV antigen.

In certain embodiments, provided herein are compositions comprising two or more arenavirus vector constructs expressing an HBV antigen as described herein. In specific embodiments, provided herein are compositions comprising three or more arenavirus vector constructs expressing an HBV antigen as described herein. In certain embodiments, the arenavirus can be LCMV.

In specific embodiments, the antigen is the HBV pre-S2/S protein or a fragment thereof (See, e.g., Section 6.2(a)).

In certain embodiments, the antigen is the HBV HBc protein or a fragment thereof. (See, e.g., Section 6.2(b)).

In certain embodiments, the antigen is the HBV HBs protein or a fragment thereof (See, e.g., Section 6.2(c)).

In certain embodiments, the antigen is a fusion of the HBV HBs and HBc proteins or antigenic fragments thereof (See, e.g., Section 6.2(d)).

In certain embodiments, the antigen is the HBV HBe protein or a fragment thereof (See, e.g., Section 6.2(e)).

In certain embodiments, the vector generated to encode one or more HBV antigens as described herein comprises one or more nucleic acids encoding an HBV antigen and combinations thereof as described. In specific embodiments the HBV antigens as described herein are separated by various linkers, spacers, and cleavage sites as described herein.

In another embodiment, the vector generated to encode one or more HBV antigens as described herein of the first infectious arenavirus may be based on LCMV Clone 13 or LCMV MP strain. (See, e.g., Section 7.1).

In another embodiment, the vector generated to encode one or more HBV antigens as described herein of the second infectious arenavirus may be based on LCMV Clone 13 or LCMV MP strain. (See, e.g., Section 7.1).

In a specific embodiment, provided herein are compositions suitable for a method of treating and/or preventing an HBV infection in a subject comprising administering to the subject a first infectious arenavirus composition expressing an HBV pre-S2/S protein or an antigenic fragment thereof and a second infectious arenavirus composition expressing an HBV HBc protein or an antigenic fragment thereof.

In a specific embodiment, provided herein are compositions suitable for a method of treating and/or preventing an infection in a subject comprising administering sequentially to the subject a first infectious arenavirus expressing an HBV pre-S2/S protein or an antigenic fragment thereof and a second infectious arenavirus expressing an HBV HBs protein or an antigenic fragment thereof.

In a specific embodiment, provided herein are compositions suitable for a an infection in a subject comprising administering simultaneously to the subject a first infectious arenavirus expressing an HBV HBc protein or an antigenic fragment thereof and a second infectious arenavirus expressing an HBV HBs protein or an antigenic fragment thereof.

In a specific embodiment, provided herein are compositions suitable for a method of treating and/or preventing an infection in a subject comprising administering sequentially to the subject a first infectious arenavirus expressing an HBV pre-S2/S protein or an antigenic fragment thereof and a second infectious arenavirus expressing a fusion of HBV HBs and HBc proteins or antigenic fragments thereof.

In a specific embodiment, provided herein are compositions suitable for a method of treating and/or preventing an infection in a subject comprising administering simultaneously to the subject a first infectious arenavirus expressing an HBV HBc protein or an antigenic fragment thereof and a second infectious arenavirus expressing a fusion of HBV HBs and HBc proteins or antigenic fragments thereof.

In a specific embodiment, provided herein are compositions suitable for a method of treating and/or preventing an infection in a subject comprising administering sequentially to the subject a first infectious arenavirus expressing an HBV HBc protein or an antigenic fragment thereof and a second infectious arenavirus expressing an HBV pre-S2/S protein or an antigenic fragment thereof.

In a specific embodiment, provided herein are compositions suitable for a method of treating and/or preventing an infection in a subject comprising administering sequentially to the subject a first infectious arenavirus expressing a fusion of HBV HBs and HBc proteins or antigenic fragments thereof and a second infectious arenavirus expressing an HBV pre-S2/S protein or an antigenic fragment thereof.

In a specific embodiment, provided herein are compositions suitable for a method of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBe protein or an antigenic fragment thereof.

In a specific embodiment, provided herein are compositions suitable for a method of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBc protein or an antigenic fragment thereof.

In a specific embodiment, provided herein are compositions suitable for a method of treating and/or preventing an infection in a subject comprising administering to the subject a first infectious arenavirus expressing an HBV pre-S2/S protein or an antigenic fragment thereof and a second infectious arenavirus expressing an HBV HBe protein or an antigenic fragment thereof.

In a specific embodiment, provided herein are compositions suitable for a method of treating and/or preventing an infection in a subject comprising administering simultaneously to the subject a first infectious arenavirus expressing an HBV HBe protein or an antigenic fragment thereof and a second infectious arenavirus expressing an HBV HBs protein or an antigenic fragment thereof.

In a specific embodiment, provided herein are compositions suitable for a method of treating and/or preventing an infection in a subject comprising administering sequentially to the subject a first infectious arenavirus expressing an HBV HBe protein or an antigenic fragment thereof and a second infectious arenavirus expressing a fusion of HBV HBs and HBc proteins or antigenic fragments thereof.

In a specific embodiment, provided herein are compositions suitable for a method of treating and/or preventing an infection in a subject comprising administering sequentially to the subject a first infectious arenavirus expressing an HBV HBs protein or an antigenic fragment thereof and a second infectious arenavirus expressing a fusion of HBV HBs and HBc proteins or antigenic fragments thereof.

In a specific embodiment, provided herein are compositions suitable for a method of treating and/or preventing an infection in a subject comprising administering sequentially to the subject a first infectious arenavirus expressing an HBV HBe protein or an antigenic fragment thereof and a second infectious arenavirus expressing an HBV pre-S2/S protein or an antigenic fragment thereof.

In a specific embodiment, provided herein are compositions suitable for a method of treating and/or preventing an infection in a subject comprising administering sequentially to the subject a first infectious arenavirus expressing a fusion of HBV HBs and HBc proteins or antigenic fragments thereof and a second infectious arenavirus expressing an HBV HBs protein or an antigenic fragment thereof.

In a specific embodiment, provided herein are compositions suitable for a method of treating and/or preventing an infection in a subject comprising administering sequentially to the subject a first infectious arenavirus expressing an HBV HBs protein or an antigenic fragment thereof and a second infectious arenavirus expressing an HBV pre-S2/S protein or an antigenic fragment thereof.

In a specific embodiment, provided herein are compositions suitable for a method of treating and/or preventing an infection in a subject comprising administering simultaneously to the subject a first infectious arenavirus expressing an HBV HBc protein or an antigenic fragment thereof and a second infectious arenavirus expressing an HBV HBe protein or an antigenic fragment thereof.

In a specific embodiment, provided herein are compositions suitable for a method of treating and/or preventing an infection in a subject comprising administering simultaneously to the subject a first infectious arenavirus expressing an HBV HBs protein or an antigenic fragment thereof and a second infectious arenavirus expressing an HBV HBe protein or an antigenic fragment thereof.

In a specific embodiment, provided herein are compositions suitable for a method of treating and/or preventing an infection in a subject comprising administering simultaneously to the subject a first infectious arenavirus expressing an HBV HBs protein or an antigenic fragment thereof and a second infectious arenavirus expressing an HBV HBc protein or an antigenic fragment thereof.

In a specific embodiment, provided herein are compositions suitable for a method of treating and/or preventing an infection in a subject comprising administering simultaneously to the subject a first infectious arenavirus expressing an HBV HBe protein or an antigenic fragment thereof and a second infectious arenavirus expressing an HBV HBc protein or an antigenic fragment thereof.

In another embodiment, the first infectious arenavirus composition expressing an HBV antigen is a primary vaccine antigen and the second infectious arenavirus expressing another HBV antigen is a secondary vaccine antigen.

In yet another embodiment, provided herein is the combined use of the replication-deficient arenaviruses compositions expressing an HBV antigen as described herein and one or more replication-defective virus vector compositions. In a more specific embodiment the replication-defective virus vector composition can be but is not limited to: poxviruses, adenoviruses, alphaviruses, herpes simplex viruses, paramyxoviruses, rhabdoviruses, poliovirus, adeno-associated virus, and Sendai virus, and mixtures thereof. In a specific embodiment, the poxvirus is a modified vaccine Ankara.

In another embodiment, two infectious arenaviruses compositions have molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, two or more infectious arenavirus compositions expressing an HBV antigen described herein are suitable for administration to subjects who have, are susceptible to, or are at risk for an HBV infection. In another embodiment, the subjects, to whom two or more infectious arenaviruses compositions expressing an HBV antigen described herein or a composition thereof is administered, are infected with, are susceptible to, or are at risk for, an infection with HBV.

In another embodiment, said two or more infectious arenavirus compositions further comprise at least one other medicament for treating and/or preventing HBV infection. Therapeutic medicaments include, but are not limited to, entecavir (BARACLUDE®; Bristol-Myers Squibb), lamivudine (EPIVIR HBV®; GlaxoSmithKline), adefovir dipivoxil (HEPSERA®; Gilead Sciences), interferon alpha 2b (INTRON A®; Schering), pegylated interferon (PEGASYS®; Roche), telbivudine (TYZEKA®, Novartis), and tenofovir (VIREAD®; Gilead Sciences).

In another embodiment, compositions are suitable for administrating to a symptomatic subject a second infectious arenavirus composition expressing an HBV antigen or a fragment thereof as described herein. In yet another embodiment, the compositions are suitable for administration to a subject with a compromised immune system, especially transplant recipients, HIV-infected persons, a pregnant subject, or a subject who has cancer, a second infectious arenavirus composition expressing an HBV antigen described herein or a fragment thereof. In another embodiment, two or more infectious arenavirus compositions expressing an HBV antigen as described herein or a fragment thereof are suitable for administrating to a subject who is a child of 0, 1, 2, 3, 4, 5, 6, 7, 8, 9, 10, 11, 12, 13, 14, 15, 16, or 17 years of age suffering from or susceptible to, or are at risk for, an infection with HBV.

In another embodiment, compositions are suitable for administrating to a subject who is a child, a first arenavirus expressing an HBV antigen, and administering to the same subject who is an adolescent a second arenavirus expressing an HBV antigen. In a specific embodiment, the administration regime can involve administering to a subject who is 0, 1, 2, 3, 4, 5, 6, 7, 8, 9, 10, 11, 12, 13, 14, 15, 16, or 17 years of age a first arenavirus expressing an HBV antigen as described herein, and to the same subject who is 12, 13, 14, 15, 16, 17, 18, 19, 20, 21, 22, 23, 24, 25 years of age a second infectious arenavirus expressing an HBV antigen.

In another embodiment, compositions are suitable for administering to a prepubescent subject a second infectious arenavirus expressing an HBV antigen. In another embodiment, the administration regime can involve administering to an adolescent male, aged 12 to 18 years a second infectious arenavirus expressing an HBV antigen as described herein. In another embodiment, the administration regime can involve administering to a female, aged 12 to 18 years a second infectious arenavirus expressing an HBV antigen.

In another embodiment, two or more infectious arenavirus compositions expressing an HBV antigen or a fragment thereof, as described herein reduce the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

In another embodiment, two or more infectious arenavirus compositions expressing an HBV antigen or a fragment thereof, as described herein, administered separately, reduce the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

In another embodiment, two or more infectious arenavirus compositions expressing an HBV antigen or a fragment thereof, as described herein, administered sequentially, reduce the risk that an individual will develop an infection with HBV by at least 10%, at least about 20%, at least about 25%, at least about 30%, at least about 40%, at least about 50%, at least about 60%, at least about 70%, at least about 80%, at least about 90%, or more, compared to the risk of developing an infection with HBV in the absence of such treatment.

In another embodiment, provided herein the invention provides a vaccine composition comprising a synergistic combination of two or more infectious replication-deficient arenaviruses expressing an HBV antigen.

In another embodiment, provided herein the invention provides a vaccine composition comprising a synergistic combination of two or more infectious replication-competent arenaviruses expressing an HBV antigen.

6.9 Assays

Assay for Measuring Arenavirus Vector Infectivity

Any assay known to the skilled artisan can be used for measuring the infectivity of an arenavirus vector preparation. For example, determination of the virus/vector titer can be done by a "focus forming unit assay" (FFU assay). In brief, complementing cells, e.g. HEK 293 cells expressing LCMV GP protein, are plated and inoculated with different dilutions of a virus/vector sample. After an incubation period, to allow cells to form a monolayer and virus to attach to cells, the monolayer is covered with Methylcellulose. When the plates are further incubated, the original infected cells release viral progeny. Due to the Methylcellulose overlay the spread of the new viruses is restricted to neighboring cells. Consequently, each infectious particle produces a circular zone of infected cells called a Focus. Such Foci can be made visible and by that countable using antibodies against LCMV-NP and a HRP-based color reaction. The titer of a virus/vector can be calculated in focus-forming units per milliliter (FFU/mL).

To determine the infectious titer (FFU/mL) of transgene-carrying vectors this assay is modified by the use of the respective transgene-specific antibody instead of anti-LCMV-NP antibody.

Serum ELISA

Determination of the humoral immune response upon vaccination of animals (e.g. mice, guinea pigs) can be done by antigen-specific serum ELISAs (enzyme-linked immunosorbent assays). In brief, plates are coated with antigen (e.g. recombinant protein), blocked to avoid unspecific binding of antibodies and incubated with serial dilutions of sera. After incubation, bound serum-antibodies can be detected, e.g., using an enzyme-coupled anti-species (e.g. mouse, guinea pig)-specific antibody (detecting total IgG or IgG subclasses) and subsequent color reaction. Antibody titers can be determined as, e.g., endpoint geometric mean titer.

Immunocapture ELISA (IC-ELISA) may also be performed (see Shanmugham et al., 2010, Clin. Vaccine Immunol. 17(8):1252-1260), wherein the capture agents are cross-linked to beads.

Neutralizing Assay in ARPE-19 Cells

Determination of the neutralizing activity of induced antibodies in sera is performed with the following cell assay using ARPE-19 cells from ATCC and a GFP-tagged virus. In addition supplemental serum as a source of exogenous complement is used. The assay is started with seeding of $6.5 \times 10^3$ cells/well (50 µl/well) in a 384 well plate one or two days before using for neutralization. The neutralization is done in 96-well sterile tissue culture plates without cells for 1 h at 37° C. After the neutralization incubation step the mixture is added to the cells and incubated for additional 4 days for GFP-detection with a plate reader. A positive neutralizing human sera is used as assay positive control on each plate to check the reliability of all results. Titers (EC50) are determined using a 4 parameter logistic curve fitting. As additional testing the wells are checked with a fluorescence microscope.

Plaque Reduction Assay

In brief, plaque reduction (neutralization) assays for Hepatitis B virus are performed by use of an isolate of HBV tagged with green fluorescent protein, 5% rabbit serum was used as a source of exogenous complement, and plaques are enumerated by fluorescence microscopy. Neutralization titers are defined as the highest dilution of serum that results in a 50% reduction in plaques, compared with that in control (pre-immune) serum samples.

Neutralization Assay in Guinea Pig Lung Fibroblast (GPL) Cells

In brief, serial dilutions of test and control (pre-vaccination) sera were prepared in GPL complete media with supplemental rabbit serum (1%) as a source of exogenous complement. The dilution series spanned 1:40 through 1:5120. Serum dilutions were incubated with eGFP tagged virus (100-200 pfu per well) for 30 min at 37° C., and then transferred to 12-well plates containing confluent GPL cells. Samples were processed in triplicate. After 2 hours incubation at 37° C. the cells were washed with PBS, re-fed with GPL complete media and incubated at 37° C./5% $CO_2$ for 5 days. Plaques were visualized by fluorescence microscopy, counted, and compared to control wells. That serum dilution resulting in a 50% reduction in plaque number compared to controls was designated as the neutralizing titer.

qPCR

LCMV RNA genomes are isolated using QIAamp Viral RNA mini Kit (QIAGEN), according to the protocol provided by the manufacturer. LCMV RNA genome equivalents are detected by quantitative PCR carried out on an StepOnePlus Real Time PCR System (Applied Biosystems) with SuperScript® III Platinum® One-Step qRT-PCR Kit (Invitrogen) and primers and probes (FAM reporter and NFQ-MGB Quencher) specific for part of the LCMV NP coding region. The temperature profile of the reaction is: 30 min at 60° C., 2 min at 95° C., followed by 45 cycles of 15 s at 95° C., 30 s at 56° C. RNA is quantified by comparison of the sample results to a standard curve prepared from a log 10 dilution series of a spectrophotometrically quantified, in vitro-transcribed RNA fragment, corresponding to a fragment of the LCMV NP coding sequence containing the primer and probe binding sites.

Western Blotting

Infected cells grown in tissue culture flasks or in suspension are lysed at indicated timepoints post infection using RIPA buffer (Thermo Scientific) or used directly without cell-lysis. Samples are heated to 99° C. for 10 minutes with reducing agent and NuPage LDS Sample buffer (NOVEX) and chilled to room temperature before loading on 4-12% SDS-gels for electrophoresis. Proteins are blotted onto membranes using Invitrogens iBlot Gel transfer Device and visualized by Ponceau staining. Finally, the preparations are probed with an primary antibodies directed against proteins of interest and alkaline phosphatase conjugated secondary antibodies followed by staining with 1-Step NBT/BCIP solution (INVITROGEN).

MHC-Peptide Multimer Staining Assay for Detection of Antigen-Specific CD8+ T-Cell Proliferation Any assay known to the skilled artisan can be used to test antigen-specific CD8+ T-cell responses. For example, the MHC-peptide tetramer staining assay can be used (see, e.g., Altman J. D. et al., Science. 1996; 274:94-96; and Murali-Krishna K. et al., Immunity. 1998; 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for an antigen specific T-cell (typically fluorescently labeled). The tetramer is then detected by flow cytometry via the fluorescent label.

ELISPOT Assay for Detection of Antigen-Specific CD4+ T-Cell Proliferation

Any assay known to the skilled artisan can be used to test antigen-specific CD4+ T-cell responses. For example, the ELISPOT assay can be used (see, e.g., Czerkinsky C. C. et al., J Immunol Methods. 1983; 65:109-121; and Hutchings P. R. Et al., J Immunol Methods. 1989; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system.

Intracellular Cytokine Assay for Detection of Functionality of CD8+ and CD4+ T-Cell Responses Any assay known to the skilled artisan can be used to test the functionality of CD8+ and CD4+ T cell responses. For example, the intracellular cytokine assay combined with flow cytometry can be used (see, e.g., Suni M. A. et al., J Immunol Methods. 1998; 212:89-98; Nomura L. E. et al., Cytometry. 2000; 40:60-68; and Ghanekar S. A. et al., Clinical and Diagnostic Laboratory Immunology. 2001; 8:628-63). Briefly, the assay comprises the following steps: activation of cells via specific peptides or protein, an inhibition of protein transport (e.g., brefeldin A) is added to retain the cytokines within the cell. After washing, antibodies to other cellular markers can be added to the cells. Cells are then fixed and permeabilized. The anti-cytokine antibody is added and the cells can be analyzed by flow cytometry.

Assay for Confirming Replication-Deficiency of Viral Vectors

Any assay known to the skilled artisan that determines concentration of infectious and replication-competent virus particles can also be used as a to measure replication-deficient viral particles in a sample. For example, FFU assays (as described in [00408]) with non-complementing cells can be used for this purpose.

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer (see, e.g., Kaufmann, S. H.; Kabelitz, D. (2002). Methods in Microbiology Vol. 32: Immunology of Infection. Academic Press. ISBN 0-12-521532-0). Plaque formation can take 3-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample.

Measuring Viral Load in the Blood or Liver

Any assay known to the skilled artisan that determines the viral load may be used to detect the number of HBV particles per volume in the blood or liver (see, e.g., Mendy et al., 2010, J. Viral Hepat. 17(2): 115-122). Non-limiting examples of such assays include nucleic acid-based tests such as PCR, as well as non-nucleic acid-based tests.

Liver Biopsy

Any procedure known to the skilled artisan that performs a liver biopsy may be used to determine the degree of liver damage, for example, to test a patient for chronic HBV infection or liver cancer. Non-limiting examples of types of liver biopsies include percutaneous needle biopsies, laparoscopic biopsies, and transvenous biopsies. In certain embodiments, a liver biopsy is used to determine the presence of ground glass hepatocytes when the cells are examined under a light microscope. The observance of ground glass hepatocytes is indicative of the presence of HBsAg in the liver cells.

Assay for Expression of Viral Antigen

Any assay known to the skilled artisan can be used for measuring expression of viral antigens. For example, FFU assays (as described in [00408]) can be performed. For detection, mono- or polyclonal antibody preparation(s) against respective viral antigens are used (transgene-specific FFU).

Furthermore, Western Blotting (as described in [00415]) can be performed.

Microparticle Enzyme Immunoassay

The AXSYM® HbsAg (Abbott) is a microparticle enzyme immunoassay (MEIA) to detect HBsAg in adult, pediatric, and neonatal serum or plasma, including in pregnant women. This assay can be used as an aid in the diagnosis of acute or chronic HBV. This assay may also be used to confirm the presence of HBV infection.

To perform the assay, a sample of the patient's blood is placed into reaction wells containing detector antibodies and microparticles coated with antibodies to HBV (e.g., to HBV antigens). If the blood sample contains HBV proteins (e.g., HBsAg), they will bind to the microparticles in the reaction wells. This reaction is detected by another substance that produces light, which is then measured to determine the presence of HBV (e.g. HBV antigens) in the blood. If the first test is positive, the patient's blood is re-tested to confirm the presence of HBV (e.g., HBV antigens). Any microparticle enzyme immunoassay known to the skilled artisan may be used to measure the presence of HBsAg or other HBV antigens.

Other HBV Assays

A sample of the patient's blood is placed in contact with either HBV antibodies or HBV antigens. The antibodies and/or antigens include HBsAg, antibodies to HBeAg, antibodies to HBsAg, HBeAg, IgM antibodies to HBcAg, and antibodies to HBcAg. If the patient is infected with HBV, antigens and/or antibodies present in the blood will cause a chemical reaction to occur when the test is run. This assay allows for the detection of the stage of HBV, according to what HBV antigens and/or antibodies are present in the patient's blood.

Any assay known to one of skill in the art may be used to evaluate levels of HBV, HBV antigens, or HBV antibodies. For non-limiting examples of such assays, see, e.g., Mayer et al., 2012, BMC Clin. Pathol. 12:8, Van Helden et al., 2004, Clin. Lab. 50(1-2):63-73, and Villar et al., 2011, J. Med. Virol. 83(9):1522-1529.

Animal Models

The safety, tolerance and immunogenic effectiveness of vaccines comprising of an infectious arenavirus expressing an HBV antigen described herein or a composition thereof can be tested in animals models. In certain embodiments, the animal models that can be used to test the safety, tolerance and immunogenic effectiveness of the vaccines and compositions thereof used herein include mouse, guinea pig, rat, monkey, and chimpanzee. In a preferred embodiment, the animal models that can be used to test the safety, tolerance and immunogenic effectiveness of the vaccines and compositions thereof used herein include mouse.

In a specific example, a transgenic mouse model may be used to assess the antiviral potential of pharmacological agents, such as immunotherapies or vaccines, and to assess physiological processes, including the immune response (see, e.g., Guidotti et al., 1995, J. Virol. 69(10):6158-69). Such transgenic mouse models may express human molecules, such as human class I and II HLA molecules, and/or the hepatitis B surface antigen (HBsAg) (see, e.g., Bourgine et al., 2012, Virology 430(1):10-9).

In another specific example, the woodchuck (*Marmota monax*) can be used as an animal model for developing and testing treatment and prevention approaches to chronic hepadnaviral infections, such as chronic hepatitis B (see, e.g., Kosinska et al., Hepat. Res. Treat. 2010:817580). The woodchuck model is applicable for evaluation of the immunogenicity and other immune responses of potential immunotherapies such as vaccines (see, e.g., Vaccine 27(25-26):3271-3275).

6.10 Sequences

The sequences in Table 3 are illustrative amino acid sequences and nucleotide sequences that can be used with the methods and compositions described herein. In some instances a DNA sequence is used to describe the RNA sequence of a viral genomic segment. The RNA sequence can be readily deduced from the DNA sequence.

TABLE 3

Illustrative amino acid sequences.

| SEQ ID NO: | Description | Sequence |
|---|---|---|
| 1 | nucleotide sequence of the HBV pre-S2/SORF | ATGCAGTGGAATTCCACAACCTTCCACCAAACTCT<br>GCAAGATCCCAGAGTGAGAGGCCTGTATTTCCCT<br>GCTGGTGGCTCCAGTTCAGGAACAGTCAACCCTG<br>TTCTGACCACTGCCTCTCCCTTGTCATCAATCTTCT<br>CCAGGATTGGGGACCCTGCTCTGAACATGGAGAA<br>CATCACATCAGGATTCCTGGGACCCCTTCTTGTGT<br>TGCAGGCAGGGTTTTTCTTGTTGACAAGAATCCTC<br>ACAATCCCTCAGAGTCTGGACTCTTGGTGGACTTC<br>TCTCAATTTTCTGGGGGGAACCACAGTGTGTCTTG<br>GCCAAAATTCTCAGTCCCCAACCTCCAATCACTCA<br>CCAACCTCTTGTCCTCCAACTTGTCCTGGTTACAG<br>ATGGATGTGTCTGAGGAGATTCATCATCTTCCTCT<br>TCATCCTGCTGCTGTGCCTCATCTTCTTGTTGGTTC<br>TTCTGGACTATCAAGGAATGTTGCCAGTTTGTCCT<br>CTGATTCCAGGATCCTCAACAACCAGCACTGGAC<br>CATGCAGGACCTGCATGACCACTGCTCAAGGAAC |

TABLE 3-continued Illustrative amino acid sequences.

| SEQ ID NO: | Description | Sequence |
|---|---|---|
| | | CTCAATGTATCCCTCCTGTTGCTGCACCAAACCTT CAGATGGAAATTGCACCTGCATTCCCATCCCATCA TCCTGGGCTTTTGGAAAATTCCTTTGGGAGTGGGC CTCAGCCAGATTCTCCTGGCTCAGTTTGCTGGTGC CATTTGTTCAGTGGTTTGTTGGGCTTTCCCCCACT GTTTGGCTTTCAGTGATTTGGATGATGTGGTATTG GGGGCCAAGTCTGTACAGCATCTTGAGTCCCTTTT TGCCTCTGTTGCCAATTTTCTTTTGTCTTTGGGTCT ACATTTAA |
| 2 | nucleotide sequence of the HBV HBc ORF | ATGGACATTGACCCTTACAAAGAATTTGGAGCAA CTGTGGAGTTGCTCTCCTTTTTGCCTTCTGACTTCT TTCCTTCAGTGAGAGATCTTCTTGACACTGCCTCA GCTCTGTACAGGGAAGCCTTGGAGTCTCCTGAGC ATTGTTCACCTCACCACACTGCACTCAGGCAAGC AATTCTTTGCTGGGGGGAACTCATGACTCTGGCA ACCTGGGTGGGTGTCAATTTGGAAGATCCAGCCT CAAGAGACCTTGTGGTCAGTTATGTCAACACAAA CATGGGCCTGAAGTTCAGGCAACTCTTGTGGTTTC ACATTTCTTGTCTCACTTTTGGAAGAGAAACAGTC ATTGAGTATTGGTGTCTTTTGGAGTGTGGATCAG GACTCCTCCAGCTTACAGACCACCAAATGCCCCA ATCCTGTCAACACTTCCAGAGACCACTGTTGTCAG AAGAAGAGGCAGGTCCCCCAGAAGAAGAACTCC CTCACCAAGAAGAAGAAGGTCTCAATCTCCCAGA AGGAGAAGATCTCAATCAAGGGAATCTCAATGTT AG |
| 3 | nucleotide sequence of the HBV HBs-HBc fusion protein ORF | ATGGGGCAGAATCTTTCCACCAGCAATCCTCTGGGATTCTT TCCAGACCACCAGTTGGATCCAGCCTTCAGAGCAAACACTG CAAATCCAGATTGGGACTTCAATCCCAACAAGGACACCTGG CCAGATGCCAACAAGGTGGGAGCTGGAGCATTTGGGCTGGG TTTTCACCCCACCCCATGGAGGCCTTTTGGGGTGGAGCCCTC AGGCTCAGGGCATTCTGCAAACTTTGCCAGCAAATCCACCT CCTGCCTCCACCAACAGGCAGTCAGGAAGGCAGCCCACCCC TCTGTCTCCACCTTTGAGAAACACTCATCCTCAGGCCATGC AGTGGAATTCCACAACCTTCCACCAAACTCTGCAAGATCCC AGAGTGAGAGGCCTGTATTTCCCTGCTGGTGGCTCCAGTTC AGGAACAGTCAACCCTGTTCTGACCACTGCCTCTCCCTTGT CATCAATCTTCTCCAGGATTGGGGACCCTGCTCTGAACATG GAGAACATCACATCAGGATTCCTGGGACCCCTTCTTGTGTT GCAGGCAGGGTTTTTCTTGTTGACAAGAATCCTCACAATCC CTCAGAGTCTGGACTCTTGGTGGACTTCTCTCAATTTTCTG GGGGGAACCACAGTGTGTCTTGGCCAAAATTCTCAGTCCCC AACCTCCAATCACTCACCAACCTCTTGTCCTCCAACTTGTC CTGGTTACAGATGGATGTGTCTGAGGAGATTCATCATCTTC CTCTTCATCCTGCTGCTGTGCCTCATCTTCTTGTTGGTTCT TCTGGACTATCAAGGAATGTTGCCAGTTTGTCCTCTGATTC CAGGATCCTCAACAACCAGCACTGGACCATGCAGGACCTGC ATGACCACTGCTCAAGGAACCTCAATGTATCCCTCCTGTTG CTGCACCAAACCTTCAGATGGAAATTGCACCTGCATTCCCA TCCCATCATCCTGGGCTTTTGGAAAATTCCTTTGGGAGTGG GCCTCAGCCAGATTCTCCTGGCTCAGTTTGCTGGTGCCATT TGTTCAGTGGTTTGTTGGGCTTTCCCCCACTGTTTGGCTTT CAGTGATTTGGATGATGTGGTATTGGGGGCCAAGTCTGTAC AGCATCTTGAGTCCCTTTTGCCTCTGTTGCCAATTTTCTT TTGTCTTTGGGTCTACATTATGGACATTGACCCTTACAAAG AATTTGGAGCAACTGTGGAGTTGCTCTCCTTTTTGCCTTCT GACTTCTTTCCTTCAGTGAGAGATCTTCTTGACACTGCCTC AGCTCTGTACAGGGAAGCCTTGGAGTCTCCTGAGCATTGTT CACCTCACCACACTGCACTCAGGCAAGCAATTCTTTGCTGG GGGGAACTCATGACTCTGGCAACCTGGGTGGGTGTCAATTT GGAAGATCCAGCCTCAAGAGACCTTGTGGTCAGTTATGTCA ACACAAACATGGGCCTGAAGTTCAGGCAACTCTTGTGGTTT CACATTTCTTGTCTCACTTTTGGAAGAGAAACAGTCATTGA GTATTTGGTGTCTTTTGGAGTGTGGATCAGGACTCCTCCAG CTTACAGACCACCAAATGCCCCAATCCTGTCAACACTTCCA GAGACCACTGTTGTCAGAAGAAGAGGCAGGTCCCCCAGAAG AAGAACTCCCTCACCAAGAAGAAGAAGGTCTCAATCTCCCA GAAGGAGAAGATCTCAATCAAGGGAATCTCAATGTTAG |
| 4 | nucleotide sequence of the LCMV S segment expressing HBV HBs- | GCGCACCGGGGATCCTAGGCTTTTTGGATTGCGCT TTCCTCTAGATCAACTGGGTGTCAGGCCCTATCCT ACAGAAGGATGGGGCAGAATCTTTCCACCAGCAA |

TABLE 3-continued

Illustrative amino acid sequences.

| SEQ ID NO: | Description | Sequence |
|---|---|---|
| | HBc fusion protein in cDNA form (The genomic segment is RNA, the sequence in SEQ ID NO: 4 is shown for DNA; however, exchanging all thymidines ("T") in SEQ ID NO: 4 for uridines ("U") provides the RNA sequence.) | TCCTCTGGGATTCTTTCCAGACCACCAGTTGGATC CAGCCCTTCAGAGCAAACACTGCAAATCCAGATTG GGACTTCAATCCCAACAAGGACACCTGGCCAGAT GCCAACAAGGTGGGAGCTGGAGCATTTGGGCTGG GTTTCACCCCACCCCATGGAGGCCTTTTGGGGTGG AGCCCTCAGGCTCAGGGCATTCTGCAAACTTTGCC AGCAAATCCACCTCCTGCCTCCACCAACAGGCAG TCAGGAAGGCAGCCCACCCCTCTGTCTCCACCTTT GAGAAACACTCATCCTCAGGCCATGCAGTGGAAT TCCACAACCTTCCACCAAACTCTGCAAGATCCCA GAGTGAGAGGCCTGTATTTCCCTGCTGGTGGCTCC AGTTCAGGAACAGTCAACCCTGTTCTGACCACTG CCTCTCCCTTGTCATCAATCTTCTCCAGGATTGGG GACCCTGCTCTGAACATGGAGAACATCACATCAG GATTCCTGGGACCCCTTCTTGTGTTGCAGGCAGGG TTTTTCTTGTTGACAAGAATCCTCACAATCCCTCA GAGTCTGGACTCTTGGTGGACTTCTCTCAATTTTC TGGGGGGAACCACAGTGTGTCTTGGCCAAAATTC TCAGTCCCCAACCTCCAATCACTCACCAACCTCTT GTCCTCCAACTTGTCCTGGTTACAGATGGATGTGT CTGAGGAGATTCATCATCTTCCTCTTCATCCTGCT GCTGTGCCTCATCTTCTTGTTGGTTCTTCTGGACTA TCAAGGAATGTTGCCAGTTTGTCCTCTGATTCCAG GATCCTCAACAACCAGCACTGGACCATGCAGGAC CTGCATGACCACTGCTCAAGGAACCTCAATGTAT CCCTCCTGTTGCTGCACCAAACCTTCAGATGGAAA TTGCACCTGCATTCCCATCCCATCATCCTGGGCTT TTGGAAAATTCCTTTGGGAGTGGGCCTCAGCCAG ATTCTCCTGGCTCAGTTTGCTGGTGCCATTTGTTC AGTGGTTTGTTGGGCTTTCCCCCACTGTTTGGCTT TCAGTGATTTGGATGATGTGGTATTGGGGGCCAA GTCTGTACAGCATCTTGAGTCCCTTTTTGCCTCTG TTGCCAATTTTCTTTTGTCTTTGGGTCTACATTATG GACATTGACCCTTACAAAGAATTTGGAGCAACTG TGGAGTTGCTCTCCTTTTTGCCTTCTGACTTCTTTC CTTCAGTGAGAGATCTTCTTGACACTGCCTCAGCT CTGTACAGGGAAGCCTTGGAGTCTCCTGAGCATT GTTCACCTCACCACACTGCACTCAGGCAAGCAAT TCTTTGCTGGGGGGAACTCATGACTCTGGCAACCT GGGTGGGTGTCAATTTGGAAGATCCAGCCTCAAG AGACCTTGTGGTCAGTTATGTCAACACAAACATG GGCCTGAAGTTCAGGCAACTCTTGTGGTTTCACAT TTCTTGTCTCACTTTTGGAAGAGAAACAGTCATTG AGTATTTGGTGTCTTTTGGAGTGTGGATCAGGACT CCTCCAGCTTACAGACCACCAAATGCCCCAATCCT GTCAACACTTCCAGAGACCACTGTTGTCAGAAGA AGAGGCAGGTCCCCCAGAAGAAGAACTCCCTCAC CAAGAAGAAGAAGGTCTCAATCTCCCAGAAGGAG AAGATCTCAATCAAGGGAATCTCAATGTTAGAGA ACAGCGCCTCCCTGACTCTCCACCTCGAAAGAGG TGGAGAGTCAGGGAGGCCCAGAGGGTCTTAGAGT GTCACAACATTTGGGCCTCTAAAAATTAGGTCAT GTGGCAGAATGTTGTGAACAGTTTTCAGATCTGG GAGCCTTGCTTTGGAGGCGCTTTCAAAAATGATG CAGTCCATGAGTGCACAGTGCGGGGTGATCTCTTT CTTCTTTTTGTCCCTTACTATTCCAGTATGCATCTT ACACAACCAGCCATATTTGTCCCACACTTTATCTT CATACTCCCTCGAAGCTTCCCTGGTCATTTCAACA TCGATAAGCTTAATGTCCTTCCTATTTTGTGAGTC CAGAAGCTTTCTGATGTCATCGGAGCCTTGACAG CTTAGAACCATCCCCTGCGGAAGAGCACCTATAA CTGACGAGGTCAACCCGGGTTGCGCATTGAAGAG GTCGGCAAGATCCATGCCGTGTGAGTACTTGGAA TCTTGCTTGAATTGTTTTTGATCAACGGGTTCCCT GTAAAAGTGTATGAACTGCCCGTTCTGTGGTTGG AAAAATTGCTATTTCCACTGGATCATTAAATCTACC CTCAATGTCAATCCATGTAGGAGCGTTGGGGTCA ATTCCTCCCATGAGGTCTTTTAAAAGCATTGTCTG GCTGTAGCTTAAGCCCACCTGAGGTGGACCTGCT GCTCCAGGCGCTGGCCTGGGTGAGTTGACTGCAG GTTTCTCGCTTGTGAGATCAATTGTTGTGTTTTCCC ATGCTCTCCCCACAATCGATGTTCTACAAGCTATG TATGGCCATCCTTCACCTGAAAGGCAAACTTTATA GAGGATGTTTTCATAAGGGTTCCTGTCCCCAACTT |

TABLE 3-continued

Illustrative amino acid sequences.

| SEQ ID NO: | Description | Sequence |
|---|---|---|
| | | GGTCTGAAACAAACATGTTGAGTTTTCTCTTGGCC<br>CCGAGAACTGCCTTCAAGAGATCCTCGCTGTTGCT<br>TGGCTTGATCAAAATTGACTCTAACATGTTACCCC<br>CATCCAACAGGGCTGCCCCTGCCTTCACGGCAGC<br>ACCAAGACTAAAGTTATAGCCAGAAATGTTGATG<br>CTGGACTGCTGTTCAGTGATGACCCCCAGAACTG<br>GGTGCTTGTCTTTCAGCCTTTCAAGATCATTAAGA<br>TTTGGATACTTGACTGTGTAAAGCAAGCCAAGGT<br>CTGTGAGCGCTTGTACAACGTCATTGAGCGGAGT<br>CTGTGACTGTTTGGCCATACAAGCCATAGTTAGAC<br>TTGGCATTGTGCCAAATTGATTGTTCAAAAGTGAT<br>GAGTCTTTCACATCCCAAACTCTTACCACACCACT<br>TGCACCCTGCTGAGGCTTTCTCATCCCAACTATCT<br>GTAGGATCTGAGATCTTTGGTCTAGTTGCTGTGTT<br>GTTAAGTTCCCCATATATACCCCTGAAGCCTGGGG<br>CCTTTCAGACCTCATGATCTTGGCCTTCAGCTTCT<br>CAAGGTCAGCCGCAAGAGACATCAGTTCTTCTGC<br>ACTGAGCCTCCCCACTTTCAAAACATTCTTCTTTG<br>ATGTTGACTTTAAATCCACAAGAGAATGTACAGT<br>CTGGTTGAGACTTCTGAGTCTCTGTAGGTCTTTGT<br>CATCTCTCTTTTCCTTCCTCATGATCCTCTGAACAT<br>TGCTGACCTCAGAGAAGTCCAACCCATTCAGAAG<br>GTTGGTTGCATCCTTAATGACAGCAGCCTTCACAT<br>CTGATGTGAAGCTCTGCAATTCTCTTCTCAATGCT<br>TGCGTCCATTGGAAGCTCTTAACTTCCTTAGACAA<br>GGACATCTTGTTGCTCAATGGTTTCTCAAGACAAA<br>TGCGCAATCAAATGCCTAGGATCCACTGTGCG |
| 5 | nucleotide sequence of the LCMV S segment expressing the HBc ORF, in cDNA form (The genomic segment is RNA, the sequence in SEQ ID NO: 5 is shown for DNA; however, exchanging all thymidines ("T") in SEQ ID NO: 5 for uridines ("U") provides the RNA sequence.) | GCGCACCGGGGATCCTAGGCTTTTTGGATTGCGCTTTCCTC<br>TAGATCAACTGGGTGTCAGGCCCTATCCTACAGAAGGATGG<br>ACATTGACCCTTACAAAGAATTTGGAGCAACTGTGGAGTTG<br>CTCTCCTTTTTGCCTTCTGACTTCTTTCCTTCAGTGAGAGA<br>TCTTCTTGACACTGCCTCAGCTCTGTACAGGGAAGCCTTGG<br>AGTCTCCTGAGCATTGTTCACCTCACCACACTGCACTCAGG<br>CAAGCAATTCTITGCTGGGGGGAACTCATGACTCTGGCAAC<br>CTGGGTGGGTGTCAATTTGGAAGATCCAGCCTCAAGAGACC<br>TTGTGGTCAGTTATGTCAACACAAACATGGGCCTGAAGTTC<br>AGGCAACTCTTGTGGTTTCACATTTCTTGTCTCACTTTTGG<br>AAGAGAAACAGTCATTGAGTATTTGGTGTCTTTTGGAGTGT<br>GGATCAGGACTCCTCCAGCTTACAGACCACCAAATGCCCCA<br>ATCCTGTCAACACTTCCAGAGACCACTGTTGTCAGAAGAAG<br>AGGCAGGTCCCCCAGAAGAAGAACTCCCTCACCAAGAAGAA<br>GAAGGTCTCAATCTCCCAGAAGGAGAAGATCTCAATCAAGG<br>GAATCTCAATGTTAGAGAACAGCGCCTCCCTGACTCTCCAC<br>CTCGAAAGAGGTGGAGAGTCAGGGAGGCCCAGAGGGTCTTA<br>GAGTGTCACAACATTTGGGCCTCTAAAAATTAGGTCATGTG<br>GCAGAATGTTGTGAACAGTTTTCAGATCTGGGAGCCTTGCT<br>TTGGAGGCGCTTTCAAAAATGATGCAGTCCATGAGTGCACA<br>GTGCGGGGTGATCTCTTTCTTCTTTTTGTCCCTTACTATTC<br>CAGTATGCATCTTACACAACCAGCCATATTTGTCCCACACT<br>TTATCTTCATACTCCCTCGAAGCTTCCCTGGTCATTTCAAC<br>ATCGATAAGCTTAATGTCCTTCCTATTTTGTGAGTCCAGAA<br>GCTTTCTGATGTCATCGGAGCCTTGACAGCTTAGAACCATC<br>CCCTGCGGAAGAGCACCTATAACTGACGAGGTCAACCCGGG<br>TTGCGCATTGAAGAGGTCGGCAAGATCCATGCCGTGTGAGT<br>ACTTGGAATCTTGCTTGAATTGTTTTTGATCAACGGGTTCC<br>CTGTAAAAGTGTATGAACTGCCCGTTCTGTGGTTGGAAAAT<br>TGCTATTTCCACTGGATCATTAAATCTACCCTCAATGTCAA<br>TCCATGTAGGAGCGTTGGGGTCAATTCCTCCCATGAGGTCT<br>TTTAAAAGCATTGTCTGGCTGTAGCTTAAGCCCACCTGAGG<br>TGGACCTGCTGCTCCAGGCGCTGGCCTGGGTGAGTTGACTG<br>CAGGTTTCTCGCTTGTGAGATCAATTGTTGTGTTTTCCCAT<br>GCTCTCCCACAATCGATGTTCTACAAGCTATGTATGGCCA<br>TCCTTCACCTGAAAGGCAAACTTTATAGAGGATGTTTTCAT<br>AAGGGTTCCTGTCCCAACTTGGTCTGAAACAAACATGTTG<br>AGTTTTCTCTTGGCCCCGAGAACTGCCTTCAAGAGATCCTC<br>GCTGTTGCTTGGCTTGATCAAAATTGACTCTAACATGTTAC<br>CCCCATCCAACAGGGCTGCCCCTGCCTTCACGGCAGCACCA<br>AGACTAAAGTTATAGCCAGAAATGTTGATGCTGGACTGCTG<br>TTCAGTGATGACCCCCAGAACTGGGTGCTTGTCTTTCAGCC<br>TTTCAAGATCATTAAGATTTGGATACTTGACTGTGTAAAGC<br>AAGCCAAGGTCTGTGAGCGCTTGTACAACGTCATTGAGCGG<br>AGTCTGTGACTGTTTGGCCATACAAGCCATAGTTAGACTTG<br>GCATTGTGCCAAATTGATTGTTCAAAAGTGATGAGTCTTTC |

TABLE 3-continued

Illustrative amino acid sequences.

| SEQ ID NO: | Description | Sequence |
|---|---|---|
| | | ACATCCCAAACTCTTACCACACCACTTGCACCCTGCTGAGG
CTTTCTCATCCCAACTATCTGTAGGATCTGAGATCTTTGGT
CTAGTTGCTGTGTTGTTAAGTTCCCCATATATACCCCTGAA
GCCTGGGGCCTTTCAGACCTCATGATCTTGGCCTTCAGCTT
CTCAAGGTCAGCCGCAAGAGACATCAGTTCTTCTGCACTGA
GCCTCCCCACTTTCAAAACATTCTTCTTTGATGTTGACTTT
AAATCCACAAGAGAATGTACAGTCTGGTTGAGACTTCTGAG
TCTCTGTAGGTCTTTGTCATCTCTCTTTTCCTTCCTCATGA
TCCTCTGAACATTGCTGACCTCAGAGAAGTCCAACCCATTC
AGAAGGTTGGTTGCATCCTTAATGACAGCAGCCTTCACATC
TGATGTGAAGCTCTGCAATTCTCTTCTCAATGCTTGCGTCC
ATTGGAAGCTCTTAACTTCCTTAGACAAGGACATCTTGTTG
CTCAATGGTTTCTCAAGACAAATGCGCAATCAAATGCCTAG
GATCCACTGTGCG |
| 6 | nucleotide sequence of the LCMV S segment expressing the pre-S2/S ORF, in cDNA form ( TABLE 3-continued Illustrative amino acid sequences.

| SEQ ID NO: | Description | Sequence |
|---|---|---|
| | | AAAGCAAGCCAAGGTCTGTGAGCGCTTGTACAAC<br>GTCATTGAGCGGAGTCTGTGACTGTTTGGCCATAC<br>AAGCCATAGTTAGACTTGGCATTGTGCCAAATTG<br>ATTGTTCAAAAGTGATGAGTCTTTCACATCCCAAA<br>CTCTTACCACACCACTTGCACCCTGCTGAGGCTTT<br>CTCATCCCAACTATCTGTAGGATCTGAGATCTTTG<br>GTCTAGTTGCTGTGTTGTTAAGTTCCCCATATATA<br>CCCCTGAAGCCTGGGGCCTTTCAGACCTCATGATC<br>TTGGCCTTCAGCTTCTCAAGGTCAGCCGCAAGAG<br>ACATCAGTTCTTCTGCACTGAGCCTCCCCACTTTC<br>AAAACATTCTTCTTTGATGTTGACTTTAAATCCAC<br>AAGAGAATGTACAGTCTGGTTGAGACTTCTGAGT<br>CTCTGTAGGTCTTTGTCATCTCTCTTTTCCTTCCTC<br>ATGATCCTCTGAACATTGCTGACCTCAGAGAAGT<br>CCAACCCATTCAGAAGGTTGGTTGCATCCTTAATG<br>ACAGCAGCCTTCACATCTGATGTGAAGCTCTGCA<br>ATTCTCTTCTCAATGCTTGCGTCCATTGGAAGCTC<br>TTAACTTCCTTAGACAAGGACATCTTGTTGCTCAA<br>TGGTTTCTCAAGACAAATGCGCAATCAAATGCCT<br>AGGATCCACTGTGCG |
| 7 | lymphocytic choriomeningitis virus clone 13 segment L, complete sequence (GenBank: DQ361066.1) (The genomic segment is RNA, the sequence in SEQ ID NO: 7 is shown for DNA; however, exchanging all thymidines ("T") in SEQ ID NO: 7 for uridines ("U") provides the RNA sequence.) | GCGCACCGGGGATCCTAGGCGTTTAGTTGCGCTG<br>TTTGGTTGCACAACTTCTTCGTGAGGCTGTCAGA<br>AGTGGACCTGGCTGATAGCGATGGGTCAAGGCAA<br>GTCCAGAGAGGAGAAAGGCACCAATAGTACAAA<br>CAGGGCCGAAATCCTACCAGATACCACCTATCTT<br>GGCCCTTTAAGCTGCAAATCTTGCTGGCAGAAATT<br>TGACAGCTTGGTAAGATGCCATGACCACTACCTTT<br>GCAGGCACTGTTTAAACCTTCTGCTGTCAGTATCC<br>GACAGGTGTCCTCTTTGTAAATATCCATTACCAAC<br>CAGATTGAAGATATCAACAGCCCCAAGCTCTCCA<br>CCTCCCTACGAAGAGTAACACCGTCCGGCCCCGG<br>CCCCGACAAACAGCCCAGCACAAGGGAACCGCAC<br>GTCaCCCAACGCACACAGACACAGCACCCAACAC<br>AGAACACGCACACACACACACACACACACCCACA<br>CGCACGCGCCCCCACCACCGGGGGGCGCCCCCCC<br>CCGGGGGGCGGCCCCCGGGAGCCCGGGCGGAG<br>CCCCACGGAGATGCCCATCAGTCGATGTCCTCGG<br>CCACCGACCCGCCcAGCCAATCGTCGCAGGACCTC<br>CCCTTGAGTCTAAACCTGCCCCCCACTgTTTCATA<br>CATCAAAGTGCTCCTAGATTTGCTAAAACAAAGT<br>CTGCAATCCTTAAAGGCGAACCAGTCTGGCAAAA<br>GCGACAGTGGAATCAGCAGAATAGATCTGTCTAT<br>ACATAGTTCCTGGAGGATTACACTTATCTCTGAAC<br>CCAACAAATGTTCACCAGTTCTGAATCGATGCAG<br>GAAGAGGTTCCCAAGGACATCACTAATCTTTTCAT<br>AGCCCTCAAGTCCTGCTAGAAAGACTTTCATGTCC<br>TTGGTCTCCAGCTTCACAATGATATTTTGGACAAG<br>GTTTCTTCCTTCAAAAAGGGCACCCATCTTTACAG<br>TCAGTGGCACAGGCTCCCACTCAGGTCCAACTCTC<br>TCAAAGTCAATAGATCTAATCCCATCCAGTATTCT<br>TTTGGAGCCCAACAACTCAAGCTCAAGAGAATCA<br>CCAAGTATCAAGGGATCTTCCATGTAATCCTCAA<br>ACTCTTCAGATCTGATATCAAAGACACCATCGTTC<br>ACCTTGAAGACAGAGTCTGTCCTCAGTAAGTGGA<br>GGCATTCATCCAACATTCTTCTATCTATCTCACCC<br>TTAAAGAGGTGAGAGCATGATAAAAGTTCAGCCA<br>CACCTGGATTCTGTAATTGGCACCTAACCAAGAA<br>TATCAATGAAAATTTCCTTAAACAGTCAGTATTAT<br>TCTGATTGTGCGTAAAGTCCACTGAAATTGAAAA<br>CTCCAATACCCCTTTTGTGTAGTTGAGCATGTAGT<br>CCCACAGATCCTTTAAGGATTTAAATGCCTTTGGG<br>TTTGTCAGGCCCTGCCTAATCAACATGGCAGCATT<br>ACACACAACATCTCCCATTCGGTAAGAGAACCAC<br>CCAAAACCAAACTGCAAATCATTCCTAAACATAG<br>GCCTCTCCACATTTTTGTTCACCACCTTTGAGACA<br>AATGATTGAAAGGGGCCCAGTGCCTCAGCACCAT<br>CTTCAGATGGCATCATTTCTTTATGAGGGAACCAT<br>GAAAAATTGCCTAATGTCCTGGTTGTTGCAACAA<br>ATTCTCGAACAAATGATTCAAAATACACCTGTTTT<br>AAGAAGTTCTTGCAGACATCCCTCGTGCTAACAA<br>CAAATTCATCAACCAGACTGGAGTCAGATCGCTG<br>ATGAGAATTGGCAAGGTCAGAAAACAGAACAGT<br>GTAATGTTCATCCCTTTTCCACTTAACAACATGAG |

TABLE 3-continued

Illustrative amino acid sequences.

| SEQ ID NO: Description | Sequence |
|---|---|
| | AAATGAGTGACAAGGATTCTGAGTTAATATCAAT |
| | TAAAACACAGAGGTCAAGGAATTTAATTCTGGGA |
| | CTCCACCTCATGTTTTTTGAGCTCATGTCAGACAT |
| | AAATGGAAGAAGCTGATCCTCAAAGATCTTGGGA |
| | TATAGCCGCCTCACAGATTGAATCACTTGGTTCAA |
| | ATTCACTTTGTCCTCCAGTAGCCTTGAGCTCTCAG |
| | GCTTTCTTGCTACATAATCACATGGGTTTAAGTGC |
| | TTAAGAGTTAGGTTCTCACTGTTATTCTTCCCTTTG |
| | GTCGGTTCTGCTAGGACCCAAACACCCAACTCAA |
| | AAGAGTTGCTCAATGAAATACAAATGTAGTCCCA |
| | AAGAAGAGGCCTTAAAAGGCATATATGATCACGG |
| | TGGGCTTCTGGATGAGACTGTTTGTCACAAATGTA |
| | CAGCGTTATACCATCCCGATTGCAAACTCTTGTCA |
| | CATGATCATCTGTGGTTAGATCCTCAAGCAGCTTT |
| | TTGATATACAGATTTTCCCTATTTTTGTTTCTCACA |
| | CACCTGCTTCCTAGAGTTTTGCAAAGGCCTATAAA |
| | GCCAGATGAGATACAACTCTGGAAAGCTGACTTG |
| | TTGATTGCTTCTGACAGCAGCTTCTGTGCACCCCT |
| | TGTGAATTTACTACAAAGTTTGTTCTGGAGTGTCT |
| | TGATCAATGATGGGATTCTTTCCTCTTGGAAAGTC |
| | ATCACTGATGGATAAACCACCTTTTGTCTTAAAAC |
| | CATCCTTAATGGGAACATTTCATTCAAATTCAACC |
| | AGTTAACATCTGCTAACTGATTCAGATCTTCTTCA |
| | AGACCGAGGAGGTCTCCCAATTGAAGAATGGCCT |
| | CCtTTTTATCTCTGTTAAATAGGTCTAAGAAAAATT |
| | CTTCATTAAATTCACCATTTTTGAGCTTATGATGC |
| | AGTTTCCTTACAAGCTTTCTTACAACCTTTGTTTCA |
| | TTAGGACACAGTTCCTCAATGAGTCTTTGTATTCT |
| | GTAACCTCTAGAACCATCCAGCCAATCTTTCACAT |
| | CAGTGTTGGTATTCAGTAGAAATGGATCCAAAGG |
| | GAAATTGGCATACTTTAGGAGGTCCAGTGTTCTCC |
| | TTTGGATACTATTAACTAGGGAGACTGGGACGCC |
| | ATTTGCGATGGCTTGATCTGCAATTGTATCTATTG |
| | TTTCACAAAGTTGATGTGGCTCTTTACACTTGACA |
| | TTGTGTAGCGCTGCAGATACAAACTTTGTGAGAA |
| | GAGGGACTTCCTCCCCCCATACATAGAATCTAGA |
| | TTTAAATTCTGCAGCGAACCTCCCAGCCACACTTT |
| | TTGGGCTGATAAATTTGTTTAACAAGCCGCTCAGA |
| | TGAGATTGGAATTCCAACAGGACAAGGACTTCCT |
| | CCGGATCACTTACAACCAGGTCACTCAGCCTCCTA |
| | TCAAATAAAGTGATCTGATCATCACTTGATGTGTA |
| | AGCCTCTGGTCTTTCGCCAAAGATAACACCAATG |
| | CAGTAGTTGATGAACCTCTCGCTAAGCAAACCAT |
| | AGAAGTCAGAAGCATTATGCAAGATTCCCTGCCC |
| | CATATCAATAAGGCTGGATATATGGGATGGCACT |
| | ATCCCCATTTCAAAATATTGTCTGAAAATTCTCTC |
| | AGTAACAGTTGTTTCTGAACCCCTGAGAAGTTTTA |
| | GCTTCGACTTGACATATGATTTCATCATTGCATTC |
| | ACAACAGGAAAGGGGACCTCGACAAGCTTATGCA |
| | TGTGCCAAGTTAACAAAGTGCTAACATGATCTTTC |
| | CCGGAACGCACATACTGGTCATCACCTAGTTTGA |
| | GATTTTGTAGAAACATTAAGAACAAAAATGGGCA |
| | CATCATTGGTCCCCATTTGCTGTGATCCATACTAT |
| | AGTTTAAGAACCCTTCCCGCACATTGATAGTCATT |
| | GACAAGATTGCATTTTCAAATTCCTTATCATTGTT |
| | TAAACAGGAGCCTGAAAAGAAACTTGAAAAAGA |
| | CTCAAAATAATCTTCTATTAACCTTGTGAACATTT |
| | TTGTCCTCAAATCTCCAATATAGAGTTCTCTATTT |
| | CCCCCAACCTGCTCTTTATAAGATAGTGCAAATTT |
| | CAGCCTTCCAGAGTCAGGACCTACTGAGGTGTAT |
| | GATGTTGGTGATTCTTCTGAGTAGAAGCACAGATT |
| | TTTCAAAGCAGCACTCATACATTgTGTCAACGACA |
| | GAGCTTTACTAAGGGACTCAGAATTACTTTCCCTC |
| | TCACTGATTCTCACGTCTTCTTCCAGTTTGTCCCA |
| | GTCAAATTTGAAATTCAAGCCTTGCCTTTGCATAT |
| | GCCTGTATTTCCCTGAGTACGCATTTGCATTCATT |
| | TGCAACAGAATCATCTTCATGCAAGAAAACCAAT |
| | CATTCTCAGAAAAGAACTTTCTACAAAGGTTTTTT |
| | GCCATCTCATCGAGGCCACACTGATCTTTAATGAC |
| | TGAGGTGAAATACAAAGGTGACAGCTCTGTGGAA |
| | CCCTCAACAGCCTCACAGATAAATTTCATGTCATC |
| | ATTGGTTAGACATGATGGGTCAAAGTCTTCTACTA |
| | AATGGAAAGATATTTCTGACAAGATAACTTTTCTT |
| | AAGTGAGCCATCTTCCCTGTTAGAATAAGCTGTA |

TABLE 3-continued

Illustrative amino acid sequences.

| SEQ ID NO: Description | Sequence |
|---|---|
| | AATGATGTAGTCCTTTTGTATTTGTAAGTTTTTCTC |
| | CATCTCCTTTGTCATTGGCCCTCCTACCTCTTCTGT |
| | ACCGTGCTATTGTGGTGTTGACCTTTTCTTCGAGA |
| | CTTTTGAAGAAGCTTGTCTCTTCTTCTCCATCAAA |
| | ACATATTTCTGCCAGGTTGTCTTCCGATCTCCCTG |
| | TCTCTTCTCCCTTGGAACCGATGACCAATCTAGAG |
| | ACTAACTTGGAAACTTTATATTCATAGTCTGAGTG |
| | GCTCAACTTATACTTTTGTTTTCTTACGAAACTCTC |
| | CGTAATTTGACTCACAGCACTAACAAGCAATTTGT |
| | TAAAGTCATATTCCAGAAGTCGTTCTCCATTTAGA |
| | TGCTTATTAACCACCACACTTTTGTTACTAGCAAG |
| | ATCTAATGCTGTCGCACATCCAGAGTTAGTCATGG |
| | GATCTAGGCTGTTTAGCTTCTTCTCTCCTTTGAAA |
| | ATTAAAGTGCCGTTGTTAAATGAAGACACCATTA |
| | GGCTAAAGGCTTCCAGATTAACACCTGGAGTTGT |
| | ATGCTGACAGTCAATTTCTTTACTAGTGAATCTCT |
| | TCATTTGCTCATAGAACACACATTCTTCCTCAGGA |
| | GTGATTGCTTCCTTGGGGTTGACAAAAAAACCAA |
| | ATTGACTTTTGGGCTCAAAGAACTTTTCAAAACAT |
| | TTTATCTGATCTGTTAGCCTGTCAGGGGTCTCCTT |
| | TGTGATCAAATGACACAGGTATGACACATTCAAC |
| | ATAAATTTAAATTTTGCACTCAACAACACCTTCTC |
| | ACCAGTACCAAAAATAGTTTTTATTAGGAATCTA |
| | AGCAGCTTATACACCACCTTCTCAGCAGGTGTGAT |
| | CAGATCCTCCCTCAACTTATCCATTAATGATGTAG |
| | ATGAAAAATCTGACACTATTGCCATCACCAAATA |
| | TCTGACACTCTGTACCTGCTTTTGATTTCTCTTTGT |
| | TGGGTTGGTGAGCATTAGCAACAATAGGGTCCTC |
| | AGTGCAACCTCAATGTCGGTGAGACAGTCTTTCA |
| | AATCAGGACATGATCTAATCCATGAAATCATGAT |
| | GTCTATCATATTGTATAAGACCTCATCTGAAAAAA |
| | TTGGTAAAAAGAACCTTTTAGGATCTGCATAGAA |
| | GGAAATTAAATGACCATCCGGGCCTTGTATGGAG |
| | TAGCACCTTGAAGATTCTCCAGTCTTCTGGTATAA |
| | TAGGTGGTATTCTTCAGAGTCCAGTTTTATTACTT |
| | GGCAAAACACTTCTTTGCATTCTACCACTTGATAT |
| | CTCACAGACCCTATTTGATTTTGCCTTAGTCTAGC |
| | AACTGAGCTAGTTTTCATACTGTTTGTTAAGGCCA |
| | GACAAACAGATGATAATCTTCTCAGGCTCTGTAT |
| | GTTCTTCAGCTGCTCTGTGCTGGGTTGGAAATTGT |
| | AATCTTCAAACTTCGTATAATACATTATCGGGTGA |
| | GCTCCAATTTTCATAAAGTTCTCAAATTCAGTGAA |
| | TGGTATGTGGCATTCTTGCTCAAGGTGTTCAGACA |
| | GTCCGTAATGCTCGAAACTCAGTCCCACCACTAA |
| | CAGGCATTTTTGAATTTTTGCAATGAACTCACTAA |
| | TAGAtGCCCTAAACAATTCCTCAAAAGACACCTTT |
| | CTAAACACCTTTGACTTTTTTCTATTCCTCAAAAG |
| | TCTAATGAACTCCTCTTTAGTGCTGTGAAAGCTTA |
| | CCAGCCTATCATTCACACTACTATAGCAACAACCC |
| | ACCCAGTGTTTATCATTTTTAACCCTTTGAATTTC |
| | GACTGTTTTATCAATGAGGAAAGACACAAAACAT |
| | CCAGATTTAACAACTGTCTCCTTCTAGTATTCAAC |
| | AGTTTCAAACTCTTGACTTTGTTTAACATAGAGAG |
| | GAGCCTCTCATATTCAGTGCTAGTCTCACTTCCCC |
| | TTTCGTGCCCATGGGTCTCTGCAGTTATGAATCTC |
| | ATCAAAGGACAGGATTCGACTGCCTCCCTGCTTA |
| | ATGTTAAGATATCATCACTATCAGCAAGGTTTTCA |
| | TAGAGCTCAGAGAATTCCTTGATCAAGCCTTCAG |
| | GGTTTACTTTCTGAAAGTTTCTCTTTAATTTCCCAC |
| | TTTCTAAATCTCTTCTAAACCTGCTGAAAAGAGAG |
| | TTTATTCCAAAAACCACATCATCACAGCTCATGTT |
| | GGGGTTGATGCCTTCGTGGCACATCCTCATAATTT |
| | CATCATTGTGAGTTGACCTCGCATCTTTCAGAATT |
| | TTCATAGAGTCCATACCGGAGCGCTTGTCGATAGT |
| | AGTCTTCAGGGACTCACAGAGTCTAAAATATTCA |
| | GACTCTTCAAAGACTTTCTCATTTTGGTTAGAATA |
| | CTCCAAAAGTTTGAATAAAAGGTCTCTAAATTTG |
| | AAGTTTGCCCACTCTGGCATAAAACTATTATCATA |
| | ATCACAACGACCATCTACTATTGGAACTAATGTG |
| | ACACCCGCAACAGCAAGGTCTTCCCTGATGCATG |
| | CCAATTTGTTAGTGTCCTCTATAAATTTCTTCTCA |
| | AAACTGGCTGGaGtGCTCCTAACAAAACACTCAAG |
| | AAGAATGAGAGAATTGTCTATCAGCTTGTAACCA |
| | TCAGGAATGATAAGTGGTAGTCCTGGGCATACAA |

US 11,214,598 B2

TABLE 3-continued

Illustrative amino acid sequences.

| SEQ ID NO: | Description | Sequence |
|---|---|---|
| | | TTCCAGACTCCACCAAAATTGTTTCCACAGACTTA<br>TCGTCGTGGTTGTGTGTGCAGCCACTCTTGTCTGC<br>ACTGTCTATTTCAATGCAGCGTGACAGCAACTTGA<br>GTCCCTCAATCAGAACCATTCTGGGTTCCCTTTGT<br>CCCAGAAAGTTGAGTTTCTGCCTTGACAACCTCTC<br>ATCCTGTTCTATATAGTTTAAACATAACTCTCTCA<br>ATTCTGAGATGATTTCATCCATTGCGCATCAAAAA<br>GCCTAGGATCCTCGGTGCG |
| 8 | amino acid sequence of an HBV HBs protein-derived epitope | VWLSVIWM |
| 9 | amino acid sequence of an HBV HBs protein-derived epitope | IPQSLDSWWTSL |
| 10 | amino acid sequence of an HBV HBc protein-derived epitope | MGLKFRQL |
| 11 | lymphocytic choriomeningitis virus segment S, complete sequence (The genomic segment is RNA, the sequence in SEQ ID NO: 11 is shown for DNA; however, exchanging all thymidines ("T") in SEQ ID NO: 11 for uridines ("U") provides the RNA sequence.) | CGCACCGGGGATCCTAGGCTTTTTGGATTGCGCTTTCCTC<br>TAGATCAACTGGGTGTCAGGCCCTATCCTACAGAAGGATG<br>GGTCAGATTGTGACAATGTTTGAGGCTCTGCCTCACATCA<br>TCGATGAGGTGATCAACATTGTCATTATTGTGCTTATCGT<br>GATCACGGGTATCAAGGCTGTCTACAATTTTGCCACCTGT<br>GGGATATTCGCATTGATCAGTTTCCTACTTCTGGCTGGCA<br>GGTCCTGTGGCATGTACGGTCTTAAGGGACCCGACATTTA<br>CAAAGGAGTTTACCAATTTAAGTCAGTGGAGTTTGATATG<br>TCACATCTGAACCTGACCATGCCCAACGCATGTTCAGCCA<br>ACAACTCCCACCATTACATCAGTATGGGGACTTCTGGACT<br>AGAATTGACCTTCACCAATGATTCCATCATCAGTCACAAC<br>TTTTGCAATCTGACCTCTGCCTTCAACAAAAAGACCTTTG<br>ACCACACACTCATGAGTATAGTTTCGAGCCTACACCTCAG<br>TATCAGAGGGAACTCCAACTATAAGGCAGTATCCTGCGAC<br>TTCAACAATGGCATAACCATCCAATACAACTTGACATTCT<br>CAGATCGACAAAGTGCTCAGAGCCAGTGTAGAACCTTCAG<br>AGGTAGAGTCCTAGATATGTTTAGAACTGCCTTCGGGGGG<br>AAATACATGAGGAGTGGCTGGGGCTGGACAGGCTCAGATG<br>GCAAGACCACCTGGTGTAGCAGACGAGTTACCAATACCT<br>GATTATACAAAATAGAACCTGGGAAAACCACTGCACATAT<br>GCAGGTCCTTTTGGGATGTCCAGGATTCTCCTTTCCCAAG<br>AGAAGACTAAGTTCTTCACTAGGAGACTAGCGGGCACATT<br>CACCTGGACTTTGTCAGACTCTTCAGGGGTGGAGAATCCA<br>GGTGGTTATTGCCTGACCAAATGGATGATTCTTGCTGCAG<br>AGCTTAAGTGTTTCGGGAACACAGCAGTTGCGAAATGCAA<br>TGTAAATCATGATGCCGAATTCTGTGACATGCTGCGACTA<br>ATTGACTACAACAAGGCTGCTTTGAGTAAGTTCAAAGAGG<br>ACGTAGAATCTGCCTTGCACTTATTCAAAACAACAGTGAA<br>TTCTTTGATTTCAGATCAACTACTGATGAGGAACCACTTG<br>AGAGATCTGATGGGGGTGCCATATTGCAATTACTCAAAGT<br>TTTGGTACCTAGAACATGCAAAGACCGGCGAAACTAGTGT<br>CCCCAAGTGCTGGCTTGTCACCAATGGTTCTTACTTAAAT<br>GAGACCCACTTCAGTGATCAAATCGAACAGGAAGCCGATA<br>ACATGATTACAGAGATGTTGAGGAAGGATTACATAAAGAG<br>GCAGGGGAGTACCCCCCTAGCATTGATGGACCTTCTGATG<br>TTTTCCACATCTGCATATCTAGTCAGCATCTTCCTGCACC<br>TTGTCAAAATACCAACACACAGGCACATAAAAGGTGGCTC<br>ATGTCCAAAGCCACACCGATTAACCAACAAAGGAATTTGT<br>AGTTGTGGTGCATTTAAGGTGCCTGGTGTAAAAACCGTCT<br>GGAAAAGACGCTGAAGAACAGCGCCTCCCTGACTCTCCAC<br>CTCGAAAGAGGTGGAGAGTCAGGGAGGCCCAGAGGGTCTT<br>AGAGTGTCACAACATTTGGGCCTCTAAAAATTAGGTCATG<br>TGGCAGAATGTTGTGAACAGTTTTCAGATCTGGGAGCCTT<br>GCTTTGGAGGCGCTTTCAAAAATGATGCAGTCCATGAGTG<br>CACAGTGCGGGTGATCTCTTTCTTCTTTTTGTCCCTTAC<br>TATTCCAGTATGCATCTTACACAACCAGCCATATTTGTCC<br>CACACTTTGTCTTCATACTCCCTCGAAGCTTCCCTGGTCA<br>TTTCAACATCGATAAGCTTAATGTCCTTCCTATTCTGTGA<br>GTCCAGAAGCTTTCTGATGTCATCGGAGCCTTGACAGCTT<br>AGAACCATCCCCTGCGGAAGAGCACCTATAACTGACGAGG<br>TCAACCCGGGTTGCGCATTGAAGAGGTCGGCAAGATCCAT<br>GCCGTGTGAGTACTTGGAATCTTGCTTGAATTGTTTTTGA<br>TCAACGGGTTCCCTGTAAAAGTGTATGAACTGCCCGTTCT |

TABLE 3-continued

Illustrative amino acid sequences.

| SEQ ID NO: | Description | Sequence |
|---|---|---|
| | | GTGGTTGGAAAATTGCTATTTCCACTGGATCATTAAATCT<br>ACCCTCAATGTCAATCCATGTAGGAGCGTTGGGGTCAATT<br>CCTCCCATGAGGTCTTTTAAAAGCATTGTCTGGCTGTAGC<br>TTAAGCCCACCTGAGGTGGACCTGCTGCTCCAGGCGCTGG<br>CCTGGGTGAATTGACTGCAGGTTTCTCGCTTGTGAGATCA<br>ATTGTTGTGTTTTCCCATGCTCTCCCCACAATCGATGTTC<br>TACAAGCTATGTATGGCCATCCTTCACCTGAAAGGCAAAC<br>TTTATAGAGGATGTTTTCATAAGGGTTCCTGTCCCCAACT<br>TGGTCTGAAACAAACATGTTGAGTTTTCTCTTGGCCCCGA<br>GAACTGCCTTCAAGAGGTCCTCGCTGTTGCTTGGCTTGAT<br>CAAAATTGACTCTAACATGTTACCCCCATCCAACAGGGCT<br>GCCCCTGCCTTCACGGCAGCACCAAGACTAAAGTTATAGC<br>CAGAAATGTTGATGCTGGACTGCTGTTCAGTGATGACCCC<br>CAGAACTGGGTGCTTGTCTTTCAGCCTTTCAAGATCATTA<br>AGATTTGGATACTTGACTGTGTAAAGCAAGCCAAGGTCTG<br>TGAGCGCTTGTACAACGTCATTGAGCGGAGTCTGTGACTG<br>TTTGGCCATACAAGCCATAGTTAGACTTGGCATTGTGCCA<br>AATTGATTGTTCAAAAGTGATGAGTCTTTCACATCCCAAA<br>CTCTTACCACACCACTTGCACCCTGCTGAGGCTTTCTCAT<br>CCCAACTATCTGTAGGATCTGAGATCTTTGGTCTAGTTGC<br>TGTGTTGTTAAGTTCCCCATATATACCCCTGAAGCCTGGG<br>GCCTTTCAGACCTCATGATCTTGGCCTTCAGCTTCTCAAG<br>GTCAGCCGCAAGAGACATCAGTTCTTCTGCACTGAGCCTC<br>CCCACTTTCAAAACATTCTTCTTTGATGTTGACTTTAAAT<br>CCACAAGAGAATGTACAGTCTGGTTGAGACTTCTGAGTCT<br>CTGTAGGTCTTTGTCATCTCTCTTTTCCTTCCTCATGATC<br>CTCTGAACATTGCTGACCTCAGAGAAGTCCAACCCATTCA<br>GAAGGTTGGTTGCATCCTTAATGACAGCAGCCTTCACATC<br>TGATGTGAAGCTCTGCAATTCTCTTCTCAATGCTTGCGTC<br>CATTGGAAGCTCTTAACTTCCTTAGACAAGGACATCTTGT<br>TGCTCAATGGTTTCTCAAGACAAATGCGCAATCAAATGCC<br>TAGGATCCACTGTGCG |
| 12 | lymphocytic choriomeningitis virus clone 13 segment S, complete sequence (GenBank: DQ361065.2) (The genomic segment is RNA, the sequence in SEQ ID NO: 12 is shown for DNA; however, exchanging all thymidines ("T") in SEQ ID NO: 12 for uridines ("U") provides the RNA sequence.) | GCGCACCGGGGATCCTAGGCTTTTTGGATTGCGCTTTCCT<br>CTAGATCAACTGGGTGTCAGGCCCTATCCTACAGAAGGAT<br>GGGTCAGATTGTGACAATGTTTGAGGCTCTGCCTCACATC<br>ATCGATGAGGTGATCAACATTGTCATTATTGTGCTTATCG<br>TGATCACGGGTATCAAGGCTGTCTACAATTTTGCCACCTG<br>TGGGATATTCGCATTGATCAGTTTCCTACTTCTGGCTGGC<br>AGGTCCTGTGGCATGTACGGTCTTAAGGGACCCGACATTG<br>ACAAAGGAGTTTACCAATTTAAGTCAGTGGAGTTTGATAT<br>GTCACATCTGAACCTGACCATGCCCAACGCATGTTCAGCC<br>AACAACTCCCACCATTACATCAGTATGGGGACTTCTGGAC<br>TAGAATTGACCTTCACCAATGATTCCATCATCAGTCACAA<br>CTTTTGCAATCTGACCTCTGCCTTCAACAAAAAGACCTTT<br>GACCACACACTCATGAGTATAGTTTCGAGCCTACACCTCA<br>GTATCAGAGGGAACTCCAACTATAAGGCAGTATCCTGCGA<br>CTTCAACAATGGCATAACCATCCAATACAACTTGACATTC<br>TCAGATGCACAAAGTGCTCAGAGCCAGTGTAGAACCTTCA<br>GAGGTAGAGTCCTAGATATGTTTAGAACTGCCTTCGGGGG<br>GAAATACATGAGGAGTGGCTGGGGCTGGACAGGCTCAGAT<br>GGCAAGACCACCTGGTGTAGCCAGACGAGTTACCAATACC<br>TGATTATACAAAATAGAACCTGGGAAAACCACTGCACATA<br>TGCAGGTCCTTTTGGGATGTCCAGGATTCTCCTTTCCCAA<br>GAGAAGACTAAGTTCCTCACTAGGAGACTAGCGGGCACAT<br>TCACCTGGACTTTGTCAGACTCTTCAGGGGTGGAGAATCC<br>AGGTGGTTATTGCCTGACCAAATGGATGATTCTTGCTGCA<br>GAGCTTAAGTGTTTCGGGAACACAGCAGTTGCGAAATGCA<br>ATGTAAATCATGATGAAGAATTCTGTGACATGCTGCGACT<br>AATTGACTACAACAAGGCTGCTTTGAGTAAGTTCAAAGAG<br>GACGTAGAATCTGCCTTGCACTTATTCAAAACAACAGTGA<br>ATTCTTTGATTTCAGATCAACTACTGATGAGGAACCACTT<br>GAGAGATCTGATGGGGTGCCATATTGCAATTACTCAAAG<br>TTTTGGTACCTAGAACATGCAAAGACCGGCGAAACTAGTG<br>TCCCCAAGTGCTGGCTTGTCACCAATGGTTCTTACTTAAA<br>TGAGACCCACTTCAGTGACCAAATCGAACAGGAAGCCGAT<br>AACATGATTACAGAGATGTTGAGGAAGGATTACATAAAGA<br>GGCAGGGGAGTACCCCCCTAGCATTGATGGACCTTCTGAT<br>GTTTTCCACATCTGCATATCTAGTCAGCATCTTCCTGCAC<br>CTTGTCAAAATACCAACACACAGGCACATAAAAGGTGGCT<br>CATGTCCAAAGCCACACCGATTAACCAACAAAGGAATTTG<br>TAGTTGTGGTGCATTTAAGGTGCCTGGTGTAAAAACCGTC<br>TGGAAAAGACGCTGAAGAACAGCGCCTCCCTGACTCTCCA<br>CCTCGAAAGAGGTGGAGAGTCAGGGAGGCCCAGAGGGTCT |

TABLE 3-continued

Illustrative amino acid sequences.

| SEQ ID NO: | Description | Sequence |
|---|---|---|
| | | TAGAGTGTCACAACATTTGGGCCTCTAAAAATTAGGTCAT<br>GTGGCAGAATGTTGTGAACAGTTTTCAGATCTGGGAGCCT<br>TGCTTTGGAGGCGCTTTCAAAAATGATGCAGTCCATGAGT<br>GCACAGTGCGGGGTGATCTCTTTCTTCTTTTTGTCCCTTA<br>CTATTCCAGTATGCATCTTACACAACCAGCCATATTTGTC<br>CCACACTTTGTCTTCATACTCCCTCGAAGCTTCCCTGGTC<br>ATTTCAACATCGATAAGCTTAATGTCCTTCCTATTCTGTG<br>AGTCCAGAAGCTTTCTGATGTCATCGGAGCCTTGACAGCT<br>TAGAACCATCCCCTGCGGAAGAGCACCTATAACTGACGAG<br>GTCAACCCGGGTTGCGCATTGAAGAGGTCGGCAAGATCCA<br>TGCCGTGTGAGTACTTGGAATCTTGCTTGAATTGTTTTTG<br>ATCAACGGGTTCCCTGTAAAAGTGTATGAACTGCCCGTTC<br>TGTGGTTGGAAAATTGCTATTTCCACTGGATCATTAAATC<br>TACCCTCAATGTCAATCCATGTAGGAGCGTTGGGGTCAAT<br>TCCTCCCATGAGGTCTTTTAAAAGCATTGTCTGGCTGTAG<br>CTTAAGCCCACCTGAGGTGGACCTGCTGCTCCAGGCGCTG<br>GCCTGGGTGAATTGACTGCAGGTTTCTCGCTTGTGAGATC<br>AATTGTTGTGTTTTCCCATGCTCTCCCCACAATCGATGTT<br>CTACAAGCTATGTATGGCCATCCTTCACCTGAAAGGCAAA<br>CTTTATAGAGGATGTTTTCATAAGGGTTCCTGTCCCCAAC<br>TTGGTCTGAAACAAACATGTTGAGTTTTCTCTTGGCCCCG<br>AGAACTGCCTTCAAGAGGTCCTCGCTGTTGCTTGGCTTGA<br>TCAAAATTGACTCTAACATGTTACCCCCATCCAACAGGGC<br>TGCCCCTGCCTTCACGGCAGCACCAAGACTAAAGTTATAG<br>CCAGAAATGTTGATGCTGGACTGCTGTTCAGTGATGACCC<br>CCAGAACTGGGTGCTTGTCTTTCAGCCTTTCAAGATCATT<br>AAGATTTGGATACTTGACTGTGTAAAGCAAGCCAAGGTCT<br>GTGAGCGCTTGTACAACGTCATTGAGCGGAGTCTGTGACT<br>GTTTGGCCATACAAGCCATAGTTAGACTTGGCATTGTGCC<br>AAATTGATTGTTCAAAAGTGATGAGTCTTTCACATCCCAA<br>ACTCTTACCACACCACTTGCACCCTGCTGAGGCTTTCTCA<br>TCCCAACTATCTGTAGGATCTGAGATCTTTGGTCTAGTTG<br>CTGTGTTGTTAAGTTCCCCATATATACCCCTGAAGCCTGG<br>GGCCTTTCAGACCTCATGATCTTGGCCTTCAGCTTCTCAA<br>GGTCAGCCGCAAGAGACATCAGTTCTTCTGCACTGAGCCT<br>CCCCACTTTCAAAACATTCTTCTTTGATGTTGACTTTAAA<br>TCCACAAGAGAATGTACAGTCTGGTTGAGACTTCTGAGTC<br>TCTGTAGGTCTTTGTCATCTCTCTTTTCCTTCCTCATGAT<br>CCTCTGAACATTGCTGACCTCAGAGAAGTCCAACCCATTC<br>AGAAGGTTGGTTGCATCCTTAATGACAGCAGCCTTCACAT<br>CTGATGTGAAGCTCTGCAATTCTCTTCTCAATGCTTGCGT<br>CCATTGGAAGCTCTTAACTTCCTTAGACAAGGACATCTTG<br>TTGCTCAATGGTTTCTCAAGACAAATGCGCAATCAAATGC<br>CTAGGATCCACTGTGCG |
| 13 | lymphocytic choriomeningitis strain MP segment L, complete sequence (The genomic segment is RNA, the sequence in SEQ ID NO: 13 is shown for DNA; however, exchanging all thymidines ("T") in SEQ ID NO: 13 for uridines ("U") provides the RNA sequence.) | GCGCACCGGGGATCCTAGGCATTTTTGTTGCGCATTTTGT<br>TGTGTTATTTGTTGCACAGCCCTTCATCGTGGGACCTTCA<br>CAAACAAACCAAACCACCAGCCATGGGCCAAGGCAAGTCC<br>AAAGAGGGAAGGGATGCCAGCAATACGAGCAGAGCTGAAA<br>TTCTGCCAGACACCACCTATCTCGGACCTCTGAACTGCAA<br>GTCATGCTGGCAGAGATTTGACAGTTTAGTCAGATGCCAT<br>GACCACTATCTCTGCAGACACTGCCTGAACCTCCTGCTGT<br>CAGTCTCCGACAGGTGCCCTCTCTGCAAACATCCATTGCC<br>AACCAAACTGAAAATATCCACGGCCCCAAGCTCTCCACCC<br>CCTTACGAGGAGTGACGCCCCGAGCCCCAACACCGACACA<br>AGGAGGCCACCAACACAACGCCCAACACGGAACACACACA<br>CACACACCCACACACACATCCACACACACGCGCCCCCACA<br>ACGGGGGCGCCCCCCCGGGGGTGGCCCCCCGGGTGCTCGG<br>GCGGAGCCCCACGGAGAGGCCAATTAGTCGATCTCCTCGA<br>CCACCGACTTGGTCAGCCAGTCATCACAGGACTTGCCCTT<br>AAGTCTGTACTTGCCCACAACTGTTTCATACATCACCGTG<br>TTCTTTGACTTACTGAAACATAGCCTACAGTCTTTGAAAG<br>TGAACCAGTCAGGCACAAGTGACAGCGGTACCAGTAGAAT<br>GGATCTATCTATACACAACTCTTGGAGAATTGTGCTAATT<br>TCCGACCCCTGTAGATGCTCACCAGTTCTGAATCGATGTA<br>GAAGAAGGCTCCCAAGGACGTCATCAAAATTTCCATAACC<br>CTCGAGCTCTGCCAAGAAAACTCTCATATCCTTGGTCTCC<br>AGTTTCACAACGATGTTCTGAACAAGGCTTCTTCCCTCAA<br>AAAGAGCACCCATTCTCACAGTCAAGGGCACAGGCTCCCA<br>TTCAGGCCCAATCCTCTCAAAATCAAGGGATCTGATCCCG<br>TCCAGTATTTTCCTTGAGCCTATCAGCTCAAGCTCAAGAG<br>AGTCACCGAGTATCAGGGGGTCCTCCATATAGTCCTCAAA<br>CTCTTCAGACCTAATGTCAAAAACACCATCGTTCACCTTG<br>AAGATAGAGTCTGATCTCAACAGGTGGAGGCATTCGTCCA |

TABLE 3-continued

Illustrative amino acid sequences.

| SEQ ID NO: | Description | Sequence |
|---|---|---|
| | | AGAACCTTCTGTCCACCTCACCTTTAAAGAGGTGAGAGCA
TGATAGGAACTCAGCTACACCTGGACCTTGTAACTGGCAC
TTCACTAAAAAGATCAATGAAAACTTCCTCAAACAATCAG
TGTTATTCTGGTTGTGAGTGAAATCTACTGTAATTGAGAA
CTCTAGCACTCCCTCTGTATTATTTATCATGTAATCCCAC
AAGTTTCTCAAAGACTTGAATGCCTTTGGATTTGTCAAGC
CTTGTTTGATTAGCATGGCAGCATTGCACACAATATCTCC
CAATCGGTAAGAGAACCATCCAAATCCAAATTGCAAGTCA
TTCCTAAACATGGGCCTCTCCATATTTTGTTCACTACTT
TTAAGATGAATGATTGGAAAGGCCCCAATGCTTCAGCGCC
ATCTTCAGATGGCATCATGTCTTTATGAGGGAACCATGAA
AAACTTCCTAGAGTTCTGCTTGTTGCTACAAATTCTCGTA
CAAATGACTCAAAATACACTTGTTTAAAAAGTTTTTGCA
GACATCCCTTGTACTAACGACAAATTCATCAACAAGGCTT
GAGTCAGAGCGCTGATGGGAATTTACAAGATCAGAAAATA
GAACAGTGTAGTGTTCGTCCCTCTTCCACTTAACTACATG
AGAAATGAGCGATAAAGATTCTGAATTGATATCGATCAAT
ACGCAAAGGTCAAGGAATTTGATTCTGGGACTCCATCTCA
TGTTTTTTGAGCTCATATCAGACATGAAGGGAAGCAGCTG
ATCTTCATAGATTTTAGGGTACAATCGCCTCACAGATTGG
ATTACATGGTTTAAACTTATCTTGTCCTCCAGTAGCCTTG
AACTCTCAGGCTTCCTTGCTACATAATCACATGGGTTCAA
GTGCTTGAGGCTTGAGCTTCCCTCATTCTTCCCTTTCACA
GGTTCAGCTAAGACCCAAACACCCAACTCAAAGGAATTAC
TCAGTGAGATGCAAATATAGTCCCAAAGGAGGGGCCTCAA
GAGACTGATGTGGTCGCAGTGAGCTTCTGGATGACTTTGC
CTGTCACAAATGTACAACATTATGCCATCATGTCTGTGGA
TTGCTGTCACATGCGCATCCATAGCTAGATCCTCAAGCAC
TTTTCTAATGTATAGATTGTCCCTATTTTTATTTCTCACA
CATCTACTTCCCAAAGTTTTGCAAAGACCTATAAAGCCTG
ATGAGATGCAACTTTGAAAGGCTGACTTATTGATTGCTTC
TGACAGCAACTTCTGTGCACCTCTTGTGAACTTACTGCAG
AGCTTGTTCTGGAGTGTCTTGATTAATGATGGGATTCTTT
CCTCTTGGAAAGTCATTACTGATGGATAAACCACTTTCTG
CCTCAAGACCATTCTTAATGGGAACAACTCATTCAAATTC
AGCCAATTTATGTTTGCCAATTGACTTAGATCCTCTTCGA
GGCCAAGGATGTTTCCCAACTGAAGAATGGCTTCCTTTTT
ATCCCTATTGAAGAGGTCTAAGAAGAATTCTTCATTGAAC
TCACCATTCTTGAGCTTATGATGTAGTCTCCTTACAAGCC
TTCTCATGACCTTCGTTTCACTAGGACACAATTCTTCAAT
AAGCCTTTGGATTCTGTAACCTCTAGAGCCATCCAACCAA
TCCTTGACATCAGTATTAGTGTTAAGCAAAAATGGGTCCA
AGGGAAAGTTGGCATATTTTAAGAGGTCTAATGTTCTCTT
CTGGATGCAGTTTACCAATGAAACTGGAACACCATTTGCA
ACAGCTTGATCGGCAATTGTATCTATTGTTTCACAGAGTT
GGTGTGGCTCTTTACACTTAACGTTGTGTAATGCTGCTGA
CACAAATTTTGTTAAAAGTGGGACCTCTTCCCCCCACACA
TAAAATCTGGATTTAAATTCTGCAGCAAATCGCCCCACCA
CACTTTTCGGACTGATGAACTTGTTAAGCAAGCCACTCAA
ATGAGAATGAAATTCCAGCAATACAAGGACTTCCTCAGGG
TCACTATCAACCAGTTCACTCAATCTCCTATCAAATAAGG
TGATCTGATCATCACTTGATGTGTAAGATTCTGGTCTCTC
ACCAAAAATGACACCGATACAATAATTAATGAATCTCTCA
CTGATTAAGCCGTAAAAGTCAGAGGCATTATGTAAGATTC
CCTGTCCCATGTCAATGAGACTGCTTATATGGGAAGGCAC
TATTCCTAATTCAAAATATTCTCGAAAGATTCTTTCAGTC
ACAGTTGTCTCTGAACCCCTAAGAAGTTTCAGCTTTGATT
TGATATATGATTTCATCATTGCATTCACAACAGGAAAAGG
GACCTCAACAAGTTTGTGCATGTGCCAAGTTAATAAGGTG
CTGATATGATCCTTTCCGGAACGCACATACTGGTCATCAC
CCAGTTTGAGATTTTGAAGGAGCATTAAAAACAAAAATGG
GCACATCATTGGCCCCATTTGCTATGATCCATACTGTAG
TTCAACAACCCCTCTCGCACATTGATGGTCATTGATAGAA
TTGCATTTTCAAATTCTTTGTCATTGTTTAAGCATGAACC
TGAGAAGAAGCTAGAAAAAGACTCAAAATAATCCTCTATC
AATCTTGTAAACATTTTTGTTCTCAAATCCCCAATATAAA
GTTCTCTGTTTCCTCCAACCTGCTCTTTGTATGATAACGC
AAACTTCAACCTTCCGGAATCAGGACCAACTGAAGTGTAT
GACGTTGGTGACTCCTCTGAGTAAAAACATAAATTCTTTA
AAGCAGCACTCATGCATTTTGTCAATGATAGAGCCTTACT
TAGAGACTCAGAATTACTTTCCCTTTCACTAATTCTAACA
TCTTCTTCAGTTTGTCCCAGTCAAACTTGAAATTCAGAC
CTTGTCTTTGCATGTGCCTGTATTTCCCTGAGTATGCATT
TGCATTCATTTGCAGTAGAATCATTTTCATACACGAAAAC |

TABLE 3-continued

Illustrative amino acid sequences.

| SEQ ID NO: | Description | Sequence |
|---|---|---|
| | | CAATCACCCTCTGAAAAAAACTTCCTGCAGAGGTTTTTG CCATTTCATCCAGACCACATTGTTCTTTGACAGCTGAAGT GAAATACAATGGTGACAGTTCTGTAGAAGTTTCAATAGCC TCACAGATAAATTTCATGTCATCATTGGTGAGACAAGATG GGTCAAAATCTTCCACAAGATGAAAAGAAATTTCTGATAA GATGACCTTCCTTAAATATGCCATTTTACCTGACAATATA GTCTGAAGGTGATGCAATCCTTTTGTATTTTCAAACCCCA CCTCATTTTCCCCTTCATTGGTCTTCTTGCTTCTTTCATA CCGCTTTATTGTGGAGTTGACCTTATCTTCTAAATTCTTG AAGAAACTTGTCTCTTCTTCCCCATCAAAGCATATGTCTG CTGAGTCACCTTCTAGTTTCCCAGCTTCTGTTTCTTTAGA GCCGATAACCAATCTAGAGACCAACTTTGAAACCTTGTAC TCGTAATCTGAGTGGTTCAATTTGTACTTCTGCTTTCTCA TGAAGCTCTCTGTGATCTGACTCACAGCACTAACAAGCAA TTTGTTAAAATCATACTCTAGGAGCCGTTCCCCATTTAAA TGTTTGTTAACAACCACACTTTTGTTGCTGGCAAGGTCTA ATGCTGTTGCACACCCAGAGTTAGTCATGGGATCCAAGCT ATTGAGCCTCTTCTCCCCTTTGAAAATCAAAGTGCCATTG TTGAATGAGGACACCATCATGCTAAAGGCCTCCAGATTGA CACCTGGGGTTGTGCGCTGACAGTCAACTTCTTTCCCAGT GAACTTCTTCATTTGGTCATAAAAAACACACTCTTCCTCA GGGGTGATTGACTCTTTAGGGTTAACAAAGAAGCCAAACT CACTTTTAGGCTCAAAGAATTTCTCAAAGCATTTAATTTG ATCTGTCAGCCTATCAGGGGTTTCCTTTGTGATTAAATGA CACAGGTATGACACATTCAACATGAACTTGAACTTTGCGC TCAACAGTACCTTTTCACCAGTCCCAAAAACAGTTTTGAT CAAAAATCTGAGCAATTTGTACACTACTTTCTCAGCAGGT GTGATCAAATCCTCCTTCAACTTGTCCATCAATGATGTGG ATGAGAAGTCTGAGACAATGGCCATCACTAAATACCTAAT GTTTTGAACCTGTTTTGATTCCTCTTTGTTGGGTTGGTG AGCATGAGTAATAATAGGGTTCTCAATGCAATCTCAACAT CATCAATGCTGTCCTTCAAGTCAGGACATGATCTGATCCA TGAGATCATGGTGTCAATCATGTTGTGCAACACTTCATCT GAGAAGATTGGTAAAAAGAACCTTTTTGGGTCTGCATAAA AAGAGATTAGATGGCCATTGGGACCTTGTATAGAATAACA CCTTGAGGATTCTCCAGTCTTTTGATACAGCAGGTGATAT TCCTCAGAGTCCAATTTTATCACTTGGCAAAATACCTCTT TACATTCCACCACTTGATACCTTACAGAGCCCAATTGGTT TTGTCTTAATCTAGCAACTGAACTTGTTTTCATACTGTTT GTCAAAGCTAGACAGACAGATGACAATCTTTTCAAACTAT GCATGTTCCTTAATTGTTCCGTATTAGGCTGGAAATCATA ATCTTCAAACTTTGTATAATACATTATAGGATGAGTTCCG GACCTCATGAAATTCTCAAACTCAATAAATGGTATGTGGC ACTCATGCTCAAGATGTTCAGACAGACCATAGTGCCCAAA ACTAAGTCCCACCACTGACAAGCACCTTTGAACTTTTAAA ATGAACTCATTTATGGATGTTCTAAACAAATCCTCAAGAG ATACCTTTCTATACGCCTTTGACTTTCTCCTGTTCCTTAG AAGTCTGATGAACTCTTCCTTGGTGCTATGAAAGCTCACC AACCTATCATTCACACTCCCATAGCAACAACCAACCCAGT GCTTATCATTTTTTGACCCTTTGAGTTTAGACTGTTTGAT CAACGAAGAGAGACACAAGACATCCAAATTCAGTAACTGT CTCCTTCTGGTGTTCAATAATTTTAAACTTTTAACTTTGT TCAACATAGAGGAGCCTCTCATACTCAGTGCTAGTCTC ACTTCCTCTCTCATAACCATGGGTATCTGCTGTGATAAAT CTCATCAAAGGACAGGATTCAACTGCCTCCTTGCTTAGTG CTGAAATGTCATCACTGTCAGCAAGAGTCTCATAAAGCTC AGAGAATTCCTTAATTAAATTTCCGGGGTTGATTTTCTGA AAACTCCTCTTGAGCTTCCCAGTTTCCAAGTCTCTTCTAA ACCTGCTGTAAAGGGAGTTTATGCCAAGAACCACATCATC GCAGTTCATGTTTGGGTTGACACCATCATGGCACATTTTC ATAATTTCATCATTGTGAAATGATCTTGCATCTTTCAAGA TTTTCATAGAGTCTATACCGGAACGCTTATCAACAGTGGT CTTGAGAGATTCGCAAAGTCTGAAGTACTCAGATTCCTCA AAGACTTTCTCATCTTGGCTAGAATACTCTAAAAGTTTAA ACAGAAGGTCTCTGAACTTGAAATTCACCCACTCTGGCAT AAAGCTGTTATCATAATCACACCGACCATCCACTATTGGG ACCAATGTGATACCCGCAATGGCAAGGTCTTCTTTGATAC AGGCTAGTTTATTGGTGTCCTCTATAAATTTCTTCTCAAA ACTAGCTGGTGTGCTTCTAACGAAGCACTCAAGAAGAATG AGGGAATTGTCAATCAGTTTATAACCATCAGGAATGATCA AAGGCAGTCCCGGCACACAATCCCAGACTCTATTAGAAT TGCCTCAACAGATTTATCATCATGGTTGTGTATGCAGCCG CTCTTGTCAGCACTGTCTATCTCTATACAACGCGACAAAA GTTTGAGTCCCTCTATCAATACCATTCTGGGTTCTCTTTG |

TABLE 3-continued

Illustrative amino acid sequences.

| SEQ ID NO: | Description | Sequence |
|---|---|---|
| | | CCCTAAAAAGTTGAGCTTCTGCCTTGACAACCTCTCATCT TGTTCTATGTGGTTTAAGCACAACTCTCTCAACTCCGAAA TAGCCTCATCCATTGCGCATCAAAAAGCCTAGGATCCTCG GTGCG |
| 14 | lymphocytic choriomeningitis strain MP segment S, complete sequence (The genomic segment is RNA, the sequence in SEQ ID NO: 14 is shown for DNA; however, exchanging all thymidines ("T") in SEQ ID NO: 14 for uridines ("U") provides the RNA sequence.) | CGCACCGGGGATCCTAGGCTTTTTGGATTGCGCTTTCCTC AGCTCCGTCTTGTGGGAGAATGGGTCAAATTGTGACGATG TTTGAGGCTCTGCCTCACATCATTGATGAGGTCATTAACA TTGTCATTATCGTGCTTATTATCATCACGAGCATCAAAGC TGTGTACAATTTCGCCACCTGCGGGATACTTGCATTGATC AGCTTTCTTTTTCTGGCTGGCAGGTCCTGTGGAATGTATG GTCTTGATGGGCCTGACATTTACAAAGGGGTTTACCGATT CAAGTCAGTGGAGTTTGACATGTCTTACCTTAACCTGACG ATGCCCAATGCATGTTCGGCAAACAACTCCCATCATTATA TAAGTATGGGGACTTCTGGATTGGAGTTAACCTTCACAAA TGACTCCATCATCACCCACAACTTTTGTAATCTGACTTCC GCCCTCAACAAGAGGACTTTTGACCACACACTTATGAGTA TAGTCTCAAGTCTGCACCTCAGCATTAGAGGGGTCCCCAG CTACAAAGCAGTGTCCTGTGATTTTAACAATGGCATCACT ATTCAATACAACCTGTCATTTTCTAATGCACAGAGCGCTC TGAGTCAATGTAAGACCTTCAGGGGGAGAGTCCTGGATAT GTTCAGAACTGCTTTTGGAGGAAAGTACATGAGGAGTGGC TGGGGCTGGACAGGTTCAGATGGCAAGACTACTTGGTGCA GCCAGACAAACTACCAATATCTGATTATACAAAACAGGAC TTGGGAAAACCACTGCAGGTACGCAGGCCCTTTCGGAATG TCTAGAATTCTCTTCGCTCAAGAAAAGACAAGGTTTCTAA CTAGAAGGCTTGCAGGCACATTCACTTGGACTTTATCAGA CTCATCAGGAGTGGAGAATCCAGGTGGTTACTGCTTGACC AAGTGGATGATCCTCGCTGCAGAGCTCAAGTGTTTTGGGA ACACAGCTGTTGCAAAGTGCAATGTAAATCATGATGAAGA GTTCTGTGATATGCTACGACTGATTGATTACAACAAGGCT GCTTTGAGTAAATTCAAAGAAGATGTAGAATCCGCTCTAC ATCTGTTCAAGACAACAGTGAATTCTTTGATTTCTGATCA GCTTTTGATGAGAAATCACCTAAGAGACTTGATGGGAGTG CCATACTGCAATTACTCGAAATTCTGGTATCTAGAGCATG CAAAGACTGGTGAGACTAGTGTCCCCAAGTGCTGGCTTGT CAGCAATGGTTCTTATTTGAATGAAACCCATTTCAGCGAC CAAATTGAGCAGGAAGCAGATAATATGATCACAGAAATGC TGAGAAAGGACTACATAAAAAGGCAAGGGAGTACCCCTCT AGCCTTGATGGATCTATTGATGTTTTCTACATCAGCATAT TTGATCAGCATCTTTCTGCATCTTGTGAGGATACCAACAC ACAGACACATAAAGGGCGGCTCATGCCCAAAACCACATCG GTTAACCAGCAAGGGAATCTGTAGTTGTGGTGCATTTAAA GTACCAGGTGTGGAAACCACCTGGAAAAGACGCTGAACAG CAGCGCCTCCCTGACTCACCACCTCGAAAGAGGTGGTGAG TCAGGGAGGCCCAGAGGGTCTTAGAGTGTTACGACATTTG GACCTCTGAAGATTAGGTCATGTGGTAGGATATTGTGGAC AGTTTTCAGGTCGGGGAGCCTTGCCTTGGAGGCGCTTTCA AAGATGATACAGTCCATGAGTGCACAGTGTGGGGTGACCT CTTTCTTTTTCTTGTCCCTCACTATTCCAGTGTGCATCTT GCATAGCCAGCCATATTTGTCCCAGACTTTGTCCTCATAT TCTCTTGAAGCTTCTTTAGTCATCTCAACATCGATGAGCT TAATGTCTCTTCTGTTTTGTGAATCTAGGAGTTTCCTGAT GTCATCAGATCCCTGACAACTTAGGACCATTCCCTGTGGA AGAGCACCTATTACTGAAGATGTCAGCCCAGGTTGTGCAT TGAAGAGGTCAGCAAGGTCCATGCCATGTGAGTATTTGGA GTCCTGCTTGAATTGTTTTTGATCAGTGGGTTCTCTATAG AAATGTATGTACTGCCCATTCTGTGGCTGAAATATTGCTA TTTCTACCGGGTCATTAAATCTGCCCTCAATGTCAATCCA TGTAGGAGCGTTAGGGTCAATACCTCCCATGAGGTCCTTC AGCAACATTGTTTGGCTGTAGCTTAAGCCCACCTGAGGTG GGCCCGCTGCCCCAGGCGCTGGTTTGGGTGAGTTGGCCAT AGGCCTCTCATTTGTCAGATCAATTGTTGTGTTCTCCCAT GCTCTCCCTACAACTGATGTTCTACAAGCTATGTATGGCC ACCCCTCCCCTGAAAGACACTTTGTAGAGGGATGTTCTC GTAAGGATTCCTGTCTCCAACCTGATCAGAAACAAACATG TTGAGTTTCTTCTTGGCCCCAAGAACTGCTTTCAGGAGAT CCTCACTGTTGCTTGGCTTAATTAAGATGGATTCCAACAT GTTACCCCCATCTAACAAGGCTGCCCTGCTTTCACAGCA GCACCGAGACTGAAATTGTAGCCAGATATGTTGATGCTAG ACTGCTGCTCAGTGATGACTCCCAAGACTGGGTGCTTGTC TTTCAGCCTTTCAAGGTCACTTAGGTTCGGGTACTTGACT GTGTAAAGCAGCCCAAGGTCTGTGAGTGCTTGCACAACGT CATTGAGTGAGGTTTGTGATTGTTTGGCCATACAAGCCAT |

TABLE 3-continued

Illustrative amino acid sequences.

| SEQ ID NO: | Description | Sequence |
|---|---|---|
| | | TGTTAAGCTTGGCATTGTGCCGAATTGATTGTTCAGAAGT GATGAGTCCTTCACATCCCAGACCCTCACCACACCATTTG CACTCTGCTGAGGTCTCCTCATTCCAACCATTTGCAGAAT CTGAGATCTTTGGTCAAGCTGTTGTGCTGTTAAGTTCCCC ATGTAGACTCCAGAAGTTAGAGGCCTTTCAGACCTCATGA TTTTAGCCTTCAGTTTTTCAAGGTCAGCTGCAAGGGACAT CAGTTCTTCTGCACTAAGCCTCCCTACTTTTAGAACATTC TTTTTTTGATGTTGACTTTAGGTCCACAAGGGAATACACAG TTTGGTTGAGGCTTCTGAGTCTCTGTAAATCTTTGTCATC CCTCTTCTCTTTCCTCATGATCCTCTGAACATTGCTCACC TCAGAGAAGTCTAATCCATTCAGAAGGCTGGTGGCATCCT TGATCACAGCAGCTTTCACATCTGATGTGAAGCCTTGAAG CTCTCTCCTCAATGCCTGGGTCCATTGAAAGCTTTTAACT TCTTTGGACAGAGACATTTTGTCACTCAGTGGATTTCCAA GTCAAATGCGCAATCAAAATGCCTAGGATCCACTGTGCG |
| 15 | amino acid sequence of the NP protein of the MP strain of LCMV | MSLSKEVKSFQWTQALRRELQGFTSDVKAAVIKDATSLLN GLDFSEVSNVQRIMRKEKRDDKDLQRLRSLNQTVYSLVDL KSTSKKNVLKVGRLSAEELMSLAADLEKLKAKIMRSERPL TSGVYMGNLTAQQLDQRSQILQMVGMRRPQQSANGVVRVW DVKDSSLLNNQFGTMPSLTMACMAKQSQTSLNDVVQALTD LGLLYTVKYPNLSDLERLKDKHPVLGVITEQQSSINISGY NFSLGAAVKAGAALLDGGNMLESILIKPSNSEDLLKAVLG AKKKLNMFVSDQVGDRNPYENILYKVCLSGEGWPYIACRT SVVGRAWENTTIDLTNERPMANSPKPAPGAAGPPQVGLSY SQTMLLKDLMGGIDPNAPTWIDIEGRFNDPVEIAIFQPQN GQYIHFYREPTDQKQFKQDSKYSHGMDLADLFNAQPGLTS SVIGALPQGMVLSCQGSDDIRKLLDSQNRRDIKLIDVEMT KEASREYEDKVWDKYGWLCKMHTGIVRDKKKKEVTPHCAL MDCIIFESASKARLPDLKTVHNILPHDLIFRGPNVVTL |
| 16 | amino acid sequence of the GP protein of the MP strain of LCMV | MGQIVTMFEALPHIIDEVINIVIIVLIIITSIKAVYNFAT CGILALISFLFLAGRSCGMYGLDGPDIYKGVYRFKSVEFD MSYLNLTMPNACSANNSHHYISMGTSGLELTFTNDSIITH NFCNLTSALNKRTFDHTLMSIVSSLHLSIRGVPSYKAVSC DFNNGITIQYNLSFSNAQSALSQCKTFRGRVLDMFRTAFG GKYMRSGWGWTGSDGKTTWCSQTNYQYLIIQNRTWENHCR YAGPFGMSRILFAQEKTRFLTRRLAGTFTWTLSDSSGVEN PGGYCLTKWMILAAELKCFGNTAVAKCNVNHDEEFCDMLR LIDYNKAALSKFKEDVESALHLFKTTVNSLISDQLLMRNH LRDLMGVPYCNYSKFWYLEHAKTGETSVPKCWLVSNGSYL NETHFSDQIEQEADNMITEMLRKDYIKRQGSTPLALMDLL MFSTSAYLISIFLHLVRIPTHRHIKGGSCPKPHRLTSKGI CSCGAFKVPGVETTWKRR |
| 17 | amino acid sequence of the L protein of the MP strain of LCMV | MDEAISELRELCLNHIEQDERLSRQKLNFLGQREPRMVLI EGLKLLSRCIEIDSADKSGCIHNDDKSVEAILIESGIVC PGLPLIIPDGYKLIDNSLILLECFVRSTPASFEKKFIEDT NKLACIKEDLAIAGITLVPIVDGRCDYDNSFMPEWVNFKF RDLLFKLLEYSSQDEKVFEESEYFRLCESLKTTVDKRSGI DSMKILKDARSFHNDEIMKMCHDGVNPNMNCDDVVLGINS LYSRFRRDLETGKLKRSFQKINPGNLIKEFSELYETLADS DDISALSKEAVESCPLMRFITADTHGYERGSETSTEYERL LSMLNKVKSLKLLNTRRRQLLNLDVLCLSSLIKQSKLKGS KNDKHWVGCCYGSVNDRLVSFHSTKEEFIRLLRNRRKSKA YRKVSLEDLFRTSINEFILKVQRCLSVVGLSFGHYGLSEH LEHECHIPFIEFENFMRSGTHPIMYYTKFEDYDFQPNTEQ LRNMHSLKRLSSVCLALTNSMKTSSVARLRQNQLGSVRYQ VVECKEVFCQVIKLDSEEYHLLYQKTGESSRCYSIQGPNG HLISFYADPKRFFLPIFSDEVLHNMIDTMISWIRSCPDLK DSIDDVEIALRTLLLLMLTNPTKRNQKQVQNIRYLVMAIV SDFSSTSLMDKLKEDLITPAEKVVYKLLRFLIKTVFGTGE KVLLSAKFKFMLNVSYLCHLITKETPDRLTDQIKCFEKFF EPKSEFGFFVNPKESITPEEECVFYDQMKKFTGKEVDCQR TTPGVNLEAFSMMVSSFNNGTLIFKGEKRLNSLDPMTNSG CATALDLASNKSVVVNKHLNGERLLEYDFNKLLVSAVSQI TESFMRKQKYKLNHSDYEYKVSKLVSRLVIGSKETEAGKL EGDSADICFDGEEETSFFKNLEDKVNSTIKRYERSKKTNE GENEVGFENTKGLHHLQTILSGKMAYLRKVILSEISFHLV EDFDPSCLTNDDMKFICEAIETSTELSPLYFTSAVKEQCG LDEMAKNLCRKFFSEGDWFSCMKMILLQMNANAYSGKYRH MQRQGLNFKFDWDKLEEDVRISERESNSESLSKALSLTKC MSAALKNLCFYSEESPTSYTSVGPDSGRLKFALSYKEQVG GNRELYIGDLRTKMFTRLIEDYFESFSSFFFSGSCLNNDKE |

TABLE 3-continued

Illustrative amino acid sequences.

| SEQ ID NO: | Description | Sequence |
|---|---|---|
| | | FENAILSMTINVREGLLNYSMDHSKWGPMMCPFLFLMLLQ<br>NLKLGDDQYVRSGKDHISTLLTWHMHKLVEVPFPVVNAMM<br>KSYIKSKLKLLRGSETTVTERIFREYFELGIVPSHISSLI<br>DMGQGILHNASDFYGLISERFINYCIGVIFGERPESYTSS<br>DDQITLFDRRLSELVDSDPEEVLVLLEFHSHLSGLLNKFI<br>SPKSVVGRFAAEFKSRFYVWGEEVPLLTKFVSAALHNVKC<br>KEPHQLCETIDTIADQAVANGVPVSLVNCIQKRTLDLLKY<br>ANFPLDPFLLNTNTDVKDWLDGSRGYRIQRLIEELCPSET<br>KVMRRLVRRLHHKLKNGEFNEEFFLDLFNRDKKEAILQLG<br>NILGLEEDLSQLANINWLNLNELFPLRMVLRQKVVYPSVM<br>TFQEERIPSLIKTLQNKLCSKFTRGAQKLLSEAINKSAFQ<br>SCISSGFIGLCKTLGSRCVRNKNRDNLYIRKVLEDLAMDA<br>HVTAIHRHDGIMLYICDRQSHPEAHCDHISLLRPLLWDYI<br>CISLSNSFELGVWVLAEPVKGKNEGSSSLKHLNPCDYVAR<br>KPESSRLLEDKISLNHVIQSVRRLYPKIYEDQLLPFMSDM<br>SSKNMRWSPRIKFLDLCVLIDINSESLSLISHVVKWKRDE<br>HYTVLFSDLVNSHQRSDSSLVDEFVVSTRDVCKNPLKQVY<br>FESFVREFVATSRTLGSFSWFPHKDMMPSEDGAEALGPFQ<br>SFILKVVNKNMERPMFRNDLQFGFGWFSYRLGDIVCNAAM<br>LIKQGLTNPKAFKSLRNLWDYMINNTEGVLEFSITVDFTH<br>NQNNTDCLRKFSLIFLVKCQLQGPGVAEFLSCSHLFKGEV<br>DRRFLDECLHLLRSDSIFKVNDGVFDIRSEEFEDYMEDPL<br>ILGDSLELELIGSRKILDGIRSLDFERIGPEWEPVPLTVR<br>MGALFEGRSLVQNIVVKLETKDMRVFLAELEGYGNFDDVL<br>GSLLLHRFRTGEHLQGSEISTILQELCIDRSILLVPLSLV<br>PDWFTFKDCRLCFSKSKNTVMYETVVGKYRLKGKSCDDWL<br>TKSVVEEID |
| 18 | amino acid sequence of the Z protein of the MP strain of LCMV | MGQGKSKEGRDASNTSRAEILPDTTYLGPLNCKSCWQRFD<br>SLVRCHDHYLCRHCLNLLLSVSDRCPLCKHPLPTKLKIST<br>APSSPPPYEE |
| 19 | Junin virus Candid#1 L segment | GCGCACCGGGGATCCTAGGCGTAACTTCATCATTAAAATCT<br>CAGATTCTGCTCTGAGTGTGACTTACTGCGAAGAGGCAGAC<br>AAATGGGCAACTGCAACGGGGCATCCAAGTCTAACCAGCCA<br>GACTCCTCAAGAGCCACACAGCCAGCCGCAGAATTTAGGAG<br>GGTAGCTCACAGCAGTCTATATGGTAGATATAACTGTAAGT<br>GCTGCTGGTTTGCTGATACCAATTTGATAACCTGTAATGAT<br>CACTACCTTTGTTTAAGGTGCCATCAGGGTATGTTAAGGAA<br>TTCAGATCTCTGCAATATCTGCTGGAAGCCCCT<br>GCCCACCACAATCACAGTACCGGTGGAGCCAACAGCACCAC<br>CACCATAGGCAGACTGCACAGGGTCAGACCCGACCCCCCGG<br>GGGGCCCCCATGGGGACCCCCCGTGGGGGAACCCCGGGGGT<br>GATGCGCCATTAGTCAATGTCTTTGATCTCGACTTTGTGCT<br>TCAGTGGCCTGCATGTCACCCCTTTCAATCTGAACTGCCCT<br>TGGGGATCTGATATCAGCAGGTCATTTAAAGATCT<br>GCTGAATGCCACCTTGAAATTTGAGAATTCCAACCAGTCAC<br>CAAATTTATCAAGTGAACGGATCAACTGCTCTTTGTGTA<br>GATCATAAACGAGGACAAAGTCCTCTTGCTGAAATAATATT<br>GTTTGTGATGTTGTTTTTAGATAAGGCCATAGTTGGCTT<br>AATAAGGTTTCCACACTATCAATGTCCTCTAGTGCTCCAAT<br>TGCCTTGACTATGACATCCCCAGACAACTCAACTCTATA<br>TGTTGACAACCTTTCATTACCTCTGTAAAAGATACCCTCTT<br>TCAAGACAAGAGGTTCTCCTGGGTTATCTGGCCCAATGA<br>GGTCATATGCATACTTGTTACTTAGTTCAGAATAAAAGTCA<br>CCAAAGTTGAACTTAACATGGCTCAGAATATTGTCATCA<br>TTTGTCGCAGCGTAGCCTGCATCAATAAACAAGCCAGCTAG<br>GTCAAAGCTCTCATGGCCTGTGAACAATGGTAGGCTAGC<br>GATAACCAGTGCACCATCCAACAATGAGTGGCTTCCCTCAG<br>ACCCAGAAACACATTGACTCATTGCATCCACATTCAGCT<br>CTAATTCAGGGGTACCGACATCATCCACTCCTAGTGAACTG<br>ACAATGGTGTAACTGTACACCATCTTTCTTCTAAGTTTA<br>AATTTTGTCGAAACTCGTGTGTGTTCTACTTGAATGATCAA<br>TTTTAGTTTCACAGCTTCTTGGCAAGCAACATTGCGCAA<br>CACAGTGTGCAGGTCCATCATGTCTTCCTGAGGCAACAAGG<br>AGATGTTGTCAACAGAGACACCCTCAAGGAAAACCTTGA<br>TATTATCAAAGCTAGAAACTACATAACCCATTGCAATGTCT<br>TCAACAAACATTGCTCTTGATACTTTATTATTCCTAACT<br>GACAAGGTAAAATCTGTGAGTTCAGCTAGATCTACTTGACT<br>GTCATCTTCTAGATCTAGAACTTCATTGAACCAAAAGAA<br>GGATTTGAGACACGATGTTGACATGACTAGTGGGTTTATCA<br>TCGAAGATAAGACAACTTGCACCATGAAGTTCCTGCAAA<br>CTTGCTGTGGGCTGATGCCAACTTCCCAATTTGTATACTCT<br>GACTGTCTAACATGGGCTGAAGCGCAATCACTCTGTTTC |

TABLE 3-continued

Illustrative amino acid sequences.

| SEQ ID NO: Description | Sequence |
|---|---|
| | ACAATATAAACATTATTATCTCTTACTTTCAATAAGTGACT
TATAATCCCTAAGTTTTCATTCATCATGTCTAGAGCCAC
ACAGACATCTAGAAACTTGAGTCTTCCACTATCCAAAGATC
TGTTCACTTGAAGATCATTCATAAAGGGTGCCAAATGTT
CTTCAAATAGTTTGGGGTAATTTCTTCGTATAGAATGCAAT
ACATGGTTCATGCCTAATTGGTCTTCTATCTGTCGTACT
GCTTTGGGTTTAACAGCCCAGAAGAAATTCTTATTACATAA
GACCAGAGGGGCCTGTGGACTCTTAATAGCAGAAAACAC
CCACTCCCTAACTCACAGGCATTTGTCAGCACCAAAGAGA
AGTAATCCCACAAAATTGGTTTAGAAAATTGGTTAACTT
CTTTAAGTGATTTTTGACAGTAAATAACTTTAGGCTTTCTC
TCACAAATTCCACAAAGACATGGCATTATTCGAGTAAAT
ATGTCCTTTATATACAGAAATCCGCCTTTACCATCCCTAAC
ACACTTACTCCCCATACTCTTACAAAACCCAATGAAGCC
TGAGGCAACAGAAGACTGAAATGCAGATTTGTTGATTGACT
CTGCCAAGATCTTCTTCACGCCTTTTGTGAAATTTCTTG
ACAGCCTGGACTGTATTGTCCTTATCAATGTTGGCATCTCT
TCTTTCTCTAACACTCTTCGACTTGTCATGAGTTTGGTC
CTCAAGACCAACCTCAAGTCCCCAAAGCTCGCTAAATTGAC
CCATCTGTAGTCTAGAGTTTGTCTGATTTCATCTTCACT
ACACCCGGCATATTGCAGGAATCCGGATAAAGCCTCATCCC
CTCCCCTGCTTATCAAGTTGATAAGGTTTTCCTCAAAGA
TTTTGCCTCTCTTAATGTCATTGAACACTTTCCTCGCGCAG
TTCCTTATAAACATTGTCTCCTTATCATCAGAAAAAATA
GCTTCAATTTTCCTCTGTAGACGGTACCCTCTAGACCCATC
AACCCAGTCTTTGACATCTTGTTCTTCAATAGCTCCAAA
CGGAGTCTCTCTGTATCCAGAGTATCTAATCAATTGGTTGA
CTCTAATGGAAATCTTTGACACTATATGAGTGCTAACCC
CATTAGCAATACATTGATCACAAATTGTGTCTATGGTCTCT
GACAGTTGTGTTGGAGTTTTACACTTAACGTTGTGTAGA
GCAGCAGACACAAACTTGGTGAGTAAAGGAGTCTCTTCACC
CATGACAAAAAATCTTGACTTAAACTCAGCAACAAAAGTTC
CTATCACACTCTTTGGGCTGATAAACTTGTTTAATTTAGAA
GATAAGAATTCATGGAAGCACACCATTTCCAGCAGTT
CTGTCCTGTCTTGAAACTTTTCATCACTAAGGCAAGGAATT
TTTTATAAGGCTAACCTGGTCATCGCTGGAGGTATAAGTG
ACAGGTATCACATCATACAATAAGTCAAGTGCATAACACAG
AAATTGTTCAGTAATTAGCCCATATAAATCTGATGTGTT
GTGCAAGATTCCCTGGCCCATGTCCAAGACAGACATTATAT
GGCTGGGGACCTGGTCCCTTGACTGCAGATACTGGTGAA
AAAACTCTTCACCAACACTAGTACAGTCACAACCCATTAAA
CCTAAAGATCTCTTCAATTTCCCTACACAGTAGGCTTCT
GCAACATTAATTGGAACTTCAACGACCTTATGAAGATGCCA
TTTGAGAATGTTCATTACTGGTTCAAGATTCACCTTTGT
TCTATCTCTGGGATTCTTCAATTCTAATGTGTACAAAAAAG
AAAGGAAAAGTGCTGGGCTCATAGTTGGTCCCCATTTGG
AGTGGTCATATGAACAGGACAAGTCACCATTGTTAACAGCC
ATTTTCATATCACAGATTGCACGTTCGAATTCCTTTTCT
GAATTCAAGCATGTGTATTTCATTGAACTACCCACAGCTTC
TGAGAAGTCTTCAACTAACCTGGTCATCAGCTTAGTGTT
GAGGTCTCCCACATACAGTTCTCTATTTGAGCCAACCTGCT
CCTTATAACTTAGTCCAAATTTCAAGTTCCCTGTATTTG
AGCTGATGCTTGTGAACTCTGTAGGAGAGTCGTCTGAATAG
AAACATAAATTCCGTAGGGCTGCATTTGTAAAATAACTT
TTGTCTAGCTTATCAGCAATGGCTTCAGAATTGCTTTCCCT
GGTACTAAGCCGAACCTCATCCTTTAGTCTCAGAACTTC
ACTGGAAAAGCCCAATCTAGATCTACTTCTATGCTCATAAC
TACCCAATTTCTGATCATAATGTCCTTGAATTAAAAGAT
ACTTGAAGCATTCAAAGAATTCATCTTCTTGGTAGGCTATT
GTTGTCAAATTTTTTAATAACAAACCCAAAGGGCAGATG
TCCTGCGGTGCTTCAAGAAAATAAGTCAATTTAAATGGAGA
TAGATAAACAGCATCACATAACTCTTTATACACATCAGA
CCTGAGCACATCTGGATCAAAATCCTTCACCTCATGCATTG
ACACCTCTGCTTTAATCTCTCTCAACACTCCAAAAGGGG
CCCACAATGACTCAAGAGACTCTCGCTCATCAACAGATGGA
TTTTTTGATTTCAACTTGGTGATCTCAACTTTTGTCCCC
TCACTATTAGCCACTTGGCTAGTGTCATTTGTACGTCATT
TCTAATACCCTCAAAGGCCCTTACTTGATCCTCTGTTAA
ACTCTCATACATCACTGATAATTCTTCTTGATTGGTTCTGG
TTCTTGAACCGGTGCTCACAAGACCTGTTAGATTTTTA
ATATTAAGTAGTCCATGGAATCAGGATCAAGATTATACCTG
CCTTTTGTTTTAAACCTCTCAGCCATAGTAGAAACGCAT
GTTGAAACAAGTTTCTCCTTATCATAAACAGAAAGAATATT
TCCAAGTTCGTCGAGCTTGGGGATTACCACACTTTTATT |

TABLE 3-continued

Illustrative amino acid sequences.

| SEQ ID NO: | Description | Sequence |
|---|---|---|
| | | GCTTGACAGATCCAGAGCTGTGCTAGTGATGTTAGGCCTGT
AGGGATTGCTTTTCAGTTCACCTGTAACTTTAAGTCTTC
CTCTATTGAAGAGAGAAATGCAGAAGGACAAAATCTCTTTA
CACACTCCTGGAATTTGAGTATCTGAGGAAGTCTTAGCC
TCTTTGGAAAAGAATCTGTCCAATCCTCTTATCATGGTGTC
CTCTTGTTCCAGTGTTAGACTCCCACTTAGAGGGGGGTT
TACAACAACACAATCAAACTTGACTTTGGGCTCAATAAACT
TCTCAAAACACTTTATTTGATCTGTCAGGCGATCAGGTG
TCTCTTTGGTTACCAAGTGACACAGATAACTAACATTTAAT
AGATATTTAAACCTTCTTGCAAAGTAAAGATCTGCATCT
TCCCCTTCACCCAAAATTGTCTGGAAAAGTTCCACAGCCAT
CCTCTGAATCAGCACCTCTGATCCAGACATGCAGTCGAC
CCTTAACTTTGACATCAAATCCACATGATGGATTTGATTTG
CATATGCCATCAAGAAATATCTTAGACCTTGTAAAAATG
TCTGGTTCCTTTTGGAAGGGGAACAGAGTACAGCTAACACT
AACAATCTTAATATTGGCCTTGTCATTGTCATGAGTTCG
TGGCTAAAATCCAACCAGCTGGTCATTTCCTCACACATTTC
AATTAACACATCCTCCGAAAATATAGGCAGGAAAAATCT
CTTTGGATCACAGTAAAAAGAGCCTTGTTCTTCCAATACCC
CATTGATGGATAGATAGATAGAATAGCACCTTGACTTCT
CACCTGTTTTTTGGTAAAACAAGAGACCAAATGTATTCTTT
GTCAGATGAAATCTTTGTACATAACACTCTCTTAGTCTA
ACATTCCCAAAATATCTAGAATACTCTCTTTCATTGATTAA
CAATCGGGAGGAAAATGATGTCTTCATCGAGTTGACCAA
TGCAAGGGAAATGGAGGACAAAATCCTAAATAATTTCTTCT
GCTCACCTTCCACTAAGCTGCTGAATGGCTGATGTCTAC
AGATTTTCTCAAATTCCTTGTTAATAGTATATCTCATCACT
GGTCTGTCAGAAACAAGTGCCTGAGCTAAAATCATCAAG
CTATCCATATCAGGGTGTTTTATTAGTTTTTCCAGCTGTGA
CCAGAGATCTTGATGAGAGTTCTTCAATGTTCTGGAACA
CGCTTGAACCCACTTGGGGCTGGTCATCAATTTCTTCCTTA
TTAGTTTAATCGCCTCCAGAATATCTAGAAGTCTGTCAT
TGACTAACATTAACATTTGTCCAACAACTATTCCCGCATTT
CTTAACCTTACAATTGCATCATCATGCGTTTTGAAAAGA
TCACAAAGTAAATTGAGTAAAACTAAGTCCAGAAACAGTAA
AGTGTTTCTCCTGGTGTTGAAAACTTTTAGACCTTTCAC
TTTGTTACACACGGAAAGGGCTTGAAGATAACACCTCTCTA
CAGCATCAATAGATATAGAATTCTCATCTGACTGGCTTT
CCATGTTGACTTCATCTATTGGATGCAATGCGATAGAGTAG
ACTACATCCATCAACTTGTTTGCACAAAAAGGGCAGCTG
GGCACATCACTGTCTTTGTGGCTTCCTAATAAGATCAAGTC
ATTTATAAGCTTAGACTTTTGTGAAAATTTGAATTTCCC
CAACTGCTTGTCAAAAATCTCCTTCTTAAACCAAAACCTTA
ACTTTATGAGTTCTTCTCTTATGACAGATTCTCTAATGT
CTCCTCTAACCCCAACAAAGAGGGATTCATTTAACCTCTCA
TCATAACCCAAAGAATTCTTTTTCAAGCATTCGATGTTT
TCTAATCCCAAGCTCTGGTTTTTTGTGTTGGACAAACTATG
GATCAATCGCTGGTATTCTTGTTCTTCAATATTAATCTC
TTGCATAAATTTTGATTTCTTTAGGATGTCGATCAGCAACC
ACCGAACTCTTTCAACAACCCAATCAGCAAGGAATCTAT
TGCTGTAGCTAGATCTGCCATCAACCACAGGAACCAACGTA
ATCCCTGCCCTTAGTAGGTCGGACTTTAGGTTTAAGAGC
TTTGACATGTCACTCTTCCATTTTCTCTCAAACTCATCAGG
ATTGACCCTAACAAAGGTTTCCAATAGGATGAGTGTTTT
CCCTGTGAGTTTGAAGCCATCCGGAATGACTTTTGGAAGGG
TGGGACATAGTATGCCATAGTCAGACAGGATCACATCAA
CAAACTTCTGATCTGAATTGATCTGACAGGCGTGTGCCTCA
CAGGACTCAAGCTCTACTAAACTTGACAGAAGTTTGAAC
CCTTCCAACAACAGAGAGCTGGGGTGATGTTGAGATAAAAA
GATGTCCCTTTGGTATGCTAGCTCCTGTCTTTCTGGAAA
ATGCTTTCTAATAAGGCTTTTTATTTCATTTACTGATTCCT
CCATGCTCAAGTGCCGCCTAGGATCCTCGGTGCG |
| 20 | Junin virus Candid+1901 S segment | GCGCACCGGGGATCCTAGGCGATTTTGGTTACGCTATAATT
GTAACTGTTTCTGTTTGGACAACATCAAAAACATCCATTG
CACAATGGGGCAGTTCATTAGCTTCATGCAAGAAATACCAA
CCTTTTTGCAGGAGGCTCTGAACATTGCTCTTGTTGC
AGTCAGTCTCATTGCCATCATTAAGGGTATAGTGAACTTGT
ACAAAAGTGGTTTATTCCAATTCTTTGTATTCCTAGCGC
TTGCAGGAAGATCCTGCACAGAAGAAGCTTTCAAAATCGGA
CTGCACACTGAGTTCCAGACTGTGTCCTTCTCAATGGTG
GGTCTCTTTTCCAACAATCCACATGACCTACCTTTGTTGTG
TACCTTAAACAAGAGCCATCTTTACATTAAGGGGGGCAA
TGCTTCATTTCAGATCAGCTTTGATGATATTGCAGTATTGT |

TABLE 3-continued

Illustrative amino acid sequences.

| SEQ ID NO: | Description | Sequence |
|---|---|---|
| | | TGCCACAGTATGATGTTATAATACAACATCCAGCAGATA
TGAGCTGGTGTTCCAAAAGTGATGATCAAATTTGGTTGTCT
CAGTGGTTCATGAATGCTGTGGGACATGATTGGCATCTA
GACCCACCATTTCTGTGTAGGAACCGTGCAAAGACAGAAGG
CTTCATCTTTCAAGTCAACACCTCCAAGACTGGTGTCAA
TGGAAATTATGCTAAGAAGTTTAAGACTGGCATGCATCATT
TATATAGAGAATATCCTGACCCTTGCTTGAATGGCAAAC
TGTGCTTAATGAAGGCACAACCTACCAGTTGGCCTCTCCAA
TGTCCACTCGACCACGTTAACACATTACACTTCCTTACA
AGAGGTAAAAACATTCAACTTCCAAGGAGGTCCTTGAAAGC
ATTCTTCTCCTGGTCTTTGACAGACTCATCCGGCAAGGA
TACCCCTGGAGGCTATTGTCTAGAAGAGTGGATGCTCGTAG
CAGCCAAAATGAAGTGTTTTGGCAATACTGCTGTAGCAA
AATGCAATTTGAATCATGACTCTGAATTCTGTGACATGTTG
AGGCTCTTTGATTACAACAAAATGCTATCAAACCCTA
AATGATGAAACTAAGAAACAAGTAAATCTGATGGGGCAGAC
AATCAATGCCCTGATATCTGACAATTTATTGATGAAAAA
CAAAATTAGGGAACTGATGAGTGTCCCTTACTGCAATTACA
CAAAATTTTGGTATGTCAACCACACACTTTCAGGACAAC
ACTCATTACCAAGGTGCTGGTTAATAAAAAACAACAGCTAT
TTGAACATCTCTGACTTCCGTAATGACTGGATATTAGAA
AGTGACTTCTTAATTTCTGAAATGCTAAGCAAAGAGTATTC
GGACAGGCAGGGTAAAACTCCTTTGACTTTAGTTGACAT
CTGTATTTGGAGCACAGTATTCTTCACAGCGTCACTCTTCC
TTCACTTGGTGGGTATACCCTCCCACAGACACATCAGGG
GCGAAGCATGCCCTTTGCCACACAGGTTGAACAGCTTGGGT
GGTTGCAGATGTGGTAAGTACCCCAATCTAAAGAAACCA
ACAGTTTGGCGTAGAGGACACTAAGACCTCCTGAGGGTCCC
CACCAGCCCGGGCACTGCCCGGGCTGGTGTGGCCCCCCAGT
CCGCGGCCTGGCCGCGGACTGGGGAGGCACTGCTTACAGTG
CATAGGCTGCCTTCGGGAGGAACAGCAAGCTCGGTGGTAAT
AGAGGTGTAGGTTCCTCCTCATAGAGCTTCCCATCTAGCAC
TGACTGAAACATTATGCAGTCTAGCAGAGCACAGTGTGGTT
CACTGGAGGCCAACTTGAAGGGAGTATCCTTTTCCCTCTTT
TTCTTATTGACAACCACTCCATTGTGATATTTG
CATAAGTGACCATATTTCTCCCAGACCTGTTGATCAAACTG
CCTGGCTTGTTCAGATGTGAGCTTAACATCAACCAGTTT
AAGATCTCTTCTTCCATGGAGGTCAAACAACTTCCTGATGT
CATCGGATCCTTGAGTAGTCACAACCATGTCTGGAGGCA
GCAAGCCGATCACGTAACTAAGAACTCCTGGCATTGCATCT
TCTATGTCCTTCATTAAGATGCCGTGAGAGTGTCTGCTA
CCATTTTTAAACCCTTTCTCATCATGTGGTTTTCTGAAGCA
GTGAATGTACTGCTTACCTGCAGGTTGGAATAATGCCAT
CTCAACAGGGTCAGTGGCTGGTCCTTCAATGTGAGCCAAA
GGGTGTTGGTGGGGTCGAGTTTCCCCACTGCCTCTCTGA
TGACAGCTTCTTGTATCTCTGTCAAGTTAGCCAATCTCAAA
TTCTGACCGTTTTTTTCCGGCTGTCTAGGACCAGCAACT
GGTTTCCTTGTCAGATCAATACTTGTGTTGTCCCATGACCT
GCCTGTGATTTGTGATCTAGAACCAATATAAGGCCAACC
ATCGCCAGAAAGACAAAGTTTGTACAAAAGGTTTTCATAAG
GATTTCTATTGCCTGGTTTCTCATCAATAAACATGCCTT
CTCTTCGTTTAACCTGAATGGTTGATTTTATGAGGGAAGAG
AAGTTTTCTGGGGTGACTCTGATTGTTTCCAACATGTTT
CCACCATCAAGAATAGATGCTCCAGCCTTTACTGCAGCTGA
AAGACTGAAGTTGTAACCAGAAATATTGATGGAGCTTTC
ATCTTTAGTCACAATCTGAAGGCAGTCATGTTCCTGAGTCA
GTCTGTCAAGGTCACTTAAGTTTGGATACTTCACAGTGT
ATAGAAGCCCAAGTGAGGTTAAAGCTTGTATGACACTGTTC
ATTGTCTCACCTCCTTGAACAGTCATGCATGCAATTGIC
AATGCAGGAACAGAGCCAAACTGATTGTTAGCTTTGAAGG
GTCTTTAACATCCCATATCCTCACCACACCATTTCCCCC
AGTCCCTTGCTGTTGAAATCCCAGTGTTCTCAATATCTCTG
ATCTTTTAGCAAGTTGTGACTGGGACAAGTTACCCATGT
AAACCCCCTGAGAGCCTGTCTCTGCTCTTCTTATCTTGTTT
TTTAATTTCTCAAGGTCAGACGCCAACTCCATCAGTTCA
TCCCTCCCCAGATCTCCCACCTTGAAAACTGTGTTTCGTTG
AACACTCCTCATGGACATGAGTCTGTCAACCTCTTTATT
CAGGTCCCTCAACTTGTTGAGGTCTTCTTCCCCCTTTTAG
TCTTTCTGAGTGCCCGCTGCACCTGTGCCACTTGGTTGA
AGTCGATGCTGTCAGCAATTAGCTTGGCGTCCTTCAAAACA
TCTGACTTGACAGTCTGAGTGAATTGGCTCAAACCTCTC
CTTAAGGACTGAGTCCATCTAAAGCTTGGAACCTCCTTGGA
GTGTGCCATGCCAGAAGTTCTGGTGATTTTGATCTAGAA |

TABLE 3-continued

Illustrative amino acid sequences.

| SEQ ID NO: | Description | Sequence |
|---|---|---|
| | | TAGAGTTGCTCAGTGAAAGTGTTAGACACTATGCCTAGGAT CCACTGTGCG |
| 21 | amino acid sequence of the NP protein of the Clone 13 strain of LCMV (GenBank Accession No. ABC96002.1; GI: 86440166) | MSLSKEVKSFQWTQALRRELQSFTSDVKAAVIKDATNLLNG LDFSEVSNVQRIMRKEKRDDKDLQRLRSLNQTVHSLVDLKS TSKKNVLKVGRLSAEELMSLAADLEKLKAKIMRSERPQASG VYMGNLTTQQLDQRSQILQIVGMRKPQQGASGVVRVWDVKD SSLLNNQFGTMPSLTMACMAKQSQTPLNDVVQALTDLGLLY TVKYPNLNDLERLKDKHPVLGVITEQQSSINISGYNFSLGA AVKAGAALLDGGNMLESILIKPSNSEDLLKAVLGAKRKLNM FVSDQVGDRNPYENILYKVCLSGEGWPYIACRTSIVGRAWE NTTIDLTSEKPAVNSPRPAPGAAGPPQVGLSYSQTMLLKDL MGGIDPNAPTWIDIEGRFNDPVEIAIFQPQNGQFIHFYREP VDQKQFKQDSKYSHGMDLADLFNAQPGLTSSVIGALPQGMV LSCQGSDDIRKLLDSQNRKDIKLIDVEMTREASREYEDKVW DKYGWLCKMHTGIVRDKKKKEITPHCALMDCIIFESASKAR LPDLKTVHNILPHDLIFRGPNVVTL |
| 22 | amino acid sequence of the GP protein of the Clone 13 strain of LCMV (GenBank Accession No. ABC96001.2; GI: 116563462) | MGQIVTMFEALPHIIDEVINIVIIVLIVITGIKAVYNFATC GIFALISFLLLAGRSCGMYGLKGPDIYKGVYQFKSVEFDMS HLNLTMPNACSANNSHHYISMGTSGLELTFTNDSIISHNFC NLTSAFNKKTFDHTLMSIVSSLHLSIRGNSNYKAVSCDFNN GITIQYNLTFSDAQSAQSQCRTFRGRVLDMFRTAFGGKYMR SGWGWTGSDGKTTWCSQTSYQYLIIQNRTWENHCTYAGPFG MSRILLSQEKTKFLTRRLAGTFTWTLSDSSGVENPGGYCLT KWMILAAELKCFGNTAVAKCNVNHDEEFCDMLRLIDYNKAA LSKFKEDVESALHLFKTTVNSLISDQLLMRNHLRDLMGVPY CNYSKFWYLEHAKTGETSVPKCWLVTNGSYLNETHFSDQIE QEADNMITEMLRKDYIKRQGSTPLALMDLLMFSTSAYLVSI FLHLVKIPTHRHIKGGSCPKPHRLTNKGICSCGAFKVPGVK TVWKRR |
| 23 | amino acid sequence of the L protein of the Clone 13 strain of LCMV (GenBank Accession No. ABC96004.1; GI: 86440169) | MDEIISELRELCLNYIEQDERLSRQKLNFLGQREPRMVLIE GLKLLSRCIEIDSADKSGCTHNHDDKSVETILVESGIVCPG LPLIIPDGYKLIDNSLILLECFVRSTPASFEKKFIEDTNKL ACIREDLAVAGVTLVPIVDGRCDYDNSFMPEWANFKFRDLL FKLLEYSNQNEKVFEESEYFRLCESLKTTIDKRSGMDSMKI LKDARSTHNDEIMRMCHEGINPNMSCDDVVFGINSLFSRFR RDLESGKLKRNFQKVNPEGLIKEFSELYENLADSDDILTLS REAVESCPLMRFITAETHGHERGSETSTEYERLLSMLNKVK SLKLLNTRRRQLLNLDVLCLSSLIKQSKFKGLKNDKHWVGC CYSSVNDRLVSFHSTKEEFIRLLRNRKKSKVFRKVSFEELF RASISEFIAKIQKCLLVVGLSFEHYGLSEHLEQECHIPFTE FENFMKIGAHPIMYYTKFEDYNFQPSTEQLKNIQSLRRLSS VCLALTNSMKTSSVARLRQNQIGSVRYQVVECKEVFCQVIK LDSEEYHLLYQKTGESSRCYSIQGPDGHLISFYADPKRFFL PIFSDEVLYNMIDIMISWIRSCPDLKDCLTDIEVALRTLLL LMLTNPTKRNQKQVQSVRYLVMAIVSDFSSTSLMDKLREDL ITPAEKVVYKLLRFLIKTIFGTGEKVLLSAKFKFMLNVSYL CHLITKETPDRLTDQIKCFEKFFEPKSQFGFFVNPKEAITP EEECVFYEQMKRFTSKEIDCQHTTPGVNLEAFSLMVSSFNN GTLIFKGEKKLNSLDPMTNSGCATALDLASNKSVVVNKHLN GERLLEYDFNKLLVSAVSQITESFVRKQKYKLSHSDYEYKV SKLVSRLVIGSKGEETGRSEDNLAEICFDGEEETSFFKSLE EKVNTTIARYRRGRRANDKGDGEKLTNTKGLHHLQLILTGK MAHLRKVILSEISFHLVEDFDPSCLTNDDMKFICEAVEGST ELSPLYFTSVIKDQCGLDEMAKNLCRKFFSENDWFSCMKMI LLQMNANAYSGKYRHMQRQGLNFKFDWDKLEEDVRISERES NSESLSKALSLIQCMSAALKNLCFYSEESPTSYTSVGPDSG RLKFALSYKEQVGGNRELYIGDLRTKMFTRLIEDYFESFSS FFSGSCLNNDKEFENAILSMTINVREGFLNYSMDHSKWGPM MCPFLFLMFLQNLKLGDDQYVRSGKDHVSTLLTWHMHKLVE VPFPVVNAMMKSYVKSKLKLLRGSETTVTERIFRQYFEMGI VPSHISSLIDMGQGILHNASDFYGLLSERFINYCIGVIFGE RPEAYTSSDDQITLFDRRLSDLVVSDPEEVLVLLEFQSHLS GLLNKFISPKSVAGRFAAEFKSRFYVWGEEVPLLTKFVSAA LHNVKCKEPHQLCETIDTIADQAIANGVPVSLVNSIQRRTL DLLKYANFPLDPFLLNTNTDVKDWLDGSRGYRIQRLIEELC PNETKVVRKLVRKLHHKLKNGEFNEEFFLDLFNRDKKEAIL QLGDLLGLEEDLNQLADVNWLNLNEMFPLRMVLRQKVVYPS VMTFQEERIPSLIKTLQNKLCSKFTRGAQKLLSEAINKSAF QSCISSGFIGLCKTLGSRCVRNKNRENLYIKKLLEDLTTDD HVTRVCNRDGITLYICDKQSHPEAHRDHICLLRPLLWDYIC ISLSNSFELGVWVLAEPTKGKNNSENLTLKHLNPCDYVARK |

TABLE 3-continued

Illustrative amino acid sequences.

| SEQ ID NO: | Description | Sequence |
|---|---|---|
| | | PESSRLLEDKVNLNQVIQSVRRLYPKIFEDQLLPFMSDMSS KNMRWSPRIKFLDLCVLIDINSESLSLISHVVKWKRDEHYT VLFSDLANSHQRSDSSLVDEFVVSTRDVCKNFLKQVYFESF VREFVATTRTLGNFSWFPHKEMMPSEDGAEALGPFQSFVSK VVNKNVERPMFRNDLQFGFGWFSYRMGDVVCNAAMLIRQGL TNPKAFKSLKDLWDYMLNYTKGVLEFSISVDFTHNQNNTDC LRKFSLIFLVRCQLQNPGVAELLSCSHLFKGEIDRRMLDEC LHLLRTDSVFKVNDGVFDIRSEEFEDYMEDPLILGDSLELE LLGSKRILDGIRSIDFERVGPEWEPVPLTVKMGALFEGRNL VQNIIVKLETKDMKVFLAGLEGYEKISDVLGNLFLHRFRTG EHLLGSEISVILQELCIDRSILLIPLSLLPDWFAFKDCRLC FSKSRSTLMYETVGGRFRLKGRSCDDWLGGSVAEDID |
| 24 | amino acid sequence of the Z protein of the Clone 13 strain of LCMV (GenBank Accession No. ABC96003.1; GI: 86440168) | MGQGKSREEKGTNSTNRAEILPDTTYLGPLSCKSCWQKFDS LVRCHDHYLCRHCLNLLLSVSDRCPLCKYPLPTRLKISTAP SSPPPYEE |
| 25 | amino acid sequence of the GP protein of the WE strain of LCMV | MGQIVTMFEALPHIIDEVINIVIIVLIIITSIKAVYNFATC GILALVSFLFLAGRSCGMYGLNGPDIYKGVYQFKSVEFDMS HLNLTMPNACSANNSHHYISMGSSGLELTFTNDSILNHNFC NLTSAFNKKTFDHTLMSIVSSLHLSIRGNSNHKAVSCDFNN GITIQYNLSFSDPQSAISQCRTFRGRVLDMFRTAFGGKYMR SGWGWAGSDGKTTWCSQTSYQYLIIQNRTWENHCRYAGPFG MSRILFAQEKTKFLTRRLAGTFTWTLSDSSGVENPGGYCLT KWMILAAELKCFGNTAVAKCNVNHDEEFCDMLRLIDYNKAA LSKFKQDVESALHVFKTTVNSLISDQLLMRNHLRDLMGVPY CNYSKFWYLEHAKTGETSVPKCWLVTNGSYLNETHFSDQIE QEADNMITEMLRKDYIKRQGSTPLALMDLLMFSTSAYLISI FLHLVKIPTHRHIKGGSCPKPHRLTNKGICSCGAFKVPGVK TIWKRR |
| 26 | nucleotide sequence of the HBV HBe antigen (GenBank Accession No. E15688.1; GI: 5710371) | ATGGACATTGACACGTATAAAGAATTTGGAGCTACTGTGGA GTTACTCTCGTTTTTGCCTTCTGACTTCTTTCCTTCCGTCA GAGATCTCCTAGACACCGCCTCAGCTCTGTATCGAGAAGCC TTAGAGTCTCCTGAGCATTGCTCACCTCACCATACTGCACT CAGGCAAGCCATTCTCTGCTGGGGGAATTGATGACTCTAG CTACCTGGGTGGGTAATAATTTGGAAGATCCAGCATCCAGG GATCTAGTAGTCAATTATGTTAATACTAACATGGGTTTAAA GATCAGGCAACTATTGTGGTTTCATATATCTTGCCTTACTT TTGGAAGAGAGACTGTACTTGAATATTTGGTCTCTTTCGGA GTGTGGATTCGCACTCCTCCAGCCTATAGACCACCAAATGC CCCTATCTTATCAACACTTCCGGAAACTACTGTTGTTTAA |

7. EXAMPLES

7.1 Design of Arenavirus Vector Genome/Vector Construction

Based on established approaches (U.S. Patent Application Publication No. US 2010/0297172 A1; and Flatz L. et al., Nat Med. 2010 March; 16(3): 339-345), LCMV- and Junin Virus (JUNV)-based vaccine vectors expressing the respective HBV antigens or certain domains thereof are designed (FIG. 1).

7.2 Vaccines Against Hepatitis B Virus

Candidate vaccines against hepatitis B virus (HBV) comprise rLCMV-based and rJUNV (Junin vaccine strain Candid#1) vectors expressing pre-S2/S (rLCMV/pre-S2/S, rJUNV/Pre-S2/S), HBc (rLCMV/HBc, rJUNV/HBc), a fusion protein consisting of the full length HBs and HBc ORFs (rLCMV/HBsHBc), and HBe (rLCMV/HBe, rJUNV/HBe). Vectors will be replication-deficient (r2LCMV, also referred to as rLCMV, r2JUNV, also referred to as rJUNV) and replication-competent trisegmented constructs (r3LCMV, r3JUNV; see, e.g., Emonet et al., 2009, PNAS, 106(9):3473-3478), wherein the transgenes are arranged in a so-called "artificial" way (r3LCMV$^{art}$, r3JUNV$^{art}$). Mice (e.g., C57BL/6 mice) are immunized with one of these constructs, or with combinations thereof in a homologous or heterologous prime-boost vaccination. Administration is performed via the intraperitoneal, intramuscular, or intravenous route. The dose will be in the range of $10^4$ to $10^7$ focus forming units (FFU). At time points ranging from 7 to 100 days after immunization, HBV-specific CD8+ T cells are measured in the blood and/or spleen. T cells may be measured, for example, by using MHC class I tetramers in combination with anti-CD8 antibodies in order to identify the magnitude of the CD8+ T cell response to HBV-derived epitopes.

In a complementary approach, synthetic peptides are used to selectively stimulate directly ex vivo blood and/or spleen-derived CD8+ T cells by means of intracellular cytokine assays. The intracellular cytokine assays measure the frequency of interferon (IFN)-γ, tumor necrosis factor (TNF)-α, and/or interleukin (IL)-2-producing CD8+ T cells. Surface expression of CD107a serves as a marker of cytolytic degranulation in flow cytometry (FACS). Peptide specificities are analyzed, including: HBs-derived epitope VWLSVIWM (SEQ ID NO: 8), HBs-derived epitope IPQSLDSWWTSL (SEQ ID NO: 9), and HBc-derived epitope MGLKFRQL (SEQ ID NO: 10).

7.3 Immunogenicity of Replication-Deficient Arenavirus-Based Vectors Expressing HBV Antigens C57BL/6 mice (5 mice per group) were immunized once with $10^5$ FFU of rLCMV/HBs-HBc (group 1), rLCMV/HBc (group 3), rLCMV/Pre-S2 (group 4), or with $10^4$ FFU of rLCMV/HBs-HBc (group 2), via the intravenous route. Control mice were left untreated. 10 days after immunization CD8+ T cells were measured in the blood by using MHC class I multimers. H-2K$^b$ dextramers complexed with the HBs-derived epitope VWLSVIWM and H-2K$^b$ dextramers complexed with the HBc-derived epitope MGLKFRQL were used in combination with anti-CD8α antibody to identify hepatitis B virus-specific CD8+ T cells. The enumerated cells were expressed as a percentage of the total CD8$^+$B220$^-$ T cell pool in peripheral blood.

Figure 3:
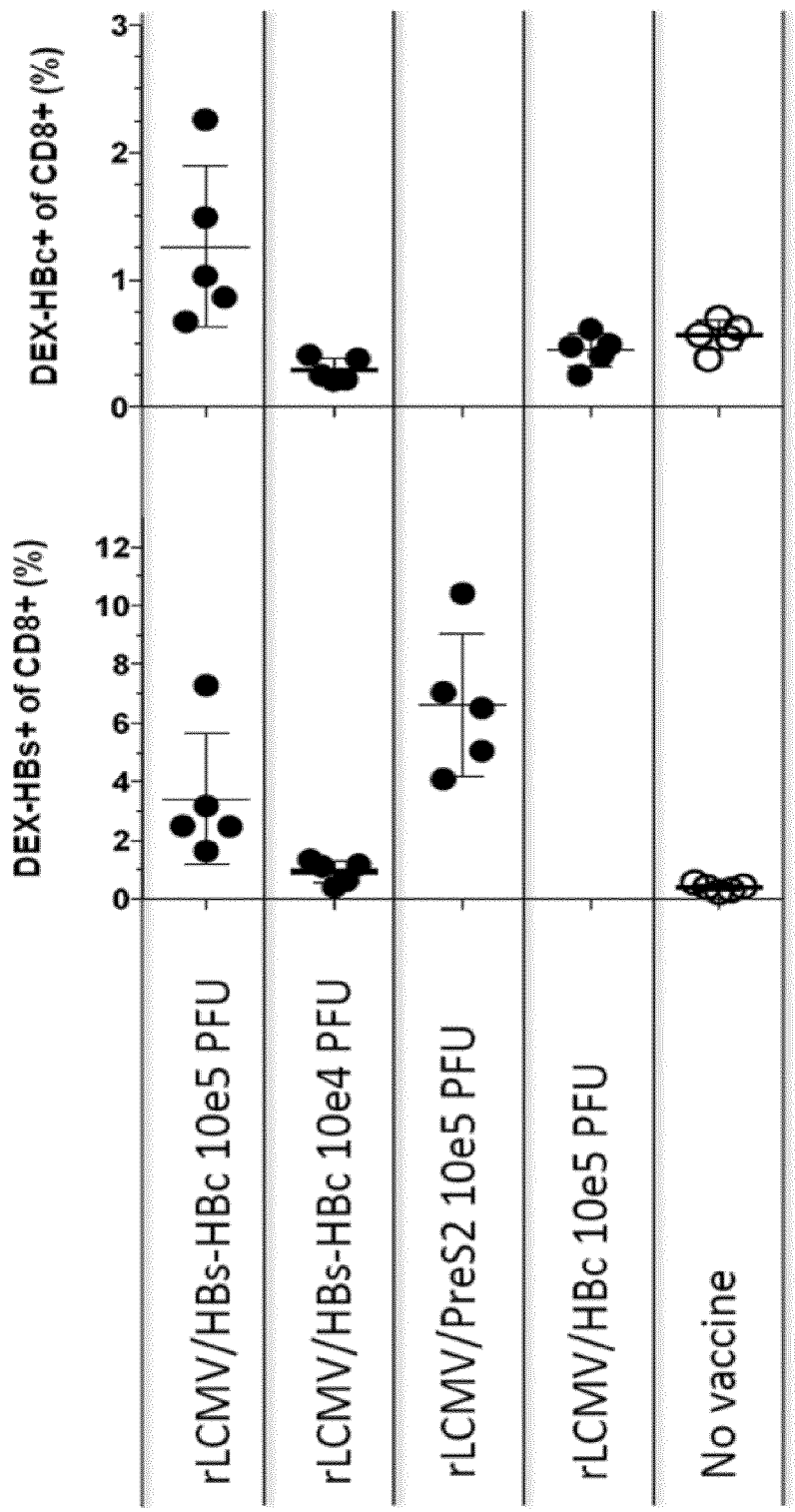

The results, as shown in FIG. 3, indicate that vaccination with rLCMV/HBs-HBc, rLCMV/HBc and rLCMV/Pre-S2 induces substantial antigen-specific CD8+ T cell responses against the antigens expressed by the respective vectors. The anti-HBs and anti-HBc CD8+ T cell responses induced by vaccination with rLCMV/HBs-HBc showed a clear dose dependency. Higher frequencies of anti-HBc CD8+ T cells upon rLCMV/HBs-HBc immunization as compared to rLCMV/HBc immunization indicate that fusion to HBs results in augmented immunogenicity of HBc.

Anti-HBs CD8+ T cell frequencies were somewhat higher after immunization with rLCMV/Pre-S2 than after immunization with rLCMV/HBs-HBc, raising the possibility that anti-HBc CD8+ T cell responses competed with anti-HBs responses for antigen availability.

Figure 4A:
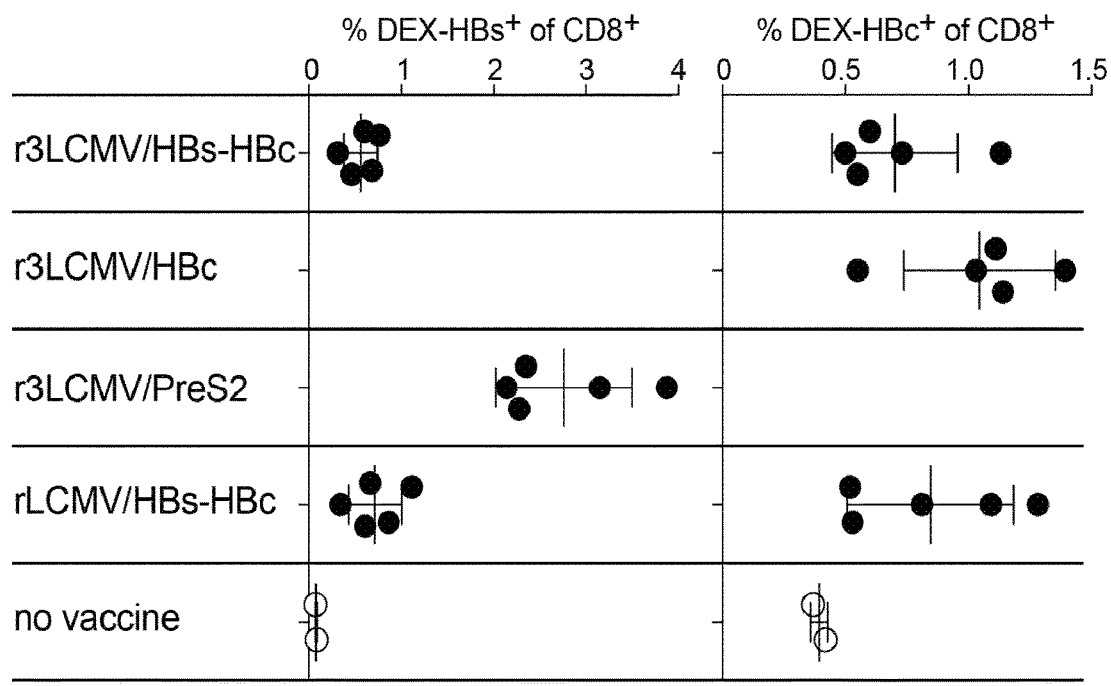
Figure 4B:
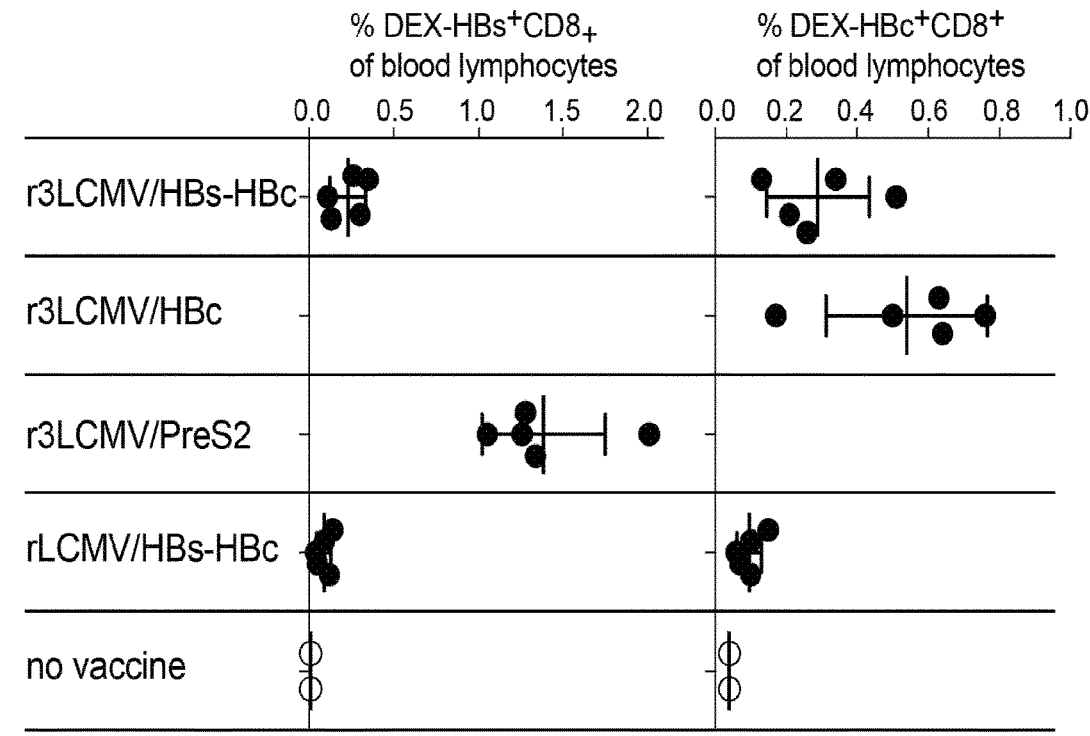

7.4 Immunogenicity of Attenuated Replication-Competent Arenavirus-Based Vectors Expressing HBV Antigens C57BL/6 mice (5 mice per group) were immunized once with $10^5$ FFU of r3LCMV/HBs-HBc (group 1), r3LCMV/HBc (group 2), r3LCMV/Pre-S2 (group 3), or with $10^5$ FFU of rLCMV/HBs-HBc (group 4), via the intravenous route. Control mice were left without vaccination. 8 days after immunization HBs- and HBc-epitope-specific CD8+ T cells were measured in the blood by using MHC class I multimers. H-2K$^b$ dextramers complexed with the HBs-derived epitope VWLSVIWM and H-2K$^b$ dextramers complexed with the HBc-derived epitope MGLKFRQL were used in combination with anti-CD8a antibody to identify hepatitis B virus-specific CD8+ T cells. The enumerated cells were expressed in two different ways, either as a percentage of the total CD8$^+$B220$^-$ T cell pool in peripheral blood (FIG. 4A) or as a percentage of circulating lymphocytes in blood (FIG. 4B).

The results, as shown in FIG. 4, indicate that all r3LCMV-based constructs as well as the replication-deficient rLCMV/HBs-HBc reference vector were immunogenic, eliciting epitope-specific CD8+ T cells against their vectorized antigens, respectively. Moreover, when enumerating epitope-specific CD8+ T cells as a percentage of circulating lymphocytes, the replicating r3LCMV/HBs-HBc is shown to be more immunogenic than its replication-deficient counterpart rLCMV/HBs-HBc.

Equivalents and Incorporation by Reference

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following embodiments. All references (including patent applications, patents, and publications) cited herein are incorporated herein by reference in their entireties and for all purposes to the same extent as if each individual publication or patent or patent application was specifically and individually indicated to be incorporated by reference in its entirety for all purposes.

What is claimed is:

1. An infectious arenavirus viral vector, wherein the arenavirus is lymphocytic choriomeningitis virus, and wherein the open reading frame encoding the glycoprotein (GP) of the arenavirus viral vector is removed and replaced by a nucleotide sequence selected from the group consisting of:
   a) a nucleotide sequence encoding an HBV middle surface antigen (pre-S2/S) protein or an antigenic fragment thereof;
   b) a nucleotide sequence encoding an HBV core antigen (HBc) protein or an antigenic fragment thereof; and
   c) a nucleotide sequence encoding a fusion of HBV surface antigen (HBs) and HBc proteins or antigenic fragments thereof.

2. The viral vector of claim 1 wherein the pre-S2/S protein or the antigenic fragment thereof comprises an amino acid sequence that is at least 80% identical to an amino acid sequence encoded by the nucleotide sequence of SEQ ID NO: 1.

3. The viral vector of claim 1 wherein the HBc protein or the antigenic fragment thereof comprises an amino acid sequence that is at least 80% identical to an amino acid sequence encoded by the nucleotide sequence of SEQ ID NO: 2.

4. The viral vector of claim 1 wherein fusion of HBV HBs and HBc proteins or antigenic fragments thereof comprise an amino acid sequence that is at least 80% identical to an amino acid sequence encoded by the nucleotide sequence of SEQ ID NO: 3.

5. The viral vector of claim 1 comprising at least two nucleotide sequences selected from the group consisting of:
   a) a nucleotide sequence encoding an HBV pre-S2/S protein or an antigenic fragment thereof;
   b) a nucleotide sequence encoding an HBV HBc protein or an antigenic fragment thereof; and
   c) a nucleotide sequence encoding a fusion of HBV HBs and HBc proteins or antigenic fragments thereof.

6. The viral vector of claim 1 comprising at least three nucleotide sequences selected from the group consisting of:
   a) a nucleotide sequence encoding an HBV pre-S2/S protein or an antigenic fragment thereof;
   b) a nucleotide sequence encoding an HBV HBc protein or an antigenic fragment thereof; and
   c) a nucleotide sequence encoding a fusion of HBV HBs and HBc proteins or antigenic fragments thereof.

7. The viral vector of claim 5 or 6 wherein expression of the nucleotide sequences produces an antigenic protein complex that elicits higher titers of neutralizing antibodies than expression of the antigenic protein complex components individually.

8. The viral vector of claim 1 wherein the lymphocytic choriomeningitis virus is the lymphocytic choriomeningitis virus Clone 13 strain or the lymphocytic choriomeningitis virus MP strain.

9. The viral vector of claim 1 wherein the viral vector comprises a genomic segment, wherein the genomic segment comprises a nucleotide sequence that is at least 90% identical to the sequence of nucleotide 1639 to 3315 of SEQ ID NO: 11 or 1640 to 3316 of SEQ ID NO: 12, or at least 90% identical to the amino acid sequence encoded by nucleotide 1639 to 3315 of SEQ ID NO: 11 or 1640 to 3316 of SEQ ID NO: 12.

10. The viral vector of claim 1, wherein the growth or infectivity of the arenavirus is not affected by the nucleotide sequence.

11. A pharmaceutical composition, immunogenic composition, or vaccine comprising the viral vector of claim 1 and a pharmaceutically acceptable carrier.

12. A method of immunizing against a HBV infection or treating or preventing a disease associated with a HBV infection or symptoms of a HBV infection in a patient, wherein said method comprises administering to the patient the viral vector of claim 1.

13. An isolated nucleic acid, wherein the nucleic acid comprises an arenavirus genomic short segment of lymphocytic choriomeningitis virus, and wherein the open reading frame encoding the glycoprotein (GP) of the genomic short segment is deleted or functionally inactivated and wherein the genomic segment comprises one or more of:
   a) a nucleotide sequence encoding an HBV middle surface antigen (pre-S2/S) protein or an antigenic fragment thereof;
   b) a nucleotide sequence encoding an HBV core antigen (HBc) protein or an antigenic fragment thereof; and
   c) a nucleotide sequence encoding a fusion of HBV surface antigen (HBs) and HBc proteins or antigenic fragments thereof.

14. A method for generating an infectious, replication-deficient arenavirus viral vector comprising:
   a) transfecting into a host cell the nucleic acid of claim 13;
   b) maintaining the host cell under conditions suitable for virus formation; and
   c) harvesting the infectious, replication-deficient arenavirus viral vector;
   wherein the host cell expresses the open reading frame encoding the glycoprotein (GP) that is deleted or functionally inactivated of the genomic segment.

15. An infectious, replication-deficient arenavirus viral vector, wherein the arenavirus is lymphocytic choriomeningitis virus engineered to contain a genome with the ability to amplify and express its genetic information in infected cells but unable to produce further infectious progeny particles in normal, not genetically engineered cells, wherein the open reading frame encoding the glycoprotein (GP) of the arenavirus viral vector is removed and replaced by a nucleotide sequence selected from the group consisting of:
   a) a nucleotide sequence encoding an HBV middle surface antigen (pre-S2/S) protein or an antigenic fragment thereof;
   b) a nucleotide sequence encoding an HBV core antigen (HBc) protein or an antigenic fragment thereof; and
   c) a nucleotide sequence encoding a fusion of HBV surface antigen (HBs) and HBc proteins or antigenic fragments thereof
   wherein administration of the arenavirus viral vector to a subject induces a long-lasting immune response against the HBV antigen or an antigenic fragment thereof.

16. The arenavirus viral vector of claim 15, wherein the long-lasting immune response:
- induces a detectable antibody titer against an HBV antigen or an antigenic fragment thereof and increases the antibody titer against the HBV antigen or an antigenic fragment thereof by at least 100%; or
- induces a detectable antibody titer against the HBV antigen or an antigenic fragment thereof for at least a minimum of 4 weeks and increases the antibody titer against the HBV antigen or an antigenic fragment thereof by at least 100%.

17. A pharmaceutical composition comprising a first infectious, replication-deficient arenavirus viral vector, wherein the arenavirus is lymphocytic choriomeningitis virus engineered to contain a genome with the ability to amplify and express its genetic information in infected cells but unable to produce further infectious progeny particles in normal, not genetically engineered cells, wherein the open reading frame encoding the glycoprotein (GP) of the arenavirus viral vector is removed and replaced by a first nucleotide sequence selected from the group consisting of:
- a) a nucleotide sequence encoding an HBV middle surface antigen (pre-S2/S) protein or an antigenic fragment thereof;
- b) a nucleotide sequence encoding an HBV core antigen (HBc) protein or an antigenic fragment thereof; and
- c) a nucleotide sequence encoding a fusion of HBV surface antigen (HBs) and HBc proteins or antigenic fragments thereof;

and a second infectious, replication-deficient arenavirus viral vector, wherein the arenavirus is lymphocytic choriomeningitis virus engineered to contain a genome with the ability to amplify and express its genetic information in infected cells but unable to produce further infectious progeny particles in normal, not genetically engineered cells, wherein the open reading frame encoding the GP of the second arenavirus viral vector is removed and replaced by a second nucleotide sequence selected from the group consisting of:
- a) a nucleotide sequence encoding an HBV middle surface antigen (pre-S2/S) protein or an antigenic fragment thereof;
- b) a nucleotide sequence encoding an HBV core antigen (HBc) protein or an antigenic fragment thereof; and
- c) a nucleotide sequence encoding a fusion of HBV surface antigen (HBs) and HBc proteins or antigenic fragments thereof.

18. The pharmaceutical composition of claim 17, wherein the first nucleotide sequence and the second nucleotide sequence are different.

19. The pharmaceutical composition of claim 17, wherein the first nucleotide sequence encodes the HBV pre-S2/S protein or fragment thereof, and wherein the second nucleotide sequence encodes:
- the HBV HBc protein or a fragment thereof; or
- the fusion of the HBV HBs and HBc proteins or fragments thereof.

20. The pharmaceutical composition of claim 17, wherein the composition is suitable for intramuscular or intravenous administration.

21. The method of claim 14 further comprises in step a) transfecting into the host cell: a cDNA of the second arenavirus genomic segment, a nucleic acid comprising the L protein ORF, and/or a nucleic acid comprising the NP protein ORF.

22. The viral vector of claim 1, wherein the arenavirus is replication-deficient and is engineered to contain a genome with the ability to amplify and express its genetic information in infected cells but unable to produce further infectious progeny particles in normal, not genetically engineered cells.

23. The viral vector of claim 1, wherein the arenavirus is bisegmented and replication-deficient.

24. The viral vector of claim 1, wherein the arenavirus is trisegmented and replication-competent.

25. The viral vector of claim 1, wherein the HBV HBs is an HBV small surface antigen.

26. The nucleic acid of claim 13, wherein the HBV HBs is an HBV small surface antigen.

27. The viral vector of claim 15, wherein the HBV HBs is an HBV small surface antigen.

28. The pharmaceutical composition of claim 17, wherein the HBV HBs is an HBV small surface antigen.

29. The viral vector of claim 1, wherein the open reading frame encoding the GP is removed and replaced by a nucleotide sequence encoding an HBV middle surface antigen (pre-S2/S) protein or an antigenic fragment thereof.

30. The viral vector of claim 1, wherein the open reading frame encoding the GP is removed and replaced by a nucleotide sequence encoding an HBV core antigen (HBc) protein or an antigenic fragment thereof.

31. The viral vector of claim 1, wherein the open reading frame encoding the GP is removed and replaced by a nucleotide sequence encoding a fusion of HBV surface antigen (HBs) and HBc proteins or antigenic fragments thereof.

32. The viral vector of claim 15, wherein the open reading frame encoding the GP is removed and replaced by a nucleotide sequence encoding an HBV middle surface antigen (pre-S2/S) protein or an antigenic fragment thereof.

33. The viral vector of claim 15, wherein the open reading frame encoding the GP is removed and replaced by a nucleotide sequence encoding an HBV core antigen (HBc) protein or an antigenic fragment thereof.

34. The viral vector of claim 15, wherein the open reading frame encoding the GP is removed and replaced by a nucleotide sequence encoding a fusion of HBV surface antigen (HBs) and HBc proteins or antigenic fragments thereof.

* * * * *

SEQUENCE LISTING

<160> NUMBER OF SEQ ID NOS: 26

<210> SEQ ID NO 1
<211> LENGTH: 846
<212> TYPE: DNA
<213> ORGANISM: Artificial Sequence
<220> FEATURE:
<223> OTHER INFORMATION: HBV pre-S2/S ORF

<400> SEQUENCE: 1

```
atgcagtgga attccacaac cttccaccaa actctgcaag atcccagagt gagaggcctg      60
tatttccctg ctggtggctc cagttcagga acagtcaacc ctgttctgac cactgcctct     120
cccttgtcat caatcttctc caggattggg gaccctgctc tgaacatgga gaacatcaca     180
tcaggattcc tgggacccct tcttgtgttg caggcagggt ttttcttgtt gacaagaatc     240
ctcacaatcc ctcagagtct ggactcttgg tggacttctc tcaattttct gggggggaacc     300 acagtgtgtc ttggccaaaa ttctcagtcc ccaacctcca atcactcacc aacctcttgt     360
cctccaactt gtcctggtta cagatggatg tgtctgagga gattcatcat cttcctcttc     420
atcctgctgc tgtgcctcat cttcttgttg gttcttctgg actatcaagg aatgttgcca     480
gtttgtcctc tgattccagg atcctcaaca accagcactg gaccatgcag gacctgcatg     540
accactgctc aaggaacctc aatgtatccc tcctgttgct gcaccaaacc ttcagatgga     600
```

-continued

```
aattgcacct gcattcccat cccatcatcc tgggcttttg gaaaattcct ttgggagtgg      660
gcctcagcca gattctcctg gctcagtttg ctggtgccat tgttcagtg gtttgttggg       720 ctttccccca ctgtttggct ttcagtgatt tggatgatgt ggtattgggg gccaagtctg      780
tacagcatct tgagtccctt tttgcctctg ttgccaattt tcttttgtct ttgggtctac      840
atttaa                                                                 846

<210> SEQ ID NO 2
<211> LENGTH: 552
<212> TYPE: DNA
<213> ORGANISM: Artificial Sequence
<220> FEATURE:
<223> OTHER INFORMATION: HBV HBc ORF

<400> SEQUENCE: 2
atggacattg acccttacaa agaatttgga gcaactgtgg agttgctctc cttttgcct       60 tctgacttct ttccttcagt gagagatctt cttgacactg cctcagctct gtacagggaa     120
gccttggagt ctcctgagca ttgttcacct caccacactg cactcaggca agcaattctt     180
tgctgggggg aactcatgac tctggcaacc tgggtgggtg tcaatttgga agatccagcc     240
tcaagagacc ttgtggtcag ttatgtcaac acaaacatgg gcctgaagtt caggcaactc     300
ttgtggtttc acatttcttg tctcactttt ggaagagaaa cagtcattga gtatttggtg     360
tcttttggag tgtggatcag gactcctcca gcttacagac caccaaatgc ccaatcctg      420 tcaacacttc cagagaccac tgttgtcaga agaagaggca ggtccccag aagaagaact     480 ccctcaccaa gaagaagaag gtctcaatct cccagaagga agatctca atcaagggaa      540 tctcaatgtt ag                                                          552

<210> SEQ ID NO 3
<211> LENGTH: 1719
<212> TYPE: DNA
<213> ORGANISM: Artificial Sequence
<220> FEATURE:
<223> OTHER INFORMATION: HBV HBs-HBc fusion protein ORF

<400> SEQUENCE: 3
atggggcaga atctttccac cagcaatcct ctgggattct ttccagacca ccagttggat      60
ccagccttca gagcaaacac tgcaaatcca gattgggact tcaatcccaa caaggacacc     120
tggccagatg ccaacaaggt gggagctgga gcatttgggc tgggtttcac cccacccccat    180 ggaggccttt gggggtggag ccctcaggct cagggcattc tgcaaacttt gccagcaaat    240
ccacctcctg cctccaccaa caggcagtca ggaaggcagc ccacccctct gtctccacct     300
ttgagaaaca ctcatcctca ggccatgcag tggaattcca caaccttcca ccaaactctg    360
caagatccca gagtgagagg cctgtatttc cctgctggtg gctccagttc aggaacagtc    420
aaccctgttc tgaccactgc ctctcccttg tcatcaatct tctccaggat tggggaccct    480
gctctgaaca tggagaacat cacatcagga ttcctgggac ccttcttgt gttgcaggca     540 gggttttct tgttgacaag aatcctcaca atccctcaga gtctggactc ttggtggact    600
tctctcaatt ttctgggggg aaccacagtg tgtcttggcc aaaattctca gtccccaacc    660
tccaatcact caccaaccct ttgtcctcca acttgtcctg gttacagatg gatgtgtctg    720
aggagattca tcatcttcct cttcatcctg ctgctgtgcc tcatcttctt gttggttctt    780
ctggactatc aaggaatgtt gccagtttgt cctctgattc caggatcctc aacaaccagc    840
```

```
actggaccat gcaggacctg catgaccact gctcaaggaa cctcaatgta tccctcctgt    900
tgctgcacca aaccttcaga tggaaattgc acctgcattc ccatcccatc atcctgggct    960
tttggaaaat tcctttggga gtgggcctca gccagattct cctggctcag tttgctggtg   1020
ccatttgttc agtggtttgt tgggcttccc ccactgtttt ggctttcagt gatttggatg   1080
atgtggtatt gggggccaag tctgtacagc atcttgagtc ccttttttgcc tctgttgcca   1140 attttctttt gtctttgggt ctacattatg acattgacc cttacaaaga atttggagca    1200
actgtggagt tgctctcctt tttgccttct gacttctttc cttcagtgag agatcttctt   1260
gacactgcct cagctctgta cagggaagcc ttggagtctc ctgagcattg ttcacctcac    1320
cacactgcac tcaggcaagc aattctttgc tgggggggaac tcatgactct ggcaacctgg   1380
gtgggtgtca atttgaaga tccagcctca agagaccttg tggtcagtta tgtcaacaca    1440
aacatgggcc tgaagttcag gcaactcttg tggttttcaca tttcttgtct cacttttgga   1500
agagaaacag tcattgagta tttggtgtct tttggagtgt ggatcaggac tcctccagct    1560
tacagaccac caaatgcccc aatcctgtca acacttccag agaccactgt tgtcagaaga    1620
agaggcaggt cccccagaag aagaactccc tcaccaagaa gaagaaggtc tcaatctccc    1680
agaaggagaa gatctcaatc aagggaatct caatgttag                           1719

<210> SEQ ID NO 4
<211> LENGTH: 3599
<212> TYPE: DNA
<213> ORGANISM: Artificial Sequence
<220> FEATURE:
<223> OTHER INFORMATION: cDNA of LCMV S segment expressing HBV HBs-HBc
      fusion protein

<400> SEQUENCE: 4
gcgcaccggg gatcctaggc tttttggatt gcgctttcct ctagatcaac tgggtgtcag    60
gccctatcct acagaaggat ggggcagaat cttttccacca gcaatcctct gggattcttt   120
ccagaccacc agttggatcc agccttcaga gcaaacactg caaatccaga ttgggacttc   180
aatcccaaca aggacacctg ccagatgcc aacaaggtgg agctggagc atttgggctg     240 ggtttcaccc caccccatgg aggccttttg gggtggagcc ctcaggctca gggcattctg    300
caaactttgc cagcaaatcc acctcctgcc tccaccaaca ggcagtcagg aaggcagccc    360 accccctctgt ctccaccttt gagaaacact catcctcagg ccatgcagtg gaattccaca   420
accttccacc aaactctgca agatcccaga gtgagaggcc tgtatttccc tgctggtggc    480
tccagttcag gaacagtcaa ccctgttctg accactgcct ctcccttgtc atcaatcttc    540
tccaggattg gggaccctgc tctgaacatg gagaacatca catcaggatt cctgggaccc    600
cttcttgtgt tgcaggcagg ttttttcttg ttgacaagaa tcctcacaat ccctcagagt    660
ctggactctt ggtggacttc tctcaatttt ctgggggaa ccacagtgtg tcttggccaa    720
aattctcagt ccccaacctc caatcactca ccaacctctt gtcctccaac ttgtcctggt    780
tacagatgga tgtgtctgag gagattcatc atcttcctct tcatcctgct gctgtgcctc    840
atcttcttgt tggttcttct ggactatcaa ggaatgttgc cagtttgtcc tctgattcca    900
ggatcctcaa caaccagcac tggaccatgc aggacctgca tgaccactgc tcaaggaacc    960
tcaatgtatc cctcctgttg ctgcaccaaa ccttcagatg gaaattgcac ctgcattccc    1020
atcccatcat cctgggcttt tggaaaattc ctttgggagt gggcctcagc cagattctcc   1080
tggctcagtt tgctggtgcc atttgttcag tggtttgttg ggctttcccc cactgtttgg   1140
```

```
ctttcagtga tttggatgat gtggtattgg gggccaagtc tgtacagcat cttgagtccc    1200 ttttttgcctc tgttgccaat tttcttttgt ctttgggtct acattatgga cattgaccct    1260
tacaaagaat ttggagcaac tgtggagttg ctctccttttt tgccttctga cttctttcct    1320
tcagtgagag atcttcttga cactgcctca gctctgtaca gggaagcctt ggagtctcct    1380
gagcattgtt cacctcacca cactgcactc aggcaagcaa ttctttgctg gggggaactc    1440
atgactctgg caacctgggt gggtgtcaat ttggaagatc cagcctcaag agaccttgtg    1500
gtcagttatg tcaacacaaa catgggcctg aagttcaggc aactcttgtg gtttcacatt    1560
tcttgtctca cttttggaag agaaacagtc attgagtatt tggtgtcttt tggagtgtgg    1620
atcaggactc ctccagctta cagaccacca aatgccccaa tcctgtcaac acttccagag    1680
accactgttg tcagaagaag aggcaggtcc cccagaagaa gaactccctc accaagaaga    1740
agaaggtctc aatctcccag aaggagaaga tctcaatcaa gggaatctca atgttagaga    1800
acagcgcctc cctgactctc cacctcgaaa gaggtggaga gtcagggagg cccagagggt    1860
cttagagtgt cacaacattt gggcctctaa aaattaggtc atgtggcaga atgttgtgaa    1920
cagttttcag atctgggagc cttgcttttgg aggcgctttc aaaaatgatg cagtccatga    1980
gtgcacagtg cgggggtgatc tctttcttct ttttgtccct tactattcca gtatgcatct    2040
tacacaacca gccatatttg tcccacactt tatcttcata ctccctcgaa gcttccctgg    2100
tcatttcaac atcgataagc ttaatgtcct tcctattttg tgagtccaga agctttctga    2160
tgtcatcgga gccttgacag cttagaacca tccccctgcgg aagagcacct ataactgacg    2220
aggtcaaccc gggttgcgca ttgaagaggt cggcaagatc catgccgtgt gagtacttgg    2280
aatcttgctt gaattgtttt tgatcaacgg gttccctgta aaagtgtatg aactgcccgt    2340
tctgtggttg gaaaattgct atttccactg gatcattaaa tctaccctca atgtcaatcc    2400
atgtaggagc gttggggtca attcctccca tgaggtcttt taaaagcatt gtctggctgt    2460
agcttaagcc cacctgaggt ggacctgctg ctccaggcgc tggcctgggt gagttgactg    2520
caggtttctc gcttgtgaga tcaattgttg tgttttccca tgctctcccc acaatcgatg    2580
ttctacaagc tatgtatggc catccttcac ctgaaaggca aactttatag aggatgtttt    2640
cataagggtt cctgtcccca acttggtctg aaacaaacat gttgagtttt ctcttggccc    2700
cgagaactgc cttcaagaga tcctcgctgt tgcttggctt gatcaaaatt gactctaaca    2760 tgttacccccc atccaacagg gctgcccctg ccttcacggc agcaccaaga ctaaagttat    2820
agccagaaat gttgatgctg gactgctgtt cagtgatgac ccccagaact gggtgcttgt    2880
ctttcagcct ttcaagatca ttaagatttg gatacttgac tgtgtaaagc aagccaaggt    2940
ctgtgagcgc ttgtacaacg tcattgagcg gagtctgtga ctgtttggcc atacaagcca    3000
tagttagact tggcattgtg ccaaattgat tgttcaaaag tgatgagtct ttcacatccc    3060
aaactcttac cacaccactt gcaccctgct gaggctttct catcccaact atctgtagga    3120
tctgagatct ttggtctagt tgctgtgttg ttaagttccc catatatacc cctgaagcct    3180
ggggcctttc agacctcatg atcttggcct tcagcttctc aaggtcagcc gcaagagaca    3240
tcagttcttc tgcactgagc ctccccactt tcaaaacatt cttctttgat gttgactttta    3300 aatccacaag agaatgtaca gtctggttga gacttctgag tctctgtagg tctttgtcat    3360
ctctcttttc cttcctcatg atcctctgaa cattgctgac ctcagagaag tccaacccat    3420
tcagaaggtt ggttgcatcc ttaatgacag cagccttcac atctgatgtg aagctctgca    3480
attctcttct caatgcttgc gtccattgga agctcttaac ttccttagac aaggacatct    3540
```
tgttgctcaa tggtttctca agacaaatgc gcaatcaaat gcctaggatc cactgtgcg   3599

<210> SEQ ID NO 5
<211> LENGTH: 2432
<212> TYPE: DNA
<213> ORGANISM: Artificial Sequence
<220> FEATURE:
<223> OTHER INFORMATION: cDNA of LCMV S segment expressing the HBc ORF

<400> SEQUENCE: 5

```
gcgcaccggg gatcctaggc tttttggatt gcgctttcct ctagatcaac tgggtgtcag    60
gccctatcct acagaaggat ggacattgac ccttacaaag aatttggagc aactgtggag   120
ttgctctcct ttttgccttc tgacttcttt ccttcagtga gagatcttct tgacactgcc   180
tcagctctgt acaggaagc cttggagtct cctgagcatt gttcacctca ccacactgca   240
ctcaggcaag caattctttg ctgggggga ctcatgactc tggcaacctg ggtgggtgtc   300
aatttggaag atccagcctc aagagacctt gtggtcagtt atgtcaacac aaacatgggc   360
ctgaagttca ggcaactctt gtggtttcac atttcttgtc tcacttttgg aagagaaaca   420
gtcattgagt atttggtgtc ttttggagtg tggatcagga ctcctccagc ttacagacca   480
ccaaatgccc caatcctgtc aacacttcca gagaccactg ttgtcagaag aagaggcagg   540
tcccccagaa gaagaactcc ctcaccaaga agaagaaggt ctcaatctcc cagaaggaga   600
agatctcaat caagggaatc tcaatgttag agaacagcgc ctccctgact ctccacctcg   660
aaagaggtgg agagtcaggg aggcccagag ggtcttagag tgtcacaaca tttgggcctc   720
taaaaattag gtcatgtggc agaatgttgt gaacagtttt cagatctggg agccttgctt   780
tggaggcgct ttcaaaaatg atgcagtcca tgagtgcaca gtgcgggtg atctctttct   840 tcttttttgtc ccttactatt ccagtatgca tcttacacaa ccagccatat tgtcccaca   900 ctttatcttc atactccctc gaagcttccc tggtcatttc aacatcgata agcttaatgt   960
ccttcctatt ttgtgagtcc agaagctttc tgatgtcatc ggagccttga cagcttagaa   1020
ccatcccctg cggaagagca cctataactg acgaggtcaa cccgggttgc gcattgaaga   1080
ggtcggcaag atccatgccg tgtgagtact tggaatcttg cttgaattgt ttttgatcaa   1140
cgggttccct gtaaaagtgt atgaactgcc cgttctgtgg ttggaaaatt gctatttcca   1200
ctggatcatt aaatctaccc tcaatgtcaa tccatgtagg agcgttgggg tcaattcctc   1260
ccatgaggtc ttttaaaagc attgtctggc tgtagcttaa gcccacctga ggtggacctg   1320
ctgctccagg cgctggcctg ggtgagttga ctgcaggttt ctcgcttgtg agatcaattg   1380
ttgtgttttc ccatgctctc cccacaatcg atgttctaca agctatgtat ggccatcctt   1440
cacctgaaag gcaaacttta tagaggatgt tttcataagg gttcctgtcc ccaacttggt   1500
ctgaaacaaa catgttgagt tttctcttgg ccccgagaac tgccttcaag agatcctcgc   1560
tgttgcttgg cttgatcaaa attgactcta acatgttacc cccatccaac agggctgccc   1620
ctgccttcac ggcagcacca agactaaagt tatagccaga aatgttgatg ctggactgct   1680
gttcagtgat gacccccaga actgggtgct tgtctttcag cctttcaaga tcattaagat   1740
ttggatactt gactgtgtaa agcaagccaa ggtctgtgag cgcttgtaca acgtcattga   1800
gcggagtctg tgactgtttg gccatacaag ccatagttag acttggcatt gtgccaaatt   1860
gattgttcaa aagtgatgag tctttcacat cccaaactct taccacacca cttgcaccct   1920
gctgaggctt tctcatccca actatctgta ggatctgaga tctttggtct agttgctgtg   1980
```

```
ttgttaagtt ccccatatat acccctgaag cctggggcct ttcagacctc atgatcttgg    2040
ccttcagctt ctcaaggtca gccgcaagag acatcagttc ttctgcactg agcctcccca    2100 cttttcaaaac attcttcttt gatgttgact ttaaatccac aagagaatgt acagtctggt    2160
tgagacttct gagtctctgt aggtctttgt catctctctt ttccttcctc atgatcctct    2220
gaacattgct gacctcagag aagtccaacc cattcagaag gttggttgca tccttaatga    2280
cagcagcctt cacatctgat gtgaagctct gcaattctct tctcaatgct tgcgtccatt    2340
ggaagctctt aacttcctta gacaaggaca tcttgttgct caatggtttc tcaagacaaa    2400
tgcgcaatca aatgcctagg atccactgtg cg                                  2432
```

<210> SEQ ID NO 6
<211> LENGTH: 2726
<212> TYPE: DNA
<213> ORGANISM: Artificial Sequence
<220> FEATURE:
<223> OTHER INFORMATION: cDNA of LCMV S segment expressing the pre-S2/S
      ORF

<400> SEQUENCE: 6

```
gcgcaccggg gatcctaggc tttttggatt gcgctttcct ctagatcaac tgggtgtcag     60
gccctatcct acagaaggat gcagtggaat tccacaacct tccaccaaac tctgcaagat    120
cccagagtga gaggcctgta tttccctgct ggtggctcca gttcaggaac agtcaaccct    180
gttctgacca ctgcctctcc cttgtcatca atcttctcca ggattgggga ccctgctctg    240
aacatggaga acatcacatc aggattcctg ggacccttc ttgtgttgca ggcagggttt    300
ttcttgttga caagaatcct cacaatccct cagagtctgg actcttggtg gacttctctc    360
aattttctgg ggggaaccac agtgtgtctt ggccaaaatt ctcagtcccc aacctccaat    420
cactcaccaa cctcttgtcc tccaacttgt cctggttaca gatggatgtg tctgaggaga    480
ttcatcatct tcctcttcat cctgctgctg tgcctcatct tcttgttggt tcttctggac    540
tatcaaggaa tgttgccagt ttgtcctctg attccaggat cctcaacaac cagcactgga    600
ccatgcagga cctgcatgac cactgctcaa ggaacctcaa tgtatccctc ctgttgctgc    660
accaaacctt cagatggaaa ttgcacctgc attcccatcc catcatcctg ggcttttgga    720
aaattccttt gggagtgggc ctcagccaga ttctcctggc tcagtttgct ggtgccattt    780
gttcagtggt ttgttgggct ttcccccact gttttggctt cagtgatttg gatgatgtgg    840 tattggggc caagtctgta cagcatcttg agtccttttt gcctctgtt gccaattttc    900 ttttgtcttt gggtctacat ttaaagaaca gcgcctccct gactctccac ctcgaaagag    960
gtggagagtc agggaggccc agagggtctt agagtgtcac aacatttggg cctctaaaaa   1020
ttaggtcatg tggcagaatg ttgtgaacag ttttcagatc tgggagcctt gctttggagg   1080
cgctttcaaa aatgatgcag tccatgagtg cacagtgcgg ggtgatctct ttcttcttt    1140 tgtcccttac tattccagta tgcatcttac acaaccagcc atatttgtcc cacactttat   1200
cttcatactc cctcgaagct tccctggtca tttcaacatc gataagctta atgtccttcc   1260
tattttgtga gtccagaagc tttctgatgt catcggagcc ttgacagctt agaaccatcc   1320
cctgcggaag agcacctata actgacgagg tcaacccggg ttgcgcattg aagaggtcgg   1380
caagatccat gccgtgtgag tacttggaat cttgcttgaa ttgttttga tcaacgggtt    1440 ccctgtaaaa gtgtatgaac tgcccgttct gtggttggaa aattgctatt tccactggat   1500
cattaaatct accctcaatg tcaatccatg taggagcgtt ggggtcaatt cctcccatga   1560
```

| | |
|---|---|
| ggtcttttaa aagcattgtc tggctgtagc ttaagcccac ctgaggtgga cctgctgctc | 1620 |
| caggcgctgg cctgggtgag ttgactgcag gtttctcgct tgtgagatca attgttgtgt | 1680 |
| tttcccatgc tctccccaca atcgatgttc tacaagctat gtatggccat ccttcacctg | 1740 |
| aaaggcaaac tttatagagg atgttttcat aagggttcct gtccccaact tggtctgaaa | 1800 |
| caaacatgtt gagttttctc ttggccccga gaactgcctt caagagatcc tcgctgttgc | 1860 |
| ttggcttgat caaaattgac tctaacatgt taccccatc caacagggct gccctgcct | 1920 |
| tcacggcagc accaagacta agttatagc cagaaatgtt gatgctggac tgctgttcag | 1980 |
| tgatgacccc cagaactggg tgcttgtctt tcagcctttc aagatcatta agatttggat | 2040 |
| acttgactgt gtaaagcaag ccaaggtctg tgagcgcttg tacaacgtca ttgagcggag | 2100 |
| tctgtgactg tttggccata caagccatag ttagacttgg cattgtgcca aattgattgt | 2160 |
| tcaaaagtga tgagtctttc acatcccaaa ctcttaccac accacttgca ccctgctgag | 2220 |
| gctttctcat cccaactatc tgtaggatct gagatctttg gtctagttgc tgtgttgtta | 2280 |
| agttccccat atataccct gaagcctggg gcctttcaga cctcatgatc ttggccttca | 2340 |
| gcttctcaag gtcagccgca agagacatca gttcttctgc actgagcctc cccactttca | 2400 |
| aaacattctt ctttgatgtt gactttaaat ccacaagaga atgtacagtc tggttgagac | 2460 |
| ttctgagtct ctgtaggtct ttgtcatctc tcttttcctt cctcatgatc ctctgaacat | 2520 |
| tgctgacctc agaagaagtcc aacccattca gaaggttggg tgcatcctta atgacagcag | 2580 |
| ccttcacatc tgatgtgaag ctctgcaatt ctcttctcaa tgcttgcgtc cattggaagc | 2640 |
| tcttaacttc cttagacaag gacatcttgt tgctcaatgg tttctcaaga caaatgcgca | 2700 |
| atcaaatgcc taggatccac tgtgcg | 2726 |

<210> SEQ ID NO 7
<211> LENGTH: 7229
<212> TYPE: DNA
<213> ORGANISM: Artificial Sequence
<220> FEATURE:
<223> OTHER INFORMATION: lymphocytic choriomeningitis virus clone 13
      segment L (GenBank: DQ361066.1)

<400> SEQUENCE: 7

| | |
|---|---|
| gcgcaccggg gatcctaggc gtttagttgc gctgtttggt tgcacaactt tcttcgtgag | 60 |
| gctgtcagaa gtggacctgg ctgatagcga tgggtcaagg caagtccaga gaggagaaag | 120 |
| gcaccaatag tacaaacagg gccgaaatcc taccagatac cacctatctt ggcccttttaa | 180 |
| gctgcaaatc ttgctggcag aaatttgaca gcttggtaag atgccatgac cactacctt | 240 |
| gcaggcactg tttaaacctt ctgctgtcag tatccgacag gtgtcctctt tgtaaatatc | 300 |
| cattaccaac cagattgaag atatcaacag ccccaagctc tccacctccc tacgaagagt | 360 |
| aacaccgtcc ggccccggcc ccgacaaaca gcccagcaca agggaaccgc acgtcaccca | 420 |
| acgcacacag acacagcacc caacacagaa cacgcacaca cacacacaca cacacccaca | 480 |
| cgcacgcgcc cccaccaccg gggggcgccc ccccccgggg ggcggccccc cgggagcccg | 540 |
| ggcggagccc cacggagatg cccatcagtc gatgtcctcg gccaccgacc cgcccagcca | 600 |
| atcgtcgcag gacctcccct tgagtctaaa cctgcccccc actgtttcat acatcaaagt | 660 |
| gctcctagat ttgctaaaac aaagtctgca atccttaaag gcgaaccagt ctggcaaaag | 720 |
| cgacagtgga atcagcagaa tagatctgtc tatacatagt tcctggagga ttacacttat | 780 |
| ctctgaaccc aacaaatgtt caccagttct gaatcgatgc aggaagaggt tcccaaggac | 840 |

```
atcactaatc ttttcatagc cctcaagtcc tgctagaaag actttcatgt ccttggtctc      900
cagcttcaca atgatatttt ggacaaggtt tcttccttca aaaagggcac ccatctttac      960
agtcagtggc acaggctccc actcaggtcc aactctctca aagtcaatag atctaatccc     1020
atccagtatt cttttggagc ccaacaactc aagctcaaga gaatcaccaa gtatcaaggg     1080
atcttccatg taatcctcaa actcttcaga tctgatatca aagacaccat cgttcacctt     1140
gaagacagag tctgtcctca gtaagtggag gcattcatcc aacattcttc tatctatctc     1200
acccttaaag aggtgagagc atgataaaag ttcagccaca cctggattct gtaattggca     1260
cctaaccaag aatatcaatg aaaatttcct taaacagtca gtattattct gattgtgcgt     1320
aaagtccact gaaattgaaa actccaatac ccctttgtg tagttgagca tgtagtccca      1380
cagatccttt aaggatttaa atgcctttgg gtttgtcagg ccctgcctaa tcaacatggc     1440
agcattacac acaacatctc ccattcggta agagaaccac ccaaaaccaa actgcaaatc     1500
attcctaaac ataggcctct ccacattttt gttcaccacc tttgagacaa atgattgaaa     1560
ggggcccagt gcctcagcac catcttcaga tggcatcatt tctttatgag gaaccatga      1620
aaaattgcct aatgtcctgg ttgttgcaac aaattctcga acaaatgatt caaaatacac     1680
ctgttttaag aagttcttgc agacatccct cgtgctaaca acaaattcat caaccagact     1740
ggagtcagat cgctgatgag aattggcaag gtcagaaaac agaacagtgt aatgttcatc     1800
cctttccac ttaacaacat gagaaatgag tgacaaggat tctgagttaa tatcaattaa      1860
aacacagagg tcaaggaatt taattctggg actccacctc atgttttttg agctcatgtc     1920
agacataaat ggaagaagct gatcctcaaa gatcttggga tatagccgcc tcacagattg     1980
aatcacttgg ttcaaattca ctttgtcctc cagtagcctt gagctctcag gctttcttgc     2040
tacataatca catgggttta agtgcttaag agttaggttc tcactgttat tcttcccttt     2100
ggtcggttct gctaggaccc aaacacccaa ctcaaaagag ttgctcaatg aaatacaaat     2160
gtagtcccaa agaagaggcc ttaaaaggca tatatgatca cggtgggctt ctggatgaga     2220
ctgtttgtca caaatgtaca gcgttatacc atcccgattg caaactcttg tcacatgatc     2280
atctgtggtt agatcctcaa gcagcttttt gatatacaga ttttccctat ttttgtttct     2340
cacacacctg cttcctagag ttttgcaaag gcctataaag ccagatgaga tacaactctg     2400
gaaagctgac ttgttgattg cttctgacag cagcttctgt gcaccccttg tgaatttact     2460
acaaagtttg ttctggagtg tcttgatcaa tgatgggatt ctttcctctt ggaaagtcat     2520
cactgatgga taaccacct tttgtcttaa aaccatcctt aatgggaaca tttcattcaa      2580
attcaaccag ttaacatctg ctaactgatt cagatcttct tcaagaccga ggaggtctcc     2640
caattgaaga atggcctcct ttttatctct gttaaatagg tctaagaaaa attcttcatt     2700
aaattcacca ttttttgagct tatgatgcag tttccttaca agctttctta caacctttgt     2760
ttcattagga cacagttcct caatgagtct ttgtattctg taacctctag aaccatccag     2820
ccaatctttc acatcagtgt tggtattcag tagaaatgga tccaaaggga aattggcata     2880
ctttaggagg tccagtgttc tcctttggat actattaact agggagactg ggacgccatt     2940
tgcgatggct tgatctgcaa ttgtatctat tgtttcacaa agttgatgtg gctctttaca     3000
cttgacattg tgtagcgctg cagatacaaa ctttgtgaga agagggactt cctccccca      3060
tacatagaat ctagatttaa attctgcagc gaacctccca gccacacttt tgggctgat      3120
aaatttgttt aacaagccgc tcagatgaga ttggaattcc aacaggacaa ggacttcctc     3180
cggatcactt acaaccaggt cactcagcct cctatcaaat aaagtgatct gatcatcact     3240
```

| | |
|---|---|
| tgatgtgtaa gcctctggtc tttcgccaaa gataacacca atgcagtagt tgatgaacct | 3300 |
| ctcgctaagc aaaccataga agtcagaagc attatgcaag attccctgcc ccatatcaat | 3360 |
| aaggctggat atatgggatg gcactatccc catttcaaaa tattgtctga aaattctctc | 3420 |
| agtaacagtt gtttctgaac ccctgagaag ttttagcttc gacttgacat atgatttcat | 3480 |
| cattgcattc acaacaggaa aggggacctc gacaagctta tgcatgtgcc aagttaacaa | 3540 |
| agtgctaaca tgatctttcc cggaacgcac atactggtca tcacctagtt tgagattttg | 3600 |
| tagaaacatt aagaacaaaa atgggcacat cattggtccc catttgctgt gatccatact | 3660 |
| atagtttaag aacccttccc gcacattgat agtcattgac aagattgcat tttcaaattc | 3720 |
| cttatcattg tttaaacagg agcctgaaaa gaaacttgaa aaagactcaa aataatcttc | 3780 |
| tattaacctt gtgaacattt ttgtcctcaa atctccaata tagagttctc tatttccccc | 3840 |
| aacctgctct ttataagata gtgcaaattt cagccttcca gagtcaggac ctactgaggt | 3900 |
| gtatgatgtt ggtgattctt ctgagtagaa gcacagattt ttcaaagcag cactcataca | 3960 |
| ttgtgtcaac gacagagctt tactaaggga ctcagaatta cttccctct cactgattct | 4020 |
| cacgtcttct tccagtttgt cccagtcaaa tttgaaattc aagccttgcc tttgcatatg | 4080 |
| cctgtatttc cctgagtacg catttgcatt catttgcaac agaatcatct tcatgcaaga | 4140 |
| aaaccaatca ttctcagaaa agaactttct acaaaggttt tttgccatct catcgaggcc | 4200 |
| acactgatct ttaatgactg aggtgaaata caaaggtgac agctctgtgg aaccctcaac | 4260 |
| agcctcacag ataaatttca tgtcatcatt ggttagacat gatgggtcaa agtcttctac | 4320 |
| taaatggaaa gatatttctg acaagataac ttttcttaag tgagccatct tccctgttag | 4380 |
| aataagctgt aaatgatgta gtccttttgt atttgtaagt ttttctccat ctcctttgtc | 4440 |
| attggccctc ctacctcttc tgtaccgtgc tattgtggtg ttgaccttt cttcgagact | 4500 |
| tttgaagaag cttgtctctt cttctccatc aaaacatatt tctgccaggt tgtcttccga | 4560 |
| tctccctgtc tcttctccct tggaaccgat gaccaatcta gagactaact tggaaacttt | 4620 |
| atattcatag tctgagtggc tcaacttata cttttgtttt cttacgaaac tctccgtaat | 4680 |
| ttgactcaca gcactaacaa gcaatttgtt aaagtcatat tccagaagtc gttctccatt | 4740 |
| tagatgctta ttaaccacca cactttttgtt actagcaaga tctaatgctg tcgcacatcc | 4800 |
| agagttagtc atgggatcta ggctgtttag cttcttctct cctttgaaaa ttaaagtgcc | 4860 |
| gttgttaaat gaagacacca ttaggctaaa ggcttccaga ttaacacctg gagttgtatg | 4920 |
| ctgacagtca atttctttac tagtgaatct cttcatttgc tcatagaaca cacattcttc | 4980 |
| ctcaggagtg attgcttcct tggggttgac aaaaaaacca aattgacttt tgggctcaaa | 5040 |
| gaacttttca aaacattta tctgatctgt tagcctgtca ggggtctcct ttgtgatcaa | 5100 |
| atgacacagg tatgacacat tcaacataaa tttaaatttt gcactcaaca acaccttctc | 5160 |
| accagtacca aaaatagttt ttattaggaa tctaagcagc ttatacacca ccttctcagc | 5220 |
| aggtgtgatc agatcctccc tcaacttatc cattaatgat gtagatgaaa aatctgacac | 5280 |
| tattgccatc accaaatatc tgacactctg tacctgcttt tgatttctct tgttgggtt | 5340 |
| ggtgagcatt agcaacaata gggtcctcag tgcaacctca atgtcggtga gacagtcttt | 5400 |
| caaatcagga catgatctaa tccatgaaat catgatgtct atcatattgt ataagacctc | 5460 |
| atctgaaaaa attggtaaaa agaacctttt aggatctgca tagaaggaaa ttaaatgacc | 5520 |
| atccgggcct tgtatggagt agcaccttga agattctcca gtcttctggt ataataggtg | 5580 |

```
gtattcttca gagtccagtt ttattacttg gcaaaacact tctttgcatt ctaccacttg    5640
atatctcaca gaccctattt gatttttgcct tagtctagca actgagctag ttttcatact   5700
gtttgttaag gccagacaaa cagatgataa tcttctcagg ctctgtatgt tcttcagctg    5760
ctctgtgctg ggttggaaat tgtaatcttc aaacttcgta taatacatta tcgggtgagc   5820
tccaattttc ataaagttct caaattcagt gaatggtatg tggcattctt gctcaaggtg   5880
ttcagacagt ccgtaatgct cgaaactcag tcccaccact aacaggcatt tttgaatttt   5940
tgcaatgaac tcactaatag atgccctaaa caattcctca aaagacacct ttctaaacac   6000
ctttgacttt tttctattcc tcaaaagtct aatgaactcc tctttagtgc tgtgaaagct   6060
taccagccta tcattcacac tactatagca acaacccacc cagtgtttat cattttttaa    6120
ccctttgaat ttcgactgtt ttatcaatga ggaaagacac aaaacatcca gatttaacaa   6180
ctgtctcctt ctagtattca acagtttcaa actcttgact ttgtttaaca tagagaggag   6240
cctctcatat tcagtgctag tctcacttcc cctttcgtgc ccatgggtct ctgcagttat   6300
gaatctcatc aaaggacagg attcgactgc ctccctgctt aatgttaaga tatcatcact   6360
atcagcaagg ttttcataga gctcagagaa ttccttgatc aagccttcag ggtttacttt   6420
ctgaaagttt ctctttaatt tcccactttc taaatctctt ctaaacctgc tgaaaagaga    6480
gtttattcca aaaccacat catcacagct catgttgggg ttgatgcctt cgtggcacat    6540
cctcataatt tcatcattgt gagttgacct cgcatctttc agaattttca tagagtccat   6600
accggagcgc ttgtcgatag tagtcttcag ggactcacag agtctaaaat attcagactc   6660
ttcaaagact ttctcatttt ggttagaata ctccaaaagt ttgaataaaa ggtctctaaa   6720
tttgaagttt gcccactctg gcataaaact attatcataa tcacaacgac catctactat   6780
tggaactaat gtgacacccg caacagcaag gtcttccctg atgcatgcca atttgttagt   6840
gtcctctata aatttcttct caaaactggc tggagtgctc taacaaaac actcaagaag    6900 aatgagagaa ttgtctatca gcttgtaacc atcaggaatg ataagtggta gtcctgggca    6960
tacaattcca gactccacca aaattgtttc cacagactta tcgtcgtggt tgtgtgtgca   7020
gccactcttg tctgcactgt ctatttcaat gcagcgtgac agcaacttga gtccctcaat   7080
cagaaccatt ctgggttccc tttgtcccag aaagttgagt ttctgccttg acaacctctc   7140
atcctgttct atatagttta aacataactc tctcaattct gagatgattt catccattgc   7200
gcatcaaaaa gcctaggatc ctcggtgcg                                      7229
```

<210> SEQ ID NO 8
<211> LENGTH: 8
<212> TYPE: PRT
<213> ORGANISM: Artificial Sequence
<220> FEATURE:
<223> OTHER INFORMATION: HBV HBs protein-derived epitope

<400> SEQUENCE: 8

Val Trp Leu Ser Val Ile Trp Met
1               5

<210> SEQ ID NO 9
<211> LENGTH: 12
<212> TYPE: PRT
<213> ORGANISM: Artificial Sequence
<220> FEATURE:
<223> OTHER INFORMATION: HBV HBs protein-derived epitope

<400> SEQUENCE: 9

-continued

```
Ile Pro Gln Ser Leu Asp Ser Trp Trp Thr Ser Leu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: HBV HBc protein-derived epitope

<400> SEQUENCE: 10

Met Gly Leu Lys Phe Arg Gln Leu
1               5

<210> SEQ ID NO 11
<211> LENGTH: 3376
<212> TYPE: DNA
<213> ORGANISM: Artificial Sequence
<220> FEATURE:
<223> OTHER INFORMATION: lymphocytic choriomeningitis virus segment S,
      complete cDNA sequence

<400> SEQUENCE: 11
cgcaccgggg atcctaggct ttttggattg cgctttcctc tagatcaact gggtgtcagg     60
ccctatccta cagaaggatg ggtcagattg tgacaatgtt tgaggctctg cctcacatca    120
tcgatgaggt gatcaacatt gtcattattg tgcttatcgt gatcacgggt atcaaggctg    180
tctacaattt tgccacctgt gggatattcg cattgatcag tttcctactt ctggctggca    240
ggtcctgtgg catgtacggt cttaagggac ccgacattta caaaggagtt taccaattta    300
agtcagtgga gtttgatatg tcacatctga acctgaccat gcccaacgca tgttcagcca    360
acaactccca ccattacatc agtatgggga cttctggact agaattgacc ttcaccaatg    420
attccatcat cagtcacaac ttttgcaatc tgacctctgc cttcaacaaa aagacctttg    480
accacacact catgagtata gtttcgagcc tacacctcag tatcagaggg aactccaact    540
ataaggcagt atcctgcgac ttcaacaatg gcataaccat ccaatacaac ttgacattct    600
cagatcgaca aagtgctcag agccagtgta gaaccttcag aggtagagtc ctagatatgt    660
ttagaactgc cttcgggggg aaatacatga ggagtggctg gggctggaca ggctcagatg    720
gcaagaccac ctggtgtagc cagacgagtt accaatacct gattatacaa aatagaacct    780
gggaaaacca ctgcacatat gcaggtcctt ttgggatgtc caggattctc ctttcccaag    840
agaagactaa gttcttcact aggagactag cgggcacatt cacctggact ttgtcagact    900
cttcaggggt ggagaatcca ggtggttatt gcctgaccaa atggatgatt cttgctgcag    960
agcttaagtg tttcgggaac acagcagttg cgaaatgcaa tgtaaatcat gatgccgaat   1020
tctgtgacat gctgcgacta attgactaca acaaggctgc tttgagtaag ttcaaagagg   1080
acgtagaatc tgccttgcac ttattcaaaa caacagtgaa ttctttgatt tcagatcaac   1140
tactgatgag gaaccacttg agagatctga tgggggtgcc atattgcaat tactcaaagt   1200
tttggtacct agaacatgca aagaccggcg aaactagtgt ccccaagtgc tggcttgtca   1260
ccaatggttc ttacttaaat gagacccact tcagtgatca aatcgaacag gaagccgata   1320
acatgattac agagatgttg aggaaggatt acataaagag gcaggggagt acccccctag   1380
cattgatgga ccttctgatg ttttccacat ctgcatatct agtcagcatc ttcctgcacc   1440
ttgtcaaaat accaacacac aggcacataa aaggtggctc atgtccaaag ccacaccgat   1500
taaccaacaa aggaatttgt agttgtggtg catttaaggt gcctggtgta aaaaccgtct   1560
```

-continued

```
ggaaaagacg ctgaagaaca gcgcctccct gactctccac ctcgaaagag gtggagagtc    1620
agggaggccc agagggtctt agagtgtcac aacatttggg cctctaaaaa ttaggtcatg    1680
tggcagaatg ttgtgaacag ttttcagatc tgggagcctt gctttggagg cgctttcaaa    1740
aatgatgcag tccatgagtg cacagtgcgg ggtgatctct ttcttctttt tgtcccttac    1800
tattccagta tgcatcttac acaaccagcc atatttgtcc cacactttgt cttcatactc    1860
cctcgaagct tccctggtca tttcaacatc gataagctta atgtccttcc tattctgtga    1920
gtccagaagc tttctgatgt catcggagcc ttgacagctt agaaccatcc cctgcggaag    1980
agcacctata actgacgagg tcaacccggg ttgcgcattg aagaggtcgg caagatccat    2040
gccgtgtgag tacttggaat cttgcttgaa ttgttttga tcaacgggtt ccctgtaaaa     2100
gtgtatgaac tgcccgttct gtggttggaa aattgctatt tccactggat cattaaatct    2160
accctcaatg tcaatccatg taggagcgtt ggggtcaatt cctcccatga ggtcttttaa    2220
aagcattgtc tggctgtagc ttaagcccac ctgaggtgga cctgctgctc caggcgctgg    2280
cctgggtgaa ttgactgcag gtttctcgct tgtgagatca attgttgtgt tttcccatgc    2340
tctccccaca atcgatgttc tacaagctat gtatggccat ccttcacctg aaaggcaaac    2400
tttatagagg atgttttcat aagggttcct gtccccaact tggtctgaaa caaacatgtt    2460
gagttttctc ttggccccga gaactgcctt caagaggtcc tcgctgttgc ttggcttgat    2520
caaaattgac tctaacatgt taccccatc caacagggct gccctgcct tcacggcagc     2580
accaagacta agttatagc cagaaatgtt gatgctggac tgctgttcag tgatgacccc    2640
cagaactggg tgcttgtctt tcagcctttc aagatcatta agatttggat acttgactgt    2700
gtaaagcaag ccaaggtctg tgagcgcttg tacaacgtca ttgagcggag tctgtgactg    2760
tttggccata caagccatag ttagacttgg cattgtgcca aattgattgt tcaaaagtga    2820
tgagtctttc acatcccaaa ctcttaccac accacttgca ccctgctgag gctttctcat    2880
cccaactatc tgtaggatct gagatctttg gtctagttgc tgtgttgtta agttccccat    2940
atataccct gaagcctggg gcctttcaga cctcatgatc ttggccttca gcttctcaag    3000
gtcagccgca agagacatca gttcttctgc actgagcctc cccactttca aaacattctt    3060
ctttgatgtt gactttaaat ccacaagaga atgtacagtc tggttgagac ttctgagtct    3120
ctgtaggtct ttgtcatctc tcttttcctt cctcatgatc ctctgaacat tgctgacctc    3180
agagaagtcc aacccattca gaaggttggt tgcatcctta atgacagcag ccttcacatc    3240
tgatgtgaag ctctgcaatt ctcttctcaa tgccttgcgtc cattggaagc tcttaacttc    3300
cttagacaag gacatcttgt tgctcaatgg tttctcaaga caaatgcgca atcaaatgcc    3360
taggatccac tgtgcg                                                    3376
```

<210> SEQ ID NO 12
<211> LENGTH: 3377
<212> TYPE: DNA
<213> ORGANISM: Artificial Sequence
<220> FEATURE:
<223> OTHER INFORMATION: lymphocytic choriomeningitis virus clone 13
      segment S, complete cDNA sequence (GenBank: DQ361065.2)

<400> SEQUENCE: 12

```
gcgcaccggg gatcctaggc ttttggatt gcgctttcct ctagatcaac tgggtgtcag       60
gccctatcct acagaaggat gggtcagatt gtgacaatgt ttgaggctct gcctcacatc     120
atcgatgagg tgatcaacat tgtcattatt gtgcttatcg tgatcacggg tatcaaggct     180
```

```
gtctacaatt ttgccacctg tgggatattc gcattgatca gtttcctact tctggctggc      240
aggtcctgtg gcatgtacgg tcttaaggga cccgacattt acaaaggagt ttaccaattt      300
aagtcagtgg agtttgatat gtcacatctg aacctgacca tgcccaacgc atgttcagcc      360
aacaactccc accattacat cagtatgggg acttctggac tagaattgac cttcaccaat      420
gattccatca tcagtcacaa cttttgcaat ctgacctctg ccttcaacaa aaagaccttt      480
gaccacacac tcatgagtat agtttcgagc ctacacctca gtatcagagg gaactccaac      540
tataaggcag tatcctgcga cttcaacaat ggcataacca tccaatacaa cttgacattc      600
tcagatgcac aaagtgctca gagccagtgt agaaccttca gaggtagagt cctagatatg      660
tttagaactg ccttcggggg gaaatacatg aggagtggct ggggctggac aggctcagat      720
ggcaagacca cctggtgtag ccagacgagt taccaatacc tgattataca aaatagaacc      780
tgggaaaacc actgcacata tgcaggtcct tttgggatgt ccaggattct cctttcccaa      840
gagaagacta agttcctcac taggagacta gcgggcacat tcacctggac tttgtcagac      900
tcttcagggg tggagaatcc aggtggttat tgcctgacca aatggatgat tcttgctgca      960
gagcttaagt gtttcgggaa cacagcagtt gcgaaatgca atgtaaatca tgatgaagaa     1020
ttctgtgaca tgctgcgact aattgactac aacaaggctg ctttgagtaa gttcaaagag     1080
gacgtagaat ctgccttgca cttattcaaa acaacagtga attctttgat ttcagatcaa     1140
ctactgatga ggaaccactt gagagatctg atggggtgc catattgcaa ttactcaaag     1200
ttttggtacc tagaacatgc aaagaccggc gaaactagtg tccccaagtg ctggcttgtc     1260
accaatggtt cttacttaaa tgagacccac ttcagtgacc aaatcgaaca ggaagccgat     1320
aacatgatta cagagatgtt gaggaaggat tacataaaga ggcaggggag taccccccta     1380
gcattgatgg accttctgat gttttccaca tctgcatatc tagtcagcat cttcctgcac     1440
cttgtcaaaa taccaacaca caggcacata aaaggtggct catgtccaaa gccacaccga     1500
ttaaccaaca aaggaatttg tagttgtggt gcatttaagg tgcctggtgt aaaaaccgtc     1560
tggaaaagac gctgaagaac agcgcctccc tgactctcca cctcgaaaga ggtggagagt     1620
cagggaggcc cagagggtct tagagtgtca caacatttgg gcctctaaaa attaggtcat     1680
gtggcagaat gttgtgaaca gttttcagat ctgggagcct tgctttggag gcgctttcaa     1740
aaaatgatgca gtccatgagt gcacagtgcg gggtgatctc tttcttcttt ttgtccctta     1800
ctattccagt atgcatctta cacaaccagc catatttgtc ccacactttg tcttcatact     1860
ccctcgaagc ttccctggtc atttcaacat cgataagctt aatgtccttc ctattctgtg     1920
agtccagaag ctttctgatg tcatcggagc cttgacagct tagaaccatc ccctgcggaa     1980
gagcacctat aactgacgag gtcaacccgg gttgcgcatt gaagaggtcg gcaagatcca     2040
tgccgtgtga gtacttggaa tcttgcttga attgttttg atcaacgggt tccctgtaaa     2100
agtgtatgaa ctgcccgttc tgtggttgga aaattgctat ttccactgga tcattaaatc     2160
taccctcaat gtcaatccat gtaggagcgt tgggtcaat tcctcccatg aggtctttta     2220
aaagcattgt ctggctgtag cttaagccca cctgaggtgg acctgctgct ccaggcgctg     2280
gcctgggtga attgactgca ggtttctcgc ttgtgagatc aattgttgtg ttttcccatg     2340
ctctccccac aatcgatgtt ctacaagcta tgtatggcca tccttcacct gaaaggcaaa     2400
ctttatagag gatgttttca taagggttcc tgtccccaac ttggtctgaa acaaacatgt     2460
tgagttttct cttggccccg agaactgcct tcaagaggtc ctcgctgttg cttggcttga     2520
tcaaaattga ctctaacatg ttaccccccat ccaacagggc tgccctgcc ttcacggcag     2580
```
caccaagact aaagttatag ccagaaatgt tgatgctgga ctgctgttca gtgatgaccc 2640
ccagaactgg gtgcttgtct ttcagccttt caagatcatt aagatttgga tacttgactg 2700
tgtaaagcaa gccaaggtct gtgagcgctt gtacaacgtc attgagcgga gtctgtgact 2760
gtttggccat acaagccata gttagacttg gcattgtgcc aaattgattg ttcaaaagtg 2820
atgagtcttt cacatcccaa actcttacca caccacttgc accctgctga ggctttctca 2880
tcccaactat ctgtaggatc tgagatcttt ggtctagttg ctgtgttgtt aagttcccca 2940
tatatacccc tgaagcctgg ggcctttcag acctcatgat cttggccttc agcttctcaa 3000
ggtcagccgc aagagacatc agttcttctg cactgagcct ccccactttc aaaacattct 3060
tctttgatgt tgactttaaa tccacaagag aatgtacagt ctggttgaga cttctgagtc 3120
tctgtaggtc tttgtcatct ctcttttcct tcctcatgat cctctgaaca ttgctgacct 3180
cagagaagtc caacccattc agaaggttgg ttgcatcctt aatgacagca gccttcacat 3240
ctgatgtgaa gctctgcaat tctcttctca atgcttgcgt ccattggaag ctcttaactt 3300
ccttagacaa ggacatcttg ttgctcaatg gtttctcaag acaaatgcgc aatcaaatgc 3360
ctaggatcca ctgtgcg 3377

<210> SEQ ID NO 13
<211> LENGTH: 7205
<212> TYPE: DNA
<213> ORGANISM: Artificial Sequence
<220> FEATURE:
<223> OTHER INFORMATION: lymphocytic choriomeningitis strain MP segment L, complete cDNA sequence

<400> SEQUENCE: 13
gcgcaccggg gatcctaggc atttttgttg cgcattttgt tgtgttattt gttgcacagc 60
ccttcatcgt gggaccttca caaacaaacc aaaccaccag ccatgggcca aggcaagtcc 120
aaagagggaa gggatgccag caatacgagc agagctgaaa ttctgccaga caccacctat 180
ctcggacctc tgaactgcaa gtcatgctgg cagagatttg acagtttagt cagatgccat 240
gaccactatc tctgcagaca ctgcctgaac ctcctgctgt cagtctccga caggtgccct 300
ctctgcaaac atccattgcc aaccaaactg aaaatatcca cggccccaag ctctccaccc 360
ccttacgagg agtgacgccc cgagccccaa caccgacaca aggaggccac caacacaacg 420
cccaacacgg aacacacaca cacacaccca cacacacatc cacacacacg cgcccccaca 480
acgggggcgc ccccccgggg gtggcccccc gggtgctcgg gcggagcccc acggagaggc 540
caattagtcg atctcctcga ccaccgactt ggtcagccag tcatcacagg acttgccctt 600
aagtctgtac ttgcccacaa ctgtttcata catcaccgtg ttctttgact tactgaaaca 660
tagcctacag tctttgaaag tgaaccagtc aggcacaagt gacagcggta ccagtagaat 720
ggatctatct atacacaact cttggagaat tgtgctaatt tccgacccct gtagatgctc 780
accagttctg aatcgatgta gaagaaggct cccaaggacg tcatcaaaat ttccataacc 840
ctcgagctct gccaagaaaa ctctcatatc cttggtctcc agtttcacaa cgatgttctg 900
aacaaggctt cttccctcaa aaagagcacc cattctcaca gtcaagggca caggctccca 960
ttcaggccca atcctctcaa aatcaaggga tctgatcccg tccagtattt tccttgagcc 1020
tatcagctca agctcaagag agtcaccgag tatcaggggg tcctccatat agtcctcaaa 1080
ctcttcagac ctaatgtcaa aaacaccatc gttcaccttg aagatagagt ctgatctcaa 1140
caggtggagg cattcgtcca agaaccttct gtccacctca cctttaaaga ggtgagagca 1200

```
tgataggaac tcagctacac ctggaccttg taactggcac ttcactaaaa agatcaatga    1260
aaacttcctc aaacaatcag tgttattctg gttgtgagtg aaatctactg taattgagaa    1320
ctctagcact ccctctgtat tatttatcat gtaatcccac aagtttctca aagacttgaa    1380
tgcctttgga tttgtcaagc cttgtttgat tagcatggca gcattgcaca caatatctcc    1440
caatcggtaa gagaaccatc caaatccaaa ttgcaagtca ttcctaaaca tgggcctctc    1500 catattttg ttcactactt ttaagatgaa tgattggaaa ggccccaatg cttcagcgcc     1560
atcttcagat ggcatcatgt ctttatgagg gaaccatgaa aaacttccta gagttctgct    1620
tgttgctaca aattctcgta caaatgactc aaaatacact tgttttaaaa agttttttgca   1680 gacatccctt gtactaacga caaattcatc aacaaggctt gagtcagagc gctgatggga    1740
atttacaaga tcagaaaata gaacagtgta gtgttcgtcc ctcttccact taactacatg    1800
agaaatgagc gataaagatt ctgaattgat atcgatcaat acgcaaaggt caaggaattt    1860
gattctggga ctccatctca tgttttttga gctcatatca gacatgaagg gaagcagctg    1920
atcttcatag attttagggt acaatcgcct cacagattgg attacatggt ttaaacttat    1980
cttgtcctcc agtagccttg aactctcagg cttccttgct acataatcac atgggttcaa    2040
gtgcttgagg cttgagcttc cctcattctt ccctttcaca ggttcagcta agacccaaac    2100
acccaactca aaggaattac tcagtgagat gcaaatatag tcccaaagga ggggcctcaa    2160
gagactgatg tggtcgcagt gagcttctgg atgactttgc ctgtcacaaa tgtacaacat    2220
tatgccatca tgtctgtgga ttgctgtcac atgcgcatcc atagctagat cctcaagcac    2280
ttttctaatg tatagattgt ccctatttt atttctcaca catctacttc ccaaagtttt     2340
gcaaagacct ataaagcctg atgagatgca actttgaaag gctgacttat tgattgcttc    2400
tgacagcaac ttctgtgcac ctcttgtgaa cttactgcag agcttgttct ggagtgtctt    2460
gattaatgat gggattcttt cctcttggaa agtcattact gatggataaa ccactttctg    2520
cctcaagacc attcttaatg ggaacaactc attcaaattc agccaattta tgtttgccaa    2580
ttgacttaga tcctcttcga ggccaaggat gtttcccaac tgaagaatgg cttccttttt    2640
atccctattg aagaggtcta agaagaattc ttcattgaac tcaccattct tgagcttatg    2700
atgtagtctc cttacaagcc ttctcatgac cttcgtttca ctaggacaca attcttcaat    2760
aagcctttgg attctgtaac ctctagagcc atccaaccaa tccttgacat cagtattagt    2820
gttaagcaaa aatgggtcca agggaaagtt ggcatatttt aagaggtcta atgttctctt    2880
ctggatgcag tttaccaatg aaactggaac accatttgca acagcttgat cggcaattgt    2940
atctattgtt tcacagagtt ggtgtggctc tttacactta acgttgtgta atgctgctga    3000
cacaaatttt gttaaaagtg ggacctcttc cccccacaca taaaatctgg atttaaattc    3060
tgcagcaaat cgccccacca cacttttcgg actgatgaac ttgttaagca agccactcaa    3120
atgagaatga aattccagca atacaaggac ttcctcaggg tcactatcaa ccagttcact    3180
caatctccta tcaaataagg tgatctgatc atcacttgat gtgtaagatt ctggtctctc    3240
accaaaaatg acaccgatac aataattaat gaatctctca ctgattaagc cgtaaaagtc    3300
agaggcatta tgtaagattc cctgtcccat gtcaatgaga ctgcttatat gggaaggcac    3360
tattcctaat tcaaaatatt ctcgaaagat tctttcagtc acagttgtct ctgaaccct     3420 aagaagtttc agctttgatt tgatatatga tttcatcatt gcattcacaa caggaaaagg    3480
gacctcaaca agtttgtgca tgtgccaagt taataaggtg ctgatatgat cctttccgga    3540
```

```
acgcacatac tggtcatcac ccagtttgag attttgaagg agcattaaaa acaaaaatgg    3600
gcacatcatt ggcccccatt tgctatgatc catactgtag ttcaacaacc cctctcgcac    3660
attgatggtc attgatagaa ttgcattttc aaattctttg tcattgttta agcatgaacc    3720
tgagaagaag ctagaaaaag actcaaaata atcctctatc aatcttgtaa acattttgt     3780 tctcaaatcc ccaatataaa gttctctgtt tcctccaacc tgctctttgt atgataacgc    3840
aaacttcaac cttccggaat caggaccaac tgaagtgtat gacgttggtg actcctctga    3900
gtaaaaacat aaattcttta agcagcact  catgcatttt gtcaatgata gagccttact    3960
tagagactca gaattacttt ccctttcact aattctaaca tcttcttcta gtttgtccca    4020
gtcaaacttg aaattcagac cttgtctttg catgtgcctg tatttccctg agtatgcatt    4080
tgcattcatt tgcagtagaa tcattttcat acacgaaaac caatcaccct ctgaaaaaaa    4140
cttcctgcag aggttttttg ccatttcatc cagaccacat tgttctttga cagctgaagt    4200
gaaatacaat ggtgacagtt ctgtagaagt ttcaatagcc tcacagataa atttcatgtc    4260
atcattggtg agacaagatg ggtcaaaatc ttccacaaga tgaaagaaa  tttctgataa    4320 gatgaccttc cttaaatatg ccattttacc tgacaatata gtctgaaggt gatgcaatcc    4380
ttttgtattt tcaaaccca  cctcattttc cccttcattg gtcttcttgc ttctttcata    4440
ccgctttatt gtggagttga ccttatcttc taaattcttg aagaaacttg tctcttcttc    4500
cccatcaaag catatgtctg ctgagtcacc ttctagtttc ccagcttctg tttctttaga    4560
gccgataacc aatctagaga ccaactttga aaccttgtac tcgtaatctg agtggttcaa    4620
tttgtacttc tgctttctca tgaagctctc tgtgatctga ctcacagcac taacaagcaa    4680
tttgttaaaa tcatactcta ggagccgttc cccatttaaa tgtttgttaa caaccacact    4740
tttgttgctg gcaaggtcta atgctgttgc acacccagag ttagtcatgg gatccaagct    4800
attgagcctc ttctccccctt tgaaaatcaa agtgccattg ttgaatgagg acaccatcat    4860
gctaaaggcc tccagattga cacctggggt tgtgcgctga cagtcaactt ctttcccagt    4920
gaacttcttc atttggtcat aaaaaacaca ctcttcctca ggggtgattg actctttagg    4980
gttaacaaag aagccaaact cacttttagg ctcaaagaat ttctcaaagc atttaatttg    5040
atctgtcagc ctatcagggg tttcctttgt gattaaatga cacaggtatg acacattcaa    5100
catgaacttg aactttgcgc tcaacagtac cttttcacca gtcccaaaaa cagttttgat    5160
caaaaatctg agcaatttgt acactacttt ctcagcaggt gtgatcaaat cctccttcaa    5220
cttgtccatc aatgatgtgg atgagaagtc tgagacaatg ccatcacta  aatacctaat    5280 gttttgaacc tgtttttgat tcctctttgt tgggttggtg agcatgagta ataatagggt    5340
tctcaatgca atctcaacat catcaatgct gtccttcaag tcaggacatg atctgatcca    5400
tgagatcatg gtgtcaatca tgttgtgcaa cacttcatct gagaagattg gtaaaaagaa    5460
ccttttgggg tctgcataaa aagagattag atggccattg ggaccttgta tagaataaca    5520
ccttgaggat tctccagtct tttgatacag caggtgatat tcctcagagt ccaatttat    5580 cacttggcaa aatacctctt tacattccac cacttgatac cttacagagc ccaattggtt    5640
ttgtcttaat ctagcaactg aacttgtttt catactgttt gtcaaagcta gacagacaga    5700
tgacaatctt ttcaaactat gcatgttcct taattgttcc gtattaggct ggaaatcata    5760
atcttcaaac tttgtataat acattatagg atgagttccg gacctcatga aattctcaaa    5820
ctcaataaat ggtatgtggc actcatgctc aagatgttca gacagaccat agtgcccaaa    5880
actaagtccc accactgaca agcacctttg aacttttaaa atgaactcat ttatggatgt    5940
```

```
tctaaacaaa tcctcaagag ataccttct atacgccttt gactttctcc tgttccttag    6000
aagtctgatg aactcttcct tggtgctatg aaagctcacc aacctatcat tcacactccc    6060
atagcaacaa ccaacccagt gcttatcatt ttttgaccct ttgagtttag actgtttgat    6120
caacgaagag agacacaaga catccaaatt cagtaactgt ctccttctgg tgttcaataa    6180
ttttaaactt ttaactttgt tcaacataga gaggagcctc tcatactcag tgctagtctc    6240
acttcctctc tcataaccat gggtatctgc tgtgataaat ctcatcaaag gacaggattc    6300
aactgcctcc ttgcttagtg ctgaaatgtc atcactgtca gcaagagtct cataaagctc    6360
agagaattcc ttaattaaat ttccgggggtt gattttctga aaactcctct tgagcttccc    6420
agtttccaag tctcttctaa acctgctgta aagggagttt atgccaagaa ccacatcatc    6480
gcagttcatg tttgggttga caccatcatg gcacattttc ataatttcat cattgtgaaa    6540
tgatcttgca tctttcaaga ttttcataga gtctataccg gaacgcttat caacagtggt    6600
cttgagagat tcgcaaagtc tgaagtactc agattcctca aagactttct catcttggct    6660
agaatactct aaaagtttaa acagaaggtc tctgaacttg aaattcaccc actctggcat    6720
aaagctgtta tcataatcac accgaccatc cactattggg accaatgtga tacccgcaat    6780
ggcaaggtct tctttgatac aggctagttt attggtgtcc tctataaatt tcttctcaaa    6840
actagctggt gtgcttctaa cgaagcactc aagaagaatg agggaattgt caatcagttt    6900
ataaccatca ggaatgatca aaggcagtcc cgggcacaca atcccagact ctattagaat    6960
tgcctcaaca gatttatcat catggttgtg tatgcagccg ctcttgtcag cactgtctat    7020
ctctatacaa cgcgacaaaa gtttgagtcc ctctatcaat accattctgg gttctctttg    7080
ccctaaaaag ttgagcttct gccttgacaa cctctcatct tgttctatgt ggtttaagca    7140
caactctctc aactccgaaa tagcctcatc cattgcgcat caaaaagcct aggatcctcg    7200
gtgcg                                                                 7205
```

<210> SEQ ID NO 14
<211> LENGTH: 3359
<212> TYPE: DNA
<213> ORGANISM: Artificial Sequence
<220> FEATURE:
<223> OTHER INFORMATION: lymphocytic choriomeningitis strain MP segment
      S, complete cDNA sequence

<400> SEQUENCE: 14
cgcaccgggg atcctaggct tttggattg cgctttcctc agctccgtct tgtgggagaa 60
tgggtcaaat tgtgacgatg tttgaggctc tgcctcacat cattgatgag gtcattaaca 120
ttgtcattat cgtgcttatt atcatcacga gcatcaaagc tgtgtacaat ttcgccacct 180
gcgggatact tgcattgatc agctttcttt ttctggctgg caggtcctgt ggaatgtatg 240
gtcttgatgg gcctgacatt tacaaagggg tttaccgatt caagtcagtg gagtttgaca 300
tgtcttacct taacctgacg atgcccaatg catgttcggc aaacaactcc catcattata 360
taagtatggg gacttctgga ttggagttaa ccttcacaaa tgactccatc atcacccaca 420
acttttgtaa tctgacttcc gccctcaaca agaggacttt tgaccacaca cttatgagta 480
tagtctcaag tctgcacctc agcattagag ggtccccag ctacaaagca gtgtcctgtg 540
attttaacaa tggcatcact attcaataca acctgtcatt ttctaatgca cagagcgctc 600
tgagtcaatg taagaccttc agggggagag tcctggatat gttcagaact gcttttggag 660
gaaagtacat gaggagtggc tggggctgga caggttcaga tggcaagact acttggtgca 720

```
gccagacaaa ctaccaatat ctgattatac aaaacaggac ttgggaaaac cactgcaggt    780
acgcaggccc tttcggaatg tctagaattc tcttcgctca agaaaagaca aggtttctaa    840
ctagaaggct tgcaggcaca ttcacttgga ctttatcaga ctcatcagga gtggagaatc    900
caggtggtta ctgcttgacc aagtggatga tcctcgctgc agagctcaag tgttttggga    960
acacagctgt tgcaaagtgc aatgtaaatc atgatgaaga gttctgtgat atgctacgac   1020
tgattgatta caacaaggct gctttgagta aattcaaaga gatgtagaa tccgctctac    1080 atctgttcaa gacaacagtg aattctttga tttctgatca gcttttgatg agaaatcacc   1140
taagagactt gatgggagtg ccatactgca attactcgaa attctggtat ctagagcatg   1200
caaagactgg tgagactagt gtccccaagt gctggcttgt cagcaatggt tcttatttga   1260
atgaaaccca tttcagcgac caaattgagc aggaagcaga taatatgatc acagaaatgc   1320
tgagaaagga ctacataaaa aggcaaggga gtaccctct agccttgatg gatctattga    1380
tgttttctac atcagcatat ttgatcagca tctttctgca tcttgtgagg ataccaacac   1440
acagacacat aaagggcggc tcatgcccaa aaccacatcg gttaaccagc aagggaatct   1500
gtagttgtgg tgcatttaaa gtaccaggtg tggaaaccac ctggaaaaga cgctgaacag   1560
cagcgcctcc ctgactcacc acctcgaaag aggtggtgag tcagggaggc ccagagggtc   1620
ttagagtgtt acgacatttg gacctctgaa gattaggtca tgtggtagga tattgtggac   1680
agttttcagg tcggggagcc ttgccttgga ggcgctttca aagatgatac agtccatgag   1740
tgcacagtgt ggggtgacct ctttcttttt cttgtccctc actattccag tgtgcatctt   1800
gcatagccag ccatatttgt cccagacttt gtcctcatat tctcttgaag cttctttagt   1860
catctcaaca tcgatgagct taatgtctct tctgttttgt gaatctagga gtttcctgat   1920
gtcatcagat ccctgacaac ttaggaccat tccctgtgga agagcaccta ttactgaaga   1980
tgtcagccca ggttgtgcat tgaagaggtc agcaaggtcc atgccatgtg agtatttgga   2040
gtcctgcttg aattgttttt gatcagtggg ttctctatag aaatgtatgt actgcccatt   2100
ctgtggctga atattgcta tttctaccgg tcattaaat ctgccctcaa tgtcaatcca    2160
tgtaggagcg ttagggtcaa tacctcccat gaggtccttc agcaacattg tttggctgta   2220
gcttaagccc acctgaggtg ggcccgctgc cccaggcgct ggtttgggtg agttggccat   2280
aggcctctca tttgtcagat caattgttgt gttctcccat gctctcccta caactgatgt   2340
tctacaagct atgtatggcc acccctcccc tgaaagacag actttgtaga ggatgttctc   2400
gtaaggattc ctgtctccaa cctgatcaga aacaaacatg ttgagtttct tcttggcccc   2460
aagaactgct ttcaggagat cctcactgtt gcttggctta attaagatgg attccaacat   2520
gttaccccca tctaacaagg ctgccctgc tttcacagca gcaccgagac tgaaattgta    2580
gccagatatg ttgatgctag actgctgctc agtgatgact cccaagactg ggtgcttgtc   2640
tttcagcctt tcaaggtcac ttaggttcgg gtacttgact gtgtaaagca gcccaaggtc   2700
tgtgagtgct tgcacaacgt cattgagtga ggtttgtgat tgtttggcca tacaagccat   2760
tgttaagctt ggcattgtgc cgaattgatt gttcagaagt gatgagtcct tcacatccca   2820
gaccctcacc acaccatttg cactctgctg aggtctcctc attccaacca tttgcagaat   2880
ctgagatctt tggtcaagct gttgtgctgt taagttcccc atgtagactc cagaagttag   2940
aggcctttca gacctcatga ttttagcctt cagttttca aggtcagctg caagggacat    3000
cagttcttct gcactaagcc tccctacttt tagaacattc ttttttgatg ttgactttag   3060
```

```
gtccacaagg gaatacacag tttggttgag gcttctgagt ctctgtaaat ctttgtcatc    3120
cctcttctct ttcctcatga tcctctgaac attgctcacc tcagagaagt ctaatccatt    3180
cagaaggctg gtggcatcct tgatcacagc agctttcaca tctgatgtga agccttgaag    3240
ctctctcctc aatgcctggg tccattgaaa gcttttaact tctttggaca gagacatttt    3300
gtcactcagt ggatttccaa gtcaaatgcg caatcaaaat gcctaggatc cactgtgcg     3359

<210> SEQ ID NO 15
<211> LENGTH: 558
<212> TYPE: PRT
<213> ORGANISM: Artificial Sequence
<220> FEATURE:
<223> OTHER INFORMATION: NP protein of the MP strain of LCMV

<400> SEQUENCE: 15

Met Ser Leu Ser Lys Glu Val Lys Ser Phe Gln Trp Thr Gln Ala Leu
1               5                   10                  15

Arg Arg Glu Leu Gln Gly Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val Tyr Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Leu Thr Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Ser Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Leu Asn Met Phe
        275                 280                 285

Val Ser Asp Gln Val Gly Asp Arg Asn Pro Tyr Glu Asn Ile Leu Tyr
    290                 295                 300

Lys Val Cys Leu Ser Gly Glu Gly Trp Pro Tyr Ile Ala Cys Arg Thr
305                 310                 315                 320
```

```
Ser Val Val Gly Arg Ala Trp Glu Asn Thr Thr Ile Asp Leu Thr Asn
            325                 330                 335

Glu Arg Pro Met Ala Asn Ser Pro Lys Pro Ala Pro Gly Ala Ala Gly
            340                 345                 350

Pro Pro Gln Val Gly Leu Ser Tyr Ser Gln Thr Met Leu Leu Lys Asp
            355                 360                 365

Leu Met Gly Gly Ile Asp Pro Asn Ala Pro Thr Trp Ile Asp Ile Glu
    370                 375                 380

Gly Arg Phe Asn Asp Pro Val Glu Ile Ala Ile Phe Gln Pro Gln Asn
385                 390                 395                 400

Gly Gln Tyr Ile His Phe Tyr Arg Glu Pro Thr Asp Gln Lys Gln Phe
            405                 410                 415

Lys Gln Asp Ser Lys Tyr Ser His Gly Met Asp Leu Ala Asp Leu Phe
            420                 425                 430

Asn Ala Gln Pro Gly Leu Thr Ser Ser Val Ile Gly Ala Leu Pro Gln
            435                 440                 445

Gly Met Val Leu Ser Cys Gln Gly Ser Asp Asp Ile Arg Lys Leu Leu
    450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
            485                 490                 495

Trp Leu Cys Lys Met His Thr Gly Ile Val Arg Asp Lys Lys Lys
            500                 505                 510

Glu Val Thr Pro His Cys Ala Leu Met Asp Cys Ile Ile Phe Glu Ser
            515                 520                 525

Ala Ser Lys Ala Arg Leu Pro Asp Leu Lys Thr Val His Asn Ile Leu
            530                 535                 540

Pro His Asp Leu Ile Phe Arg Gly Pro Asn Val Val Thr Leu
545                 550                 555

<210> SEQ ID NO 16
<211> LENGTH: 498
<212> TYPE: PRT
<213> ORGANISM: Artificial Sequence
<220> FEATURE:
<223> OTHER INFORMATION: GP protein of the MP strain of LCMV

<400> SEQUENCE: 16

Met Gly Gln Ile Val Thr Met Phe Glu Ala Leu Pro His Ile Ile Asp
1               5                  10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Ile Ser
            35                  40                  45

Phe Leu Phe Leu Ala Gly Arg Ser Cys Gly Met Tyr Gly Leu Asp Gly
            50                  55                  60

Pro Asp Ile Tyr Lys Gly Val Tyr Arg Phe Lys Ser Val Glu Phe Asp
65                  70                  75                  80

Met Ser Tyr Leu Asn Leu Thr Met Pro Asn Ala Cys Ser Ala Asn Asn
            85                  90                  95

Ser His His Tyr Ile Ser Met Gly Thr Ser Gly Leu Glu Leu Thr Phe
            100                 105                 110

Thr Asn Asp Ser Ile Ile Thr His Asn Phe Cys Asn Leu Thr Ser Ala
            115                 120                 125
```

```
Leu Asn Lys Arg Thr Phe Asp His Thr Leu Met Ser Ile Val Ser Ser
130                 135                 140

Leu His Leu Ser Ile Arg Gly Val Pro Ser Tyr Lys Ala Val Ser Cys
145                 150                 155                 160

Asp Phe Asn Asn Gly Ile Thr Ile Gln Tyr Asn Leu Ser Phe Ser Asn
        165                 170                 175

Ala Gln Ser Ala Leu Ser Gln Cys Lys Thr Phe Arg Gly Arg Val Leu
        180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Asn
210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Arg Phe Leu Thr Arg Arg Leu Ala Gly Thr Phe Thr Trp Thr Leu
                260                 265                 270

Ser Asp Ser Ser Gly Val Glu Asn Pro Gly Gly Tyr Cys Leu Thr Lys
                275                 280                 285

Trp Met Ile Leu Ala Ala Glu Leu Lys Cys Phe Gly Asn Thr Ala Val
290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
                340                 345                 350

Asp Gln Leu Leu Met Arg Asn His Leu Arg Asp Leu Met Gly Val Pro
                355                 360                 365

Tyr Cys Asn Tyr Ser Lys Phe Trp Tyr Leu Glu His Ala Lys Thr Gly
                370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
                420                 425                 430

Pro Leu Ala Leu Met Asp Leu Leu Met Phe Ser Thr Ser Ala Tyr Leu
                435                 440                 445

Ile Ser Ile Phe Leu His Leu Val Arg Ile Pro Thr His Arg His Ile
450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Glu Thr Thr Trp Lys
                485                 490                 495

Arg Arg
```

<210> SEQ ID NO 17
<211> LENGTH: 2209
<212> TYPE: PRT
<213> ORGANISM: Artificial Sequence
<220> FEATURE:
<223> OTHER INFORMATION: L protein of the MP strain of LCMV

<400> SEQUENCE: 17

```
Met Asp Glu Ala Ile Ser Glu Leu Arg Glu Leu Cys Leu Asn His Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
50                  55                  60

Asp Asp Lys Ser Val Glu Ala Ile Leu Ile Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Ile Ala Gly Ile Thr Leu Val Pro Ile Val Asp Gly Arg
130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Ile Asp Ser Met Lys Ile Leu Lys Asp
        195                 200                 205

Ala Arg Ser Phe His Asn Asp Glu Ile Met Lys Met Cys His Asp Gly
210                 215                 220

Val Asn Pro Asn Met Asn Cys Asp Asp Val Val Leu Gly Ile Asn Ser
225                 230                 235                 240

Leu Tyr Ser Arg Phe Arg Arg Asp Leu Glu Thr Gly Lys Leu Lys Arg
                245                 250                 255

Ser Phe Gln Lys Ile Asn Pro Gly Asn Leu Ile Lys Glu Phe Ser Glu
            260                 265                 270

Leu Tyr Glu Thr Leu Ala Asp Ser Asp Ile Ser Ala Leu Ser Lys
        275                 280                 285

Glu Ala Val Glu Ser Cys Pro Leu Met Arg Phe Ile Thr Ala Asp Thr
290                 295                 300

His Gly Tyr Glu Arg Gly Ser Glu Thr Ser Thr Glu Tyr Glu Arg Leu
305                 310                 315                 320

Leu Ser Met Leu Asn Lys Val Lys Ser Leu Lys Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Leu Lys Gly Ser Lys Asn Asp Lys His Trp Val Gly
        355                 360                 365

Cys Cys Tyr Gly Ser Val Asn Asp Arg Leu Val Ser Phe His Ser Thr
370                 375                 380

Lys Glu Glu Phe Ile Arg Leu Leu Arg Asn Arg Lys Ser Lys Ala
385                 390                 395                 400

Tyr Arg Lys Val Ser Leu Glu Asp Leu Phe Arg Thr Ser Ile Asn Glu
```

-continued

```
                405                 410                 415
Phe Ile Leu Lys Val Gln Arg Cys Leu Ser Val Gly Leu Ser Phe
            420                 425                 430

Gly His Tyr Gly Leu Ser Glu His Leu Glu His Glu Cys His Ile Pro
            435                 440                 445

Phe Ile Glu Phe Glu Asn Phe Met Arg Ser Gly Thr His Pro Ile Met
450                 455                 460

Tyr Tyr Thr Lys Phe Glu Asp Tyr Asp Phe Gln Pro Asn Thr Glu Gln
465                 470                 475                 480

Leu Arg Asn Met His Ser Leu Lys Arg Leu Ser Ser Val Cys Leu Ala
                485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
            515                 520                 525

Cys Gln Val Ile Lys Leu Asp Ser Glu Glu Tyr His Leu Leu Tyr Gln
530                 535                 540

Lys Thr Gly Glu Ser Ser Arg Cys Tyr Ser Ile Gln Gly Pro Asn Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Ile Asp Asp Val Glu Ile
            595                 600                 605

Ala Leu Arg Thr Leu Leu Leu Met Leu Thr Asn Pro Thr Lys Arg
610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Lys Leu Leu Arg Phe Leu Ile
            660                 665                 670

Lys Thr Val Phe Gly Thr Gly Glu Lys Val Leu Leu Ser Ala Lys Phe
            675                 680                 685

Lys Phe Met Leu Asn Val Ser Tyr Leu Cys His Leu Ile Thr Lys Glu
690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Val Asn Pro Lys Glu Ser Ile
                725                 730                 735

Thr Pro Glu Glu Cys Val Phe Tyr Asp Gln Met Lys Lys Phe Thr
            740                 745                 750

Gly Lys Glu Val Asp Cys Gln Arg Thr Thr Pro Gly Val Asn Leu Glu
            755                 760                 765

Ala Phe Ser Met Met Val Ser Ser Phe Asn Asn Gly Thr Leu Ile Phe
770                 775                 780

Lys Gly Glu Lys Arg Leu Asn Ser Leu Asp Pro Met Thr Asn Ser Gly
785                 790                 795                 800

Cys Ala Thr Ala Leu Asp Leu Ala Ser Asn Lys Ser Val Val Asn
                805                 810                 815

Lys His Leu Asn Gly Glu Arg Leu Leu Glu Tyr Asp Phe Asn Lys Leu
            820                 825                 830
```

```
Leu Val Ser Ala Val Ser Gln Ile Thr Glu Ser Phe Met Arg Lys Gln
    835                 840                 845

Lys Tyr Lys Leu Asn His Ser Asp Tyr Glu Tyr Lys Val Ser Lys Leu
    850                 855                 860

Val Ser Arg Leu Val Ile Gly Ser Lys Glu Thr Glu Ala Gly Lys Leu
865                 870                 875                 880

Glu Gly Asp Ser Ala Asp Ile Cys Phe Asp Gly Glu Glu Thr Ser
                885                 890                 895

Phe Phe Lys Asn Leu Glu Asp Lys Val Asn Ser Thr Ile Lys Arg Tyr
            900                 905                 910

Glu Arg Ser Lys Lys Thr Asn Glu Gly Glu Asn Glu Val Gly Phe Glu
            915                 920                 925

Asn Thr Lys Gly Leu His His Leu Gln Thr Ile Leu Ser Gly Lys Met
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Met Lys Phe Ile
                965                 970                 975

Cys Glu Ala Ile Glu Thr Ser Thr Glu Leu Ser Pro Leu Tyr Phe Thr
            980                 985                 990

Ser Ala Val Lys Glu Gln Cys Gly  Leu Asp Glu Met Ala  Lys Asn Leu
            995                1000                1005

Cys Arg  Lys Phe Phe Ser Glu  Gly Asp Trp Phe  Ser Cys Met Lys
    1010                1015                1020

Met Ile  Leu Leu Gln Met Asn  Ala Asn Ala Tyr Ser  Gly Lys Tyr
    1025                1030                1035

Arg His  Met Gln Arg Gln Gly  Leu Asn Phe Lys Phe  Asp Trp Asp
    1040                1045                1050

Lys Leu  Glu Glu Asp Val Arg  Ile Ser Glu Arg Glu  Ser Asn Ser
    1055                1060                1065

Glu Ser  Leu Ser Lys Ala Leu  Ser Leu Thr Lys Cys  Met Ser Ala
    1070                1075                1080

Ala Leu  Lys Asn Leu Cys Phe  Tyr Ser Glu Glu Ser  Pro Thr Ser
    1085                1090                1095

Tyr Thr  Ser Val Gly Pro Asp  Ser Gly Arg Leu Lys  Phe Ala Leu
    1100                1105                1110

Ser Tyr  Lys Glu Gln Val Gly  Gly Asn Arg Glu Leu  Tyr Ile Gly
    1115                1120                1125

Asp Leu  Arg Thr Lys Met Phe  Thr Arg Leu Ile Glu  Asp Tyr Phe
    1130                1135                1140

Glu Ser  Phe Ser Ser Phe Phe  Ser Gly Ser Cys Leu  Asn Asn Asp
    1145                1150                1155

Lys Glu  Phe Glu Asn Ala Ile  Leu Ser Met Thr Ile  Asn Val Arg
    1160                1165                1170

Glu Gly  Leu Leu Asn Tyr Ser  Met Asp His Ser Lys  Trp Gly Pro
    1175                1180                1185

Met Met  Cys Pro Phe Leu Phe  Leu Met Leu Leu Gln  Asn Leu Lys
    1190                1195                1200

Leu Gly  Asp Asp Gln Tyr Val  Arg Ser Gly Lys Asp  His Ile Ser
    1205                1210                1215

Thr Leu  Leu Thr Trp His Met  His Lys Leu Val Glu  Val Pro Phe
    1220                1225                1230
```

-continued

Pro Val Val Asn Ala Met Met Lys Ser Tyr Ile Lys Ser Lys Leu
1235                1240                1245

Lys Leu Leu Arg Gly Ser Glu Thr Thr Val Thr Glu Arg Ile Phe
1250                1255                1260

Arg Glu Tyr Phe Glu Leu Gly Ile Val Pro Ser His Ile Ser Ser
1265                1270                1275

Leu Ile Asp Met Gly Gln Gly Ile Leu His Asn Ala Ser Asp Phe
1280                1285                1290

Tyr Gly Leu Ile Ser Glu Arg Phe Ile Asn Tyr Cys Ile Gly Val
1295                1300                1305

Ile Phe Gly Glu Arg Pro Glu Ser Tyr Thr Ser Ser Asp Asp Gln
1310                1315                1320

Ile Thr Leu Phe Asp Arg Arg Leu Ser Glu Leu Val Asp Ser Asp
1325                1330                1335

Pro Glu Glu Val Leu Val Leu Leu Glu Phe His Ser His Leu Ser
1340                1345                1350

Gly Leu Leu Asn Lys Phe Ile Ser Pro Lys Ser Val Val Gly Arg
1355                1360                1365

Phe Ala Ala Glu Phe Lys Ser Arg Phe Tyr Val Trp Gly Glu Glu
1370                1375                1380

Val Pro Leu Leu Thr Lys Phe Val Ser Ala Ala Leu His Asn Val
1385                1390                1395

Lys Cys Lys Glu Pro His Gln Leu Cys Glu Thr Ile Asp Thr Ile
1400                1405                1410

Ala Asp Gln Ala Val Ala Asn Gly Val Pro Val Ser Leu Val Asn
1415                1420                1425

Cys Ile Gln Lys Arg Thr Leu Asp Leu Leu Lys Tyr Ala Asn Phe
1430                1435                1440

Pro Leu Asp Pro Phe Leu Leu Asn Thr Asn Thr Asp Val Lys Asp
1445                1450                1455

Trp Leu Asp Gly Ser Arg Gly Tyr Arg Ile Gln Arg Leu Ile Glu
1460                1465                1470

Glu Leu Cys Pro Ser Glu Thr Lys Val Met Arg Arg Leu Val Arg
1475                1480                1485

Arg Leu His His Lys Leu Lys Asn Gly Glu Phe Asn Glu Glu Phe
1490                1495                1500

Phe Leu Asp Leu Phe Asn Arg Asp Lys Lys Glu Ala Ile Leu Gln
1505                1510                1515

Leu Gly Asn Ile Leu Gly Leu Glu Glu Asp Leu Ser Gln Leu Ala
1520                1525                1530

Asn Ile Asn Trp Leu Asn Leu Asn Glu Leu Phe Pro Leu Arg Met
1535                1540                1545

Val Leu Arg Gln Lys Val Val Tyr Pro Ser Val Met Thr Phe Gln
1550                1555                1560

Glu Glu Arg Ile Pro Ser Leu Ile Lys Thr Leu Gln Asn Lys Leu
1565                1570                1575

Cys Ser Lys Phe Thr Arg Gly Ala Gln Lys Leu Leu Ser Glu Ala
1580                1585                1590

Ile Asn Lys Ser Ala Phe Gln Ser Cys Ile Ser Ser Gly Phe Ile
1595                1600                1605

Gly Leu Cys Lys Thr Leu Gly Ser Arg Cys Val Arg Asn Lys Asn
1610                1615                1620

Arg Asp Asn Leu Tyr Ile Arg Lys Val Leu Glu Asp Leu Ala Met

```
            1625                1630                1635

Asp Ala His Val Thr Ala Ile His Arg His Asp Gly Ile Met Leu
        1640                1645                1650

Tyr Ile Cys Asp Arg Gln Ser His Pro Glu Ala His Cys Asp His
        1655                1660                1665

Ile Ser Leu Leu Arg Pro Leu Leu Trp Asp Tyr Ile Cys Ile Ser
        1670                1675                1680

Leu Ser Asn Ser Phe Glu Leu Gly Val Trp Val Leu Ala Glu Pro
        1685                1690                1695

Val Lys Gly Lys Asn Glu Gly Ser Ser Ser Leu Lys His Leu Asn
        1700                1705                1710

Pro Cys Asp Tyr Val Ala Arg Lys Pro Glu Ser Ser Arg Leu Leu
        1715                1720                1725

Glu Asp Lys Ile Ser Leu Asn His Val Ile Gln Ser Val Arg Arg
        1730                1735                1740

Leu Tyr Pro Lys Ile Tyr Glu Asp Gln Leu Leu Pro Phe Met Ser
        1745                1750                1755

Asp Met Ser Ser Lys Asn Met Arg Trp Ser Pro Arg Ile Lys Phe
        1760                1765                1770

Leu Asp Leu Cys Val Leu Ile Asp Ile Asn Ser Glu Ser Leu Ser
        1775                1780                1785

Leu Ile Ser His Val Val Lys Trp Lys Arg Asp Glu His Tyr Thr
        1790                1795                1800

Val Leu Phe Ser Asp Leu Val Asn Ser His Gln Arg Ser Asp Ser
        1805                1810                1815

Ser Leu Val Asp Glu Phe Val Val Ser Thr Arg Asp Val Cys Lys
        1820                1825                1830

Asn Phe Leu Lys Gln Val Tyr Phe Glu Ser Phe Val Arg Glu Phe
        1835                1840                1845

Val Ala Thr Ser Arg Thr Leu Gly Ser Phe Ser Trp Phe Pro His
        1850                1855                1860

Lys Asp Met Met Pro Ser Glu Asp Gly Ala Glu Ala Leu Gly Pro
        1865                1870                1875

Phe Gln Ser Phe Ile Leu Lys Val Val Asn Lys Asn Met Glu Arg
        1880                1885                1890

Pro Met Phe Arg Asn Asp Leu Gln Phe Gly Phe Gly Trp Phe Ser
        1895                1900                1905

Tyr Arg Leu Gly Asp Ile Val Cys Asn Ala Ala Met Leu Ile Lys
        1910                1915                1920

Gln Gly Leu Thr Asn Pro Lys Ala Phe Lys Ser Leu Arg Asn Leu
        1925                1930                1935

Trp Asp Tyr Met Ile Asn Asn Thr Glu Gly Val Leu Glu Phe Ser
        1940                1945                1950

Ile Thr Val Asp Phe Thr His Asn Gln Asn Asn Thr Asp Cys Leu
        1955                1960                1965

Arg Lys Phe Ser Leu Ile Phe Leu Val Lys Cys Gln Leu Gln Gly
        1970                1975                1980

Pro Gly Val Ala Glu Phe Leu Ser Cys Ser His Leu Phe Lys Gly
        1985                1990                1995

Glu Val Asp Arg Arg Phe Leu Asp Glu Cys Leu His Leu Leu Arg
        2000                2005                2010

Ser Asp Ser Ile Phe Lys Val Asn Asp Gly Val Phe Asp Ile Arg
        2015                2020                2025
```

```
Ser Glu Glu Phe Glu Asp Tyr Met Glu Asp Pro Leu Ile Leu Gly
        2030                2035                2040

Asp Ser Leu Glu Leu Glu Leu Ile Gly Ser Arg Lys Ile Leu Asp
        2045                2050                2055

Gly Ile Arg Ser Leu Asp Phe Glu Arg Ile Gly Pro Glu Trp Glu
        2060                2065                2070

Pro Val Pro Leu Thr Val Arg Met Gly Ala Leu Phe Glu Gly Arg
        2075                2080                2085

Ser Leu Val Gln Asn Ile Val Val Lys Leu Glu Thr Lys Asp Met
        2090                2095                2100

Arg Val Phe Leu Ala Glu Leu Glu Gly Tyr Gly Asn Phe Asp Asp
        2105                2110                2115

Val Leu Gly Ser Leu Leu His Arg Phe Arg Thr Gly Glu His
        2120                2125                2130

Leu Gln Gly Ser Glu Ile Ser Thr Ile Leu Gln Glu Leu Cys Ile
        2135                2140                2145

Asp Arg Ser Ile Leu Leu Val Pro Leu Ser Leu Val Pro Asp Trp
        2150                2155                2160

Phe Thr Phe Lys Asp Cys Arg Leu Cys Phe Ser Lys Ser Lys Asn
        2165                2170                2175

Thr Val Met Tyr Glu Thr Val Val Gly Lys Tyr Arg Leu Lys Gly
        2180                2185                2190

Lys Ser Cys Asp Asp Trp Leu Thr Lys Ser Val Val Glu Glu Ile
        2195                2200                2205

Asp

<210> SEQ ID NO 18
<211> LENGTH: 90
<212> TYPE: PRT
<213> ORGANISM: Artificial Sequence
<220> FEATURE:
<223> OTHER INFORMATION: Z protein of the MP strain of LCMV

<400> SEQUENCE: 18

Met Gly Gln Gly Lys Ser Lys Glu Gly Arg Asp Ala Ser Asn Thr Ser
1               5                   10                  15

Arg Ala Glu Ile Leu Pro Asp Thr Thr Tyr Leu Gly Pro Leu Asn Cys
            20                  25                  30

Lys Ser Cys Trp Gln Arg Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys His Pro Leu Pro Thr Lys Leu Lys Ile Ser Thr
65                  70                  75                  80

Ala Pro Ser Ser Pro Pro Tyr Glu Glu
                85                  90

<210> SEQ ID NO 19
<211> LENGTH: 7115
<212> TYPE: DNA
<213> ORGANISM: Artificial Sequence
<220> FEATURE:
<223> OTHER INFORMATION: Junin virus Candid No.1 L segment

<400> SEQUENCE: 19
gcgcaccggg gatcctaggc gtaacttcat cattaaaatc tcagattctg ctctgagtgt    60
```

```
gacttactgc gaagaggcag acaaatgggc aactgcaacg gggcatccaa gtctaaccag    120
ccagactcct caagagccac acagccagcc gcagaattta ggagggtagc tcacagcagt    180
ctatatggta gatataactg taagtgctgc tggtttgctg ataccaattt gataacctgt    240
aatgatcact acctttgttt aaggtgccat cagggtatgt taaggaattc agatctctgc    300
aatatctgct ggaagcccct gcccaccaca atcacagtac cggtggagcc aacagcacca    360
ccaccatagg cagactgcac agggtcagac ccgacccccc ggggggcccc catggggacc    420
ccccgtgggg gaaccccggg ggtgatgcgc cattagtcaa tgtctttgat ctcgactttg    480
tgcttcagtg gcctgcatgt cacccctttc aatctgaact gcccttgggg atctgatatc    540
agcaggtcat ttaaagatct gctgaatgcc accttgaaat ttgagaattc caaccagtca    600
ccaaatttat caagtgaacg gatcaactgc tctttgtgta gatcataaac gaggacaaag    660
tcctcttgct gaaataatat tgtttgtgat gttgttttta gataaggcca tagttggctt    720
aataaggttt ccacactatc aatgtcctct agtgctccaa ttgccttgac tatgacatcc    780
ccagacaact caactctata tgttgacaac cttttcattac ctctgtaaaa gatacc ctct    840 ttcaagacaa gaggttctcc tgggttatct ggcccaatga ggtcatatgc atacttgtta    900
cttagttcag aataaaagtc accaaagttg aacttaacat ggctcagaat attgtcatca    960
tttgtcgcag cgtagcctgc atcaataaac aagccagcta ggtcaaagct ctcatggcct    1020
gtgaacaatg gtaggctagc gataaccagt gcaccatcca acaatgagtg gcttccctca    1080
gacccagaaa cacattgact cattgcatcc acattcagct ctaattcagg ggtaccgaca    1140
tcatccactc ctagtgaact gacaatggtg taactgtaca ccatctttct tctaagttta    1200
aattttgtcg aaactcgtgt gtgttctact tgaatgatca attttagttt cacagcttct    1260
tggcaagcaa cattgcgcaa cacagtgtgc aggtccatca tgtcttcctg aggcaacaag    1320
gagatgttgt caacagagac ccctcaagg aaaaccttga tattatcaaa gctagaaact    1380
acataaccca ttgcaatgtc ttcaacaaac attgctcttg atactttatt attcctaact    1440
gacaaggtaa aatctgtgag ttcagctaga tctacttgac tgtcatcttc tagatctaga    1500
acttcattga accaaaagaa ggatttgaga cacgatgttg acatgactag tgggtttatc    1560
atcgaagata agacaacttg caccatgaag ttcctgcaaa cttgctgtgg gctgatgcca    1620
acttcccaat ttgtatactc tgactgtcta acatgggctg aagcgcaatc actctgtttc    1680
acaatataaa cattattatc tcttactttc aataagtgac ttataatccc taagttttca    1740
ttcatcatgt ctagagccac acagacatct agaaacttga gtcttccact atccaaagat    1800
ctgttcactt gaagatcatt cataaagggt gccaaatgtt cttcaaatag tttggggtaa    1860
tttcttcgta tagaatgcaa tacatggttc atgcctaatt ggtcttctat ctgtcgtact    1920
gctttgggtt taacagccca gaagaaattc ttattacata agaccagagg ggcctgtgga    1980
ctcttaatag cagaaaacac ccactcccct aactcacagg catttgtcag caccaaagag    2040
aagtaatccc acaaaattgg tttagaaaat tggttaactt ctttaagtga ttttgacag    2100 taaataactt taggctttct ctcacaaatt ccacaaagac atggcattat tcgagtaaat    2160
atgtccttta tatacagaaa tccgccttta ccatccctaa cacacttact ccccatactc    2220
ttacaaaacc caatgaagcc tgaggcaaca gaagactgaa atgcagattt gttgattgac    2280
tctgccaaga tcttcttcac gccttttgtg aaatttcttg acagcctgga ctgtattgtc    2340
cttatcaatg ttggcatctc ttcttt ctct aacactcttc gacttgtcat gagtttggtc    2400
ctcaagacca acctcaagtc cccaaagctc gctaaattga cccatctgta gtctagagtt    2460
```

```
tgtctgattt catcttcact acacccggca tattgcagga atccggataa agcctcatcc    2520
cctcccctgc ttatcaagtt gataaggttt cctcaaaga ttttgcctct cttaatgtca    2580
ttgaacactt tcctcgcgca gttccttata acattgtct ccttatcatc agaaaaata    2640 gcttcaattt tcctctgtag acggtaccct ctagacccat caacccagtc tttgacatct   2700
tgttcttcaa tagctccaaa cggagtctct ctgtatccag agtatctaat caattggttg   2760
actctaatgg aaatctttga cactatatga gtgctaaccc cattagcaat acattgatca   2820
caaattgtgt ctatggtctc tgacagttgt gttggagttt tacacttaac gttgtgtaga   2880
gcagcagaca caaacttggt gagtaaagga gtctcttcac ccatgacaaa aaatcttgac   2940
ttaaactcag caacaaaagt tcctatcaca ctctttgggc tgataaactt gtttaattta   3000
gaagataaga attcatggaa gcacaccatt tccagcagtt ctgtcctgtc ttgaaacttt   3060
tcatcactaa ggcaaggaat ttttataagg ctaacctggt catcgctgga ggtataagtg   3120
acaggtatca catcatacaa taagtcaagt gcataacaca gaaattgttc agtaattagc   3180
ccatataaat ctgatgtgtt gtgcaagatt ccctggccca tgtccaagac agacattata   3240
tggctgggga cctggtccct tgactgcaga tactggtgaa aaaactcttc accaacacta   3300
gtacagtcac aacccattaa acctaaagat ctcttcaatt tccctacaca gtaggcttct   3360
gcaacattaa ttggaacttc aacgaccttta tgaagatgcc atttgagaat gttcattact   3420
ggttcaagat tcacctttgt tctatctctg ggattcttca attctaatgt gtacaaaaaa   3480
gaaaggaaaa gtgctgggct catagttggt ccccatttgg agtggtcata tgaacaggac   3540
aagtcaccat tgttaacagc catttttcata tcacagattg cacgttcgaa ttccttttct   3600
gaattcaagc atgtgtattt cattgaacta cccacagctt ctgagaagtc ttcaactaac   3660
ctggtcatca gcttagtgtt gaggtctccc acatacagtt ctctatttga gccaacctgc   3720
tccttataac ttagtccaaa tttcaagttc cctgtatttg agctgatgct tgtgaactct   3780
gtaggagagt cgtctgaata gaaacataaa ttccgtaggg ctgcatttgt aaataacttt   3840
ttgtctagct tatcagcaat ggcttcagaa ttgctttccc tggtactaag ccgaaccctca   3900 tcctttagtc tcagaacttc actggaaaag cccaatctag atctacttct atgctcataa    3960
ctacccaatt tctgatcata atgtccttga attaaaagat acttgaagca ttcaaagaat   4020
tcatcttctt ggtaggctat tgttgtcaaa tttttttaata acaaacccaa agggcagatg   4080
tcctgcggtg cttcaagaaa ataagtcaat ttaaatggag atagataaac agcatcacat   4140
aactctttat acacatcaga cctgagcaca tctggatcaa aatccttcac ctcatgcatt   4200
gacacctctg ctttaatctc tctcaacact ccaaaggggg cccacaatga ctcaagagac   4260
tctcgctcat caacagatgg atttttttgat ttcaacttgg tgatctcaac ttttgtcccc   4320
tcactattag ccatcttggc tagtgtcatt tgtacgtcat ttctaatacc ctcaaaggcc   4380
cttacttgat cctctgttaa actctcatac atcactgata attcttcttg attggttctg   4440
gttcttgaac cggtgctcac aagacctgtt agatttttta atattaagta gtccatggaa   4500
tcaggatcaa gattatacct gccttttgtt ttaaacctct cagccatagt agaaacgcat   4560
gttgaaacaa gtttctcctt atcataaaca gaaagaatat ttccaagttc gtcgagcttg   4620
gggattacca cacttttatt gcttgacaga tccagagctg tgctagtgat gttaggcctg   4680
tagggattgc ttttcagttc acctgtaact ttaagtcttc ctctattgaa gagagaaatg   4740
cagaaggaca aaatctcttt acacactcct ggaatttgag tatctgagga agtcttagcc   4800
```

```
tctttggaaa agaatctgtc caatcctctt atcatggtgt cctcttgttc cagtgttaga    4860
ctcccactta gagggggtt tacaacaaca caatcaaact tgactttggg ctcaataaac     4920
ttctcaaaac actttatttg atctgtcagg cgatcaggtg tctctttggt taccaagtga    4980
cacagataac taacatttaa tagatattta aaccttcttg caaagtaaag atctgcatct    5040
tcccccttcac ccaaaattgt ctggaaaagt tccacagcca tcctctgaat cagcacctct   5100
gatccagaca tgcagtcgac ccttaacttt gacatcaaat ccacatgatg gatttgattt    5160
gcatatgcca tcaagaaata tcttagacct tgtaaaaatg tctggttcct tttggaaggg    5220
gaacagagta cagctaacac taacaatctt aatattggcc ttgtcattgt catgagttcg    5280
tggctaaaat ccaaccagct ggtcatttcc tcacacattt caattaacac atcctccgaa    5340
aatataggca ggaaaaatct ctttggatca cagtaaaaag agccttgttc ttccaatacc    5400
ccattgatgg atagatagat agaatagcac cttgacttct cacctgtttt ttggtaaaac    5460
aagagaccaa atgtattctt tgtcagatga aatctttgta cataacactc tcttagtcta    5520
acattcccaa aatatctaga atactctctt tcattgatta caatcggga ggaaaatgat     5580
gtcttcatcg agttgaccaa tgcaagggaa atggaggaca aaatcctaaa taatttcttc    5640
tgctcacctt ccactaagct gctgaatggc tgatgtctac agattttctc aaattccttg    5700
ttaatagtat atctcatcac tggtctgtca gaaacaagtg cctgagctaa aatcatcaag    5760
ctatccatat cagggtgttt tattagtttt tccagctgtg accagagatc ttgatgagag    5820
ttcttcaatg ttctggaaca cgcttgaacc cacttggggc tggtcatcaa tttcttcctt    5880
attagtttaa tcgcctccag aatatctaga agtctgtcat tgactaacat taacatttgt    5940
ccaacaacta ttcccgcatt tcttaacctt acaattgcat catcatgcgt tttgaaaaga    6000
tcacaaagta aattgagtaa aactaagtcc agaaacagta aagtgtttct cctggtgttg    6060
aaaactttta gaccttcac tttgttacac acggaaaggg cttgaagata cacctctct     6120
acagcatcaa tagatataga attctcatct gactggcttt ccatgttgac ttcatctatt    6180
ggatgcaatg cgatagagta gactacatcc atcaacttgt ttgcacaaaa agggcagctg    6240
ggcacatcac tgtctttgtg gcttcctaat aagatcaagt catttataag cttagacttt    6300
tgtgaaaatt tgaatttccc caactgcttg tcaaaaatct ccttcttaaa ccaaaacctt    6360
aactttatga gttcttctct tatgacagat tctctaatgt ctcctctaac cccaacaaag    6420
agggattcat ttaacctctc atcataaccc aaagaattct ttttcaagca ttcgatgttt    6480
tctaatccca agctctggtt ttttgtgttg acaaactat ggatcaatcg ctggtattct     6540
tgttcttcaa tattaatctc ttgcataaat tttgatttct ttaggatgtc gatcagcaac    6600
caccgaactc tttcaacaac ccaatcagca aggaatctat tgctgtagct agatctgcca    6660
tcaaccacag gaaccaacgt aatccctgcc cttagtaggt cggactttag gtttaagagc    6720
tttgacatgt cactcttcca ttttctctca aactcatcag gattgaccct aacaaaggtt    6780
tccaatagga tgagtgtttt ccctgtgagt ttgaagccat ccggaatgac ttttggaagg    6840
gtgggacata gtatgccata gtcagacagg atcacatcaa caaacttctg atctgaattg    6900
atctgacagg cgtgtgcctc acaggactca agctctacta aacttgacag aagtttgaac    6960
ccttccaaca acagagagct ggggtgatgt tgagataaaa agatgtccct ttggtatgct    7020
agctcctgtc tttctggaaa atgctttcta ataaggcttt ttatttcatt tactgattcc    7080
tccatgctca agtgccgcct aggatcctcg gtgcg                               7115
```

<210> SEQ ID NO 20
<211> LENGTH: 3411
<212> TYPE: DNA
<213> ORGANISM: Artificial Sequence
<220> FEATURE:
<223> OTHER INFORMATION: Junin virus Candid No. 1 S segment

<400> SEQUENCE: 20

| | | | | | | |
|---|---|---|---|---|---|---|
| gcgcaccggg | gatcctaggc | gattttggtt | acgctataat | tgtaactgtt | ttctgtttgg | 60 |
| acaacatcaa | aaacatccat | tgcacaatgg | ggcagttcat | tagcttcatg | caagaaatac | 120 |
| caacctttt | gcaggaggct | ctgaacattg | ctcttgttgc | agtcagtctc | attgccatca | 180 |
| ttaagggtat | agtgaacttg | tacaaaagtg | gtttattcca | attctttgta | ttcctagcgc | 240 |
| ttgcaggaag | atcctgcaca | gaagaagctt | tcaaaatcgg | actgcacact | gagttccaga | 300 |
| ctgtgtcctt | ctcaatggtg | gtctcttttt | ccaacaatcc | acatgaccta | cctttgttgt | 360 |
| gtaccttaaa | caagagccat | ctttacatta | aggggggcaa | tgcttcattt | cagatcagct | 420 |
| ttgatgatat | tgcagtattg | ttgccacagt | atgatgttat | aatacaacat | ccagcagata | 480 |
| tgagctggtg | ttccaaaagt | gatgatcaaa | tttggttgtc | tcagtggttc | atgaatgctg | 540 |
| tgggacatga | ttggcatcta | gacccaccat | ttctgtgtag | gaaccgtgca | aagacagaag | 600 |
| gcttcatctt | tcaagtcaac | acctccaaga | ctggtgtcaa | tggaaattat | gctaagaagt | 660 |
| ttaagactgg | catgcatcat | ttatatagag | aatatcctga | cccttgcttg | aatggcaaac | 720 |
| tgtgcttaat | gaaggcacaa | cctaccagtt | ggcctctcca | atgtccactc | gaccacgtta | 780 |
| acacattaca | cttccttaca | agaggtaaaa | acattcaact | tccaaggagg | tccttgaaag | 840 |
| cattcttctc | ctggtctttg | acagactcat | ccggcaagga | taccctgga | ggctattgtc | 900 |
| tagaagagtg | gatgctcgta | gcagccaaaa | tgaagtgttt | tggcaatact | gctgtagcaa | 960 |
| aatgcaattt | gaatcatgac | tctgaattct | gtgacatgtt | gaggctcttt | gattacaaca | 1020 |
| aaaatgctat | caaaccccta | atgatgaaa | ctaagaaaca | agtaaatctg | atgggggaga | 1080 |
| caatcaatgc | cctgatatct | gacaatttat | tgatgaaaaa | caaaattagg | gaactgatga | 1140 |
| gtgtccctta | ctgcaattac | acaaaatttt | ggtatgtcaa | ccacacactt | tcaggacaac | 1200 |
| actcattacc | aaggtgctgg | ttaataaaaa | acaacagcta | tttgaacatc | tctgacttcc | 1260 |
| gtaatgactg | atattagaa | agtgacttct | taatttctga | aatgctaagc | aaagagtatt | 1320 |
| cggacaggca | gggtaaaact | cctttgactt | tagttgacat | ctgtatttgg | agcacagtat | 1380 |
| tcttcacagc | gtcactcttc | cttcacttgg | tgggtatacc | ctcccacaga | cacatcaggg | 1440 |
| gcgaagcatg | ccctttgcca | cacaggttga | acagcttggg | tggttgcaga | tgtggtaagt | 1500 |
| accccaatct | aaagaaacca | acagtttggc | gtagaggaca | ctaagacctc | ctgagggtcc | 1560 |
| ccaccagccc | gggcactgcc | cgggctggtg | tggccccca | gtccgcggcc | tggccgcgga | 1620 |
| ctggggaggc | actgcttaca | gtgcataggc | tgccttcggg | aggaacagca | agctcggtgg | 1680 |
| taatagaggt | gtaggttcct | cctcatagag | cttcccatct | agcactgact | gaaacattat | 1740 |
| gcagtctagc | agagcacagt | gtggttcact | ggaggccaac | ttgaagggag | tatccttttc | 1800 |
| cctctttttc | ttattgacaa | ccactccatt | gtgatatttg | cataagtgac | catatttctc | 1860 |
| ccagacctgt | tgatcaaact | gcctggcttg | ttcagatgtg | agcttaacat | caaccagttt | 1920 |
| aagatctctt | cttccatgga | ggtcaaacaa | cttcctgatg | tcatcggatc | cttgagtagt | 1980 |
| cacaaccatg | tctggaggca | gcaagccgat | cacgtaacta | agaactcctg | gcattgcatc | 2040 |
| ttctatgtcc | ttcattaaga | tgccgtgaga | gtgtctgcta | ccattttaa | accctttctc | 2100 |

```
atcatgtggt tttctgaagc agtgaatgta ctgcttacct gcaggttgga ataatgccat    2160
ctcaacaggg tcagtggctg gtccttcaat gtcgagccaa agggtgttgg tggggtcgag    2220
tttccccact gcctctctga tgacagcttc ttgtatctct gtcaagttag ccaatctcaa    2280
attctgaccg ttttttttccg gctgtctagg accagcaact ggtttccttg tcagatcaat    2340
acttgtgttg tcccatgacc tgcctgtgat tgtgatctca gaaccaatat aaggccaacc    2400
atcgccagaa agacaaagtt tgtacaaaag gttttcataa ggatttctat tgcctggttt    2460
ctcatcaata acatgccttc tcttcgtttt aacctgaatg gttgatttta tgagggaaga    2520
gaagttttct ggggtgactc tgattgtttc caacatgttt ccaccatcaa gaatagatgc    2580
tccagccttt actgcagctg aaagactgaa gttgtaacca gaaatattga tggagctttc    2640
atctttagtc acaatctgaa ggcagtcatg ttcctgagtc agtctgtcaa ggtcacttaa    2700
gtttggatac ttcacagtgt atagaagccc aagtgaggtt aaagcttgta tgacactgtt    2760
cattgtctca cctccttgaa cagtcatgca tgcaattgtc aatgcaggaa cagagccaaa    2820
ctgattgttt agctttgaag ggtctttaac atcccatatc ctcaccacac catttccccc    2880
agtcccttgc tgttgaaatc ccagtgttct caatatctct gatcttttag caagttgtga    2940
ctgggacaag ttacccatgt aaaccccctg agagcctgtc tctgctcttc ttatcttgtt    3000
ttttaatttc tcaaggtcag acgccaactc catcagttca tccctcccca gatctcccac    3060
cttgaaaact gtgtttcgtt gaacactcct catggacatg agtctgtcaa cctctttatt    3120
caggtccctc aacttgttga ggtcttcttc ccccttttta gtctttctga gtgcccgctg    3180
cacctgtgcc acttggttga agtcgatgct gtcagcaatt agcttggcgt ccttcaaaac    3240
atctgacttg acagtctgag tgaattggct caaacctctc cttaaggact gagtccatct    3300
aaagcttgga acctccttgg agtgtgccat gccagaagtt ctggtgattt tgatctagaa    3360
tagagttgct cagtgaaagt gttagacact atgcctagga tccactgtgc g             3411
```

<210> SEQ ID NO 21
<211> LENGTH: 558
<212> TYPE: PRT
<213> ORGANISM: Artificial Sequence
<220> FEATURE:
<223> OTHER INFORMATION: NP protein of the Clone 13 strain of LCMV
      (GenBank Accession No. ABC96002.1; GI:86440166)

<400> SEQUENCE: 21

```
Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
        115                 120                 125
```

-continued

```
Leu Thr Thr Gln Gln Leu Asp Gln Arg Ser Gln Ile Leu Gln Ile Val
    130                 135                 140
Gly Met Arg Lys Pro Gln Gln Gly Ala Ser Gly Val Val Arg Val Trp
145                 150                 155                 160
Asp Val Lys Asp Ser Ser Leu Leu Asn Asn Gln Phe Gly Thr Met Pro
                165                 170                 175
Ser Leu Thr Met Ala Cys Met Ala Lys Gln Ser Gln Thr Pro Leu Asn
            180                 185                 190
Asp Val Gln Ala Leu Thr Asp Leu Gly Leu Leu Tyr Thr Val Lys
        195                 200                 205
Tyr Pro Asn Leu Asn Asp Leu Glu Arg Leu Lys Asp Lys His Pro Val
210                 215                 220
Leu Gly Val Ile Thr Glu Gln Gln Ser Ser Ile Asn Ile Ser Gly Tyr
225                 230                 235                 240
Asn Phe Ser Leu Gly Ala Ala Val Lys Ala Gly Ala Ala Leu Leu Asp
                245                 250                 255
Gly Gly Asn Met Leu Glu Ser Ile Leu Ile Lys Pro Ser Asn Ser Glu
            260                 265                 270
Asp Leu Leu Lys Ala Val Leu Gly Ala Lys Arg Lys Leu Asn Met Phe
        275                 280                 285
Val Ser Asp Gln Val Gly Asp Arg Asn Pro Tyr Glu Asn Ile Leu Tyr
290                 295                 300
Lys Val Cys Leu Ser Gly Glu Gly Trp Pro Tyr Ile Ala Cys Arg Thr
305                 310                 315                 320
Ser Ile Val Gly Arg Ala Trp Glu Asn Thr Thr Ile Asp Leu Thr Ser
                325                 330                 335
Glu Lys Pro Ala Val Asn Ser Pro Arg Pro Ala Pro Gly Ala Ala Gly
            340                 345                 350
Pro Pro Gln Val Gly Leu Ser Tyr Ser Gln Thr Met Leu Leu Lys Asp
        355                 360                 365
Leu Met Gly Gly Ile Asp Pro Asn Ala Pro Thr Trp Ile Asp Ile Glu
370                 375                 380
Gly Arg Phe Asn Asp Pro Val Glu Ile Ala Ile Phe Gln Pro Gln Asn
385                 390                 395                 400
Gly Gln Phe Ile His Phe Tyr Arg Glu Pro Val Asp Gln Lys Gln Phe
                405                 410                 415
Lys Gln Asp Ser Lys Tyr Ser His Gly Met Asp Leu Ala Asp Leu Phe
            420                 425                 430
Asn Ala Gln Pro Gly Leu Thr Ser Ser Val Ile Gly Ala Leu Pro Gln
        435                 440                 445
Gly Met Val Leu Ser Cys Gln Gly Ser Asp Asp Ile Arg Lys Leu Leu
450                 455                 460
Asp Ser Gln Asn Arg Lys Asp Ile Lys Leu Ile Asp Val Glu Met Thr
465                 470                 475                 480
Arg Glu Ala Ser Arg Glu Tyr Glu Asp Lys Val Trp Asp Lys Tyr Gly
                485                 490                 495
Trp Leu Cys Lys Met His Thr Gly Ile Val Arg Asp Lys Lys Lys
            500                 505                 510
Glu Ile Thr Pro His Cys Ala Leu Met Asp Cys Ile Ile Phe Glu Ser
        515                 520                 525
Ala Ser Lys Ala Arg Leu Pro Asp Leu Lys Thr Val His Asn Ile Leu
530                 535                 540
Pro His Asp Leu Ile Phe Arg Gly Pro Asn Val Val Thr Leu
```

-continued

<210> SEQ ID NO 22
<211> LENGTH: 498
<212> TYPE: PRT
<213> ORGANISM: Artificial Sequence
<220> FEATURE:
<223> OTHER INFORMATION: GP protein of the Clone 13 strain of LCMV
      (GenBank Accession No. ABC96001.2; GI:116563462)

<400> SEQUENCE: 22

```
Met Gly Gln Ile Val Thr Met Phe Glu Ala Leu Pro His Ile Ile Asp
1               5                   10                  15

Glu Val Ile Asn Ile Val Ile Val Leu Ile Val Ile Thr Gly Ile
            20                  25                  30

Lys Ala Val Tyr Asn Phe Ala Thr Cys Gly Ile Phe Ala Leu Ile Ser
        35                  40                  45

Phe Leu Leu Leu Ala Gly Arg Ser Cys Gly Met Tyr Gly Leu Lys Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350
```

-continued

```
Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Val Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg
```

<210> SEQ ID NO 23
<211> LENGTH: 2210
<212> TYPE: PRT
<213> ORGANISM: Artificial Sequence
<220> FEATURE:
<223> OTHER INFORMATION: L protein of the Clone 13 strain of LCMV (GenBank Accession No. ABC96004.1; GI:86440169)

<400> SEQUENCE: 23

```
Met Asp Glu Ile Ile Ser Glu Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Thr His Asn His
    50                  55                  60

Asp Asp Lys Ser Val Glu Thr Ile Leu Val Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Arg Glu
        115                 120                 125

Asp Leu Ala Val Ala Gly Val Thr Leu Val Pro Ile Val Asp Gly Arg
    130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205
```

-continued

```
Ala Arg Ser Thr His Asn Asp Glu Ile Met Arg Met Cys His Glu Gly
    210                 215                 220
Ile Asn Pro Asn Met Ser Cys Asp Asp Val Val Phe Gly Ile Asn Ser
225                 230                 235                 240
Leu Phe Ser Arg Phe Arg Arg Asp Leu Glu Ser Gly Lys Leu Lys Arg
                245                 250                 255
Asn Phe Gln Lys Val Asn Pro Glu Gly Leu Ile Lys Glu Phe Ser Glu
            260                 265                 270
Leu Tyr Glu Asn Leu Ala Asp Ser Asp Asp Ile Leu Thr Leu Ser Arg
        275                 280                 285
Glu Ala Val Glu Ser Cys Pro Leu Met Arg Phe Ile Thr Ala Glu Thr
    290                 295                 300
His Gly His Glu Arg Gly Ser Glu Thr Ser Thr Glu Tyr Glu Arg Leu
305                 310                 315                 320
Leu Ser Met Leu Asn Lys Val Lys Ser Leu Lys Leu Asn Thr Arg
                325                 330                 335
Arg Arg Gln Leu Leu Asn Leu Asp Val Leu Cys Leu Ser Ser Leu Ile
            340                 345                 350
Lys Gln Ser Lys Phe Lys Gly Leu Lys Asn Asp Lys His Trp Val Gly
        355                 360                 365
Cys Cys Tyr Ser Ser Val Asn Asp Arg Leu Val Ser Phe His Ser Thr
    370                 375                 380
Lys Glu Glu Phe Ile Arg Leu Leu Arg Asn Arg Lys Lys Ser Lys Val
385                 390                 395                 400
Phe Arg Lys Val Ser Phe Glu Glu Leu Phe Arg Ala Ser Ile Ser Glu
                405                 410                 415
Phe Ile Ala Lys Ile Gln Lys Cys Leu Leu Val Val Gly Leu Ser Phe
            420                 425                 430
Glu His Tyr Gly Leu Ser Glu His Leu Glu Gln Glu Cys His Ile Pro
        435                 440                 445
Phe Thr Glu Phe Glu Asn Phe Met Lys Ile Gly Ala His Pro Ile Met
    450                 455                 460
Tyr Tyr Thr Lys Phe Glu Asp Tyr Asn Phe Gln Pro Ser Thr Glu Gln
465                 470                 475                 480
Leu Lys Asn Ile Gln Ser Leu Arg Arg Leu Ser Ser Val Cys Leu Ala
                485                 490                 495
Leu Thr Asn Ser Met Lys Thr Ser Ser Val Ala Arg Leu Arg Gln Asn
            500                 505                 510
Gln Ile Gly Ser Val Arg Tyr Gln Val Val Glu Cys Lys Glu Val Phe
        515                 520                 525
Cys Gln Val Ile Lys Leu Asp Ser Glu Glu Tyr His Leu Leu Tyr Gln
    530                 535                 540
Lys Thr Gly Glu Ser Ser Arg Cys Tyr Ser Ile Gln Gly Pro Asp Gly
545                 550                 555                 560
His Leu Ile Ser Phe Tyr Ala Asp Pro Lys Arg Phe Phe Leu Pro Ile
                565                 570                 575
Phe Ser Asp Glu Val Leu Tyr Asn Met Ile Asp Ile Met Ile Ser Trp
            580                 585                 590
Ile Arg Ser Cys Pro Asp Leu Lys Asp Cys Leu Thr Asp Ile Glu Val
        595                 600                 605
Ala Leu Arg Thr Leu Leu Leu Leu Met Leu Thr Asn Pro Thr Lys Arg
    610                 615                 620
Asn Gln Lys Gln Val Gln Ser Val Arg Tyr Leu Val Met Ala Ile Val
```

-continued

```
            625                 630                 635                 640
        Ser Asp Phe Ser Ser Thr Ser Leu Met Asp Lys Leu Arg Glu Asp Leu
                        645                 650                 655

Ile Thr Pro Ala Glu Lys Val Val Tyr Lys Leu Leu Arg Phe Leu Ile
                        660                 665                 670

Lys Thr Ile Phe Gly Thr Gly Glu Lys Val Leu Leu Ser Ala Lys Phe
                        675                 680                 685

Lys Phe Met Leu Asn Val Ser Tyr Leu Cys His Leu Ile Thr Lys Glu
                690                 695                 700

Thr Pro Asp Arg Leu Thr Asp Gln Ile Lys Cys Phe Glu Lys Phe Phe
        705                 710                 715                 720

Glu Pro Lys Ser Gln Phe Gly Phe Phe Val Asn Pro Lys Glu Ala Ile
                        725                 730                 735

Thr Pro Glu Glu Glu Cys Val Phe Tyr Glu Gln Met Lys Arg Phe Thr
                        740                 745                 750

Ser Lys Glu Ile Asp Cys Gln His Thr Thr Pro Gly Val Asn Leu Glu
                        755                 760                 765

Ala Phe Ser Leu Met Val Ser Ser Phe Asn Asn Gly Thr Leu Ile Phe
                        770                 775                 780

Lys Gly Glu Lys Lys Leu Asn Ser Leu Asp Pro Met Thr Asn Ser Gly
        785                 790                 795                 800

Cys Ala Thr Ala Leu Asp Leu Ala Ser Asn Lys Ser Val Val Val Asn
                        805                 810                 815

Lys His Leu Asn Gly Glu Arg Leu Leu Glu Tyr Asp Phe Asn Lys Leu
                        820                 825                 830

Leu Val Ser Ala Val Ser Gln Ile Thr Glu Ser Phe Val Arg Lys Gln
                        835                 840                 845

Lys Tyr Lys Leu Ser His Ser Asp Tyr Glu Tyr Lys Val Ser Lys Leu
                        850                 855                 860

Val Ser Arg Leu Val Ile Gly Ser Lys Gly Glu Thr Gly Arg Ser
        865                 870                 875                 880

Glu Asp Asn Leu Ala Glu Ile Cys Phe Asp Gly Glu Glu Thr Ser
                        885                 890                 895

Phe Phe Lys Ser Leu Glu Glu Lys Val Asn Thr Thr Ile Ala Arg Tyr
                        900                 905                 910

Arg Arg Gly Arg Arg Ala Asn Asp Lys Gly Asp Gly Glu Lys Leu Thr
                        915                 920                 925

Asn Thr Lys Gly Leu His His Leu Gln Leu Ile Leu Thr Gly Lys Met
                930                 935                 940

Ala His Leu Arg Lys Val Ile Leu Ser Glu Ile Ser Phe His Leu Val
        945                 950                 955                 960

Glu Asp Phe Asp Pro Ser Cys Leu Thr Asn Asp Met Lys Phe Ile
                        965                 970                 975

Cys Glu Ala Val Glu Gly Ser Thr Glu Leu Ser Pro Leu Tyr Phe Thr
                        980                 985                 990

Ser Val Ile Lys Asp Gln Cys Gly  Leu Asp Glu Met Ala  Lys Asn Leu
                    995                 1000                1005

Cys Arg Lys Phe Phe Ser Glu  Asn Asp Trp Phe Ser  Cys Met Lys
                    1010                1015                1020

Met Ile Leu Leu Gln Met Asn  Ala Asn Ala Tyr Ser  Gly Lys Tyr
                    1025                1030                1035

Arg His Met Gln Arg Gln Gly  Leu Asn Phe Lys Phe  Asp Trp Asp
                    1040                1045                1050
```

-continued

```
Lys Leu Glu Glu Asp Val Arg Ile Ser Glu Arg Glu Ser Asn Ser
1055                1060                1065

Glu Ser Leu Ser Lys Ala Leu Ser Leu Thr Gln Cys Met Ser Ala
1070                1075                1080

Ala Leu Lys Asn Leu Cys Phe Tyr Ser Glu Ser Pro Thr Ser
1085                1090                1095

Tyr Thr Ser Val Gly Pro Asp Ser Gly Arg Leu Lys Phe Ala Leu
1100                1105                1110

Ser Tyr Lys Glu Gln Val Gly Gly Asn Arg Glu Leu Tyr Ile Gly
1115                1120                1125

Asp Leu Arg Thr Lys Met Phe Thr Arg Leu Ile Glu Asp Tyr Phe
1130                1135                1140

Glu Ser Phe Ser Ser Phe Ser Gly Ser Cys Leu Asn Asn Asp
1145                1150                1155

Lys Glu Phe Glu Asn Ala Ile Leu Ser Met Thr Ile Asn Val Arg
1160                1165                1170

Glu Gly Phe Leu Asn Tyr Ser Met Asp His Ser Lys Trp Gly Pro
1175                1180                1185

Met Met Cys Pro Phe Leu Phe Leu Met Phe Leu Gln Asn Leu Lys
1190                1195                1200

Leu Gly Asp Asp Gln Tyr Val Arg Ser Gly Lys Asp His Val Ser
1205                1210                1215

Thr Leu Leu Thr Trp His Met His Lys Leu Val Glu Val Pro Phe
1220                1225                1230

Pro Val Val Asn Ala Met Met Lys Ser Tyr Val Lys Ser Lys Leu
1235                1240                1245

Lys Leu Leu Arg Gly Ser Glu Thr Thr Val Thr Glu Arg Ile Phe
1250                1255                1260

Arg Gln Tyr Phe Glu Met Gly Ile Val Pro Ser His Ile Ser Ser
1265                1270                1275

Leu Ile Asp Met Gly Gln Gly Ile Leu His Asn Ala Ser Asp Phe
1280                1285                1290

Tyr Gly Leu Leu Ser Glu Arg Phe Ile Asn Tyr Cys Ile Gly Val
1295                1300                1305

Ile Phe Gly Glu Arg Pro Glu Ala Tyr Thr Ser Ser Asp Asp Gln
1310                1315                1320

Ile Thr Leu Phe Asp Arg Arg Leu Ser Asp Leu Val Val Ser Asp
1325                1330                1335

Pro Glu Val Leu Val Leu Leu Glu Phe Gln Ser His Leu Ser
1340                1345                1350

Gly Leu Leu Asn Lys Phe Ile Ser Pro Lys Ser Val Ala Gly Arg
1355                1360                1365

Phe Ala Ala Glu Phe Lys Ser Arg Phe Tyr Val Trp Gly Glu Glu
1370                1375                1380

Val Pro Leu Leu Thr Lys Phe Val Ser Ala Ala Leu His Asn Val
1385                1390                1395

Lys Cys Lys Glu Pro His Gln Leu Cys Glu Thr Ile Asp Thr Ile
1400                1405                1410

Ala Asp Gln Ala Ile Ala Asn Gly Val Pro Val Ser Leu Val Asn
1415                1420                1425

Ser Ile Gln Arg Arg Thr Leu Asp Leu Leu Lys Tyr Ala Asn Phe
1430                1435                1440
```

```
Pro Leu Asp Pro Phe Leu Leu Asn Thr Asn Thr Asp Val Lys Asp
    1445            1450                1455

Trp Leu Asp Gly Ser Arg Gly Tyr Arg Ile Gln Arg Leu Ile Glu
    1460            1465                1470

Glu Leu Cys Pro Asn Glu Thr Lys Val Val Arg Lys Leu Val Arg
    1475            1480                1485

Lys Leu His His Lys Leu Lys Asn Gly Glu Phe Asn Glu Glu Phe
    1490            1495                1500

Phe Leu Asp Leu Phe Asn Arg Asp Lys Lys Glu Ala Ile Leu Gln
    1505            1510                1515

Leu Gly Asp Leu Leu Gly Leu Glu Glu Asp Leu Asn Gln Leu Ala
    1520            1525                1530

Asp Val Asn Trp Leu Asn Leu Asn Glu Met Phe Pro Leu Arg Met
    1535            1540                1545

Val Leu Arg Gln Lys Val Val Tyr Pro Ser Val Met Thr Phe Gln
    1550            1555                1560

Glu Glu Arg Ile Pro Ser Leu Ile Lys Thr Leu Gln Asn Lys Leu
    1565            1570                1575

Cys Ser Lys Phe Thr Arg Gly Ala Gln Lys Leu Leu Ser Glu Ala
    1580            1585                1590

Ile Asn Lys Ser Ala Phe Gln Ser Cys Ile Ser Ser Gly Phe Ile
    1595            1600                1605

Gly Leu Cys Lys Thr Leu Gly Ser Arg Cys Val Arg Asn Lys Asn
    1610            1615                1620

Arg Glu Asn Leu Tyr Ile Lys Lys Leu Leu Glu Asp Leu Thr Thr
    1625            1630                1635

Asp Asp His Val Thr Arg Val Cys Asn Arg Asp Gly Ile Thr Leu
    1640            1645                1650

Tyr Ile Cys Asp Lys Gln Ser His Pro Glu Ala His Arg Asp His
    1655            1660                1665

Ile Cys Leu Leu Arg Pro Leu Leu Trp Asp Tyr Ile Cys Ile Ser
    1670            1675                1680

Leu Ser Asn Ser Phe Glu Leu Gly Val Trp Val Leu Ala Glu Pro
    1685            1690                1695

Thr Lys Gly Lys Asn Asn Ser Glu Asn Leu Thr Leu Lys His Leu
    1700            1705                1710

Asn Pro Cys Asp Tyr Val Ala Arg Lys Pro Glu Ser Ser Arg Leu
    1715            1720                1725

Leu Glu Asp Lys Val Asn Leu Asn Gln Val Ile Gln Ser Val Arg
    1730            1735                1740

Arg Leu Tyr Pro Lys Ile Phe Glu Asp Gln Leu Leu Pro Phe Met
    1745            1750                1755

Ser Asp Met Ser Ser Lys Asn Met Arg Trp Ser Pro Arg Ile Lys
    1760            1765                1770

Phe Leu Asp Leu Cys Val Leu Ile Asp Ile Asn Ser Glu Ser Leu
    1775            1780                1785

Ser Leu Ile Ser His Val Val Lys Trp Lys Arg Asp Glu His Tyr
    1790            1795                1800

Thr Val Leu Phe Ser Asp Leu Ala Asn Ser His Gln Arg Ser Asp
    1805            1810                1815

Ser Ser Leu Val Asp Glu Phe Val Val Ser Thr Arg Asp Val Cys
    1820            1825                1830

Lys Asn Phe Leu Lys Gln Val Tyr Phe Glu Ser Phe Val Arg Glu
```

```
                1835                1840                1845
Phe Val Ala Thr Thr Arg Thr Leu Gly Asn Phe Ser Trp Phe Pro
                1850                1855                1860

His Lys Glu Met Met Pro Ser Glu Asp Gly Ala Glu Ala Leu Gly
                1865                1870                1875

Pro Phe Gln Ser Phe Val Ser Lys Val Val Asn Lys Asn Val Glu
                1880                1885                1890

Arg Pro Met Phe Arg Asn Asp Leu Gln Phe Gly Phe Gly Trp Phe
                1895                1900                1905

Ser Tyr Arg Met Gly Asp Val Val Cys Asn Ala Ala Met Leu Ile
                1910                1915                1920

Arg Gln Gly Leu Thr Asn Pro Lys Ala Phe Lys Ser Leu Lys Asp
                1925                1930                1935

Leu Trp Asp Tyr Met Leu Asn Tyr Thr Lys Gly Val Leu Glu Phe
                1940                1945                1950

Ser Ile Ser Val Asp Phe Thr His Asn Gln Asn Asn Thr Asp Cys
                1955                1960                1965

Leu Arg Lys Phe Ser Leu Ile Phe Leu Val Arg Cys Gln Leu Gln
                1970                1975                1980

Asn Pro Gly Val Ala Glu Leu Leu Ser Cys Ser His Leu Phe Lys
                1985                1990                1995

Gly Glu Ile Asp Arg Arg Met Leu Asp Glu Cys Leu His Leu Leu
                2000                2005                2010

Arg Thr Asp Ser Val Phe Lys Val Asn Asp Gly Val Phe Asp Ile
                2015                2020                2025

Arg Ser Glu Glu Phe Glu Asp Tyr Met Glu Asp Pro Leu Ile Leu
                2030                2035                2040

Gly Asp Ser Leu Glu Leu Leu Leu Gly Ser Lys Arg Ile Leu
                2045                2050                2055

Asp Gly Ile Arg Ser Ile Asp Phe Glu Arg Val Gly Pro Glu Trp
                2060                2065                2070

Glu Pro Val Pro Leu Thr Val Lys Met Gly Ala Leu Phe Glu Gly
                2075                2080                2085

Arg Asn Leu Val Gln Asn Ile Ile Val Lys Leu Glu Thr Lys Asp
                2090                2095                2100

Met Lys Val Phe Leu Ala Gly Leu Glu Gly Tyr Glu Lys Ile Ser
                2105                2110                2115

Asp Val Leu Gly Asn Leu Phe Leu His Arg Phe Arg Thr Gly Glu
                2120                2125                2130

His Leu Leu Gly Ser Glu Ile Ser Val Ile Leu Gln Glu Leu Cys
                2135                2140                2145

Ile Asp Arg Ser Ile Leu Leu Ile Pro Leu Ser Leu Leu Pro Asp
                2150                2155                2160

Trp Phe Ala Phe Lys Asp Cys Arg Leu Cys Phe Ser Lys Ser Arg
                2165                2170                2175

Ser Thr Leu Met Tyr Glu Thr Val Gly Gly Arg Phe Arg Leu Lys
                2180                2185                2190

Gly Arg Ser Cys Asp Asp Trp Leu Gly Gly Ser Val Ala Glu Asp
                2195                2200                2205

Ile Asp
                2210
```

<210> SEQ ID NO 24

```
<211> LENGTH: 90
<212> TYPE: PRT
<213> ORGANISM: Artificial Sequence
<220> FEATURE:
<223> OTHER INFORMATION: Z protein of the Clone 13 strain of LCMV
      (GenBank Accession No. ABC96003.1; GI:86440168)

<400> SEQUENCE: 24

Met Gly Gln Gly Lys Ser Arg Glu Glu Lys Gly Thr Asn Ser Thr Asn
1               5                   10                  15

Arg Ala Glu Ile Leu Pro Asp Thr Thr Tyr Leu Gly Pro Leu Ser Cys
            20                  25                  30

Lys Ser Cys Trp Gln Lys Phe Asp Ser Leu Val Arg Cys His Asp His
        35                  40                  45

Tyr Leu Cys Arg His Cys Leu Asn Leu Leu Ser Val Ser Asp Arg
    50                  55                  60

Cys Pro Leu Cys Lys Tyr Pro Leu Pro Thr Arg Leu Lys Ile Ser Thr
65                  70                  75                  80

Ala Pro Ser Ser Pro Pro Tyr Glu Glu
                85                  90

<210> SEQ ID NO 25
<211> LENGTH: 498
<212> TYPE: PRT
<213> ORGANISM: Artificial Sequence
<220> FEATURE:
<223> OTHER INFORMATION: GP protein of the WE strain of LCMV

<400> SEQUENCE: 25

Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Val Ser
        35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
            100                 105                 110

Thr Asn Asp Ser Ile Leu Asn His Asn Phe Cys Asn Leu Thr Ser Ala
        115                 120                 125

Phe Asn Lys Lys Thr Phe Asp His Thr Leu Met Ser Ile Val Ser Ser
    130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Ile Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
    210                 215                 220
```

```
Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
            245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
            325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Lys Thr Gly
370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
            405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
            435                 440                 445

Ile Ser Ile Phe Leu His Leu Val Lys Ile Pro Thr His Arg His Ile
            450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
            485                 490                 495

Arg Arg

<210> SEQ ID NO 26
<211> LENGTH: 450
<212> TYPE: DNA
<213> ORGANISM: Artificial Sequence
<220> FEATURE:
<223> OTHER INFORMATION: HBV HBe antigen (GenBank Accession No.
      E15688.1; GI: 5710371)

<400> SEQUENCE: 26
atggacattg acacgtataa agaatttgga gctactgtgg agttactctc gtttttgcct      60
tctgacttct ttccttccgt cagagatctc ctagacaccg cctcagctct gtatcgagaa     120
gccttagagt ctcctgagca ttgctcacct caccatactg cactcaggca agccattctc     180
tgctgggggg aattgatgac tctagctacc tgggtgggta ataatttgga agatccagca     240
tccagggatc tagtagtcaa ttatgttaat actaacatgg gtttaaagat caggcaacta     300
ttgtggtttc atatatcttg ccttactttt ggaagagaga ctgtacttga atatttggtc     360
```

```
tctttcggag tgtggattcg cactcctcca gcctatagac caccaaatgc ccctatctta    420
tcaacacttc cggaaactac tgttgtttaa                                    450
```